US007202253B2

(12) United States Patent
Lloyd et al.

(10) Patent No.: US 7,202,253 B2
(45) Date of Patent: Apr. 10, 2007

(54) CYCLOALKYL INHIBITORS OF POTASSIUM CHANNEL FUNCTION

(75) Inventors: John Lloyd, Yardley, PA (US); Yoon T. Jeon, Belle Meade, NJ (US); Heather Finlay, Skillman, NJ (US); Lin Yan, East Brunswick, NJ (US); Michael F. Gross, Durham, NC (US); Serge Beaudoin, Morrisville, NC (US)

(73) Assignees: Bristol-Myers Squibb Company, Princeton, NJ (US); Icagen, Inc., Durham, NC (US)

( * ) Notice: Subject to any disclaimer, the term of this patent is extended or adjusted under 35 U.S.C. 154(b) by 0 days.

(21) Appl. No.: 10/997,734

(22) Filed: Nov. 24, 2004

(65) Prior Publication Data

US 2005/0234106 A1     Oct. 20, 2005

Related U.S. Application Data

(63) Continuation of application No. 10/356,158, filed on Jan. 31, 2003, now abandoned.

(60) Provisional application No. 60/353,884, filed on Feb. 1, 2002.

(51) Int. Cl.
  *A61K 31/4709* (2006.01)
  *A61K 31/519* (2006.01)
  *C07D 217/22* (2006.01)
  *C07D 239/84* (2006.01)
  *C07D 471/06* (2006.01)

(52) U.S. Cl. .................. 514/266.4; 514/300; 514/310; 544/293; 546/122; 546/143

(58) Field of Classification Search ...................... None
  See application file for complete search history.

(56) References Cited

U.S. PATENT DOCUMENTS

| 3,406,199 | A |  | 10/1968 | Weber et al. |
| 4,611,004 | A |  | 9/1986 | Ackermann et al. |
| 4,755,594 | A |  | 7/1988 | Bridges et al. |
| 5,281,625 | A | * | 1/1994 | Zipplies et al. ............. 514/634 |
| 5,612,359 | A |  | 3/1997 | Murugesan |
| 5,631,282 | A |  | 5/1997 | Goetz |
| 5,646,162 | A |  | 7/1997 | Müller et al. |
| 5,670,504 | A |  | 9/1997 | Bochis et al. |
| 5,679,705 | A |  | 10/1997 | Baker et al. |
| 5,696,156 | A |  | 12/1997 | Baker et al. |
| 5,900,415 | A |  | 5/1999 | Peterson et al. |
| 5,952,363 | A | * | 9/1999 | Kristiansen et al. ........ 514/408 |
| 6,043,265 | A |  | 3/2000 | Murugesan et al. |
| 6,426,365 | B1 |  | 7/2002 | Shinkai et al. |
| 6,455,550 | B1 |  | 9/2002 | Chen et al. |
| 6,632,836 | B1 |  | 10/2003 | Baker et al. |
| 6,660,742 | B2 |  | 12/2003 | Lee |
| 6,953,792 | B2 |  | 10/2005 | Castro Pineiro et al. |
| 2004/0014748 | A1 |  | 1/2004 | Grutzmann et al. |
| 2004/0171642 | A1 |  | 9/2004 | Pineiro et al. |

FOREIGN PATENT DOCUMENTS

WO    WO 00/01389    1/2000

OTHER PUBLICATIONS

Balser, J.R. et al., "Suppression of Time-Dependent Outward Current in Guinea Pig Ventricular Myocytes: Actions of Quinidine and Amiodarone", Circulation Research, vol. 69, No. 2, pp. 519-529 (1991).
Bowlby, M.R. et al., "Block of Cloned Voltage-Gated Potassium Channels by the Second Messenger Diacylglycerol Independent of Protein Kinase C", Journal of Neurophysiology, vol. 73, No. 6, pp. 2221-2229 (1995).
Chandy, K.G. et al., "Voltage-Gated Potassium Channels are Required for Human T Lymphocyte Activation", J. Exp. Med., vol. 160, pp. 369-385 (1984).
DeCoursey, T.E. et al., "Voltage-gated $K^+$ channels in human T lymphocytes: a role in mitogenesis?", Nature, vol. 307, pp. 465-468 (1984).
Doupnik, C.A. et al., "The inward rectifier potassium channel family", Current Opinion in Neurobiology, vol. 5, pp. 268-277 (1995).
Fedida, D. et al., "Identity of a Novel Delayed Rectifier Current From Human Heart With a Cloned $K^+$ Channel Current", Circulation Research, vol. 73, No. 1, pp. 210-216 (1993).
Greene, T.W. et al., Protective Groups in Organic Synthesis, Second Edition, John Wiley and Sons, publ., pp. ix-x (table of contents) (1991).
Grissmer, S. et al., "Pharmacological Characterization of Five Cloned Voltage-Gated $K^+$ Channels, Types Kv1.1, 1.2, 1.3, 1.5, and 3.1, Stably Expressed in Mammalian Cell Lines", Molecular Pharmacology, vol. 45, pp. 1227-1234 (1994).
Hondeghem, L.M., "Development of Class III Antiarrhythmic Agents", Journal of Cadiovascular Pharmacology, vol. 20, Suppl. 2, S17-S22 (1992).
Kalman, K. et al., "Genomic Organization, Chromosomal Localization, Tissue Distribution, and Biophysical Characterization of a Novel Mammalian *Shaker*-related Voltage-gated Potassium Channel, Kv1.7", The Journal of Biological Chemistry, vol. 273, No. 10, pp. 5851-5857 (1998).
Leonard, R.J. et al., "Selective blockers of voltage-gated $K^+$ channels depolarize human T lymphocytes: Mechanism of the antiproliferative effect of charybdotoxin", Proc. Natl. Acad. Sci. USA, vol. 89, pp. 10094-10098 (1992).

(Continued)

*Primary Examiner*—Kamal A. Saeed
*Assistant Examiner*—Andrew B. Freistein
(74) *Attorney, Agent, or Firm*—Terrence J. Bogie

(57) ABSTRACT

Novel cycloalkyl compounds useful as inhibitors of potassium channel function (especially inhibitors of the $K_v1$ subfamily of voltage gated $K^+$ channels, especially inhibitors $K_v1.5$ which has been linked to the ultra-rapidly activating delayed rectifier $K^+$ current $I_{Kur}$), methods of using such compounds in the prevention and treatment of arrhythmia and $I_{Kur}$-associated conditions, and pharmaceutical compositions containing such compounds.

9 Claims, No Drawings

OTHER PUBLICATIONS

Lin, S.C. et al., "Voltage-gated Potassium Channels Regulate Calcium-dependent Pathways Involved in Human T Lymphocyte Activation", J. Exp. Med., vol. 177, pp. 637-645 (1993).

Nademanee, K., "The Amiodarone Odyssey", J. Am. Coll. Cardiol., vol. 20, No. 5, pp. 1063-1065 (1992).

Petersen, K.R. et al., "Expression environment determines $K^+$ current properties: Kv1 and Kv4 α-subunit-induced $K^+$ currents in mammalian cell lines and cardiac myocytes", Pflugers Arch.—Eur. J. Physiol., vol. 437, pp. 381-392 (1999).

Price, M. et al., "Charybdotoxin inhibits proliferation and interleukin 2 production in human peripheral blood lymphocytes", Proc. Natl. Acad. Sci. USA, vol. 86, pp. 10171-10175 (1989).

Roden, D.M., "Current Status of Class III Antiarrhythmic Drug Therapy", The American Journal of Cardiology, vol. 72, pp. 44B-49B (1993).

Sanguinetti, M.C. et al.,, "Two Components Of Cardiac Delayed Rectifier $K^+$ Current: Differential Sensitivity to Block by Class III Antiarrhythmic Agents", J. Gen. Physiol., vol. 96, pp. 195-215 (1990).

Singh, B.N. et al., "A third class of anti-arrhythmic action: Effects on atrial and ventricular intracellular potentials, and other pharmacological actions on cardiac muscle, of MJ 1999 and AH 3747", Br. J. Pharmac., vol. 39, pp. 675-687 (1970).

Singh, B.N. et al., "The effect of amiodarone, A new anti-anginal drug, on cardiac muscle", Br. J. Pharmac., vol. 39, pp. 657-667 (1970).

Snyders, D.J. et al., "A Rapidly Activating and Slowly Inactivating Potassium Channel Cloned from Human Heart: Functional Analysis after Stable Mammalian Cell Culture Expression", J. Gen. Physiol., vol. 101, pp. 513-543 (1993).

Swanson, R. et al., "Cloning and Expression of cDNA and Genomic Clones Encoding Three Delayed Rectifier Potassium Channels in Rat Brain", Neuron, vol. 4, pp. 929-939 (1990).

Wang, Z. et al., "Sustained Depolarization-Induced Outward Current in Human Atrial Myocytes: Evidence for a Novel Delayed Rectifier $K^+$ Current Similar to Kv1.5 Cloned Channel Currents", Circulation Research, vol. 73, No. 6, pp. 1061-1076 (1993).

Yang, T. et al., "Mechanism of block of a human cardiac potassium channel by terfenadine racemate and enantiomers", British Journal of Pharmacology, vol. 115, pp. 267-274 (1995).

Vaughan Williams, EM, Classification of Anti-Arrhythmic Drugs, Sandoe E., Flensted-Jensen E., Olesen K., eds., Cardiac Arrhythmias, Sodertaljie, Swden: AB Astra, 1971, 449-472.

Shinkai, H. et al., "Bis(2-(Acylamino)phenyl) Disulfides . . . ", Journal of Med. Chem., vol. 43, No. 19, pp. 3566-3572 (2000).

* cited by examiner

US 7,202,253 B2

CYCLOALKYL INHIBITORS OF POTASSIUM CHANNEL FUNCTION

This application is a continuation of Ser. No. 10/356,158 filed on Jan. 3, 2003 now abandoned which claims priority to U.S. Provisional Application Ser. No. 60/353,884 filed Feb. 1, 2002 the entirety of which is incorporated herein by reference.

FIELD OF THE INVENTION

The present invention provides for cycloalkyl compounds useful as inhibitors of potassium channel function (especially inhibitors of the $K_v1$ subfamily of voltage gated $K^+$ channels, more especially inhibitors $K_v1.5$ which has been linked to the ultra-rapidly activating delayed rectifier $K^+$ current $I_{Kur}$) and to pharmaceutical compositions containing such compounds. The present invention further provides for methods of using such compounds in the treatment of arrhythmia, $I_{Kur}$-associated disorders, and other disorders mediated by ion channel function.

BACKGROUND OF THE INVENTION

The importance of potassium channels was first recognized approximately fifty years ago when Hodgkin and Huxley discovered that potassium ions contributed to the current that excited the squid giant axon. Research in the area, however, was hampered by the lack of selective, high affinity ligands for potassium channels. But the advent of recombinant DNA techniques and single cell and whole cell voltage clamp techniques has changed the slow pace of the field. Indeed, potassium channels that exhibit functional, pharmacological and tissue distribution characteristics have been cloned. These cloned potassim channels are useful targets in assays for identifying candidate compounds for the treatment of various disease states. Potassium channels have turned out to be the most diverse family of ion channels discovered to date. They modulate a number of cellular events such as muscle contraction, neuro-endocrine secretion, frequency and duration of action potentials, electrolyte homeostatis, and resting membrane potential.

Potassium channels are expressed in eukaryotic and procaryotic cells and are elements in the control of electrical and non-electrical cellular functions. Potassium channels have been classified according to their biophysical and pharmacological characteristics. Subclasses of these channels have been named based on amino acid sequence and functional properties. Salient among these are the voltage dependent potassium channels, for example voltage gated potassium channels (e.g., $K_v1$, $K_v2$, $K_v3$, $K_v4$). Subtypes within these subclasses have been characterized as to their putative function, pharmacology and distribution in cells and tissues (Chandy and Gutman, "Voltage-gated potassium channel genes" in Handbook of Receptors and Channels— Ligand and Voltage-gated Ion Channels, ed. R. A. North, 1995; Doupnik et al., Curr. Opin. Neurobiol. 5:268, 1995). For example, the $K_v1$ class of potassium channels is further subdivided depending on the molecular sequence of the channel, for example $K_v1.1$, $K_v1.2$, $K_v1.3$, $K_v1.4$, $K_v1.5$, $K_v1.6$, and $K_v1.7$. Functional voltage-gated $K^+$ channels can exist as multimeric structures formed by the association of either identical or dissimilar subunits. This phenomena is thought to account for the wide diversity of $K_+$ channels. However, subunit compositions of native $K^+$ channels and the physiologic role that particular channels play are, in most cases, still unclear.

Membrane depolarization by $K_v1.3$ inhibition has been shown to be an effective method to prevent T-cell proliferation and therefore has applications in many autoimmune conditions. Inhibition of $K^+$ channels in the plasma membrane of human T-lymphocytes has been postulated to play a role in eliciting immunosuppressive responses by regulating intracellular $Ca^{++}$ homeostasis, which has been found to be important in T-cell activation.

The $K_v1.3$ voltage-gated potassium channel is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., J. Exp. Med. 160, 369, 1984; Decoursey et al., Nature, 307, 465, 1984). However, the $K^+$ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., Proc. Natl, Acad. Sci. USA, 86, 10171, 1989) showed that charybdotoxin would block $K_v1.3$ in human T-cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., Proc. Natl, Acad. Sci, USA, 89, 10094, 1992). Margatoxin, on the other hand, blocks only $K_v1.3$ in T-cells, and has immunosuppressant activity on both in in vitro and in vivo models. (Lin et al., J. exp. Med, 177, 637, 1993). The therapeutic utility of this compound, however, is limited by its potent toxicity. Recently, a class of compounds has been reported that may be an attractive alternative to the above mentioned drugs, see for example U.S. Pat. Nos. 5,670,504; 5,631,282; 5,696,156; 5,679,705; and 5,696,156. While addressing some of the activity/toxicity problems of previous drugs, these compounds tend to be of large molecular weight and are generally produced by synthetic manipulation of a natural product, isolation of which is cumbersome and labor intensive.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort. Therefore, a selective immunosuppressant without these side effects still remains to be developed. Potassium channel inhibitors promise to be the solution to this problem.

Atrial fibrillation (AF) and atrial flutter are the most common cardiac arrhythmias in clinical practice and are likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse effects including ventricular proarrhythmia. Because current therapy is inadequate and fraught with side effects, there is a clear need to develop new therapeutic approaches Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class of Anti-Arrhythmic Action: Effects On Atrial And Ventricular Intracellular Potentials And Other Pharmacological Actions On Cardiac Muscle, of M J 1999 and A H 3747" Br. J. Pharmacol 1970; 39:675–689. and Singh B. N., Vaughan Williams E. M, "The Effect of Amiodarone, A New Anti-Anginal Drug, On Cardiac Muscle", Br J. Pharmacol 1970; 39:657–667), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited by side effects (Nademanee, K. "The Amiodarone Odessey". J. Am. Coll. Cardiol. 1992; 20:1063–1065.) Drugs of this class are expected to be effective in preventing ventricular fibrillation. Selective class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. Na$^+$ or Ca$^{2+}$ currents; hereinafter $I_{Na}$ and $I_{Ca}$, respectively) or by reducing outward repolarizing potassium (K$^+$) currents. The delayed rectifier ($I_K$) K$^+$ current is the main outward current involved in the overall repolarization process during the action potential plateau, whereas the transient outward ($I_{to}$) and inward rectifier ($I_{KI}$) K$^+$ currents are responsible for the rapid initial and terminal phases of repolarization, respectively. Cellular electrophysiologic studies have demonstrated that $I_K$ consists of two pharmacologically and kinetically distinct K$^+$ current subtypes, $I_{Kr}$ (rapidly activating and deactivating) and $I_{Ks}$ (slowly activating and deactivating) (Sanguinetti and Jurkiewicz, Two Components Of Cardiac Delayed Rectifier K$^+$ Current: Differential Sensitivity To Block By Class III Antiarrhythmic Agents, J Gen Physiol 1990, 96:195–215). Class III antiarrhythmic agents currently in development, including d-sotalol, dofetilide (UK-68,798), almokalant (H234/09), E-4031 and methanesulfonamide-N-[1'-6-cyano-1,2,3,4-tetrahydro-2-naphthalenyl)-3,4-dihydro-4-hydroxyspiro[2H-1-benzopyran-2,4'-piperidin]-6yl]monochloride, predominantly, if not exclusively, block $I_{Kr}$. Although, amiodarone is a blocker of $I_{Ks}$ (Balser J. R. Bennett, P. B., Hondeghem, L. M. and Roden, D. M. "Suppression Of Time-Dependent Outward Current In Guinea Pig Ventricular Myocytes: Actions Of Quinidine And Amiodarone. Circ. Res. 1991, 69:519–529), it also blocks $I_{Na}$ and $I_{Ca}$, effects thyroid function, is as a nonspecific adrenergic blocker, and acts as an inhibitor of the enzyme phospholipase (Nademanee, K. "The Amiodarone Odessey".J.Am. Coll. Cardiol. 1992; 20:1063–1065). Therefore its method of treating arrhythmia is uncertain. Most Class III agents that are known to be in development predominantly block $I_{Kr}$.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD), prevents and/or terminates reentrant arrhythmias. Most selective Class III antiarrhythmic agents currently in development, such as d-sotalol and dofetilide predominantly, if not exclusively, block $I_{kr}$, the rapidly activating component of $I_K$ found both in the human atrium and ventricle.

Since these $I_{kr}$ blockers increase APD and refractoriness both in atria and ventricle without affecting conduction per se, theoretically they represent potential useful agents for the treatment of arrhythmias like AF. These agents have a liability in that they have an enhanced risk of proarrhythmia at slow heart rates. For example, torsades de points has been observed when these compounds are utilized (Roden, D. M. "Current Status of Class III Antiarrhythmic Drug Therapy", Am J. Cardiol, 1993; 72:44B–49B). This exaggerated effect at slow heart rates has been termed "reverse frequency-dependence", and is in contrast to frequency-independent or frequency-dependent actions (Hondeghem, L. M. "Development of Class III Antiarrhythmic Agents". J.Cadiovasc.Cardiol. 20 (Suppl.2):S17–S22).

The slowly activating component of the delayed rectifier ($I_{ks}$) potentially overcomes some of the limitations of $I_{kr}$ blockers associated with ventricular arrhythmias. Because of its slow activation kinetics however, the role of $I_{ks}$ in atrial repolarization may be limited due to the relatively short APD of the atrium. Consequently, although $I_{ks}$ blockers may provide distinct advantage in the case of ventricular arrhythmias, their ability to affect SVT is considered to be minimal.

The ultra-rapidly activating delayed rectifier K$^+$ current ($I_{kur}$) is believed to represent the native counterpart to a cloned potassium channel designated K$_v$1.5 and, while present in human atrium, it appears to be absent in human ventricle. Furthermore, because of its rapidity of activation and limited slow inactivation, $I_{kur}$ is believed to contribute significantly to repolarization in human atrium. Consequently, a specific blocker of $I_{kur}$, that is a compound which blocks $K_v1.5$, would overcome the short coming of other compounds by prolonging refractoriness by retarding repolarization in the human atrium without causing the delays in ventricular reporlarization that underlie arrhythmogenic after depolarizations and acquired long QT syndrome observed during treatment with current Class III drugs.

In intact human atrial myocytes an ultra-rapidly activating delayed rectifier $K^+$ current $I_{kur}$ which is also known as the sustained outward current, $I_{sus}$ or $I_{so}$, has been identified and this current has properties and kinetics identical to those expressed by the human $K^+$ channel clone (hKv1.5, HK2) when isolated from human heart and stably expressed in human (HEK-293) cell lines (Wang et al., 1993, Circ Res 73:1061–1076; Fedida et al., 1993, Circ Res 73:210–216; Snyders et al., 1993, J Gen Physiol 101:513–543) and originally cloned from rat brain (Swanson et al., 10, Neuron 4:929–939). Although various antiarrythmic agents are now available on the market, those having both satisfactory efficacy and a high margin of safety have not been obtained. For example, antiarrythmic agents of Class I according to the classification scheme of Vaughan-Williams ("Classification Of Antiarrhythmic Drugs: In: Cardiac Arrhythmias, edited by: E. Sandoe, E. Flensted-Jensen, K. Olesen; Sweden, Astra, Sodertalje, pp 449–472, 1981) which cause a selective inhibition of the maximum velocity of the upstroke of the action potential ($_{max}$) are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

SUMMARY OF THE INVENTION

The present invention provides cycloalkyl compounds of the following formula I, including enantiomers, diastereomers, and salts thereof, useful as inhibitors of potassium channel function (especially inhibitors of the $K_v1$ subfamily of voltage gated $K^+$ channels, more especially inhibitors of $K_v1.5$ which has been linked to the ultra-rapidly activating delayed rectifier $K^+$ current, $I_{Kur}$) for the treatment of disorders such as arrhythmia and $I_{Kur}$-associated disorders:

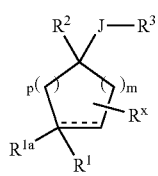

I including enantiomers, diastereomers and salts thereof wherein the dashed line represents an optional double bond, provided that $R^{1a}$ is absent when a double bond is present;

m and p are independently 0, 1, 2 or 3;

$R^1$ is

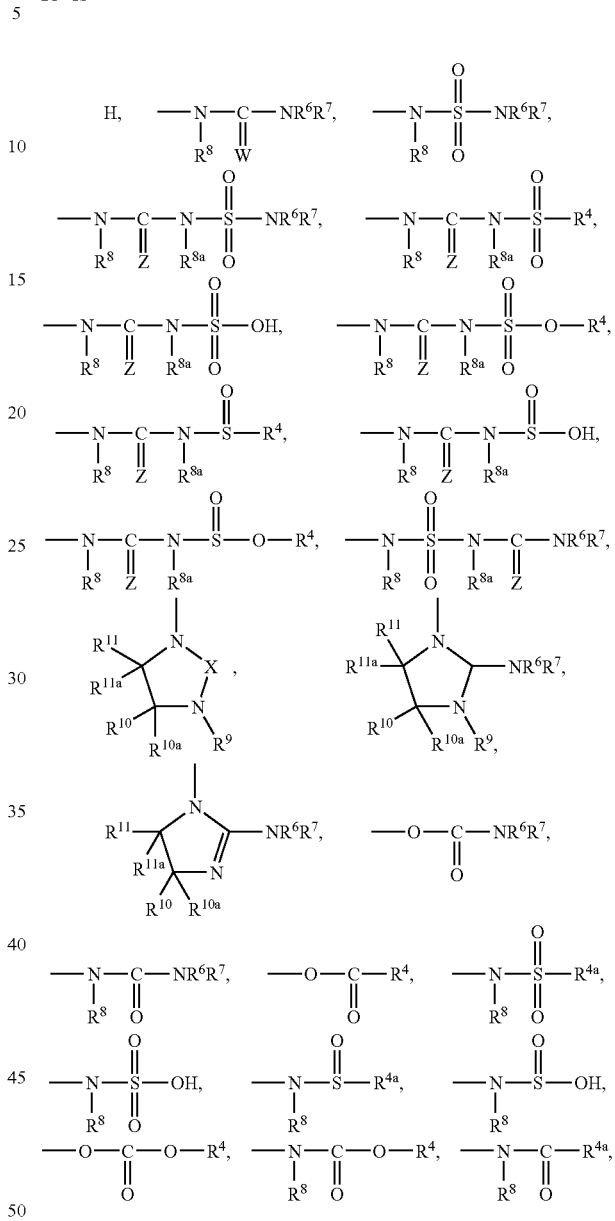

—$N(R^8)R^{14}$, —$N(R^8)C(O)R^{14}$, —$C(=NR^{8b})R^{8c}$, —$SO_2R^{8c}$, —$CO_2H$, —$OC(O)CCl_3$, —$C(O)R^{8c}$, —$CO_2R^{8c}$, —$C(=S)R^{8c}$, —$NR^6R^7$, —$OC(O)NR^6R^7$, —$N_3$, optionally substituted aryl, optionally substituted heteroaryl, optionally substituted heterocyclo, halo, perfluoroalkyl, cyano, nitro, hydroxy, optionally substituted alkoxy, optionally substituted aryloxy, optionally substituted heteroaryloxy, optionally substituted alkyl, optionally subsituted alkenyl, or optionally subsituted alkynyl;

$R^{1a}$ is H or $R^X$;

or $R^1$ and $R^{1a}$ together form oxo;

or $R^1$ and $R^{1a}$ together with the carbon atom to which they are attached combine to form an optionally substituted spiro-fused heterocyclo group;

or $R^1$ and $R^{1a}$ together combine to form a group

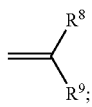

R² is heteroaryl, (heteroaryl)alkyl, aryl, (aryl)alkyl, heterocyclo, (heterocyclo)alkyl, alkyl, alkenyl or cycloalkyl, any of which may be optionally independently substituted with one or more groups $T^1$, $T^2$ or $T^3$;

J is a bond, $C_{1-4}$ alkylene optionally independently substituted with one or more groups $T^{1a}$, $T^{2a}$ or $T^{3a}$, or $C_{1-4}$ alkenylene optionally independently substituted with one or more groups $T^{1a}$, $T^{2a}$ or $T^{3a}$;

R³ is

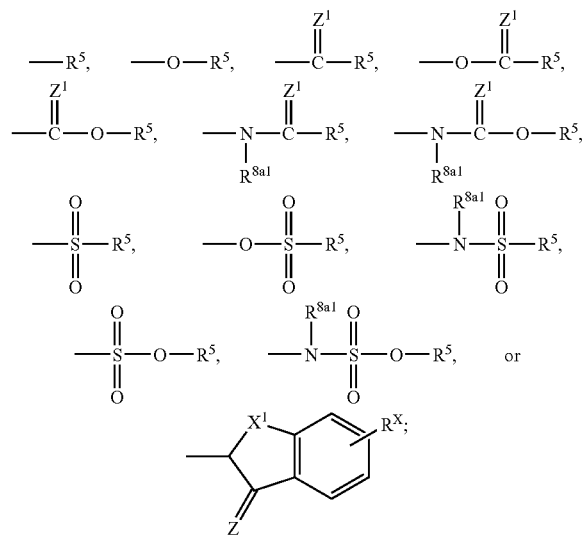

R⁴ is alkyl, haloalkyl, alkenyl, cycloalkyl, heterocyclo, aryl, or heteroaryl any of which may be optionally independently substituted with one or more groups $T^{1b}$, $T^{2b}$ or $T^{3b}$;

$R^{4a}$ is R⁴ or OR⁴;

R⁵ is —NR$^{6a}$R$^{7a}$, or heteroaryl, (heteroaryl)alkyl, aryl, (aryl)alkyl, alkyl, cycloalkyl, (cycloalkyl)alkyl, heterocyclo, (heterocyclo)alkyl, alkyl, alkenyl or alkynyl any of which may be optionally independently substituted with one or more groups $T^{1c}$, $T^{2c}$ or $T^{3c}$;

R⁶, R$^{6a}$, R⁷, R$^{7a}$, R⁸, R$^{8a}$, R$^{8a1}$, R$^{8a2}$, R$^{8a3}$, R$^{8a4}$, R$^{8a5}$ and R⁹ are independently H, alkyl, hydroxy, alkoxy, aryloxy, heterocyclooxy, heteroaryloxy, (hydroxy)alkyl, (alkoxy)alkyl, (aryloxy)alkyl, (heterocyclooxy)alkyl, (heteroaryloxy)alkyl, (cyano)alkyl, (alkenyl)alkyl, (alkynyl)alkyl, cycloalkyl, (cycloalkyl)alkyl, aryl, (aryl)alkyl, heteroaryl, (heteroaryl)alkyl, heterocyclo, (heterocyclo)alkyl, —C(O)R¹², —CO₂R¹², —C(O)—NR¹²R¹³, or —NR¹²R¹³ any of which may be optionally independently substituted with one or more groups $T^{1d}$, $T^{2d}$ or $T^{3d}$;

or R⁶ and R⁷, or R$^{6a}$ and R$^{7a}$ together with the nitrogen atom to which they are attached may combine to form a saturated or unsaturated 4 to 8 membered ring (either cycloalkyl or heterocylco) optionally independently substituted with one or more groups $T^{1d}$, $T^{2d}$ or $T^{3d}$;

or one of R⁶ or R⁷, may combine with one of R⁸, R$^{8a}$ or R⁹ to form a saturated or unsaturated 5 to 8 membered ring (either cycloalkyl or heterocylco) optionally independently substituted with one or more groups $T^{1d}$, $T^{2d}$ or $T^{3d}$.

or one of R$^{6a}$ or R$^{7a}$, may combine with R$^{8a1}$ to form a saturated or unsaturated 5 to 8 membered ring (either cycloalkyl or heterocylco) optionally independently substituted with one or more groups $T^{1d}$, $T^{2d}$ or $T^{3d}$ R$^{8b}$ is independently H, alkyl, aryl, cyano, nitro, acyl or —SO₂(alkyl);

R$^{8c}$ is independently H, alkyl, cycloalkyl, alkenyl, alkynyl, aryl, arylalkyl, cycloheteroalkyl, heteroaryl, amino or alkoxy;

R$^{8d}$ is R⁴, COR⁴, CO₂R⁴, SO₂R⁴, CONR⁶R⁷, or SO₂—NR⁶⁷;

R¹⁰R$^{10a}$, R¹¹ and R$^{11a}$ are independently H, alkyl, aryl, (aryl)alkyl, alkoxy, (alkoxy)alkyl, halo, hydroxy, (hydroxy)alkyl, amino, amido, heteroaryl, (heteroaryl)alkyl, heterocyclo, (heterocyclo)alkyl, sulfonamido, cycloalkyl, (cycloalkyl)alkyl, or cyano any of which may be optionally independently substituted on available atoms (as allowed by valence) with one or more groups $T^{1e}$, $T^{2e}$ or $T^{3e}$;

or R¹⁰ and R$^{10a}$, or R¹¹ and R$^{11a}$ may combine to form oxo;

or R$^{10a}$ may combine with R$^{11a}$ to form a bond;

or R¹⁰ may combine with R⁹ to form a saturated or unsaturated ring;

R¹² and R¹³ are independently H, alkyl, hydroxy, alkoxy, aryloxy, heterocyclooxy, heteroaryloxy, (hydroxy)alkyl, (alkoxy)alkyl, (aryloxy)alkyl, (heterocylooxy)alkyl, (heteroaryloxy)alkyl, cycloalkyl, (cycloalkyl)alkyl, aryl, (aryl)alkyl, heteroaryl, (heteroaryl)alkyl, heterocyclo, or (heterocyclo)alkyl any of which may be optionally independently substituted with one or more groups $T^{1f}$, $T^{2f}$ or $T^{3f}$ or R¹² and R¹³ together with the nitrogen atom to which they are attached may combine to form a saturated or unsaturated ring (either cycloalkyl or heterocylco) which may be optionally independently substituted with one or more groups $T^{1f}$, $T^{2f}$ or $T^{3f}$;

W is =NR$^{8a2}$, =N—CO₂R$^{8a2}$, =N—COR$^{8a2}$, =N—CN, or =N—SO₂R$^{8a2}$;

X is

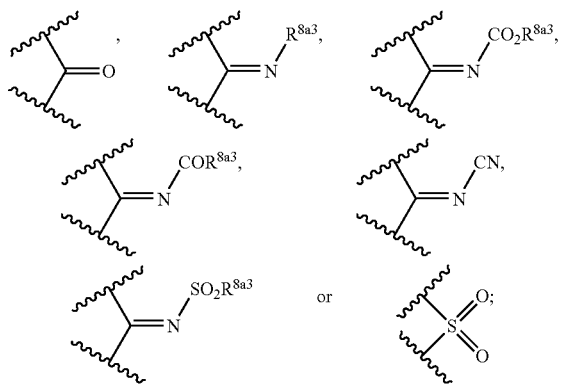

Z, Z¹ and Z² are independently =O, =S, =NR$^{8a4}$ or =N—CN;

$R^{14}$ is independently

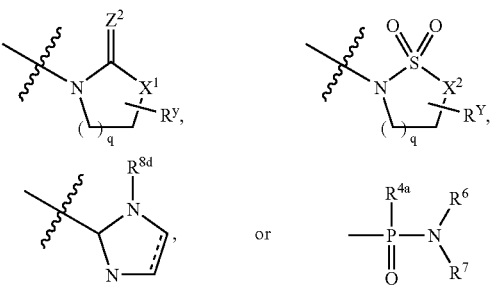

where q is 1, 2 or 3;

$R^Y$ is an optional oxo substituent attached to any available ring carbon atom;

$X^1$ is O, S, $NR^{8a5}$ or $CH_2$; and $X^2$ is $NR^{8a5}$ or $CH_2$;

$R^X$ is one or more optional substituents, attached to any available ring carbon atom, independently selected from $T^{1g}$, $T^{2g}$ or $T^{3g}$;

$T^{1-1g}$, $T^{2-2g}$, and $T^{3-3g}$ are are each independently (1) hydrogen or $T^6$, where $T^6$ is (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

(ii) (ii) a group (i) which is itself substituted by one or more of the same or different groups (i); or (iii) (iii) a group (i) or (ii) which is independently substituted by one or more (preferably 1 to 3) of the following groups (2) to (13) of the definition of $T^{1-1g}$, $T^{2-2g}$ and $T^{3-3g}$, (2) —OH or —$OT^6$, (3) —SH or —$ST^6$, (4) —C(O)$_t$H, —C(O)$_t$$T^6$, or —O—C(O)$T^6$, where t is 1 or 2;

(5) —$SO_3H$, —S(O)$_t$$T^6$, or S(O)$_t$N($T^9$)$T^6$, (6) halo, (7) cyano, (8) nitro, (9) —$T^4$—$NT^7T^8$,

(10) —$T^4$—N($T^9$)—$T^5$—$NT^7T^8$,

(11) —$T^4$—N($T^{10}$)—$T^5$—$T^6$,

(12) —$T^4$—N($T^{10}$)—$T^5$—H,

(13) oxo, $T^4$ and $T^5$ are each independently (1) a single bond, (2) —$T^{11}$—S(O)$_t$—$T^{12}$—, (3) —$T^{11}$—C(O)—$T^{12}$—, (4) —$T^{11}$—C(S)—$T^{12}$—, (5) —$T^{11}$—O—$T^{12}$—, (6) —$T^{11}$—S—$T^{12}$—, (7) —$T^{11}$—O—C(O)—$T^{12}$—, (8) —$T^{11}$—C(O)—O—$T^{12}$—, (9) —$T^{11}$—C(=$NT^{9a}$)—$T^{12}$—, or

(10) —$T^{11}$—C(O)—C(O)—$T^{12}$—

$T^7$, $T^8$, $T^9$, $T^{9a}$ and $T^{10}$ (1) are each independently hydrogen or a group provided in the definition of $T^6$, or (2) $T^7$ and $T^8$ may together be alkylene or alkenylene, completing a 3- to 8-membered saturated or unsaturated ring together with the atoms to which they are attached, which ring is unsubstituted or substituted with one or more groups listed in the description of $T^{1-1g}$, $T^{2-2g}$ and $T^{3-3g}$, or (3) $T^7$ or $T^8$, together with $T^9$, may be alkylene or alkenylene completing a 3-to 8-membered saturated or unsaturated ring together with the nitrogen atoms to which they are attached, which ring is unsubstituted or substituted with one or more groups listed in the description of $T^{1-1g}$, $T^{2-2g}$ and $T^{3-3g}$, or (4) $T^7$ and $T^8$ or $T^9$ and $T^{10}$ together with the nitrogen atom to which they are attached may combine to form a group —N=$CT^{13}T^{14}$ where $T^{13}$ and $T^{14}$ are each independently H or a group provided in the definition of $T^6$; and $T^{11}$ and $T^{12}$ are each independently (1) a single bond, (2) alkylene, (3) alkenylene, or (4) alkynylene.

The present invention provides novel methods for the prevention and treatment of arrhythmia and $I_{Kur}$-associated disorders employing one or more compounds of the formula I, enantiomers, diastereomers or pharmaceutically acceptable salts thereof. In particular the present invention provides a novel method for the selective prevention and treatment of supraventricular arrhythmias.

Preferred compounds within the scope of formula I include compounds of formula $I_a$, $I_b$ and $I_c$:

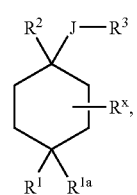

$I_a$

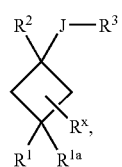

$I_b$

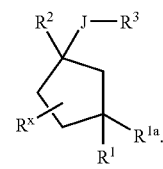

$I_c$

Preferred compounds within the scope of formula I include compounds and salts thereof wherein one or more, and especially all of $R^1$, $R^{1a}$, $R^2$, J and $R^3$ are selected from the following definitions:

$R^1$ is hydrogen, hydroxy, —$NR^6R^7$, —O—C(O)—$NR^6R^7$, —O—C(O)—$R^4$, —N($R^8$)—$SO_2$—$NR^6R^7$, —N($R^8$)—C(Z)—N($R^{8a}$)—$SO_2$—$R^4$, —N($R^8$)—C(Z)—N($R^{8a}$)—$SO_2$—OH, —$SO_2$—$R^{8c}$, —N($R^8$)—C(W)—$NR^6R^7$, or a group

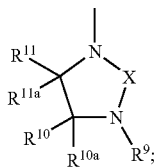

$R^{1a}$ is H, or $R^{1a}$ and $R^1$ combine from oxo or an optionally substituted spiro-fused heterocyclo group;

$R^2$ is optionally substituted alkyl, optionally substituted alkenyl, optionally substituted aryl (especially phenyl or napthyl), optionally substituted (aryl)alkyl (especially benzyl), or optionally substituted heteroaryl (especially thienyl, benzothienyl, pyridinyl or isoxazolyl);

J is a bond, optionally substituted $C_{1-4}$ alkylene (especially methylene) or optionally substituted $C_{1-4}$ alkenylene (especially ethenylene);

$R^3$ is $-R^5$, $-OR^5$, $-C(Z^1)-R^5$, $-C(Z^1)-O-R^5$, $-O-C(Z^1)-R^5$, $-N(R^{8a1})-C(Z^1)-R^5$, $-N(R^{8a1})-C(Z^1)-O-R^5$, or $-N(R^{8a1})-SO_2-R^5$;

$R^5$ is optionally substituted aryl, optionally substituted (aryl)alkyl, optionally substituted heteroaryl, optionally substituted (heteroaryl)alkyl, optionally substituted heterocylco, optionally substituted (heterocylco)alkyl, optionally subsituted cycloalkyl, optionally substituted (cycloalkyl)alkyl, optionally substituted alkyl, optionally substituted alkenyl, optionally substituted alkynyl, $-NR^{6a}R^{7a}$ or a group,

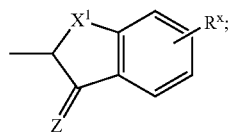

$R^6$, $R^{6a}$, $R^7$ and $R^{7a}$ are independently H, optionally substituted aryl, optionally substituted heteroaryl, optionally substituted cycloalkyl, optionally substituted heterocyclo, optionally substituted (aryl)alkyl, optionally substituted (heteroaryl)alkyl, optionally substituted (heterocylco)alkyl, optionally substituted alkyl, or $COR^{12}$;

or $R^6$ and $R^{6a}$, or $R^7$ and $R^{7a}$ together with the nitrogen to which they are attached combine to form an optionally substituted saturated or unsaturated 5 to 8 membered ring; and $R^4$, $R^8$, $R^{8a1}$, $R^{8c}$, $R^9$, $R^{10}$, $R^{10a}$, $R^{11}$, $R^{11a}$, $R^X$, X, $X^1$, $Z^1$ and W are as defined above.

More preferred compounds within the scope of formula I include compounds and salts thereof wherein one or more, and especially all of $R^1$, $R^{1a}$, $R^2$, J and $R^3$ are selected from the following definitions:

$R^1$ is hydrogen, hydroxy, $-O-C(O)-NR^6R^7$, $-O-C(O)-R^4$, $-N(R^8)-SO_2-NR^6R^7$, $-SO_2-R^{8c}$, $-N(R^8)-C(W)-NR^6R^7$, $-N(R^8)-C(Z)-N(R^{8a})-SO_2-R^4$, $-N(R^8)-C(Z)-N(R^{8a})-SO_2-OH$, or a group $R^{1a}$ is H;

$R^2$ is phenyl, napthyl, thienyl benzothienyl, alkyl or alkenyl any of which may be optionally substituted as described above;

J is a bond, methylene or ethylene;

$R^3$ is $-R^5$, $-C(Z^1)-R^5$, $-O-C(Z^1)-R^5$, or $-N(R^{8a1})-C(Z^1)-R^5$;

$R^5$ is optionally substituted alkyl, optionally substituted cycloalkyl, optionally substituted heteroayl, optionally substituted aryl or $-NR^{6a}R^{7a}$;

$R^6$, $R^{6a}$, $R^7$ and $R^{7a}$ are independently H, optionally substituted aryl, optionally substituted heteroaryl, optionally substituted cycloalkyl, optionally substituted heterocyclo, optionally substituted (aryl)alkyl, optionally substituted (heteroaryl)alkyl, optionally substituted (heterocylco)alkyl, optionally substituted alkyl, or $COR^{12}$;

or $R^6$ and $R^{6a}$, or $R^7$ and $R^{7a}$ together with the nitrogen to which they are attached combine to form an optionally substituted saturated or unsaturated 5 to 8 membered ring; and $R^4$, $R^8$, $R^{8a1}$, $R^{8c}$, $R^9$, $R^{10}$, $R^{10a}$, $R^{11}$, $R^{11a}$, X, $Z^1$ and W are as defined above.

Most preferred compounds within the scope of formula I include compounds and salts thereof wherein one or more, and especially all of $R^1$, $R^{1a}$, $R^2$, J and $R^3$ are selected from the following definitions:

$R^1$ is
(a) hydrogen, or hydroxy;
(b) $-O-C(O)-NR^6R^7$, $-N(R^8)-SO_2-NR^6R^7$, or $-N(R^8)-C(W)-NR^6R^7$
where
$R^6$ and $R^7$ are independently
(i) H, or
(ii) alkyl, cycloalkyl, alkenyl, alkynyl, aryl, heteroaryl, heterocyclo, alkoxy, (aryl)alkyl, (cycloalkyl)alkyl, (heteroaryl)alkyl, (heterocyclo)alkyl, (alkoxy)alkyl, or $NR^{12}R^{13}$ any of which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, $(OT^6)$alkyl, $(ST^6)$alkyl, $(C(O)_tT^6)$alkyl, $(NT^7T^8)$alkyl, (cyano)alkyl, (aryl)alkyl, (heteroaryl)alkyl or (heterocyclo)alkyl, or $R^6$ and $R^7$ combine to form a heterocylo ring optionally substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, $(OT^6)$alkyl, $(ST^6)$alkyl, $(C(O)_tT^6)$alkyl, $(NT^7T^8)$alkyl, (cyano)alkyl, (aryl)alkyl, (heteroaryl)alkyl or (heterocyclo)alkyl; and $R^8$ is
(i) H; or
(ii) alkyl, cycloalkyl, aryl, heteroaryl, heterocyclo, (cycloalkyl)alky, (aryl)alkyl, (heteroaryl)alkyl or (heterocyclo)alkyl any of which may be optionally independently substituted with one or more OH, SH, OT⁶, ST⁶, C(O)$_t$T⁶, NT⁷T⁸, cyano, halo, oxo, alkyl, haloalkyl, aryl, heteroaryl, heterocyclo, (OH)alkyl, (SH)alkyl, (OT⁶)alkyl, (ST⁶)alkyl, (C(O)$_t$T⁶)alkyl, (NT⁷T⁸)alkyl, (cyano)alkyl, (aryl)alkyl, (heteroaryl)alkyl or (heterocyclo)alkyl, (c) —O—C(O)—R⁴, —N(R⁸)—C(Z)—N(R⁸$^a$)—SO₂—R⁴ or —N(R⁸)—C(Z)—N(R⁸$^a$)—SO₂—OH where R⁴ is (i) H, or (ii) alkyl, cycloalkyl, alkenyl, alkynyl, aryl, heteroaryl, heterocyclo, alkoxy, (aryl)alkyl, (cycloalkyl)alkyl, (heteroaryl)alkyl, (heterocyclo)alkyl, (alkoxy)alkyl, or NR¹²R¹³ any of which may be optionally independently substituted with one or more OH, SH, OT⁶, ST⁶, C(O)$_t$T⁶, NT⁷T⁸, cyano, halo, oxo, alkyl, haloalkyl, aryl, heteroaryl, heterocyclo, (OH)alkyl, (SH)alkyl, (OT⁶)alkyl, (ST⁶)alkyl, (C(O)$_t$T⁶)alkyl, (NT⁷T⁸)alkyl, (cyano)alkyl, (aryl)alkyl, (heteroaryl)alkyl or (heterocyclo)alkyl; and R⁸ and R⁸a are independently (i) H; or (ii) alkyl, cycloalkyl, aryl, heteroaryl, heterocyclo, (cycloalkyl)alky, (aryl)alkyl, (heteroaryl)alkyl or (heterocyclo)alkyl any of which may be optionally independently substituted with one or more OH, SH, OT⁶, ST⁶, C(O)$_t$T⁶, NT⁷T⁸, cyano, halo, oxo, alkyl, haloalkyl, aryl, heteroaryl, heterocyclo, (OH)alkyl, (SH)alkyl, (OT⁶)alkyl, (ST⁶)alkyl, (C(O)$_t$T⁶)alkyl, (NT⁷T⁸)alkyl, (cyano)alkyl, (aryl)alkyl, (heteroaryl)alkyl or (heterocyclo)alkyl; or (d) or a group

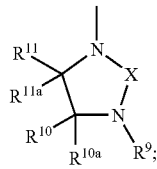

R¹$^a$ is H;

R² is phenyl, (phenyl)alkyl, napthyl, thienyl benzothienyl, alkyl or alkenyl any of which may be optionally independently substituted with one or more OH, SH, OT⁶, ST⁶, C(O)$_t$T⁶, NT⁷T⁸, cyano, halo, oxo, alkyl, haloalkyl, aryl, heteroaryl, heterocyclo, (OH)alkyl, (SH)alkyl, (OT⁶) alkyl, (ST⁶)alkyl, (C(O)$_t$T⁶)alkyl, (NT⁷T⁸)alkyl, (cyano) alkyl, (aryl)alkyl, (heteroaryl)alkyl or (heterocyclo)alkyl;

J is a bond, methylene or ethylene;

R³ is (a) —R⁵ or where R⁵ is heteroaryl, heterocyclo or —NR⁶$^a$R⁷$^a$ any of which may be optionally independently substituted with one or more OH, SH, OT⁶, ST⁶, C(O)$_t$T⁶, NT⁷T⁸, cyano, halo, oxo, alkyl, haloalkyl, aryl, heteroaryl, heterocyclo, (OH)alkyl, (SH)alkyl, (OT⁶)alkyl, (ST⁶)alkyl, (C(O)$_t$T⁶)alkyl, (NT⁷T⁸)alkyl, (cyano)alkyl, (aryl)alkyl, (heteroaryl)alkyl or (heterocyclo)alkyl;

(b) —C(Z¹)—R⁵, or —O—C(Z¹)—R⁵, where

R⁵ is aryl, (aryl)alkyl, heteroaryl, (heteroaryl)alkyl) or —NR⁶$^a$R⁷$^a$; and

R⁶$^a$ and R⁷$^a$ are independently (i) H; or (ii) alkyl, cylcoalkyl, aryl, (aryl)alkyl, heteroaryl (heteroaryl)alkyl, heterocyclo or (heterocyclo) alkyl any of which may be optionally independently substituted with one or more OH, SH, OT⁶, ST⁶, C(O)$_t$T⁶, NT⁷T⁸, cyano, halo, oxo, alkyl, haloalkyl, aryl, heteroaryl, heterocyclo, (OH) alkyl, (SH)alkyl, (OT⁶)alkyl, (ST⁶)alkyl, (C(O)$_t$T⁶)alkyl, (NT⁷T⁸)alkyl, (cyano)alkyl, (aryl)alkyl, (heteroaryl)alkyl or (heterocyclo)alkyl; or (c) —N(R⁸$^{a1}$)—C(Z)—R⁵, or —N(R⁸$^{a1}$)—SO₂—R⁵ where

R⁵ is aryl, (aryl)alkyl, hetreoaryl, (heteroaryl)alkyl, heterocyclo, (heterocyclo)alkyl, alkyl, alkenyl, alkynyl, cycloalkyl, (alkoxy)alkyl, or (cycloalkoxy)alkyl any of which may be optionally independently substituted with one or more OH, SH, OT⁶, ST⁶, C(O)$_t$T⁶, NT⁷T⁸, cyano, halo, oxo, alkyl, haloalkyl, aryl, heteroaryl, heterocyclo, (OH)alkyl, (SH)alkyl, (OT⁶) alkyl, (ST⁶)alkyl, (C(O)$_t$T⁶)alkyl, (NT⁷T⁸)alkyl, (cyano)alkyl, (aryl)alkyl, (heteroaryl)alkyl or (heterocyclo)alkyl; and R⁸$^{a1}$ is (i) H; or (ii) alkyl, cycloalkyl, aryl, heteroaryl, heterocyclo, (cycloalkyl)alky, (aryl)alkyl, (heteroaryl)alkyl or (heterocyclo)alkyl any of which may be optionally independently substituted with one or more OH, SH, OT⁶, ST⁶, C(O)$_t$T⁶, NT⁷T⁸, cyano, halo, oxo, alkyl, haloalkyl, aryl, heteroaryl, heterocyclo, (OH)alkyl, (SH)alkyl, (OT⁶)alkyl, (ST⁶)alkyl, (C(O)$_t$T⁶)alkyl, (NT⁷T⁸)alkyl, (cyano)alkyl, (aryl) alkyl, (heteroaryl)alkyl or (heterocyclo)alkyl, R⁵ is optionally substituted alkyl, optionally substituted cycloalkyl, optionally substituted heteroayl, optionally substituted aryl or —NR⁶$^a$R⁷$^a$;

R⁶, R⁶$^a$, R⁷ and R⁷$^a$ are independently H, optionally substituted aryl, optionally substituted heteroaryl, optionally substituted cycloalkyl, optionally substituted heterocyclo, optionally substituted (aryl)alkyl, optionally substituted (heteroaryl)alkyl, optionally substituted (heterocylco) alkyl, optionally substituted alkyl, or COR¹²;

or R⁶ and R⁷, or R⁶$^a$ and R⁷$^a$ together with the nitrogen to which they are attached combine to form an optionally substituted saturated or unsaturated 5 to 8 membered ring; and R⁴, R⁸, R⁸$^{a1}$, R⁸$^c$, R⁹, R¹⁰, R¹⁰$^a$, R¹¹, R¹¹$^a$, X, Z¹ and W are as defined above.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred. The term "substituted alkyl" refers to alkyl groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, —T—$NT^7T^8$, —$T^4$—$N(T^9)$—$T^5$—$T^6$, —$S(O)_tT^6$ or —$S(O)_tN(T^9)T^6$.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. The term "substituted alkenyl" refers to alkenyl groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, —$T^4$—$NT^7T^8$, —$T^4$—$N(T^9)$—$T^5$—$T^6$, —$S(O)_tT^6$ or —$S(O)_tN(T^9)T^6$.

The term "alkynyl" refers to straight or branched chain hydrocarbon groups having 2 to 12 carbon atoms, preferably 2 to 4 carbon atoms, and at least one triple carbon to carbon bond, such as ethynyl. The term "substituted alkynyl" refers to alkynyl groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$—$T^4$—$NT^7T^8$, —$T^4$—$N(T^9)$—$T^5$—$T^6$, —$S(O)_tT^6$ or —$S(O)_tN(T^9)T^6$.

The term "alkylene" refers to a straight chain bridge of 1 to 4 carbon atoms connected by single bonds (e.g., —$(CH_2)_x$— wherein x is 1 to 5), which may be substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, —$T^4$—$NT^7T^8$, —$T^4$—$N(T^9)$—$T^5$—$T^6$, —$S(O)_tT^6$ or —$S(O)'N(T^9)T^6$.

The term "alkenylene" refers to a straight chain bridge of 2 to 5 carbon atoms having one or two double bonds that is connected by single bonds and may be substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —$OC(O)T^6$, —$T^4$—$NT^7T^8$, —$T^4$—$N(T^9)$—$T^5$—$T^6$, —$S(O)_tT^6$ or —$S(O)_tN(T^9)T^6$. Exemplary alkenylene groups are —CH=CH—CH=CH—, —$CH_2$—CH=CH—, —$CH_2$—CH=CH—$CH_2$—, —$C(CH_3)_2$CH=CH— and —$CH(C_2H_5)$—CH=CH—.

The term "alkynylene" refers to a straight chain bridge of 2 to 5 carbon atoms that has a triple bond therein, is connected by single bonds, and may be substituted with one or more groups listed in the definition of $T_{1-1g}$, $T^{2-2g}$ and $T^{3-3g}$, preferably selected from cyano, halo, oxo, hydroxy, —$OT^6$, —$C(O)_tT^6$, —$OC(O)T^6$, —$T^4$—$NT^7T^8$, —$T^4$—$N(T^9)$—$T^5$—$T^6$, —$S(O)_tT^6$ or —$S(O)_tN(T^9)T^6$. Exemplary alkynylene groups are —C≡C—, —$CH_2$—C≡C—, —CH($CH_3$)—C≡C— and —C≡C—$CH(C_2H_5)CH_2$—.

The terms "ar" or "aryl" refer to aromatic homocyclic (i.e., hydrocarbon) mono-, bi- or tricyclic ring-containing groups preferably having 6 to 14 members such as phenyl, naphthyl and biphenyl, as well as such rings fused to a cycloalkyl, cycloalkenyl, heterocyclo, or heteroaryl ring. Examples include:

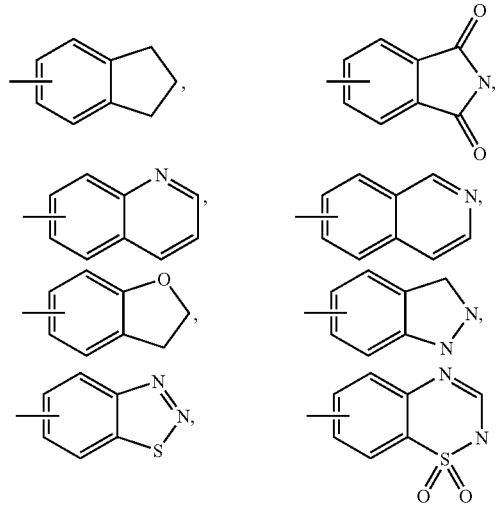

and the like.

The term "substituted aryl" refers to aryl groups substituted with one or more groups listed in the definition of $T^{1-1g}$, $T^{2-2g}$ and $T^{3-3g}$, preferably selected cyano, halo, oxo, hydroxy, —$OT^6$, —$C(O)_tT^6$, —$OC(O)T^6$, —$T^4$—$NT^7T^8$, —T—N(T9)—$T^5$—$T^6$, —$S(O)_tT^6$ or —$S(O)_tN(T^9)T^6$.

The term "cycloalkyl" refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring and which may be fused to 1 or 2 aromatic or heterocyclo rings, which include cyclopropyl, cyclobutyl, cyclopentyl, cyclohexyl, cycloheptyl, cyclooctyl, cyclodecyl, cyclododecyl, cyclohexenyl,

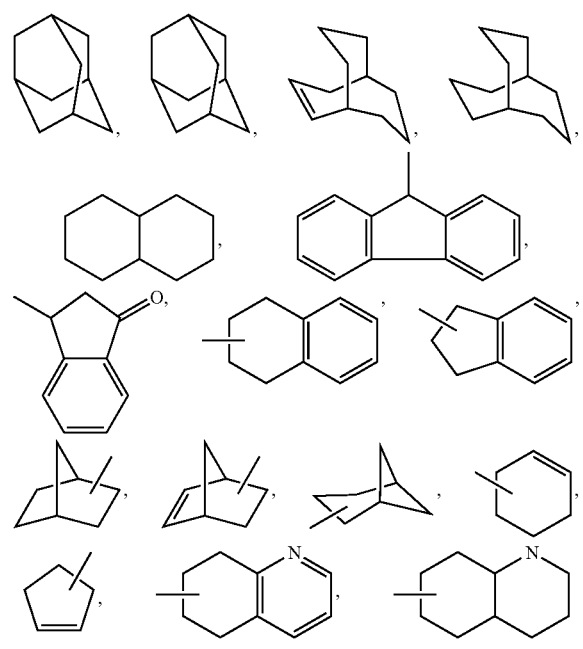

and the like. The terms "substituted cycloalkyl" refers to cycloalkyl groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —OC$(O)T^6$, —$T^4$—$NT^7T^8$, —$T^4$—$N(T^9)$—$T^5$—$T^6$, —$S(O)_tT^6$ or —$S(O)_tN(T^9)T^6$.

The terms "halogen" and "halo" refer to fluorine, chlorine, bromine and iodine.

The terms "heterocycle", "heterocyclic", "heterocyclic group" or "heterocyclo" refer to fully saturated or partially or unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be substituted or quaternized. The heterocyclic group may be attached at any heteroatom or carbon atom of the ring or ring system. The rings of multi-ring heterocycles may be either fused, bridged and/or joined through one or more spiro unions. Exemplary heterocyclic groups include

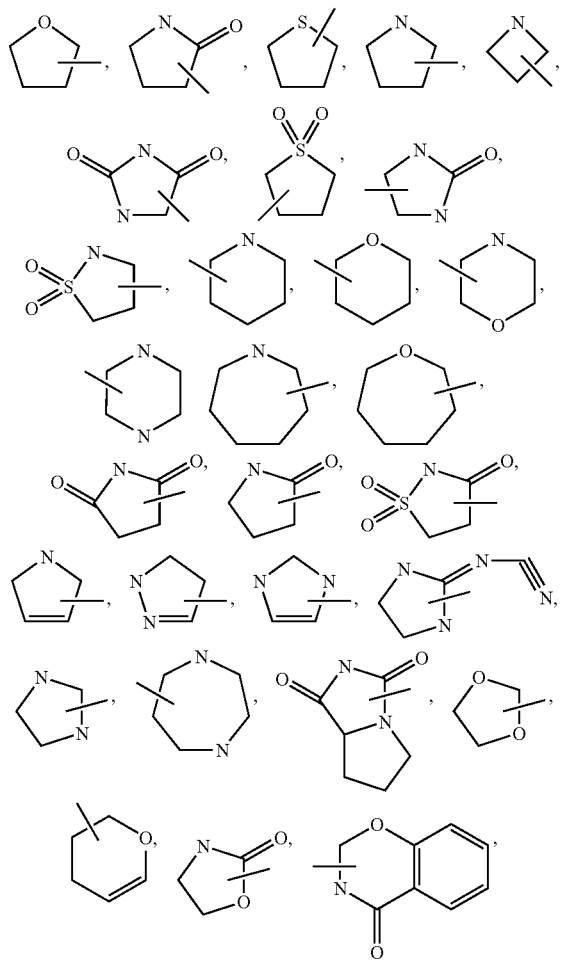

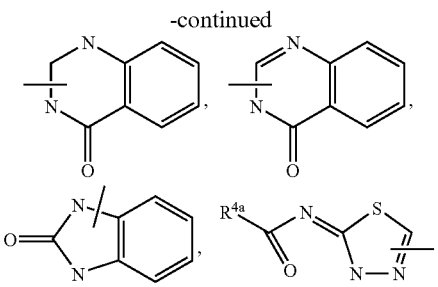

and the like.

The terms "substituted heterocycle", "substituted heterocyclic", "substituted heterocyclic group" and "substituted heterocyclo" refer to heterocycle, heterocyclic and heterocyclo groups substituted with one or more groups listed in the definition of $T^{1-1g}$, $T^{2-2g}$ and $T^{3-3g}$, preferably selected from cyano, halo, oxo, hydroxy, —$OT^6$, —$C(O)_tT^6$, —OC$(O)T^6$, —$T^4$—$NT^7T^8$, —$T^4$—$N(T^9)$—$T^5$—$T^6$, —$S(O)_tT^6$ or —$S(O)_tN(T^9)T^6$.

The term "heteroaryl" as used herein alone or as part of another group refers to a 5- 6- or 7-membered aromatic rings containing from 1 to 4 nitrogen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are such rings fused to a cycloalkyl, aryl, cycloheteroalkyl, or another heteroaryl ring. One, two, or three available carbon or nitrogen atoms in the heteroaryl ring can be optionally substituted with substituents listed in the description of $T_1$, $T_2$ and $T_3$. Also an available nitrogen or sulfur atom in the heteroaryl ring can be oxidized. Examples of heteroaryl rings include

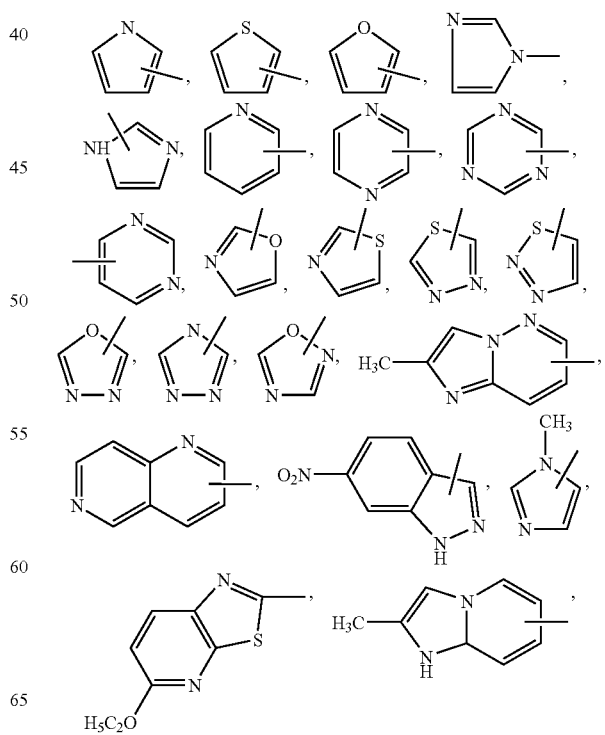

-continued

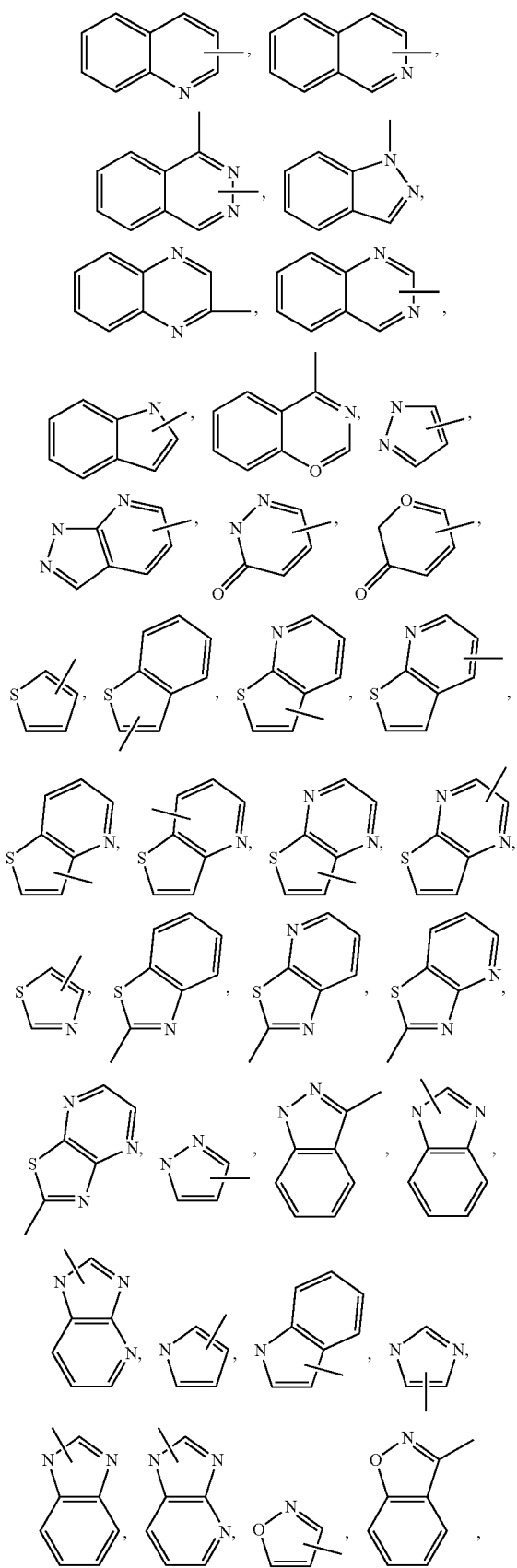

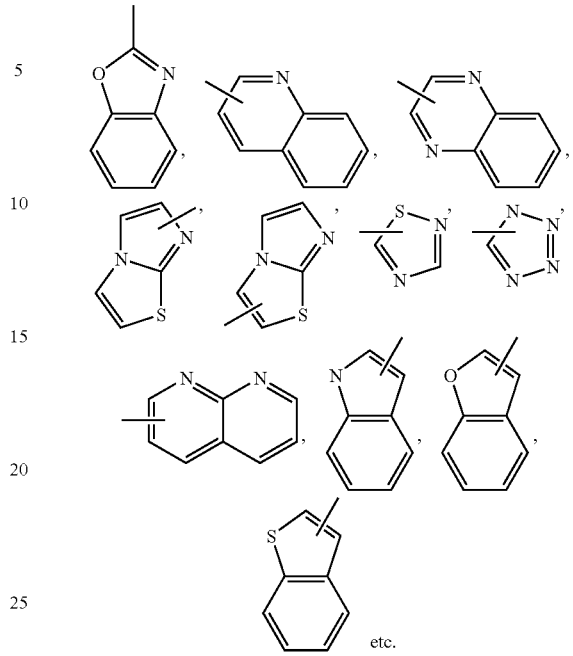

etc.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various R and Z substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The terms "including", "such as", "for example" and the like are intended to refer to exemplary embodiments and not to limit the scope of the present invention.

Schemes

Compounds of the formula I may be prepared using the sequence of steps outlined below. Specifically, compounds of the formula I where R1 is —O—CO—NR$^6$R$^7$, R$^2$ is aryl, substituted aryl or heteroaryl and —J—R$^3$ is —CH$^2$—H—CO—R$^5$ may be prepared using Scheme 1.

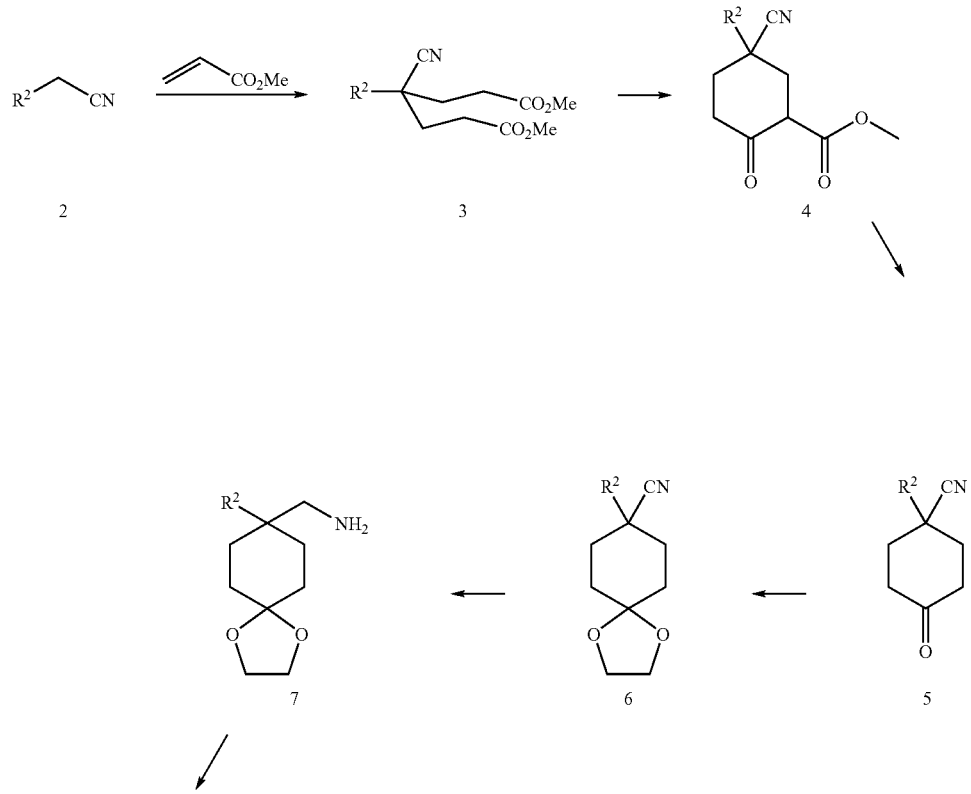

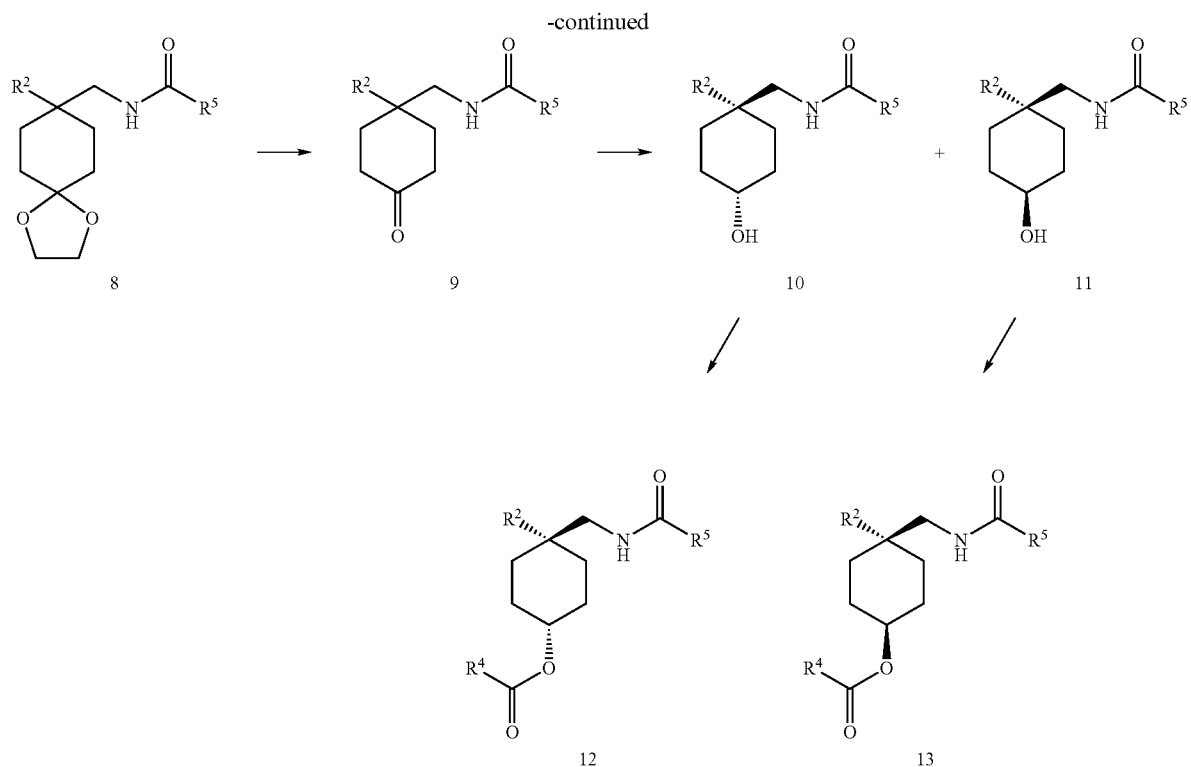

Bis Michael addition to acetonitrile 2 and subsequent Dieckmann condensation yields the intermediate cyclohexyl β-keto ester 4. Krapcho decarboxylation to the ketone followed by ketone protection and reduction of the nitrile 6 generates the primary amine 7. The amine is subsequently acylated, deprotected and the resulting ketone 9 reduced. The cis and trans alcohols may be separated and taken on to final product esters and carbamates.

Compounds of the formula I where $R^1$ is —$NR^8$—C(NCN)—$NR^6R^7$, $R^2$ is aryl, substituted aryl or heteroaryl and —J—$R^3$ is —$CH_2$—NH—C)—$R^5$ may be prepared using Scheme 2.

Scheme 2

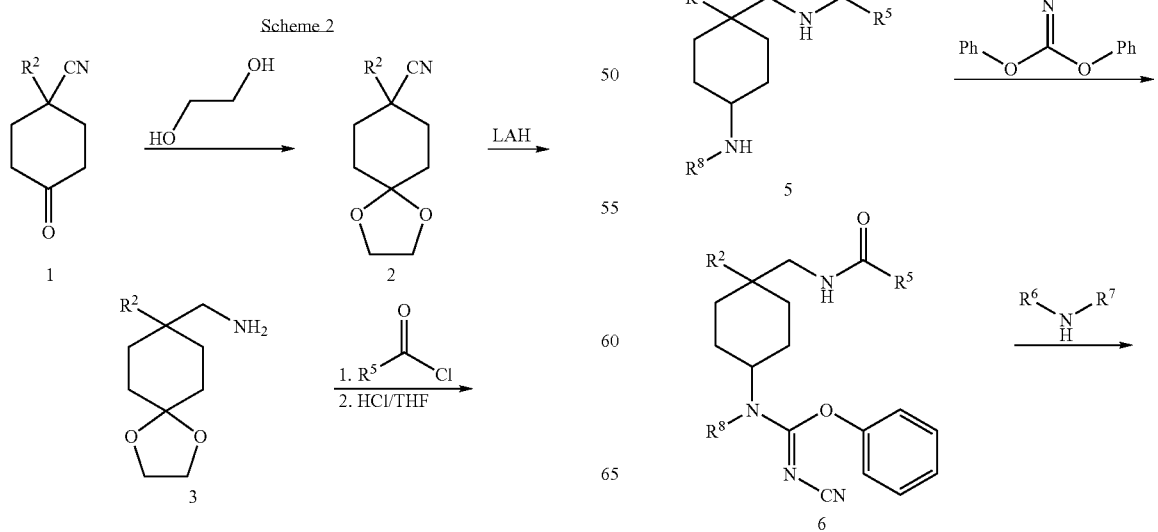

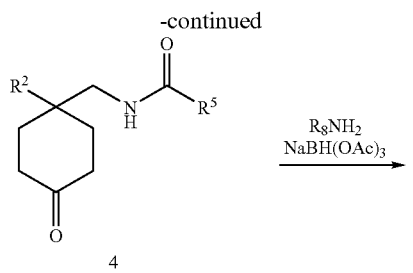

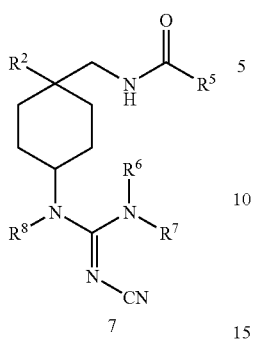

7

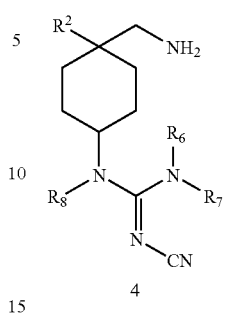

4

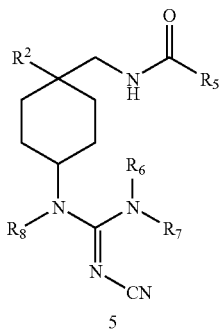

5

Compound 1 used in this preparation is readily prepared from commercially available reagents by the methods well known to those skilled in the art. Assembly of substituted cyclohexyl cyanoguanidines such as compound 3 can be done using methodology described in Scheme 2. Hydrolysis of the TFA protecting group and acylation of the amine 4 may provide the compounds of formula 5.

Compounds of the formula I where $R^1$ is —NH—SO$_2$—NR$^6$R$^7$, $R^2$ is aryl, substituted aryl or heteroaryl and —J—R$^3$ is —CH$_2$—NH—CO—R$^5$ may be prepared using Scheme 4.

Protection of the ketone moiety of commercially available compound 1, followed by reduction of nitrile with LAH provides the amine 3. The amine is acylated and the ketal moiety deprotected to provide the ketone 4. Reductive amination produces the amine 5. Compounds of formula 6 may be prepared by displacement of phenoxy group from diphenyl cyanourea. Warming 6 and an amine at 60–75° C. in alcoholic solvents provides the compound 7.

Alternatively, compounds of the formula I where $R^1$ is —NR$^8$—C(NCN)—NR$^6$R$^7$, $R^2$ is aryl, substituted aryl or heteroaryl and —J—R$^3$ is —CH$_2$—NH—CO—R$^5$ may be prepared using Scheme 3.

Scheme 3

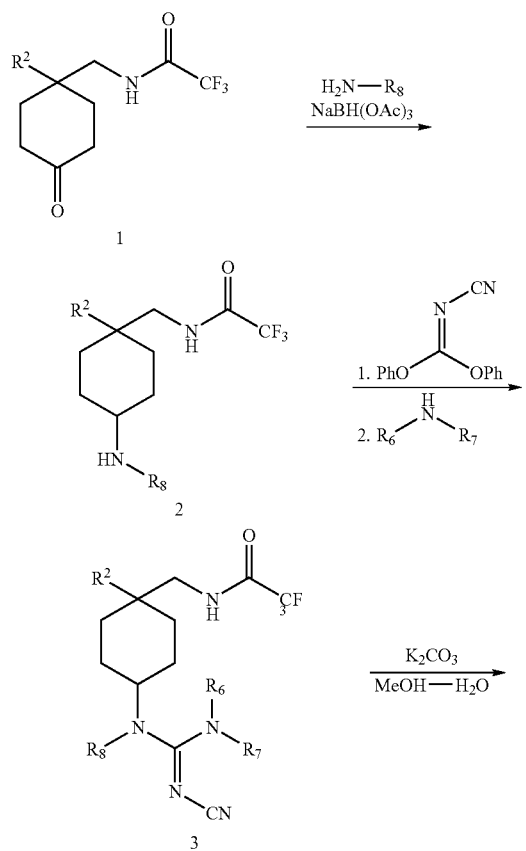

Scheme 4

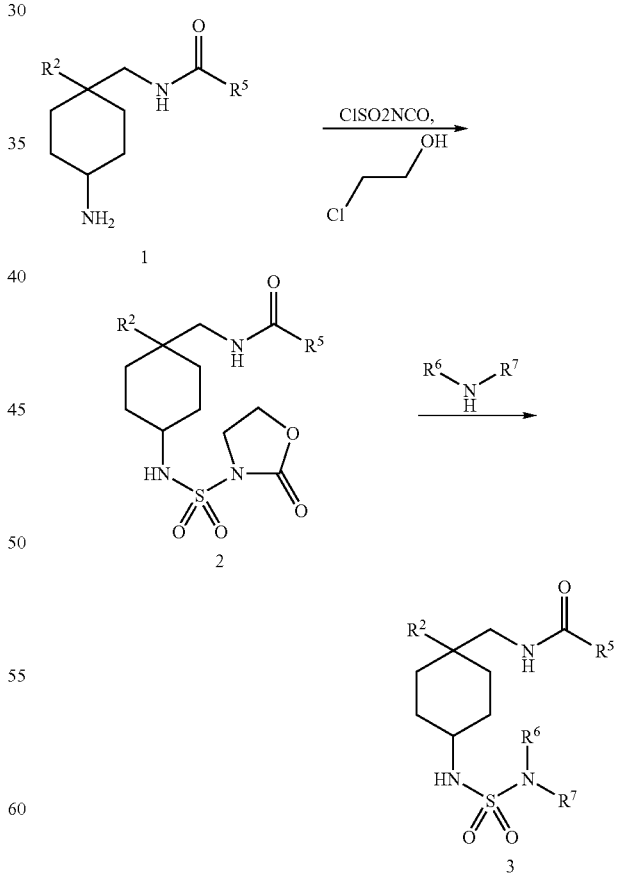

The amine 1 may be converted to the corresponding sulfonyl oxazolidine in a way described in the literature (Dewynter, G., et als. Tetrahedron, 1996, 52, 14217–14224). Compounds of formula 3 may be prepared by displacement reaction of oxazolidine 2 with amines at temperature of 65–75° C. in alcholic solvents such as ethanol and isopropanol.

Compounds of the formula I where $R^1$ is —NH—C(=NCO$_2$R$^8$)—NR$^6$R$^7$, $R^2$ is aryl, substituted aryl or heteroaryl and —J—$R^3$ is —CH$_2$—NH—CO—$R^5$ may be prepared using Scheme 5.

Scheme 5

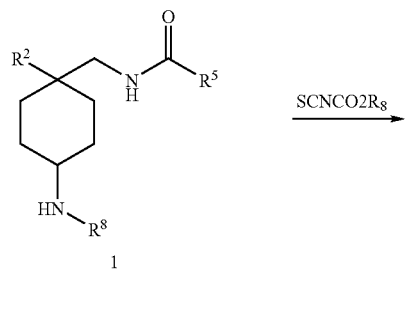

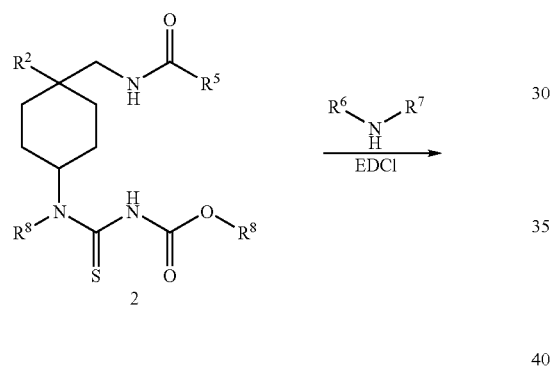

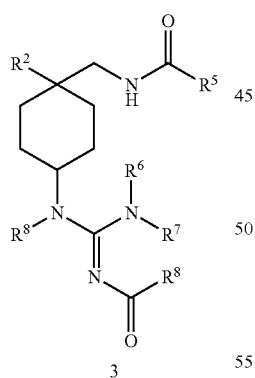

Treatment of the amine 1 with isothiocyanoformate may provide the thiourea 2, which would provide the compounds of formula 3 by the coupling with the amine in the presence of EDCI.

Compounds of the formula I where $R^1$ is a hydantoin heterocycle, $R^2$ is aryl, substituted aryl or heteroaryl and —J—$R^3$ is —CH$_2$—NH—CO—$R^5$ may be prepared using Scheme 6.

Scheme 6

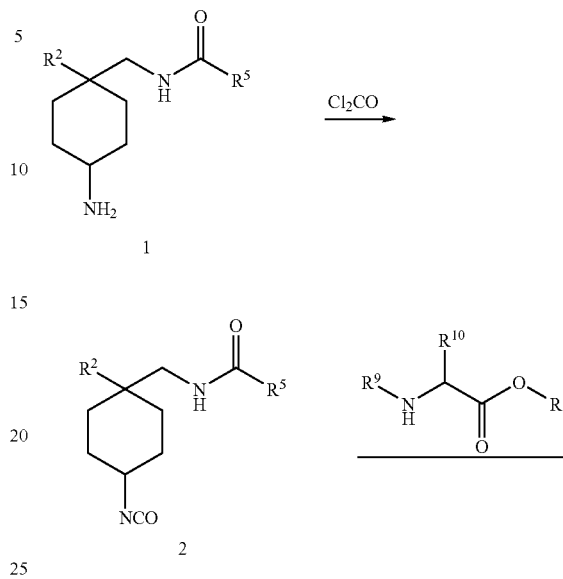

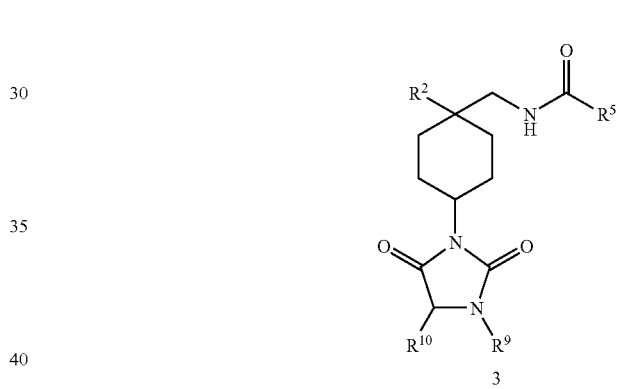

The isocyanate 2 could be obtained upon treating the amine 1 with phosgene. Treatment of the isocyanate 2 with substituted aminoester at 65–75° C. in alcoholic solvents such as ethanol or isopropanol can provide the compounds of formula 3.

Alternatively, compounds of formula 3 could be obtained by treating the amine 1 with substituted isocyanoactate in proper solvents such as dichloromethane or THF, followed by ring closure under acidic conditions according to Scheme 7.

Scheme 7

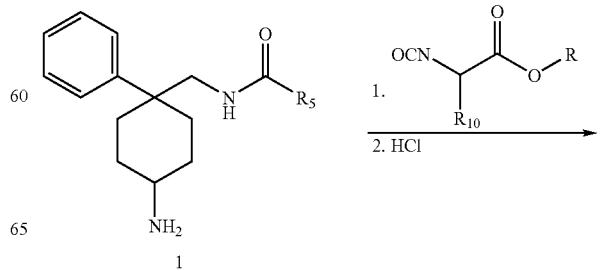

-continued

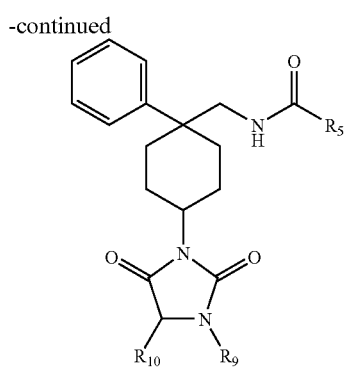
3

Compounds of the formula I where R¹ is an imidazolidine-2-one heterocycle, R² is aryl, substituted aryl or heteroaryl and —J—R³ is —CH₂—NH—CO—R⁵ may be prepared using Scheme 8.

Scheme 8

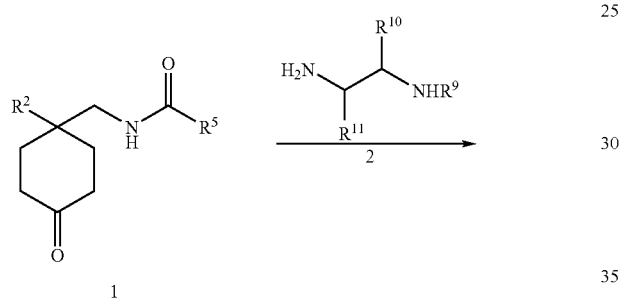

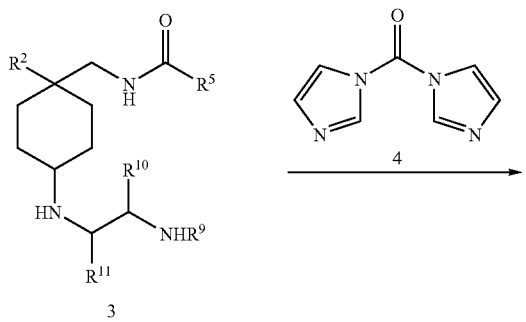

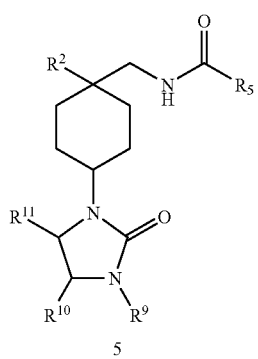
5

Reductive amination of the ketone 1 with the substituted ethylenediamine 2 may provide cyclohexylamine 3. The amine 3 can be converted to the corresponding cyclic ureas of formula 5 upon treatment with carbonyl diimidazole 4 in a solvent such as THF or dichloromethane.

Compounds of the formula I where R¹ is an imidazolidine-2-ylidine cyanamide heterocycle, R² is aryl, substituted aryl or heteroaryl and —J—R³ is —CH₂—NH—CO—R⁵ may be prepared using Scheme 9.

Scheme 9

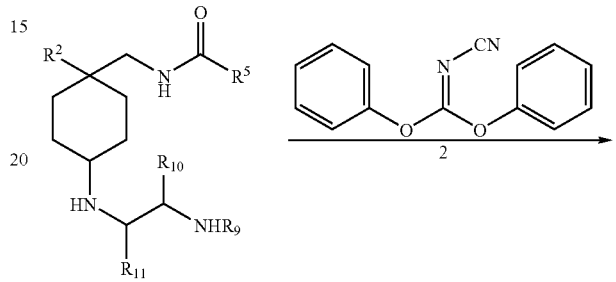

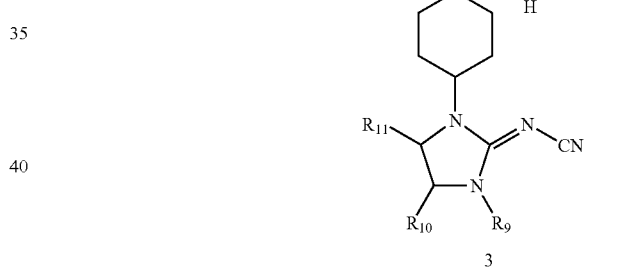
3

The same intermediate 1 from Scheme 7 may produce the compounds of formula 3 upon treating it with diphenyl cyanocarbonidate 2 at temperature of 65–75° C. in alcholic solvents such as ethanol or isopropanol.

Compounds of the formula I where —J—R³ is —CH²—NH—R⁶ where R6 is aryl or heteroaryl may be prepared using Scheme 10.

Scheme 10

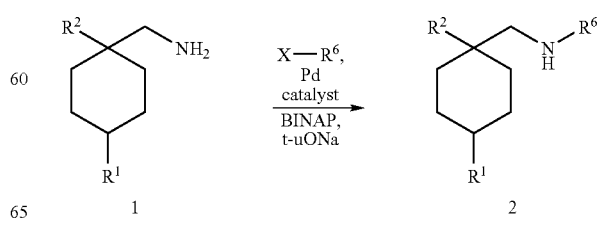

The intermediate 1 may react with a substituted aryl or heteroaryl compound where X is Cl, Br, I, OTf or similar leaving group in the presence of a palladium catalyst such as $Pd_2(dba)_3$ to produce compound 2.

Compounds of the formula I where —J—$R^3$ is —$CONR^6R^7$ may be prepared using Scheme 11

Scheme 11

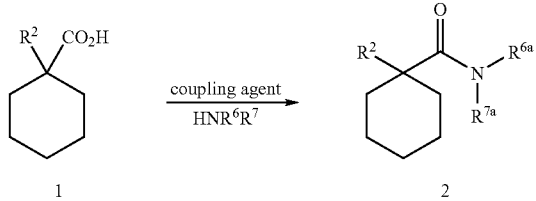

The carboxylic acid 1 may be made to react with amine $HNR^6R^7$ using a variety of standard coupling procedures known in the literature to give amide compounds of formula 2. Activation of the carboxylic acid by conversion to the carboxylic acid chloride or carboxylic acid fluoride in a solvent such as methylene chloride or acetonitrile followed by reaction with an amine in the presence of a base such as triethylamine or pyridine is a particularly useful coupling procedure.

Compounds of the formula I where $R^1$ is —O—CO—$NR^6R^7$, and —J—$R^3$ is a heterocycle, for example oxadiazole, can be prepared using Scheme 12.

-continued

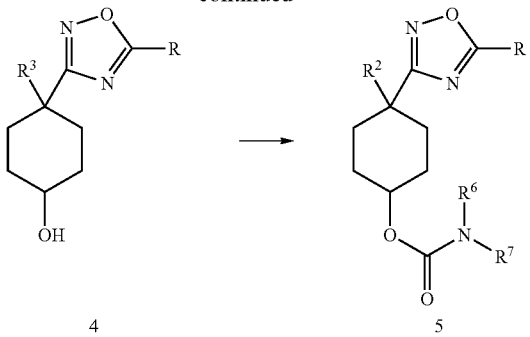

Nitrile 1 may be made to react with hydoxylamine in an organic solvent such as n-propanol to give carboxamidine 2. Carboxamidine 2 may be acylated with a variety of carboxylic acids, carboxylic acid chlorides or carboxylic acid fluorides using standard coupling procedures and the resulting intermediates may be made to undergo cyclization upon heating to give 1,2,4-oxadiazole 3. Deprotection of the ketal group of the 1,2,4-oxadiazole 3 followed by reduction of the ketone using a reducing agent such sodium borohydride in an organic solvent such as tetrahydrofuran gives hydroxy compound 4. The hydroxy compound 4 may be converted to the carbamate 5 by first reacting the hydroxy derivative with 4-nitrophenyl chloroformate to obtain the carbonate intermediate which is then reacted with an amine to form the carbamate.

Compounds of the formula I where R1 is —O—CO—$NR^6$ $R^7$, and —J—R3 is a heterocycle, for example tetrazole, can be prepared using Scheme 13.

Scheme 12

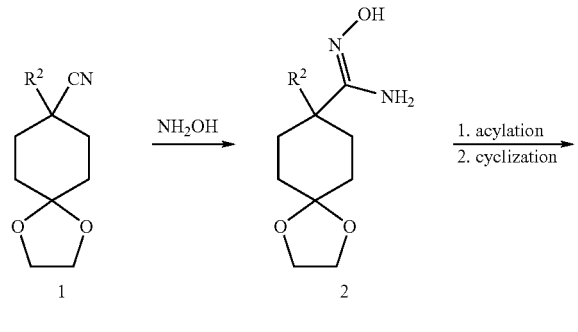

Scheme 13

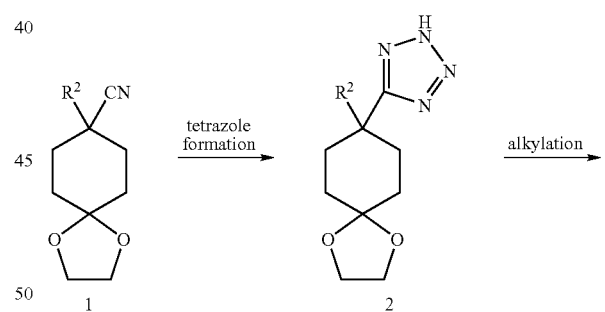

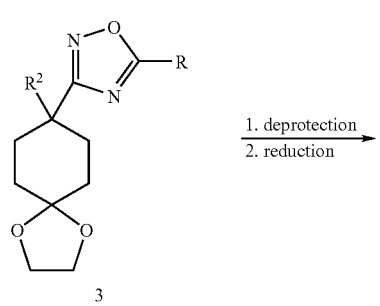

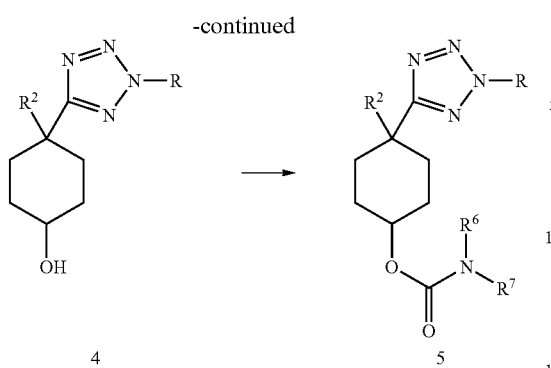

Nitrile 1 may be made to react with sodium azide in a organic solvent such as N,N-dimethylformamide at elevated temperatures to form the tetrazole 2. The tetrazole 2 may be alkylated by treatment with an alkyl halide in the presence of a base such as potassium carbonate in an organic solvent such as aceteonitrile. Deprotection of the ketal group of the alkylated tetrazole 3 followed by reduction of the ketone using a reducing agent such sodium borohydride in an organic solvent such as tetrahydrofuran gives the hydroxy compound 4. The hydroxy compound 4 may be converted to the carbamate 5 by first reacting the hydroxy derivative with 4-nitrophenyl chloroformate to obtain the carbonate intermediate which is then reacted with an amine to form the carbamate.

Compounds of the formula I where —J—$R^3$ is a heterocycle, for example 3H-quinazolin-4-one, can be prepared using Scheme 14.

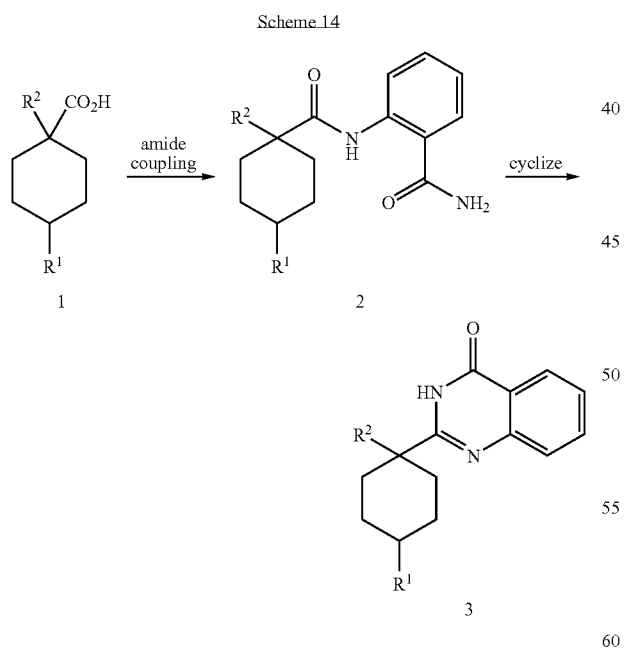

The carboxylic acid 1 may react with an anthranilic acid using a variety of standard coupling procedures known in the literature to give amide compound 2. Cyclization of compound 2 under basic conditions in an organic solvent such as ethanol at elevated temperatures would give compounds of formula 3.

Compounds of the formula I where —J—$R^3$ is a heterocycle, for example benzoxazole, can be prepared using Scheme 15.

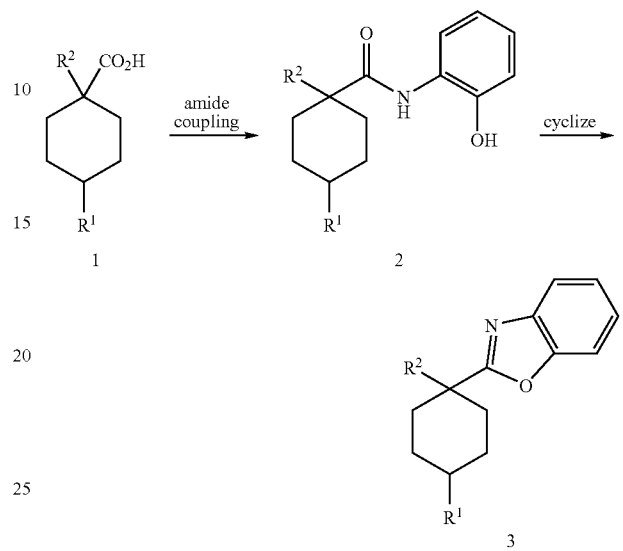

The carboxylic acid 1 may be made to react with a 2-aminophenol derivative using a variety of standard coupling procedures known in the literature to give amide compound 2. Cyclization of compound 2 under acidic conditions in an organic solvent such as p-xylene at elevated temperatures would give compounds of formula 3

Compounds of the formula I where —J—$R^3$ is a heterocycle, for example benzimidazole, can be prepared using Scheme 16.

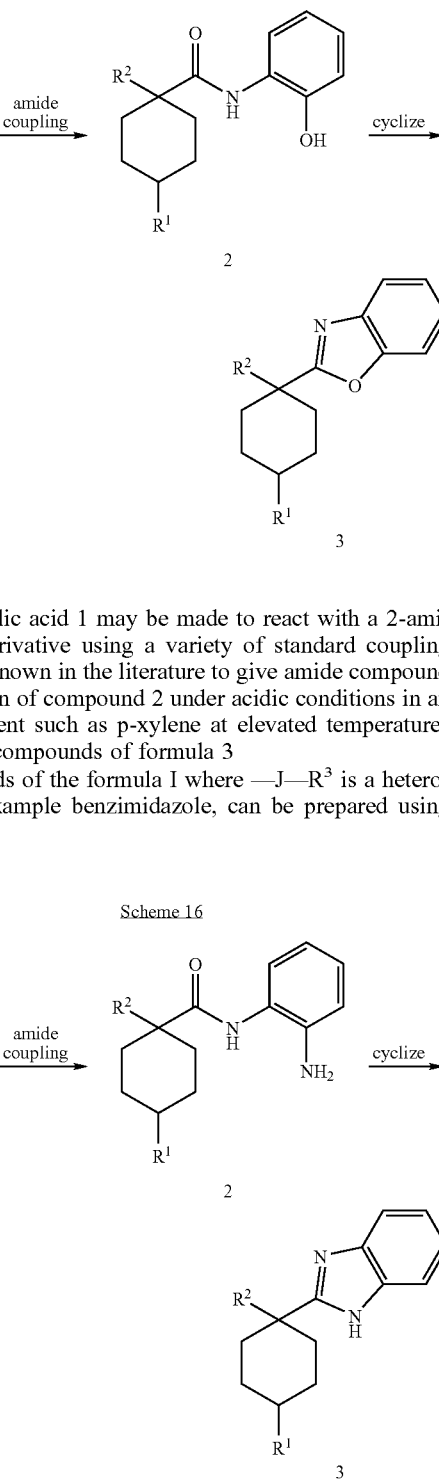

The carboxylic acid 1 may be made to react with an o-phenylenediamine derivative using a variety of standard coupling procedures known in the literature to give amide compound 2. Cyclization of compound 2 under acidic conditions in a solvent such as acetic acid at elevated temperatures would give compounds of formula 3.

Compounds of the formula I where —J—$R^3$ is —CO—$NR^{6a}R^{7a}$ and $R^1$ is —O—CO—$NR^6R^7$ can be prepared using Scheme 17.

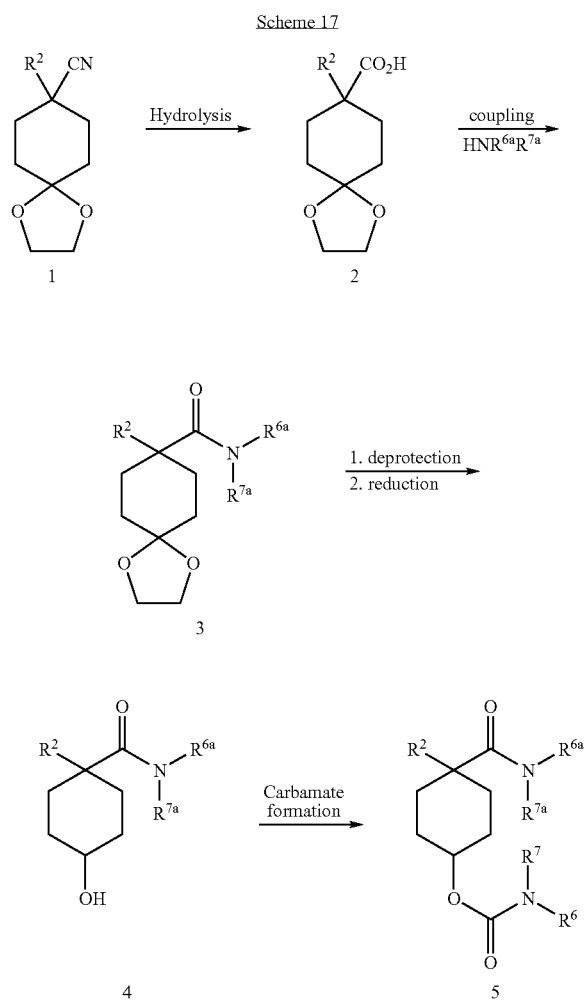

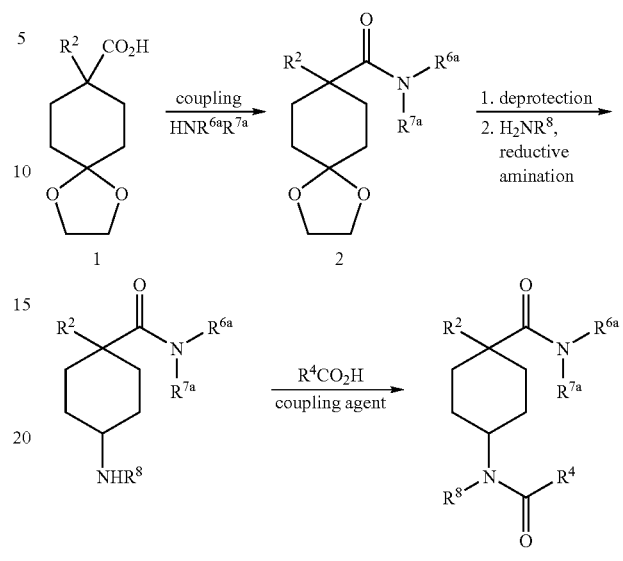

The nitrile 1 may be converted to the carboxylic acid 2 by treatment with a base such as sodium hydroxide in a solvent such as ethylene glycol at elevated temperatures. The carboxylic acid 2 may be made to react with an amine $HNR^{6a}R^{7a}$ using a variety of standard coupling procedures known in the literature to give amide compounds 3. Deprotection of the ketal group of the amide 3 followed by reduction of the ketone using a reducing agent such as sodium borohydride in an organic solvent such as tetrahydrofuran gives the hydroxy compound 4. The hydroxy compound 4 may be converted to the carbamate of formula 5 by first reacting the hydroxy derivative 4 with 4-nitrophenyl chloroformate to obtain the carbonate intermediate which is then reacted with $HNR^6R^7$ to form the carbamate.

Compounds of the formula I where —J—$R^3$ is —CO—$NR^{6a}R^{7a}$ and $R^1$ is —$NR^8$—CO—$R^4$ can be prepared using Scheme 18.

The carboxylic acid 1 may be made to react with an amine $HNR^{6a}R^{7a}$ using a variety of standard coupling procedures known in the literature to give amide compounds 2. Deprotection of the ketal group of the amide 2 followed by reductive amination of the ketone by first treating the ketone with amine $H_2NR^8$ to form the imine intermediate followed by reduction of the imine with a reducing agent such as and sodium cyanoborohydride in an organic solvent such as methanol gives the amino compound 3. The amino compound 3 may be made to react with a carboxylic acid $R^4CO_2H$ using a variety of standard coupling procedures to give compound 4.

Compounds of the formula I where —J—$R^3$ is —$CONR^{6a}R^{7a}$ and $R^1$ is —$NR^8$—C(NCN)—$NR^6R^7$ can be prepared using Scheme 19.

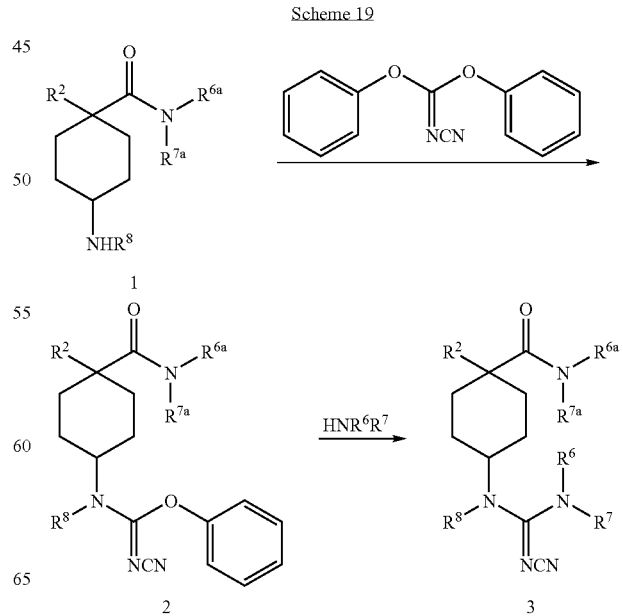

Amine 1 may react with diphenylcyanocarbonimidate in a solvent such as acetonitrile at elevated temperature to give an intermediate 2 which can further react with amine $HNR^6R^7$ to give compound 3.

Compounds of formula I wherein —J—$R^3$ is an (amino) methyl group may be prepared using methodology such as that described in Example 323 or the following schemes 20 and 21.

Scheme 20

Scheme 21

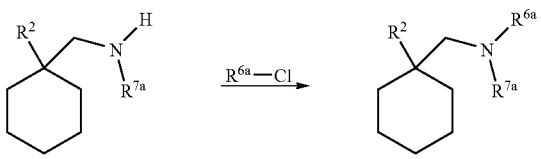

Additional compounds within the scope of the present invention can be prepared from the compounds obtained by the above described methods through conversion of the substituent groups to other functionality by the usual methods of chemical synthesis, as illustrated in the following examples.

Compounds of formula I that contain chiral centers may be obtained in non-racemic form by non-racemic synthesis or resolution by methods well known to those skilled in the art. Compounds that are non-racemic are designated as "chiral" in the examples.

In the examples described below it may be necessary to protect reactive functionality such as hydroxy, amino, thio or carboxy groups, where these are desired in the final product, to avoid their unwanted participation in reactions. The introduction and removal of protecting groups are well known to those skilled in the art, for example see (Green, T. W. in "Protective Groups in Organic Synthesis", John Wiley and Sons, 1991).

Utility

Compounds within the scope of the present invention inhibit the $K_v1$ subfamily of voltage-gated $K^+$ channels, and as such are useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents; angina pectoris including relief of Prinzmetal's symptoms, vasospastic symptoms and variant symptoms; gastrointestinal disorders including reflux esauphagitis, functional dispepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma, chronic obstructive pulmonary disease, cystic fibrosis and atherosclerosis; cell poliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the $K_v1$ subfamily of voltage-gated $K^+$ channels compounds of the present invention are useful to treat a variety of disorders including resistance by transplantation of organs or tissue, graft-versus-host diseases brought about by medulla ossium transplantation, rheumatoid arthritis, systemic lupus erythematosus, hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenicmicroorganisms, inflammatory and hyperproliferative skin diseases, psoriasis, atopical dermatitis, contact dermatitis, eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, Lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-$C_4$ release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are antiarrhythmic agents which are useful in the prevention and treatment (including partial alleviation or cure) of arrhythmias. As inhibitors of $K_v1.5$ compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio is preferably greater than 4:1, more preferably greater than 10:1, and most preferably such that prolongation of the atrial effective refractory response period is achieved without significantly detectable prolongation of the ventricular effective refractory period.

In addition, the compounds within the scope of the present invention block $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The $K_v1.5$ gene is known to be expressed in stomach tissue, intestinal/colon tissue, the pulmonary artery, and pancreatic beta cells. Thus, administration of an $I_{Kur}$ blocker could provide useful treatment for disorders such as: reflux esauphagitis, functional dispepsia, constipation, asthma, and diabetes. Additionally, $K_v1.5$ is known to be expressed in the anterior pituitary. Thus, administration of an $I_{Kur}$ blocker could stimulate growth hormone secretion. $I_{Kur}$ inhibitors can additionally be useful in cell poliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula I. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the formula I or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; bucally; parenterally, such as by subcutaneous, intravenous, intramuscular, or intrastemal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula I are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inibitors (i.e., COX-1 and/or COX-2 inhibitors) such as aspirin, indomethacin, ibuprofen, piroxicam, naproxen, celebrex, vioxx and NSAIDs; anti-platelet agents such as GPIIb/IIIa blockers (e.g., abciximab, eptifibatide and tirofiban), $P2Y_{12}$ antagonists (e.g., clopidogrel, ticlopidine and CS-747), thromboxane receptor antagonists (e.g., ifetroban), aspirin, and PDE-III inhibitors (e.g., dipyridamole) with or without aspirin; diruetics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g. sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; antithrombotic/thrombolytic agents such as tissue plasminogen activator (tPA), recombinant tPA, tenecteplase (TNK), lanoteplase (nPA), factor VIIa inhibitors, factor Xa inhibitors, thromin inibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., questran); antipoliferative agents such as cyclosporin A, taxol, FK 506, and adriamycin; antitumor agents such as taxol, adriamycin, epothilones, cisplatin and carboplatin; anti-diabetic agents such as biguanides (e.g. metformin), glucosidase inhibitors (e.g. acarbose), insulins, meglitinides (e.g. repaglinide), sulfonylureas (e.g. glimepiride, glyburide and glipizide), biguanide/glyburide combinations (i.e,. glucovance), thiozolidinediones (e.g. troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inibitors including PDE III inhibitors (e.g. cilostazol), and PDE V inhibitors (e.g., sildenafil); protein tyrosine kinase inhibitors; steroidal anti-inflammatory agents such as prednisone, and dexamethasone; and other anti-inflammatory agents such as enbrel.

The above other therapeutic agents, when employed in combination with the compounds of the present invention, may be used, for example, in those amounts indicated in the Physicians' Desk Reference (PDR) or as otherwise determined by one of ordinary skill in the art.

Assays to determine the degree of activity of a compound as an $I_{Kur}$ inhibitor are well known in the art and are described in references such as *J. Gen. Physiol.* April; 101(4):513–43, and *Br. J. Pharmacol.* 1995 May; 115(2): 267–74.

Assays to determine the degree of activity of a compound as an inhibitor of other members of the $K_v1$ subfamily are also well known in the art. For example, inhibition of Kv1.1, $K_v1.2$ and $K_v1.3$ can be measured using procedures described by Grissmer S, et al., *Mol Pharmacol* 1994 June; 45(6):1227–34. Inhibition of Kv1.4 can be measured using procedures described by Petersen K R, and Nerbonne J M, *Pflugers Arch* 1999 February; 437(3):381–92. Inhibition of Kv1.6 can be measured using procedures described by Bowlby M R, and Levitan I B, *J Neurophysiol* 1995 June; 73(6):2221–9. And inhibition of Kv1.7 can be measured using procedures described by Kalman K, et al., *J Biol Chem* 1998 March 6; 273(10):5851–7.

Compounds within the scope of the present invention demonstrate activity in $K_v1$ assays such as the ones described above.

All documents cited in the present specification are incorporated herein by reference in their entirety.

The following examples and preparations describe the manner and process of making and using the invention and are illustrative rather than limiting. It is to be understood that there may be other embodiments which fall within the spirit and scope of the invention as defined by the claims appended hereto.

EXAMPLE 1

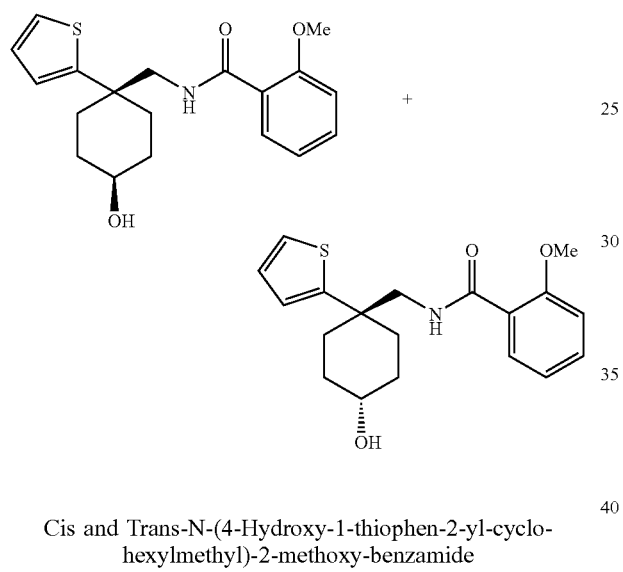

Cis and Trans-N-(4-Hydroxy-1-thiophen-2-yl-cyclohexylmethyl)-2-methoxy-benzamide Synthesis:

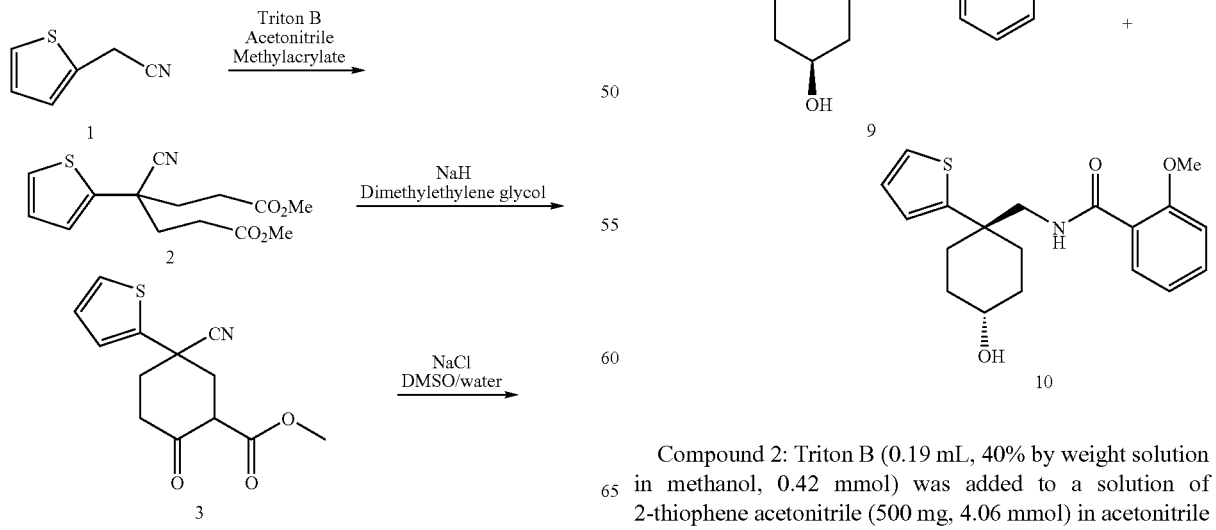

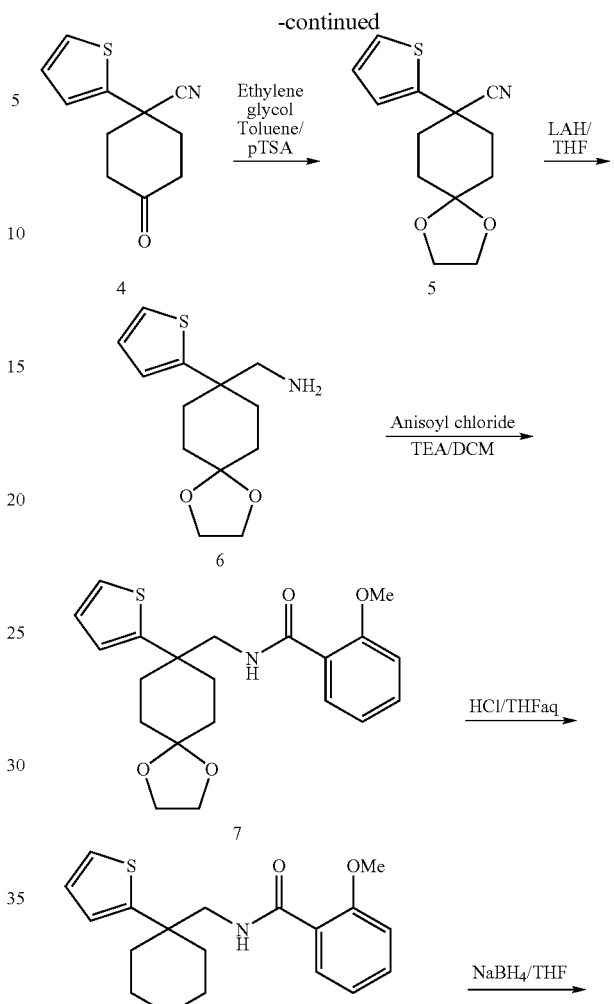

Compound 2: Triton B (0.19 mL, 40% by weight solution in methanol, 0.42 mmol) was added to a solution of 2-thiophene acetonitrile (500 mg, 4.06 mmol) in acetonitrile (27 mL) at room temperature. The reaction mixture was heated under nitrogen to 95° C. and methylacrylate (3.6 mL, 40 mmol) was added slowly (vigorous exotherm). After 5 h, the reaction mixture was allowed to cool and diluted with 50 mL of ether. The solution was transferred to a separation funnel and washed successively with HCl (1N, 2×20 mL) and saturated NaCl (1×20 mL). The organic portion was dried over anhydrous $Na_2SO_4$, decanted and concentrated yielding 1.10 g (92% crude yield) of 2 as a dark brown oil $^1$H NMR ($CDCl_3$) 2.2 ppm, 2H, multiplet; 2.3 ppm, 2H, multiplet; 2.4 ppm, 2H, multiplet; 3.65 ppm, 6H, singlet; 6.97 ppm, 1H, dd, J=3.6 and 6.2 Hz; 7.13 ppm, 1H, dd, J=1.2 and 3.6 Hz; 7.32 ppm, 1H, dd, J=1.2 and 5.1 Hz.

Compound 3: Compound 2 (1.10 g, 3.72 mmol) was dissolved in anhydrous dimethylethylene glycol (20 mL). Sodium hydride (60% dispersion in mineral oil, 360 mg, 11.2 mmol) was added slowly to the solution and the resulting brown slurry was heated under nitrogen to 95° C. for 4.5 h then allowed to cool overnight (12 h). The slurry was poured carefully into 15 mL of water and diluted with 100 mL ether. The organic portion was washed with HCl (3.7N, 2×20 mL), dried over anhydrous $Na_2SO_4$, decanted and concentrated yielding a brown oil. The crude oil was purified by silica gel flash chromatography elution with 3:1 hexane:ethylacetate yielding 298 mg (31% isolated yield) of 3 as a pale brown oil. HPLC Rt 3.10 min, Purity 100%, YMC S5 column 4.6×50 mm, 4 min gradient 0 to 100% MeOH (90% in water, 0.2% $H_3PO_4$) UV detection at 220 nm. LCMS Rt 1.61 min, [M+Na] 286.10 YMC S5 column 4.6×30 mm, 2 min gradient 0 to 100% MeOH (90% in water, 0.1% TFA) UV detection at 220 nm. $^1$H NMR ($CDCl_3$) 2.2 ppm, 2H, multiplet; 2.4 ppm, 2H, multiplet; 2.7 ppm, 2H, multiplet; 2.75 ppm, 1H, d, J=13.6 Hz; 3.15 ppm, 1H, d, J=15.0 Hz; 7.00 ppm, 1H, dd, J=3.6 and 5.1 Hz; 7.18 ppm, 1H, dd, J=1.2 and 3.6 Hz; 7.29 ppm, 1H, dd, J=1.2 and 5.2 Hz; 12.2 ppm, 1H, singlet.

Compound 4: To a solution of β-keto ester 3 (298 mg, 1.13 mmol) in DMSO (8 mL containing 0.5 mL water) was added NaCl (420 mg, 7.24 mmol). The reaction mixture was heated to 150° C. for 5 h then allowed to cool to ambient temperature. The solution was diluted with 1:1 ether:ethylacetate (50 mL), transferred to a separation funnel and washed with 10% LiCl (3×20 mL). The organic portion was dried over anhydrous $Na_2SO_4$, decanted and concentrated yielding 4 as a pale brown powder sufficiently pure to be used in the next step, (184 mg, 80% yield). HPLC Rt 2.36 min, Purity 97%, YMC S5 column 4.6×50 mm, 4 min gradient 0 to 100% MeOH (90% in water, 0.2% $H_3PO_4$) UV detection at 220 nm. $^1$H NMR ($CDCl_3$) 2.3 ppm, 2H, multiplet; 2.6 ppm, 4H, multiplet; 2.9 ppm, 2H, multiplet; 7.00 ppm, 1H, dd, J=3.6 and 6.2 Hz; 7.20 ppm, 1H, dd, J=1.2 and 3.6 Hz; 7.32 ppm, 1H, dd, J=1.2 and 5.1 Hz.

Compound 5: was dissolved in toluene (2 mL) and ethylene glycol (0.54 mL, 9.6 mmol) and toluene sulfonic acid (9 mg, 0.05 mmol) added. The solution was heated to reflux with Dean-Stark azeotropic removal of water for 14 h. The cooled reaction mixture was diluted with ether (100 mL) and washed with water (3×20 mL). The organic portion was dried over anhydrous $Na_2SO_4$, decanted and concentrated yielding 5 as a pale brown oil, (323 mg, crude quantative yield). HPLC Rt 2.90 min, Purity 83.0%, YMC S5 column 4.6×50 mm, 4 min gradient 0 to 100% MeOH (90% in water, 0.2% $H_3PO_4$) UV detection at 220 nm. $^1$H NMR ($CDCl_3$) 1.9 ppm, 2H, multiplet; 2.0 ppm, 2H, multiplet; 2.1 ppm, 2H, multiplet; 2.2 ppm, 2H, multiplet; 4.00 ppm, 4H, multiplet; 6.98 ppm, 1H, dd, J=1.2 and 3.6 Hz; 7.14 ppm, 1H, dd, J=1.2 and 5.1 Hz; 7.27 ppm, 1H, dd, J=1.2 and 5.1 Hz.

Compound 6: At ambient temperature a solution of $LiAlH_4$ (1.0M in THF, 1.35 mL, 1.35 mmol) was added to a solution of 5 in THF (5 mL). The resulting slurry was heated to reflux under nitrogen for 3 h then cooled to 0° C. 1N NaOH (0.3 mL) was added dropwise and after 10 min of vigorous stirring, anhydrous $Na_2SO_4$ was added. The slurry was filtered through a glass frit and the filter washed with THF, then the filtrate concentrated to yield 151 mg (66% yield) of 6 as a colorless oil. HPLC Rt 1.47 min, Purity 98%, YMC S5 column 4.6×50 mm, 4 min gradient 0 to 100% MeOH (90% in water, 0.2% $H_3PO_4$) UV detection at 220 nm. $^1$H NMR ($CDCl_3$) 1.7 ppm, 4H, multiplet; 1.8 ppm, 2H, multiplet; 2. 1 ppm, 2H, multiplet; 2.7 ppm, 2H, multiplet; 3.92, 4H, multiplet; 6.86, 1H, dd, J=0.9 and 3.5 Hz; 6.97, 1H, dd, J=3.5 and 5.0 Hz; 7.21, 1H, dd, J=0.9 and 5.0 Hz.

Compound 7 At ambient temperature ortho-anisoyl chloride (107 mg, 0.597 mmol) was added to a solution of amine 6 in dichloromethane (2 mL) and TEA (63 mg, 0.63 mmol). The resulting pale yellow solution was stirred for 1 h then loaded directly onto a silica gel chromatography column. The column was eluted with 1:1 hexane:ethylacetate to provide 195 mg (85% yield) of the amide 7 as a colorless oil. HPLC Rt 3.34 min, Purity 97%, YMC S5 column 4.6×50 mm, 4 min gradient 0 to 100% MeOH (90% in water, 0.2% $H_3PO_4$) UV detection at 220 nm. LCMS Rt 1.73 min, [M+1] 388.13 YMC S5 column 4.6×30 mm, 2 min gradient 0 to 100% MeOH (90% in water, 0.1% TFA) UV detection at 220 nm. $^1$H NMR ($CDCl_3$) 1.7 ppm, 4H, multiplet; 2.0 ppm, 2H, multiplet; 2.2 ppm, 2H, multiplet; 3.68 ppm, 2H, d, J=6.0 Hz; 3.73, 3H, s; 4.1 ppm, 4H, multiplet; 6.89 ppm, 1H, d, J=8.3 Hz; 6.95 ppm, 1H, dd, J=0.9 and 3.5Hz; 7.01 ppm, 1H, dd, J=3.5 and 5.1 Hz; 7.06 ppm, 1H, dd, J=7.4 and 8.0 Hz; 7.27 ppm, 1H, dd, J=0.8 and 4.9 Hz; 7.40 ppm, 1H, dd, J=1.1 and 1.7 Hz; 7.8 ppm, 1H, br s; 8.19 ppm, 1H, dd, J=1.8 and 7.8 Hz.

Compound 8: (195 mg, 0.504 mmol) was dissolved in THF (4 mL) and 2N HCl was added (1 mL). The resulting solution was heated to 40° C. for 3 h, allowed to cool, diluted with ether (50 mL) and washed with sat. $NaHCO_3$ (3×20 mL). The organic portion was dried over anhydrous $Na_2SO_4$, decanted and concentrated yielding 200 mg (crude quantative yield) of 9 as a colorless oil. HPLC Rt 3.00 min, Purity 92%, YMC S5 column 4.6×50 mm, 4 min gradient 0 to 100% MeOH (90% in water, 0.2% $H_3PO_4$) UV detection at 220 nm. LCMS Rt 1.55 min, [M+1] 333.08 YMC S5 column 4.6×30 mm, 2 min gradient 0 to 100% MeOH (90% in water, 0.1% TFA) UV detection at 220 nm. $^1$H NMR ($CDCl_3$) 2.2 ppm, 2H, multiplet; 2.5 ppm, 6H, multiplet; 3.75, 3H, s; 3.79 ppm, 1H, d, J=6.2 Hz; 6.92 ppm, 1H, d, J=8.3 Hz; 7.03 ppm, 1H, dd, J=0.9 and 3.5 Hz; 7.08 ppm, 2H, multiplet; 7.35 ppm, 1H, dd, J=0.8 and 5.1 Hz; 7.43 ppm, 1H, ddd, J=1.8, 7.5 and 8.5 Hz; 7.9 ppm, 1H, br t; 8.20 ppm, 1H, dd, J=1.8 and 7.8 Hz.

Compounds 9 and 10: To a solution of crude ketone 8 (200 mg crude, 0.504 mmol) in THF (4 mL) was added $NaBH_4$ (44 mg, 1.5 mmol). The reaction mixture was stirred at ambient temperature under nitrogen for 14 h then the slurry diluted with dichloromethane (100 mL). The slurry was transferred to a separatory funnel and the organic portion washed with 1N HCl (2×20 mL), dried over anhydrous $Na_2SO_4$, decanted and concentrated yielding a mixture of 9 and 10 as a colorless oil. The isomers were separated by preparative thin layer chromatography (25×25 cm, 1 mm plate with UV indicator at 254 nm) using 2:1 dichloromethane:MTBE as eluent. Compound 9 (43 mg) was isolated as the less polar constituent: HPLC Rt 3.16 min, Purity 95%, YMC S5 column 4.6×50 mm, 4 min gradient 0 to 100% MeOH (90% in water, 0.2% H₃PO₄) UV detection at 220 nm. LCMS Rt 1.64 min, [M+1] 346.10 YMC S5 column 4.6×30 mm, 2 min gradient 0 to 100% MeOH (90% in water, 0.1% TFA) UV detection at 220 nm. 1H NMR (MeOD) 1.3 ppm, 2H, multiplet; 1.5 ppm, 2H, multiplet; 2.1 ppm, 2H, br d; 3.37 ppm, 2H, s; 3.5 ppm, 1H, multiplet; 3.64 ppm, 3H, s; 6.8 ppm, 4H, multiplet; 7.22 ppm, 1H, dd, J=0.7 and 5.4 Hz; 7.32 ppm, 1H, dd, J=1.8 and 8.7 Hz; 7.78 ppm, 1H, dd, J=1.7 and 7.8 Hz; 8.0 ppm, 1H, br s. Compound 10 (47 mg) was isolated as the more polar constituent: HPLC Rt 2.95 min, Purity 94%, YMC S5 column 4.6×50 mm, 4 min gradient 0 to 100% MeOH (90% in water, 0.2% H₃PO₄) UV detection at 220 nm. LCMS Rt 1.52 min, [M+1] 346.13 YMC S5 column 4.6×30 mm, 2 min gradient 0 to 100% MeOH (90% in water, 0.1% TFA) UV detection at 220 nm. ¹H NMR (MeOD) 1.6 ppm, 4H, multiplet; 1.8 ppm, 2H, multiplet; 2.0 ppm, 2H, multiplet; 3.62 ppm, 1H, d, J=5.9 Hz; 3.63, 1H, br multiplet; 3.64 ppm, 3H, s; 6.9 ppm, 4H, multiplet; 7.26 ppm, 1H, dd, J=0.6 and 4.6 Hz; 7.36 ppm, 1H, dd, J=1.8 and 8.7 Hz; 7.87 ppm, 1H, dd, J=1.8 and 7.8 Hz; 8.0 ppm, 1H, br t.

EXAMPLES 2–12

Examples 2 to 12 were prepared using methodology described in Example 1.

| Ex. | Structure | Name | [M + 1] |
|---|---|---|---|
| 2 | 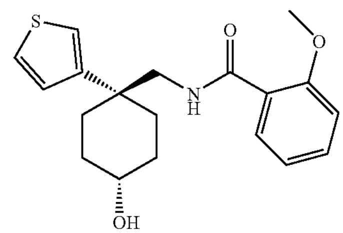 | N-(4-Hydroxy-1-thiophen-3-yl-cyclohexylmethyl)-2-methoxy-benzamide | 346 |
| 3 | 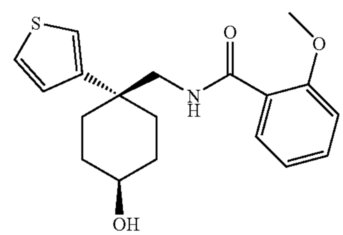 | N-(4-Hydroxy-1-thiophen-3-yl-cyclohexylmethyl)-2-methoxy-benzamide | 346 |
| 4 | 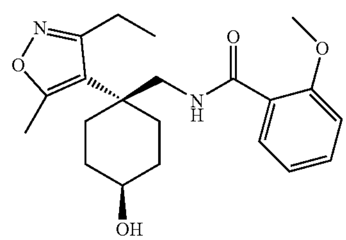 | N-[1-(3-Ethyl-5-methyl-isoxazol-4-yl)-4-hydroxy-cyclohexylmethyl]-2-methoxy-benzamide | 373 |
| 5 | 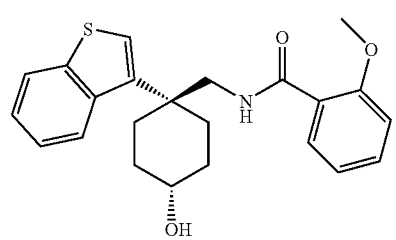 | N-(1-Benzo[b]thiophen-3-yl-4-hydroxy-cyclohexylmethyl)-2-methoxy-benzamide | 396 |
| 6 | 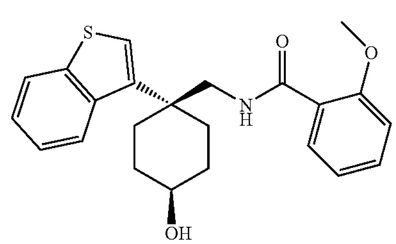 | N-(1-Benzo[b]thiophen-3-yl-4-hydroxy-cyclohexylmethyl)-2-methoxy-benzamide | 396 |

-continued

| Ex. | Structure | Name | [M + 1] |
|---|---|---|---|
| 7 | 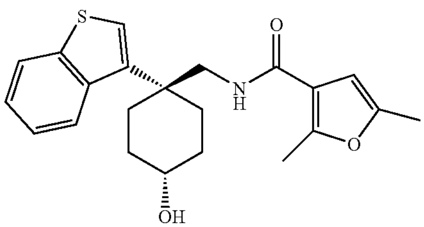 | 2,5-Dimethyl-furan-3-carboxylic acid (1-benzo[b]thiophen-3-yl-4-hydroxy-cyclohexylmethyl)-amide | 384 |
| 8 | 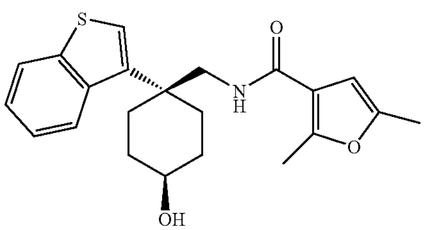 | 2,5-Dimethyl-furan-3-carboxylic acid (1-benzo[b]thiophen-3-yl-4-hydroxy-cyclohexylmethyl)-amide | 384 |
| 9 | 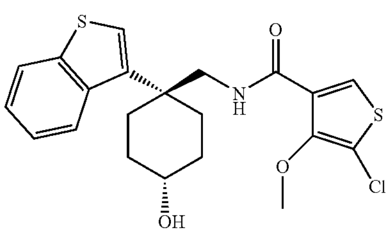 | 5-Chloro-4-methoxy-thiophene-3-carboxylic acid (1-benzo[b]thiophen-3-yl-4-hydroxy-cyclohexylmethyl)-amide | 437 |
| 10 | 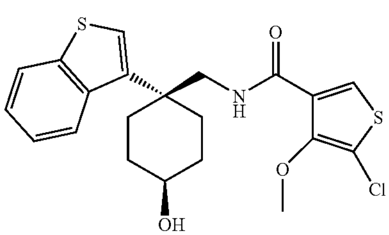 | 5-Chloro-4-methoxy-thiophene-3-carboxylic acid (1-benzo[b]thiophen-3-yl-4-hydroxy-cyclohexylmethyl)-amide | 437 |
| 11 | 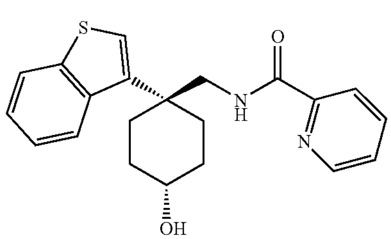 | Pyridine-2-carboxylic acid (1-benzo[b]thiophen-3-yl-4-hydroxy-cyclohexylmethyl)-amide | 367 |

| Ex. | Structure | Name | [M + 1] |
|---|---|---|---|
| 12 | 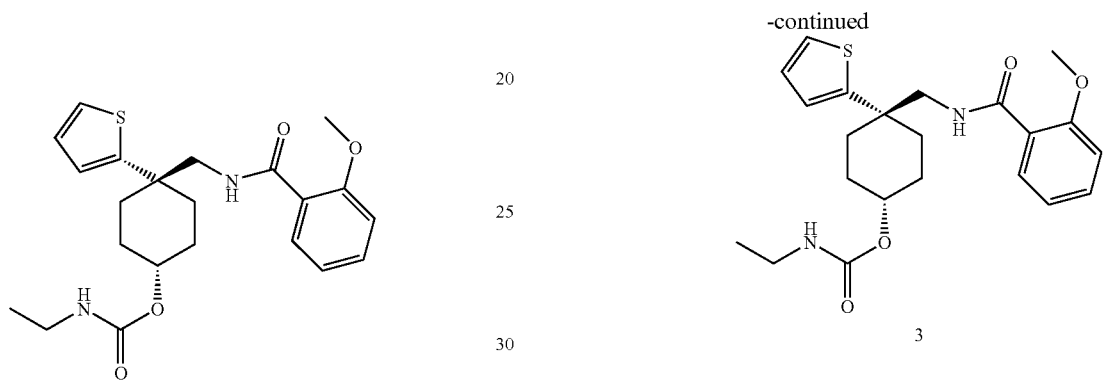 | Pyridine-2-carboxylic acid (1-benzo[b]thiophen-3-yl-4-hydroxy-cyclohexylmethyl)-amide | 367 |

EXAMPLE 13

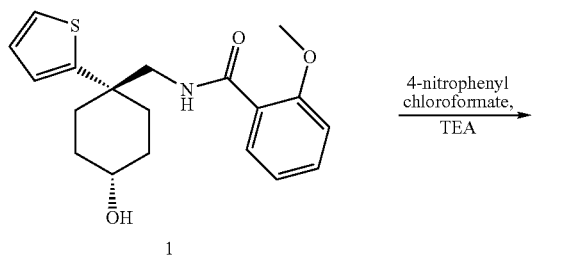

Trans-Ethyl-carbamic acid 4-[(2-methoxy-benzoylamino)-methyl]-4-thiophen-2-yl-cyclohexyl ester Synthesis:

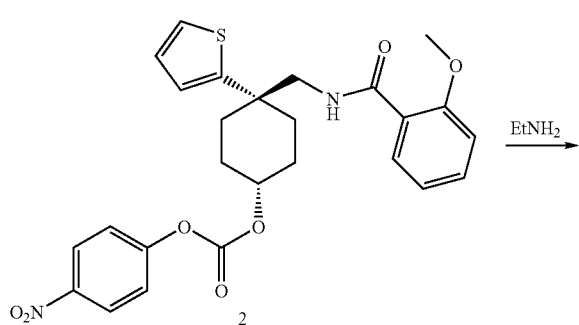

-continued

[structure 3 with EtNH on carbamate, thiophene, methoxybenzamide]

Compound 1 The synthesis of 1 is described in Example 1.

Compound 2: At ambient temperature 4-nitrophenylchloroformate (45 mg, 0.22 mmol) was added to a solution of alcohol 1 (43 mg, 0.12 mmol) in dichloromethane (10 mL) containing triethylamine (ca. 38 mg). The resulting yellow solution was stirred for 72 h then purified directly by silica gel chromatography elution with 2:1 hexane:ethylacetate yielding 32 mg (52% yield) of 2 as a colorless oil. HPLC Rt 3.91 min, Purity 84%, YMC S5 column 4.6×50 mm, 4 min gradient 0 to 100% MeOH (90% in water, 0.2% $H_3PO_4$) UV detection at 220 nm. $^1$H NMR ($CDCl_3$) 1.8 ppm, 4H, multiplet; 2.1 ppm, 2H, multiplet; 2.3 ppm, 2H, multiplet; 3.69 ppm, 1H, d, J=6.0 Hz; 3.75 ppm, 3H, s; 4.8 ppm, 1H, multiplet; 6.9 ppm, 3H, multiplet; 7.05 ppm, 2H, multiplet; 7.32 ppm, 1H, d, J=8.0 Hz; 7.45 ppm, 1H, dd, J=1.8 and 8.7Hz; 7.9 ppm, 1H, br t; 8.15 ppm, 1H, d, J=8.0 Hz; 8.20 ppm, 1H, dd, J=1.8 and 7.8 Hz.

Compound 3: A solution of ethylamine (0.8 mL, 2.0M in THF) was added to a solution of 2 (32 mg, 0.062 mmol) in dichloromethane (3 mL) at ambient temperature. After 1 h the yellow solution was loaded directly onto a preparative thin layer chrmoatography plate (25×25 cm, 1 mm with UV indicator at 254 nm). The plate was eluted using 1:1 hexane:ethylacetate to provide 11 mg (43% yield) of 3 as a colorless glass. HPLC Rt 3.37 min, Purity 96%, YMC S5 column 4.6×50 mm, 4 min gradient 0 to 100% MeOH (90% in water, 0.2% $H_3PO_4$) UV detection at 220 nm. LCMS Rt 1.71 min, [M+1] 417.14 YMC S5 column 4.6×30 mm, 2 min gradient 0 to 100% MeOH (90% in water, 0.1% TFA) UV detection at 220 nm. ¹H NMR (CDCl₃) 1.09 ppm, 3H, t, J=7.1 Hz; 1.6 ppm, 2H, multiplet; 1.8 ppm, 2H, multiplet; 2.0 ppm, 2H, multiplet; 2.2 ppm, 2H, multiplet; 3.18 ppm, 2H, multiplet; 3.65 ppm, 2H, d, J=6.0 Hz; 3.74 ppm, 3H, s; 4.72 ppm, 1H, br s; 4.48 ppm, 1H, br s; 6.90 ppm, 1H, d, J=8.2 Hz; 6.95 ppm, 1H, d, J=3.0 Hz; 7.15 ppm, 2H, multiplet; 7.28 ppm, 1H, d, J=5.0 Hz; 7.45 ppm, 1H, dd, J=1.8 and 8.8 Hz; 7.8 ppm, 1H, br s; 8.20 ppm, 1H, d, J=2.2 and 7.7 Hz.

EXAMPLES 14–27

Examples 14 to 27 were prepared using methodology described in Example 13.

| Ex. | Structure | Name | [M + 1] |
|---|---|---|---|
| 14 | 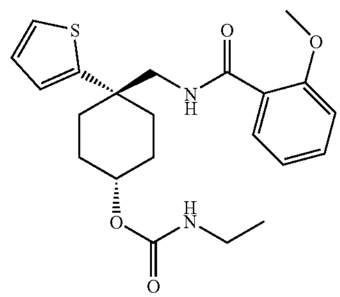 | Ethyl-carbamic acid 4-[(2-methoxy-benzoylamino)-methyl]-4-thiophen-2-yl-cyclohexyl ester | 417 |
| 15 | 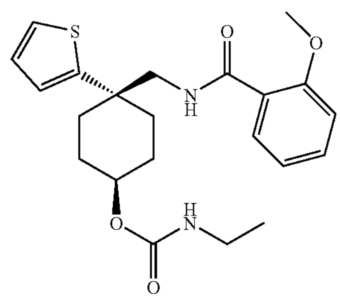 | Ethyl-carbamic acid 4-[(2-methoxy-benzoylamino)-methyl]-4-thiophen-2-yl-cyclohexyl ester | 417 |
| 16 | 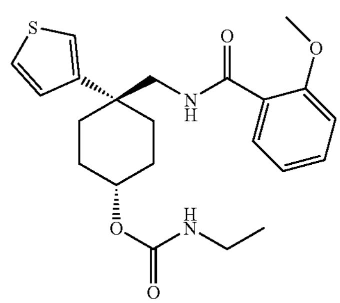 | Ethyl-carbamic acid 4-[(2-methoxy-benzoylamino)-methyl]-4-thiophen-3-yl-cyclohexyl ester | 417 |
| 17 | 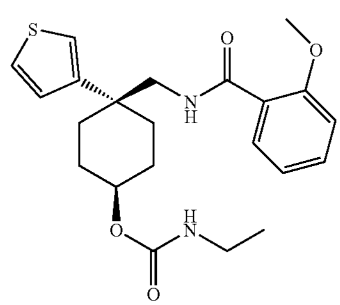 | Ethyl-carbamic acid 4-[(2-methoxy-benzoylamino)-methyl]-4-thiophen-3-yl-cyclohexyl ester | 417 |

| Ex. | Structure | Name | [M + 1] |
|---|---|---|---|
| 18 | 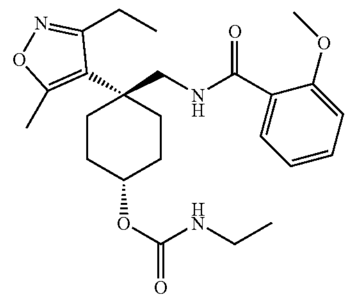 | Ethyl-carbamic acid 4-(3-ethyl-5-methyl-isoxazol-4-yl)-4-[(2-methoxy-benzoylamino)-methyl]-cyclohexyl ester | 444 |
| 19 | 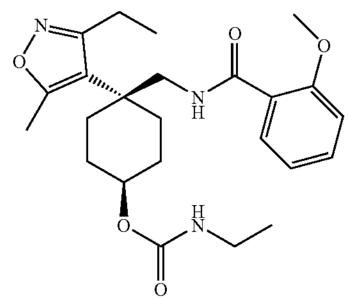 | Ethyl-carbamic acid 4-(3-ethyl-5-methyl-isoxazol-4-yl)-4-[(2-methoxy-benzoylamino)-methyl]-cyclohexyl ester | 444 |
| 20 | 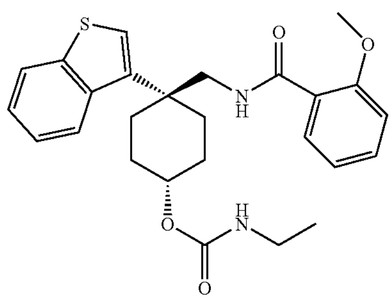 | Ethyl-carbamic acid 4-benzo[b]thiophen-3-yl-4-[(2-methoxy-benzoylamino)-methyl]-cyclohexyl ester | 467 |
| 21 | 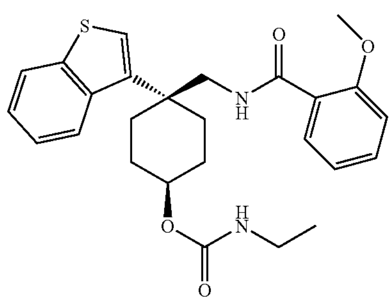 | Ethyl-carbamic acid 4-benzo[b]thiophen-3-yl-4-[(2-methoxy-benzoylamino)-methyl]-cyclohexyl ester | 467 |
| 22 | 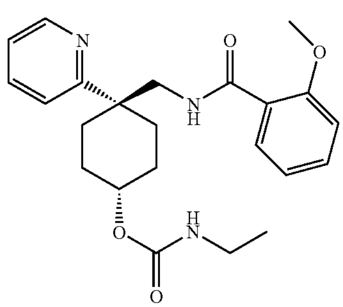 | Ethyl-carbamic acid 4-[(2-methoxy-benzoylamino)-methyl]-4-pyridin-2-yl-cyclohexyl ester | 412 |

-continued

| Ex. | Structure | Name | [M + 1] |
|---|---|---|---|
| 23 | 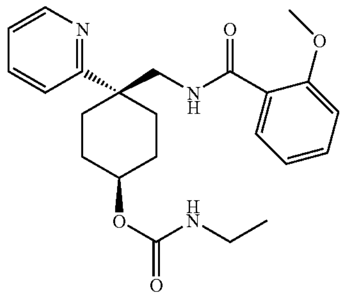 | Ethyl-carbamic acid 4-[(2-methoxy-benzoylamino)-methyl]-4-pyridin-2-yl-cyclohexyl ester | 455 |
| 24 | 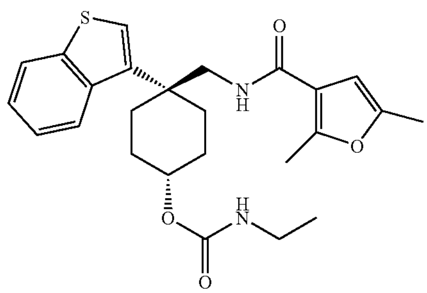 | Ethyl-carbamic acid 4-benzo[b]thiophen-3-yl-4-{[(2,5-dimethyl-furan-3-carbonyl)-amino]-methyl}-cyclohexyl ester | 455 |
| 25 | 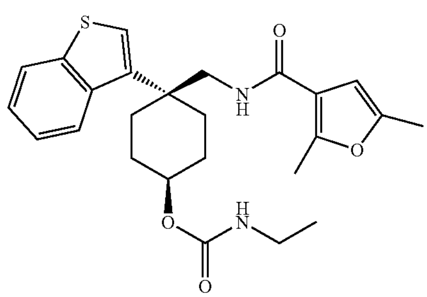 | Ethyl-carbamic acid 4-benzo[b]thiophen-3-yl-4-{[(2,5-dimethyl-furan-3-carbonyl)-amino]-methyl}-cyclohexyl ester | 507 |
| 26 | 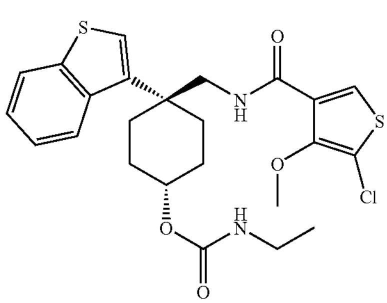 | Ethyl-carbamic acid 4-benzo[b]thiophen-3-yl-4-{[(5-chloro-4-methoxy-thiophene-3-carbonyl)-amino]-methyl}-cyclohexyl ester | 507 |

| Ex. | Structure | Name | [M + 1] |
|---|---|---|---|
| 27 | 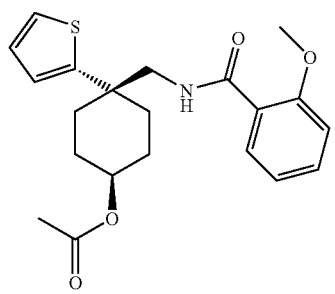 | Ethyl-carbamic acid 4-benzo[b]thiophen-3-yl-4-{[(5-chloro-4-methoxy-thiophene-3-carbonyl)-amino]-methyl}-cyclohexyl ester | 418 |

EXAMPLE 28

Acetic acid 4[(2-methoxy-benzoylamino)-methyl]-4-thiophen-3-yl-cyclohexyl ester

Synthesis:

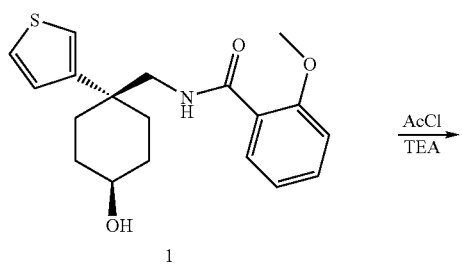

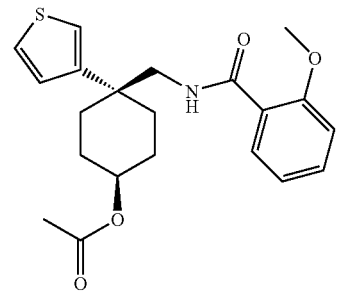

Compound 1: The synthesis of 1 is described in Example 1.

Compound 2: At ambient temperature acetyl chloride (6 mg, 0.08 mmol) was added to a solution of alcohol 1 (14 mg, 0.040 mmol) in dichloromethane (10 mL) containing TEA (ca. 8 mg). The resulting yellow solution was stirred for 16 h then purified directly by preparative HPLC YMC ODS S5 20×100 mm column 30–100% MeOH (90% in water, 0.1%TFA) gradient over 8 min with flow rate 20 mL/min and UV detection at 220 nm. The ester 2 eluted at a retention time of 8.6 min. and was isolated as a colorless oil (6.6 mg, yield 43%). HPLC Rt 3.42 min, Purity 100%, YMC S5 column 4.6×50 mm, 4 min gradient 0 to 100% MeOH (90% in water, 0.2% $H_3PO_4$) UV detection at 220 nm. LCMS Rt 1.78 min, [M+1] 388.13 YMC S5 column 4.6×30 mm, 2 min gradient 0 to 100% MeOH (90% in water, 0.1% TFA) UV detection at 220 nm. $^1H$ NMR (CDCl$_3$) 1.7 ppm, 2H, multiplet; 1.8 ppm, 2H, multiplet; 1.9 ppm, 4H, multiplet; 2.06 ppm, 3H, s; 3.71 ppm, 3H, s; 3.71 ppm, 2H, d, J=8.0 Hz; 5.3 ppm, 1H, septet; 6.90 ppm, 1H, d, J=8.3 Hz; 7.06 ppm, 1H, t; 7.1 ppm, 2H, multiplet; 7.4 ppm, 2H, multiplet; 7.74 ppm, 1H, br t; 8.19 ppm, 1H, dd, J=1.8 Hz and 7.8 Hz.

EXAMPLES 29–30
Examples 29 to 30 were synthesized using methodology described in Example 28.
| Ex. | Structure | Name | [M + 1] |
|---|---|---|---|
| 29 | 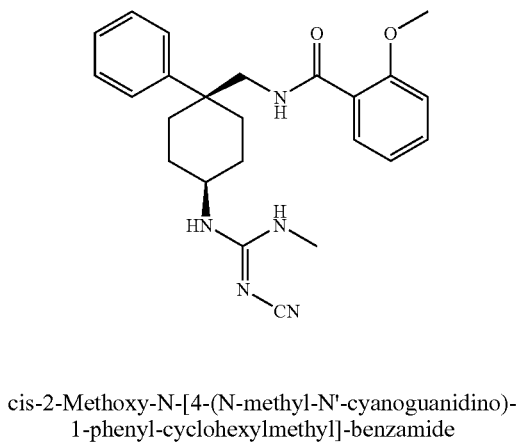 | Butyric acid 4-[(2-methoxy-benzoylamino)-methyl]-4-thiophen-3-yl-cyclohexyl ester | 416 |
| 30 | 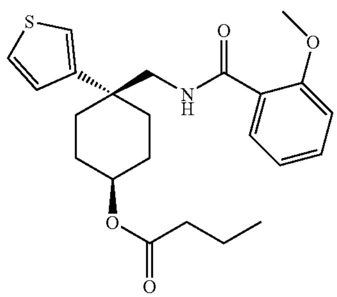 | Butyric acid 4-[(2-methoxy-benzoylamino)-methyl]-4-thiophen-3-yl-cyclohexyl ester | 416 |
EXAMPLE 31
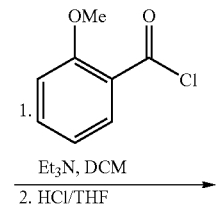
cis-2-Methoxy-N-[4-(N-methyl-N'-cyanoguanidino)-1-phenyl-cyclohexylmethyl]-benzamide
Synthesis:
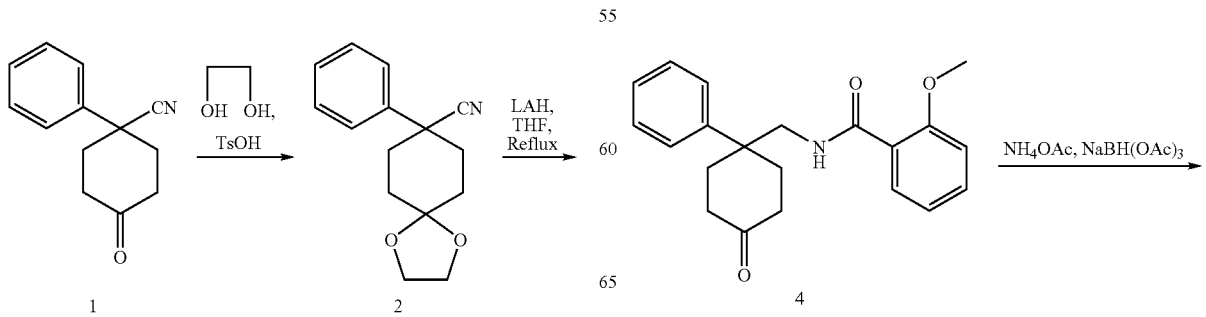

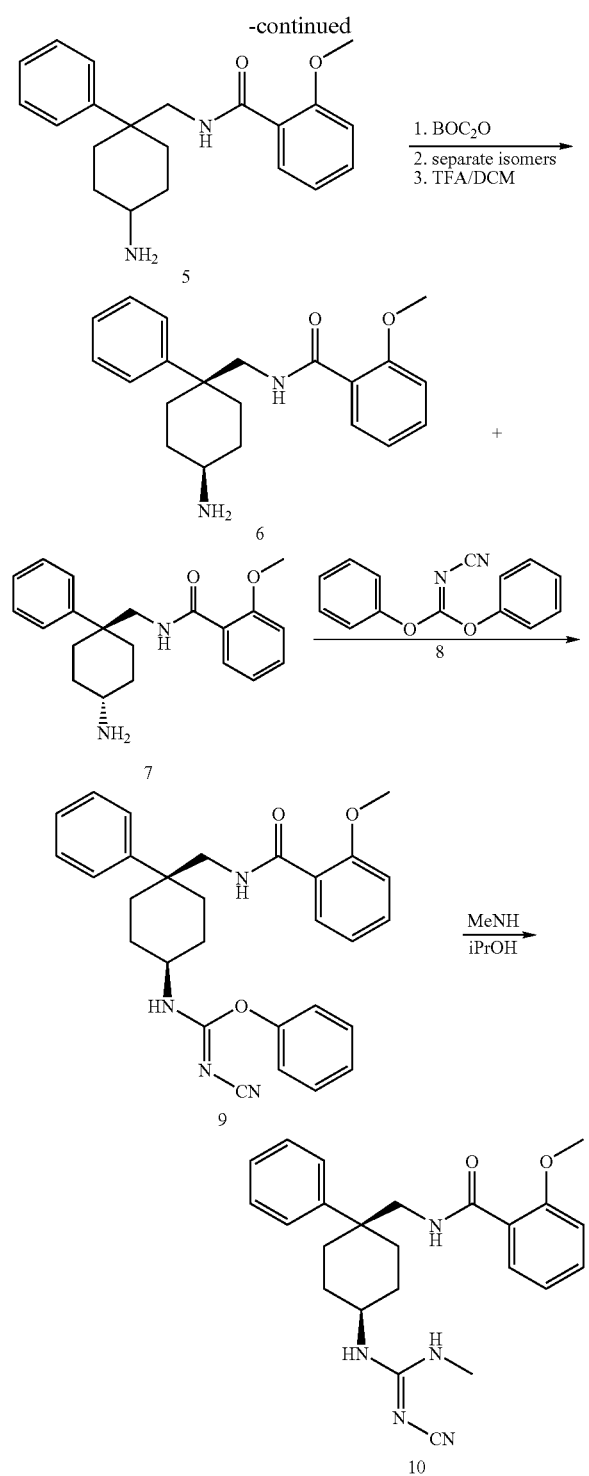

Compound 1: Compound 1 is commercially available.

Compound 2: To a solution of 4-phenyl-4-cyano-cyclohexane-1-one 1 (10 g, 50 mmol) in 200 ml of toluene was added p-toluenesulfonic acid monohydrate (2.5 g, 13.1 mmol) and ethylene glycol (20 ml, 360 mmol) in a portion, respectively. The resulting solution was stirred at reflux for 5 h. The reaction mixture was concentrated in vacuo to yield oily residue. It was then diluted with EtOAc (200 ml) and washed with aq. NaHCO$_3$ (50 ml×2) and brine (50 ml×1). The organic layer was dried over MgSO$_4$ and concentrated in vacuo to provide an oil (12. 9 g, >95%), which was subjected to the following reaction without any further purification.

Compound 3: Into a solution of the nitrile 2 (12.9 g) in 100 ml of THF was added 60 ml of 1M LAH/THF dropwide and the resulting solution was stirred at reflux for 2 h. The reaction mixture was cooled to 0° C. and quenched carefully with water. The reaction mixture was diluted with EtOAc (500 ml) and washed with aq. LiOH—NaCl (50 ml×3). The organic layer was dried over MgSO$_4$ and concentrated in vacuo to provide an oil (13.6 g, >95%), which was subjected to the following reaction without further purification.

Compound 4: To a solution of amine 3 (5.9 g, 24 mmol) and Et$_3$N (6.0 ml, 43 mmol) in 100 ml of CH$_2$Cl$_2$ was added anisoyl chloride (4.5 ml, 30.4 mmol) dropwise at 0° C. and the resulting solution was stirred for 2 h. The reaction mixture was concentrated in vacuo, yielding a white solid residue which was partitioned between EtOAc (200 ml) and aq. NaHCO$_3$ (50 ml). The organic layer was dried over MgSO$_4$ and concentrated in vacuo to provide an oil, which was diluted in 50 ml of THF and 50 ml of 2N aq. HCl. The resulting solution was stirred for 12 h at 25° C. The reaction mixture was diluted with EtOAc (200 ml). The organic layer was separated, washed with brine (50 ml×2), and dried over MgSO$_4$. Concentration of the organic layer produced an oily residue, which was purified on column chromatography (50% EtOAc/Hex) to yield 6.8 g (20.2 mmol, 84% for two steps) of the desired product.

Compound 5: To a solution of the ketone 4 (13 g, 38.6 mmol) in 100 ml of MeOH was added NH$_4$OAc (23.2 g, 300 mmol) and NaBH(OAc)$_3$ (12.2 g, 57.8 mmol) and the resulting mixture was stirred for 12 h at 25° C. The reaction mixture was concentrated in vacuo to produce a solid residue, which was partitioned between EtOAc (200 ml) and 1N aq. NaOH (30 ml×2). The organic layer was dried over MgSO$_4$. Concentration of the organic solution provided oily residue, which was subjected to column chromatography (10% NH$_3$—MeOH/CH$_2$Cl$_2$) to obtain 10.8 g of the desired product as 1:1 mixture of two diastereoisomers.

Compounds 6 and 7: The amine 5 (3.6 g, 10.7 mmol) was dissolved in CH$_3$CN (100 ml). A solution of di-tert-butyl-dicarbonate (3.5 g, 16 mmol) dissolved in 30 ml of CH$_3$CN was added dropwise. The mixture was stirred for 2 h at 25° C. Reaction mixture was concentrated in vacuo to provide an oily residue, which was subjected to column chromatography (50% Hex/EtOAc) to yeild 2.1 g of trans-isomer (retention time: 2.43 min) and 1.9 g of the cis-isomer (retention time: 2.67 min)of the boc-protected amine. Each of the amines were dissolved in 40 ml of 25% TFA/CH$_2$Cl$_2$ and stirred at 25° C. for 2 h. They were concentrated in vacuo to provide oily residues, which were dissolved in EtOAc (150 ml, respectively) and washed with 1N aq. NaOH (100 ml×2). The organic layers were dried over MgSO$_4$ and concentrated in vacuo to provide an oil, which corresponds to the amine of a single diastereoisomer.

Compound 9: To a solution of the cis-isomer of the amine 6 (700 mg, 2.07 mmol) in 40 ml of 2-propanol was added diphenyl cyanocarbonimidate (0.48 g, 2.07 mmol) and the reaction mixture was stirred at reflux for 4 h. It was concentrated in vacuo to provide an oil, which was used in a following reactions without any further purification.

Compound 10: To a solution of 9 (100 mg, 0.21 mmol) in 2 ml of 2-propanol was added 2 ml of MeNH$_2$ (2N in THF).

The mixture was stirred for 2 h at 75° C. in a sealed tube. The reaction mixture was cooled to room temperature and concentrated in vacuo to provide oily residue, which was purified by preparative HPLC (YMC S5 ODS 30×250 mm reverse phase column; 30 min gradient from 70:30 A:B to 100% B, where solvent A=90:10:0.1 H₂O:MeOH:TFA and solvent B=90:10:0.1 MeOH:H₂O:TFA) to provide 53.4 mg (0.13 mmol, 62%) of the desired product as a white solid after lyophilization (MeOH/H₂O). [M+H]=420.

EXAMPLES 32–52

Examples 32 to 52 were synthesized using methodology described in Example 31.

| Ex. | Structure | Name | (M + H) |
|---|---|---|---|
| 32 | 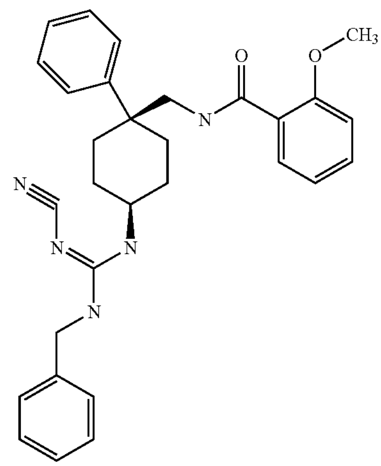 | cis-2-Methoxy-N-[4-(N-benzyl-N'-cyano-guanidino)-1-phenyl-cyclohexylmethyl]-benzamide | 496 |
| 33 | 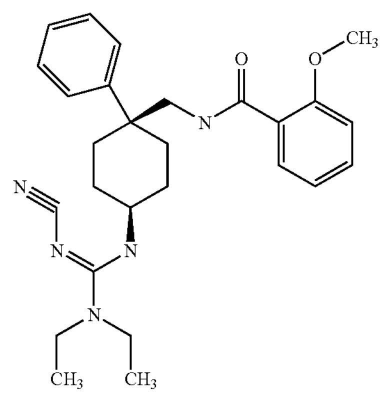 | cis-2-Methoxy-N-[4-(N,N-diethyl-cyano-guanidino)-1-phenyl-cyclohexylmethyl]-benzamide | 462 |
| 34 | 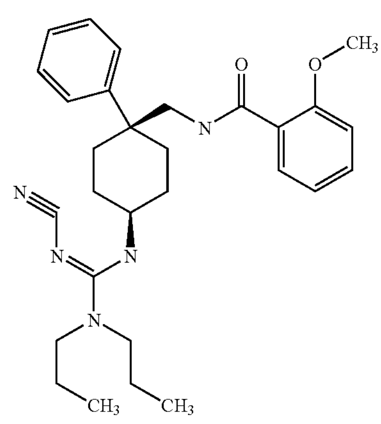 | cis-2-Methoxy-N-[4-(N,N-dipropyl-N'-cyano-guanidino)-1-phenyl-cyclohexylmethyl]-benzamide | 490 |

-continued

| Ex. | Structure | Name | (M + H) |
|---|---|---|---|
| 35 | Chiral | cis-2-Methoxy-N-[4-(N-propyl-N'-cyano-guanidino)-1-phenyl-cyclohexylmethyl]-benzamide | 448 |
| 36 | 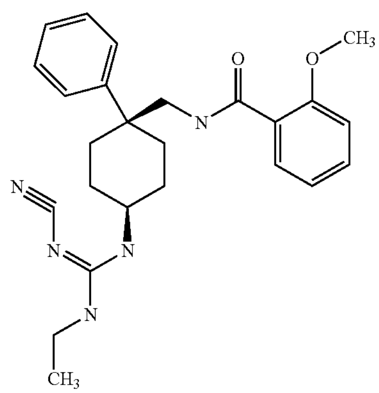 | cis-2-Methoxy-N-[4-(N-ethyl-N'-cyano-guanidino)-1-phenyl-cyclohexylmethyl]-benzamide | 434 |
| 37 | 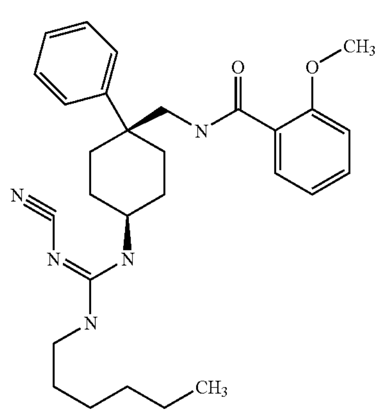 | cis-2-Methoxy-N-[4-(N-hexyl-N'-cyano-guanidino)-1-phenyl-cyclohexylmethyl]-benzamide | 490 |

-continued

| Ex. | Structure | Name | (M + H) |
|---|---|---|---|
| 38 | 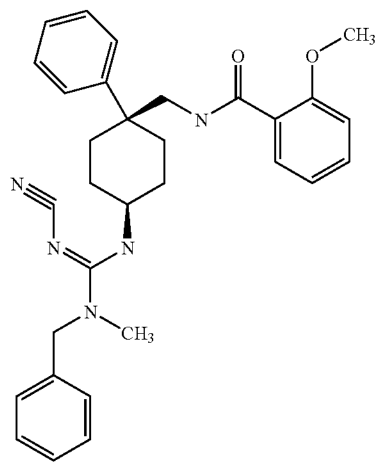 | cis-2-Methoxy-N-[4-(N-methyl-N-benzyl-N'-cyano-guanidino)-1-phenyl-cyclohexyl-methyl]-benzamide | 510 |
| 39 | 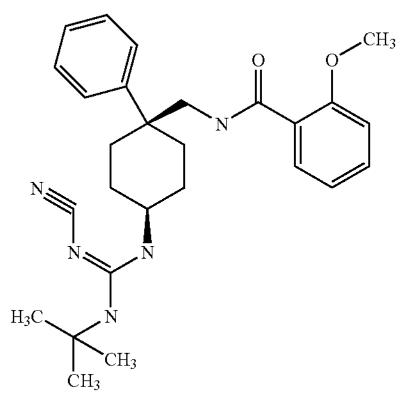 | cis-2-Methoxy-N-[4-(N-tert-butyl-N'-cyano-guanidino)-1-phenyl-cyclohexylmethyl]-benzamide | 462 |
| 40 | 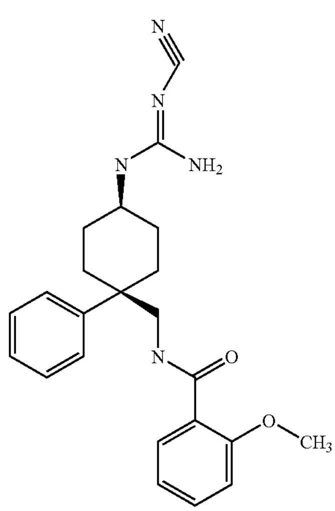 | cis-2-Methoxy-N-[4-(N-cyanoguanidino)-1-phenyl-cyclohexyl-methyl]-benzamide | 406 |

-continued

| Ex. | Structure | Name | (M + H) |
|---|---|---|---|
| 41 | 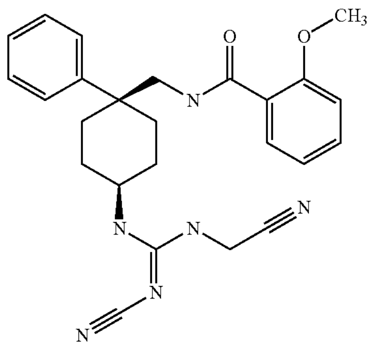 | cis-2-Methoxy-N-[4-(N-acetonitrilo-N'-cyano-guanidino)-1-phenyl-cyclohexyl-methyl]-benzamide | 445 |
| 42 | 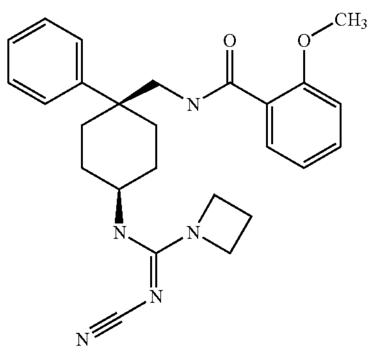 | cis-2-Methoxy-N-[4-(azetidinyl-N-cyano-guanidino)-1-phenyl-cyclohexylmethyl]-benzamide | 446 |
| 43 | 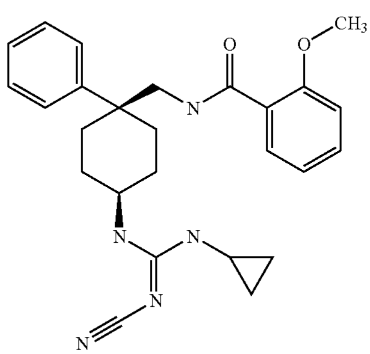 | cis-2-Methoxy-N-[4-(N-cyclopropyl-N'-cyano-guanidino)-1-phenyl-cyclohexyl-methyl]-benzamide | 446 |
| 44 | 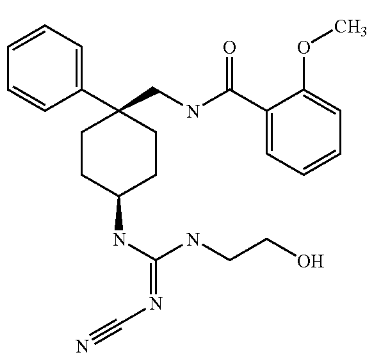 | cis-2-Methoxy-N-[4-(N-(2-hydroxyethyl)-N'-cyano-guanidino)-1-phenyl-cyclohexyl-methyl]-benzamide | 450 |

-continued

| Ex. | Structure | Name | (M + H) |
|---|---|---|---|
| 45 | 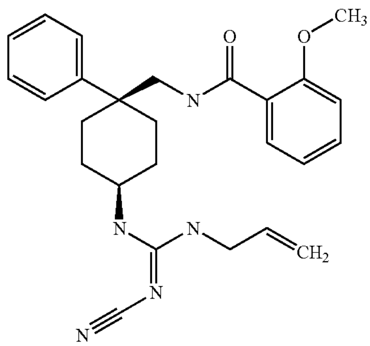 | cis-2-Methoxy-N-[4-(N-allylic-N'-cyano-guanidino)-1-phenyl-cyclohexylmethyl]-benzamide | 446 |
| 46 | 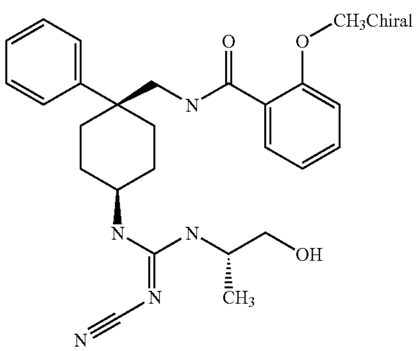 | cis-N-{4-[N'-hydroxy-1-methyl-ethyl)-N''-cyanoguanidino]-1-phenyl-cyclohexyl-methyl}-2-methoxy-benzamide | 464 |
| 47 | 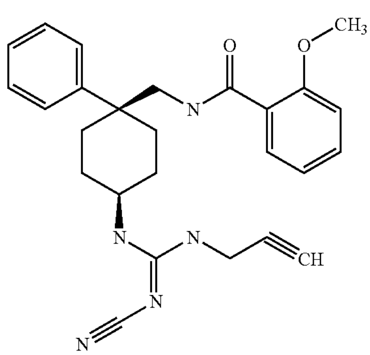 | cis-2-Methoxy-N-[4-(N-prop-2-ylnyl-N'-cyano-guanidino)-1-phenyl-cyclohexyl-methyl]-benzamide | 444 |
| 48 | 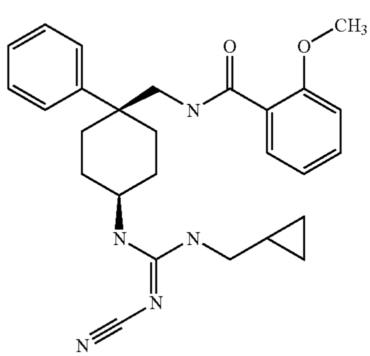 | cis-2-Methoxy-N-[4-(N-cyclopropylmethyl-N'-cyano-guanidino)-1-phenyl-cyclohexyl-methyl]-benzamide | 460 |

| Ex. | Structure | Name | (M + H) |
| --- | --- | --- | --- |
| 49 | 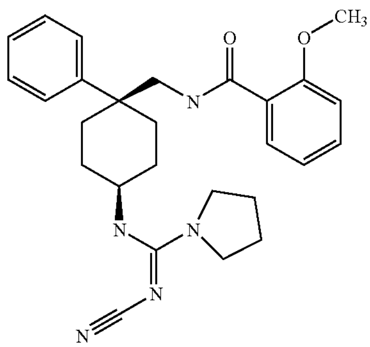 | cis-2-Methoxy-N-[4-(pyrrolidinyl-N-cyano-guanidino)-1-phenyl-cyclohexyl-methyl]-benzamide | 460 |
| 50 | 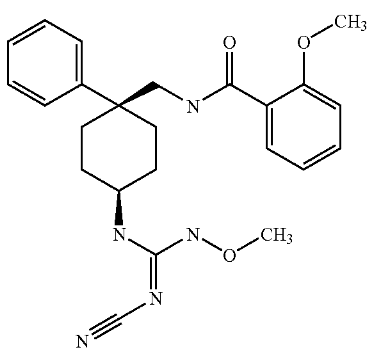 | cis-2-Methoxy-N-[4-(N-methoxy-N'-cyano-guanidino)-1-phenyl-cyclohexylmethyl]-benzamide | 436 |
| 51 | 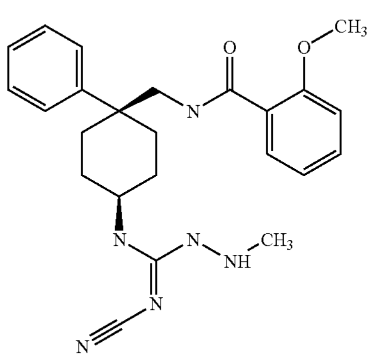 | cis-2-Methoxy-N-[4-(N-methylamino-N'-cyano-guanidino)-1-phenyl-cyclohexyl-methyl]-benzamide | 435 |

| Ex. | Structure | Name | (M + H) |
|---|---|---|---|
| 52 | 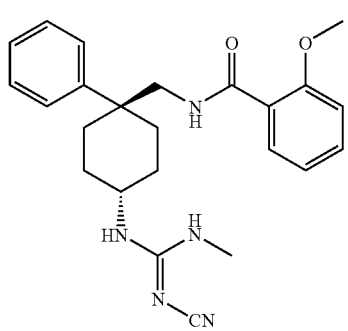 | cis-2-Methoxy-N-[4-(N,N-dimethyl-N'-cyano-guanidino)-1-phenyl-cyclohexylmethyl]-benzamide | 434 |

EXAMPLE 53

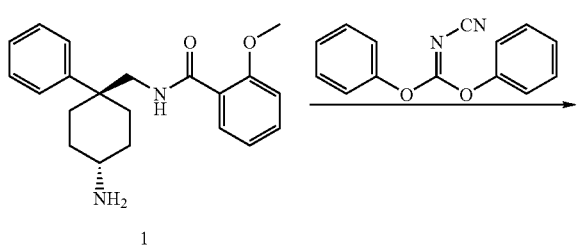

trans-2-Methoxy-N-[4-(N-methyl-N'-cyanoguanidino)-1-phenyl-cyclohexylmethyl]-benzamide Synthesis:

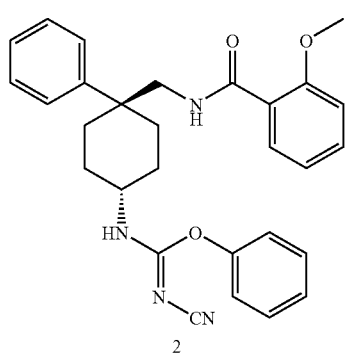

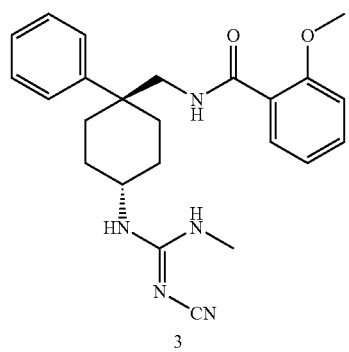

Compound 1: compound 1 was synthesized as described in Example 31.

Compound 2: To a solution of the trans-amine 1 (300 mg, 1.26 mmol) in 20 ml of 2-propanol was added diphenyl cyanocarbonidate (0.24 g, 1.26 mmol) and the resulting mixture was stirred at reflux for 4 h. The reaction mixture was concentrated in vacuo to provide an oil, which was used in a following reaction without any further purification.

Compound 3: To solution of intermediate 2 (100 mg, 0.21 mmol) in 2 ml of 2-propanol was added 2 ml of methylaamine (2N in THF). The mixture was stirred for 2 h at 75° C. in a sealed tube. The reaction mixture was cooled down and concentrated in vacuo to provide oily residue, which was purified by preparative HPLC (described in Example 1) to provide 49.3 mg (0.12 mmol, 57%) of the desired product as a white solid after lyophilization (MeOH/H2O). [M+H]=420.

EXAMPLES 54–61

Examples 54 to 61 were synthesized using methodology described in Example 53.

| Ex. | Structure | Name | (M + H) |
|---|---|---|---|
| 54 | Chiral | trans-2-Methoxy-N-[4-(N-benzyl-N'-cyanoguanidino)-1-phenyl-cyclohexyl-methyl]-benzamide | 434 |
| 55 | 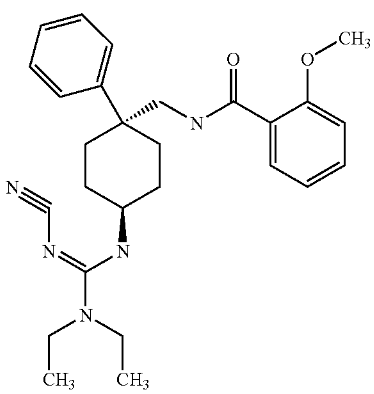 | trans-2-Methoxy-N-[4-(N,N-diethyl-N'-cyanoguanidino)-1-phenyl-cyclohexyl-methyl]-benzamide | 490 |
| 56 | 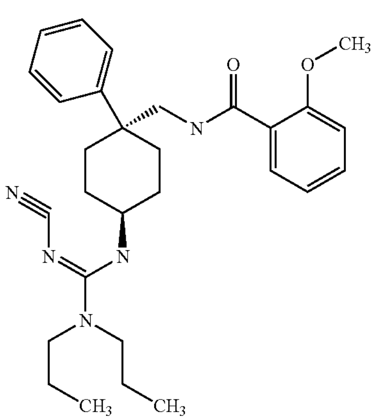 | trans-2-Methoxy-N-[4-(N,N-dipropyl-N'-cyanoguanidino)-1-phenyl-cyclohexyl-methyl]-benzamide | 510 |

-continued

| Ex. | Structure | Name | (M + H) |
|---|---|---|---|
| 57 | 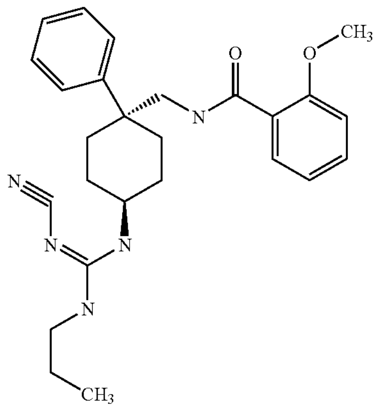 | trans-2-Methoxy-N-[4-(N-propyl-N'-cyanoguanidino)-1-phenyl-cyclohexyl-methyl]-benzamide | 462 |
| 58 | 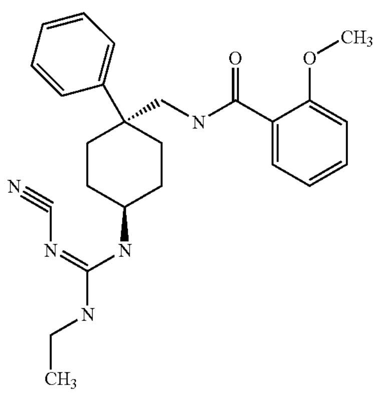 | trans-2-Methoxy-N-[4-(N-ethyl-N'-cyanoguanidino)-1-phenyl-cyclohexyl-methyl]-benzamide | 434 |
| 59 | 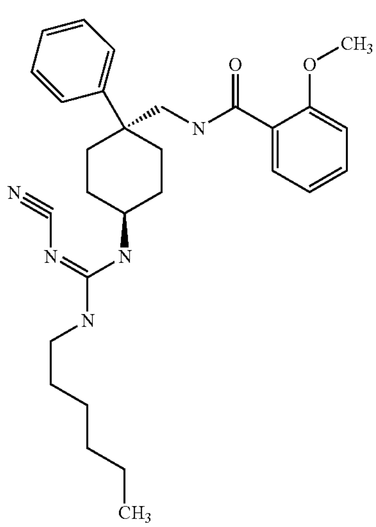 | trans-2-Methoxy-N-[4-(N-n-hexyl-N'-cyanoguanidino)-1-phenyl-cyclohexyl-methyl]-benzamide | 490 |

-continued
| Ex. | Structure | Name | (M + H) |
|---|---|---|---|
| 60 | 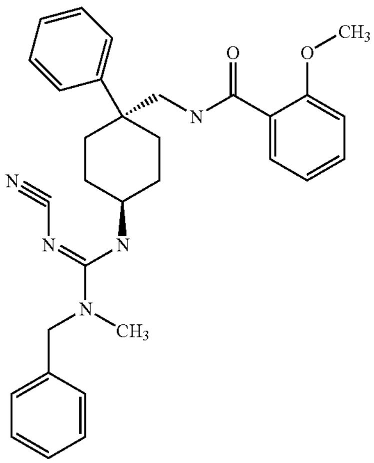 | trans-2-Methoxy-N-[4-(N-methyl-N-benzyl-N'-cyanoguanidino)-1-phenyl-cyclohexyl-methyl]-benzamide | 10 |
| 61 | 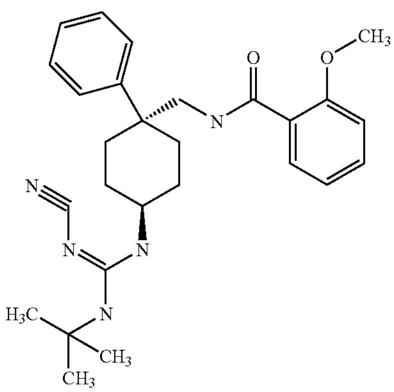 | trans-2-Methoxy-N-[4-(N-tert-butyl-N'-cyanoguanidino)-1-phenyl-cyclohexyl-methyl]-benzamide | 462 |
EXAMPLE 62 and 63
trans and cis-N-[4-(N,N'-Diethyl-cyanoguanidino)-1-phenyl-1-cyclohexylmethyl]-2-methoxy-benzamide
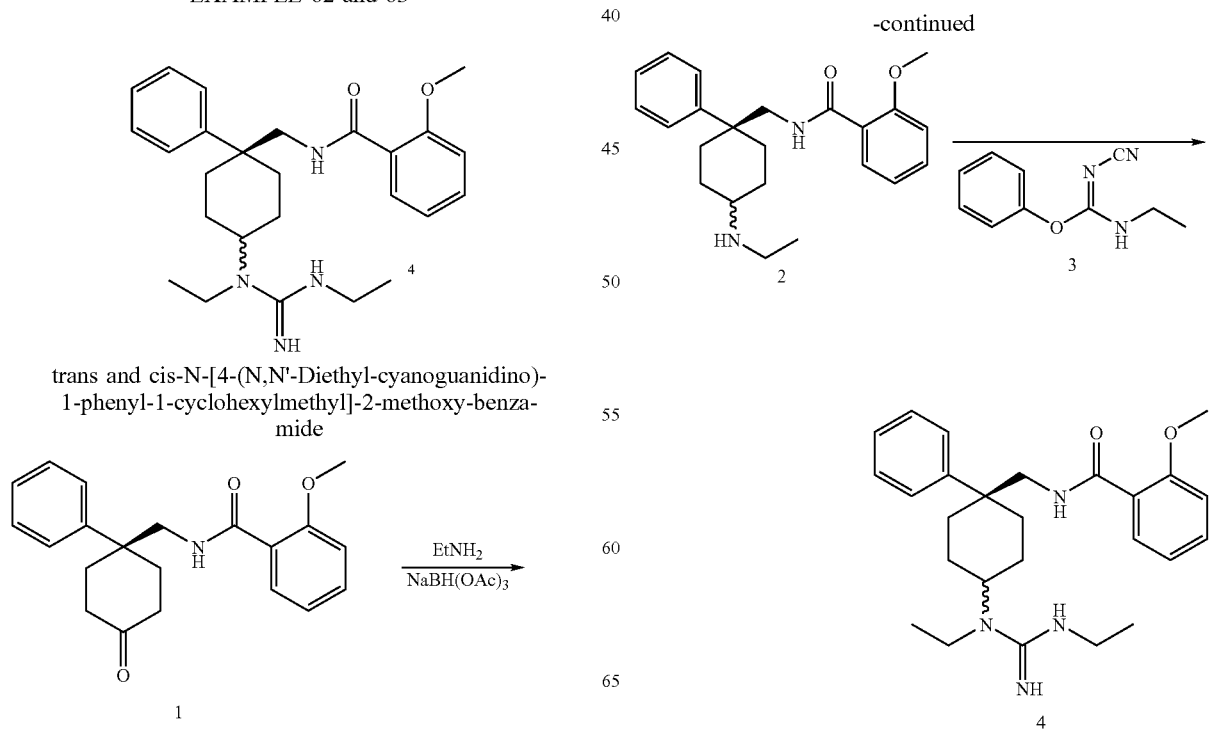

Compound 1: The synthesis of 1 is described in example 31.

Compound 2: To a solution of the ketone 1 (0.34 g, 1 mmol) in 35 ml of dichloromethane was addded EtNH₂ (1 ml of 2M solution in THF, 2 mmol), NaBH(OAc)₃ (0.42 g, 2 mmol) and drops of AcOH (cat. amount). The resulting solution was stirred at 25° C. for 3 h. Reaction mixture was concentrated in vacuo yielding oily residue, which was diluted in 250 ml of AcOH and washed with 1N aq. NaOH (20 ml×2). The organic layer was dried over Na₂SO₄ and concentrated in vacuo to provide 2 as an oil (0.35 g, >95%), which was subjected to the following reaction without further purification.

Compound 3: A solution of diphenyl cyanocarbonidate (2.4 g, 10 mmol) and EtNH₂ (5 ml of 2M solution in MeOH, 10 mmol) in 10 ml of 2-propanol was stirred for 4 h at 70° C. in a sealed tube. The reaction mixture was concentrated in vacuo yielding a white solid, which was purified on column chromatography (30% EtOAc/Hex) to yield 1.6 g (85%) of the desired product 3 as a white solid.

Compound 4: A solution of compound 2 (110 mg, 0.3 mmol) and compound 3 (74 mg, 0.39 mmol) in 5 ml of 2-propanol was stirred for 12 h at 70° C. The reaction mixture was concentrated and purified on preparative-HPLC (described in a synthesis of Example 31) to provide the cis and trans diastereoisomers. Trans compound (retention time: 3.19 min) (23 mg) and cis compound (retention time: 3036 min) (14 mg) were obtained as colorless oils. Mass Spec [M+H]⁺ 462.

EXAMPLE 64

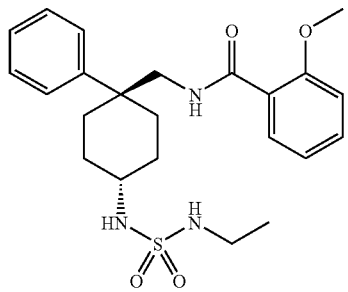

trans-2-Methoxy-N-[4-(N-ethyl-N'-sulfenylureido)-1-phenyl-cyclohexylmethyl]-benzamnide Synthesis:

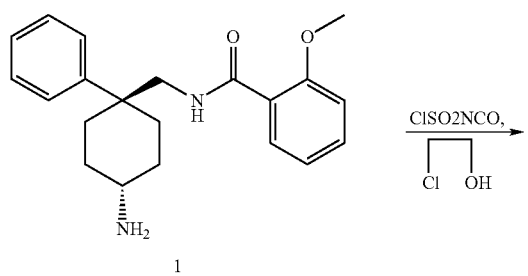

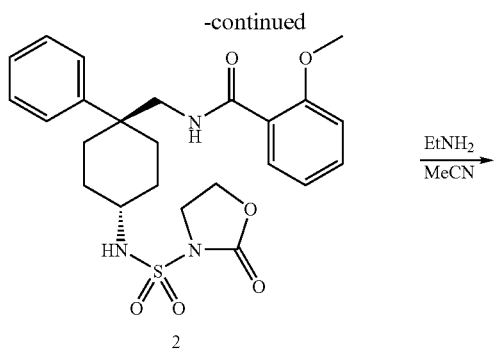

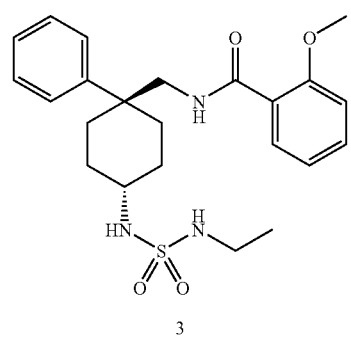

Compound 1: The synthesis of 1 was described in Example 31.

Compound 2: Chlorosulfonyl isocyanate (0.37 ml, 4.1 mmmol) was dissolved in 40 ml of dichloromethane and cooled to 0° C. Chloroethanol (0.27 ml, 4.1 mmol) was added slowly and the reaction mixture was stirred for additional 1.5 h at 0° C. A solution of the amine 1 (1.4 g, 4.1 mmol) and Et₃N (1.3 ml, 12.4 mmol) in 50 ml of dichloromethane was added slowly into the reaction mixture so that reaction temperature did not exceed 5° C. The reaction mixture was allowed to warm to 25° C. and stirred overnight. The reaction was quenched by dropwise addition of 2N HCl and saturated with NaCl. The organic layer was separated and the aqueous layer was extracted with dichloromethane (100 ml×3). The combined organic layer was dried over MgSO₄ and concentrated in vacuo to provide 2 as a white solid (2.0 g), which was subjected to the following reactions without further purification.

Compound 3: A solution of 2 (90 mg, 0.18 mmol), EtNH₂ (0.4 mmol, 0.2 ml of 2M solution in MeOH) and Et₃N (0.1 ml) in 2 ml of CH₃CN was stirred for 2 h at 65° C. The reaction mixture was purified in preparative HPLC (described in the synthesis of Example 31) to yield 12.1 mg of 3 as a colorless oil. Mass Spec [M+H]⁺=446.

EXAMPLES 65–72

Examples 65 to 72 were synthesized using methodology described in Example 64.

| Ex. | Structure | Name | (M + H) |
|---|---|---|---|
| 65 | 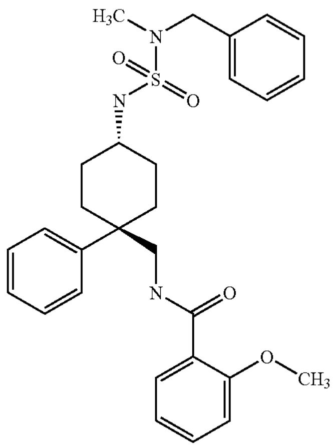 | trans-2-Methoxy-N-[4-(N-methyl-N-benzyl-N'-sulfenylureido)-1-phenyl-cyclohexyl-methyl]-benzamide | 522 |
| 66 | 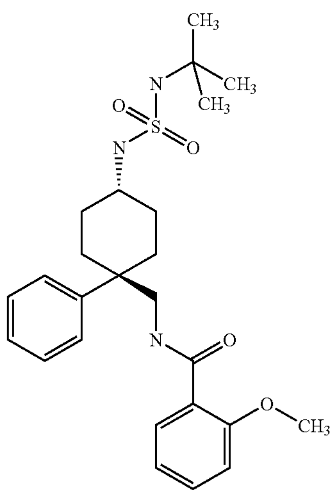 | trans-2-Methoxy-N-[4-(N-tert-butyl-N'-sulfenylureido)-1-phenyl-cyclohexyl-methyl]-benzamide | 474 |
| 67 | 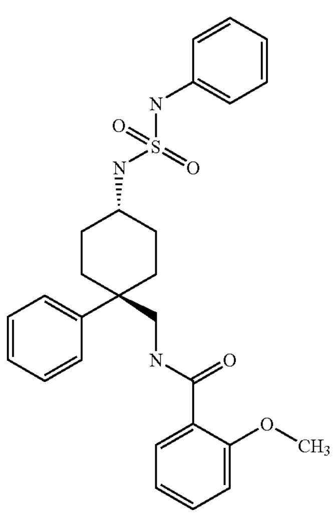 | trans-2-Methoxy-N-[4-(N-phenyl-N'-sulfenylureido)-1-phenyl-cyclohexyl-methyl]-benzamide | 494 |

-continued

| Ex. | Structure | Name | (M + H) |
|---|---|---|---|
| 68 | 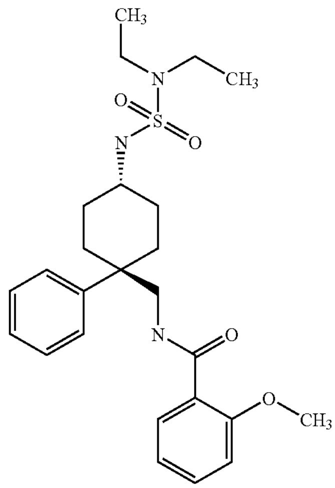 | trans-2-Methoxy-N-[4-(N,N-diethyl-N'-sulfenylureido)-1-phenyl-cyclohexyl-methyl]-benzamide | 474 |
| 69 | 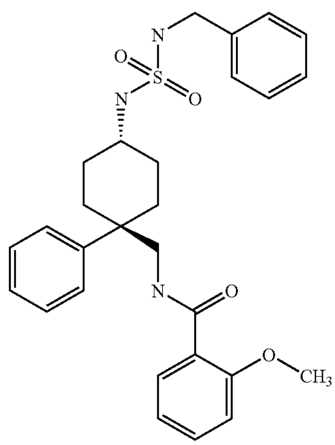 | trans-2-Methoxy-N-[4-(N-benzyl-N'-sulfenylureido)-1-phenyl-cyclohexyl-methyl]-benzamide | 508 |
| 70 | 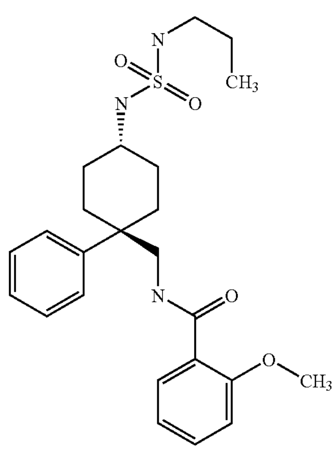 | trans-2-Methoxy-N-[4-(N-propyl-N'-sulfenylureido)-1-phenyl-cyclohexyl-methyl]-benzamide | 500 |

-continued
| Ex. | Structure | Name | (M + H) |
|---|---|---|---|
| 71 | 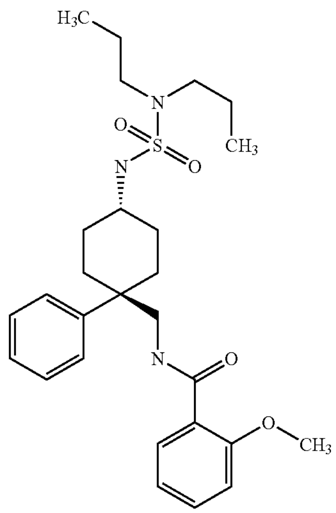 | trans-2-Methoxy-N-[4-(N,N-dipropyl-N'-sulfenylureido)-1-phenyl-cyclohexyl-methyl]-benzamide | 502 |
| 72 | 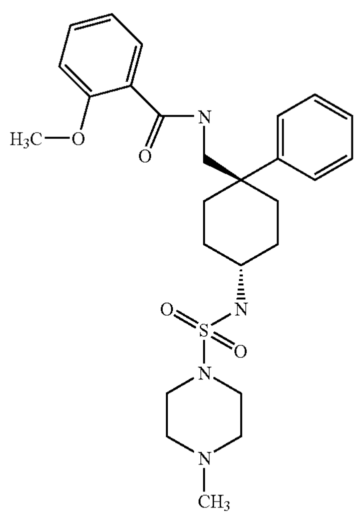 | trans-2-Methoxy-N-[4-(N-(4-N-methylpiperazinyl)-N'-sulfenylureido)-1-phenyl-cyclohexyl-methyl]-benzamide | 501 |
EXAMPLE 73
cis-2-Methoxy-N-{4-[N-(4-anisoyl)-N'-sulfenylureido]-1-phenyl-cyclohexylmethyl}-benzamide
Synthesis:
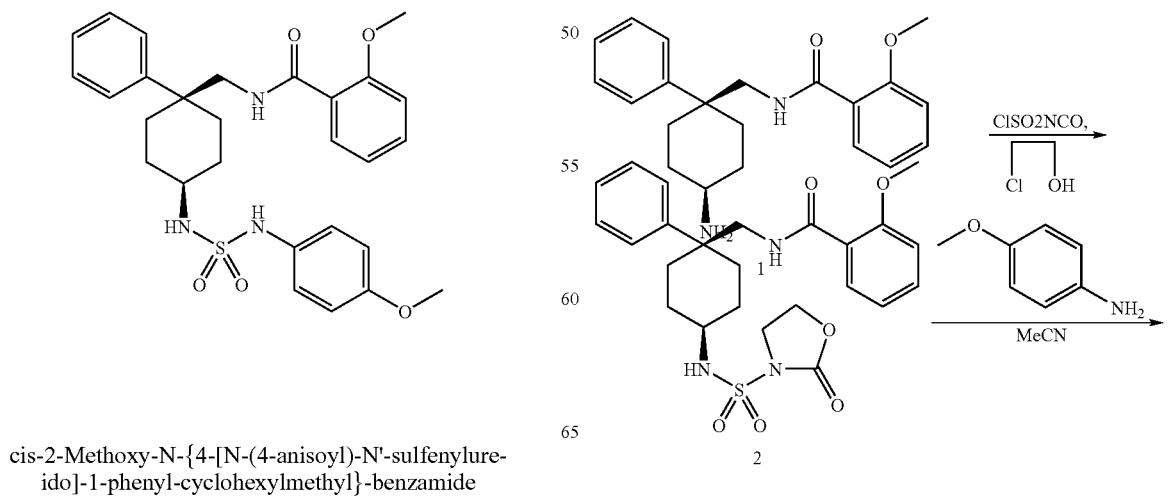

-continued

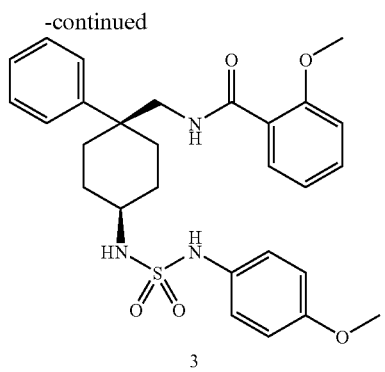

3

Compound 1: The synthesis of 1 was described in Example 31.

Compound 2: Chlorosulfonyl isocyanate (0.22 ml, 2.5 mmol) was dissolved in 2 ml of dichloromethane and cooled to 0° C. Chloroethanol (0.16 ml, 0.25 mmol) was added slowly and the reaction mixture was stirred for additional 1.5 h at 0° C. A solution of the cis-amine 1 (0.85 g, 2.5 mmol) and Et$_3$N (0.8 ml, 7.6 mmol) in 30 ml of dichloromethane was added slowly into the reaction mixture. The solution was allowed to warm to 25° C. and stirred overnight. The reaction was quenched by dropwise addition of 2N HCl and saturated with NaCl. The organic layer was separated and the aqueous layer was extracted with dichloromethane (60 ml×3). The combined organic layer was dried over MgSO$_4$ and concentrated in vacuo, yielding a white solid, which was purified by column chromatograophy (50% Hex/EtOAc) to provide 1.1 g (2.2 mmol, 87%) of 2 as a white solid.

Compound 3: A solution of 2 (17 mg, 0.035 mmol), and p-anisidine (10 mg, 0.08 mmol) in 1 ml of CH$_3$CN was stirred for 2 h at 65° C. The reaction mixture was purified by preparative HPLC (described in a synthesis of Example 31) to yield 3.2 mg of the 3 as a colorless oil. Mass Spec [M+H]$^+$ 524.

EXAMPLES 74–147

Examples 74 to 147 were synthesized using methodology described in Example 73.

| Ex. | Structure | Name | (M + H) |
|---|---|---|---|
| 74 | 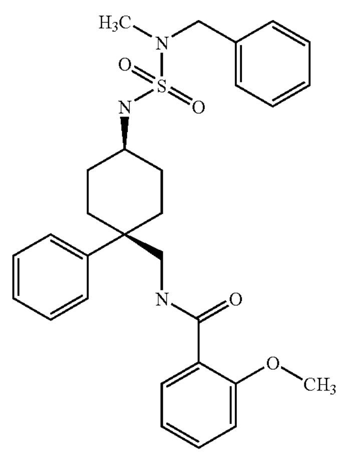 | cis-2-Methoxy-N-[4-(N-methyl-N-benzyl-N'-sulfenylureido)-1-phenyl-cyclohexyl-methyl]-benzamide | 522 |
| 75 | 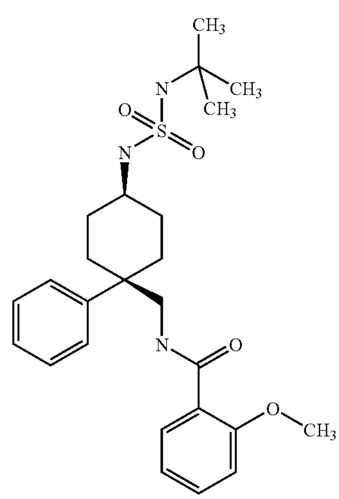 | cis-2-Methoxy-N-[4-(N-tert-butyl-N'-sulfenylurido)-1-phenyl-cyclohexyl-methyl]-benzamide | 474 |

| Ex. | Structure | Name | (M + H) |
|---|---|---|---|
| 76 | 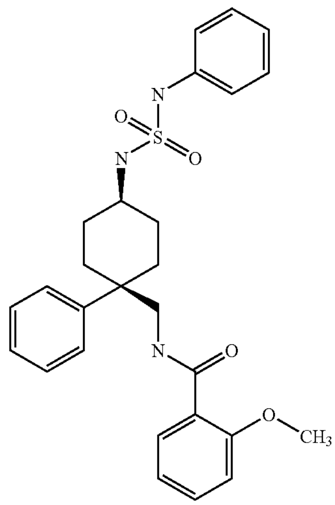 | cis-2-Methoxy-N-[4-(N-phenyl-N'-sulfenylurido)-1-phenyl-cyclohexyl-methyl]-benzamide | 494 |
| 77 | 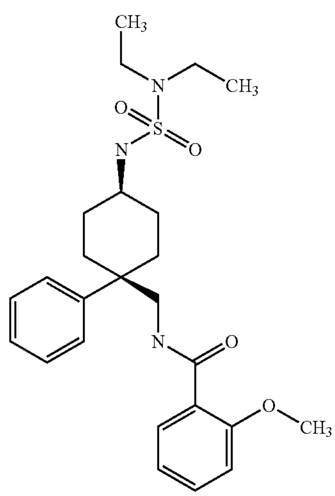 | cis-2-Methoxy-N-[4-(N,N-diethyl-N'-sulfenylurido)-1-phenyl-cyclohexyl-methyl]-benzamide | 474 |
| 78 | 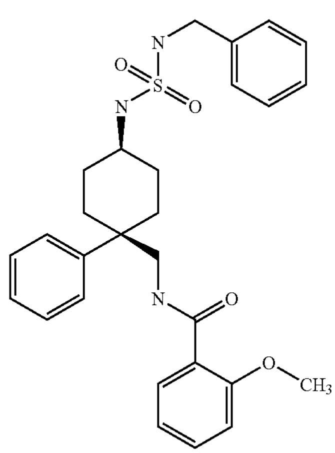 | cis-2-Methoxy-N-[4-(N-benzyl-N'-sulfenylurido)-1-phenyl-cyclohexyl-methyl]-benzamide | 508 |

-continued

| Ex. | Structure | Name | (M + H) |
|---|---|---|---|
| 79 | 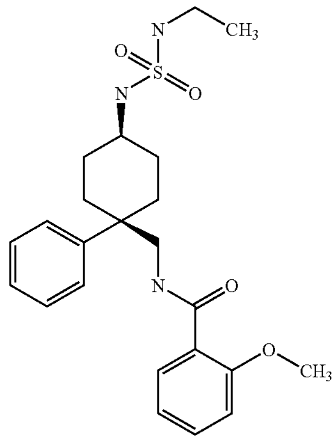 | cis-2-Methoxy-N-[4-(N-ethyl-N'-sulfenylurido)-1-phenyl-cyclohexyl-methyl]-benzamide | 446 |
| 80 | 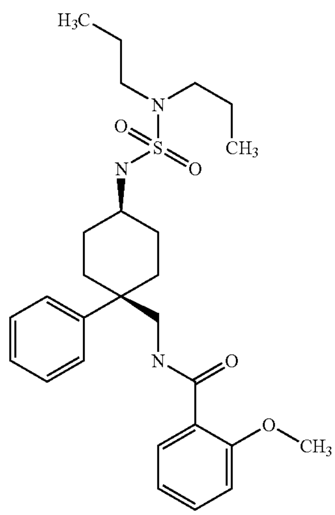 | cis-2-Methoxy-N-[4-(N,N-dipropyl-N'-sulfenylurido)-1-phenyl-cyclohexyl-methyl]-benzamide | 502 |
| 81 | 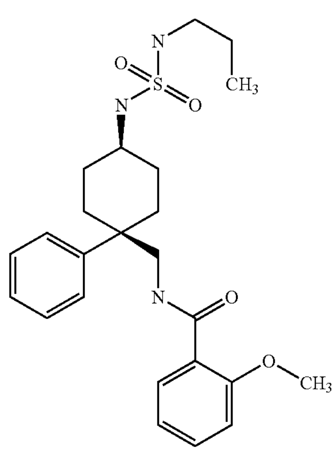 | cis-2-Methoxy-N-[4-(N-propyl-N'-sulfenylurido)-1-phenyl-cyclohexyl-methyl]-benzamide | 460 |

| Ex. | Structure | Name | (M + H) |
|---|---|---|---|
| 82 | 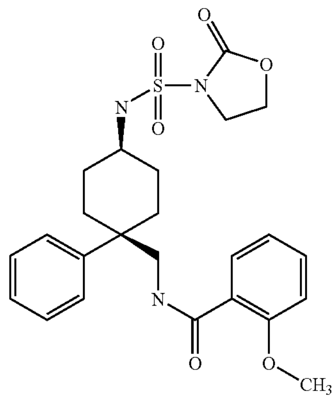 | cis-2-Methoxy-N-[4-(2-oxo-oxazolidine-3-sulfonylamino)-1-phenyl-cyclohexyl-methyl]-benzamide | 488 |
| 83 | 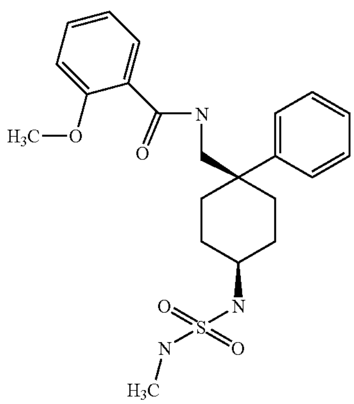 | cis-2-Methoxy-N-[4-(N-methyl-N'-sulfenylurido)-1-phenyl-cyclohexyl-methyl[-benzamide | 432 |
| 84 | 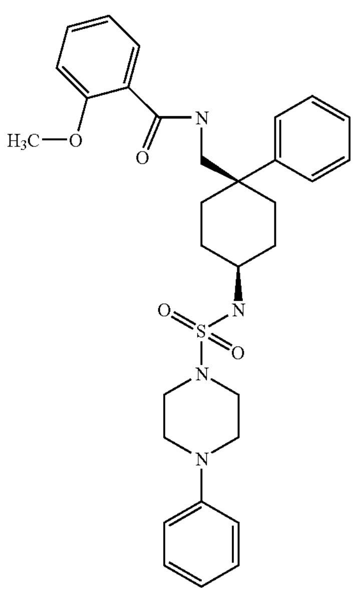 | cis-N-[4-(4-Phenyl-piperidine-1-sulfonylamino)-1-phenyl-cyclohexyl-methyl]-2-methoxy-benzamide | 563 |

-continued

| Ex. | Structure | Name | (M + H) |
|---|---|---|---|
| 85 | 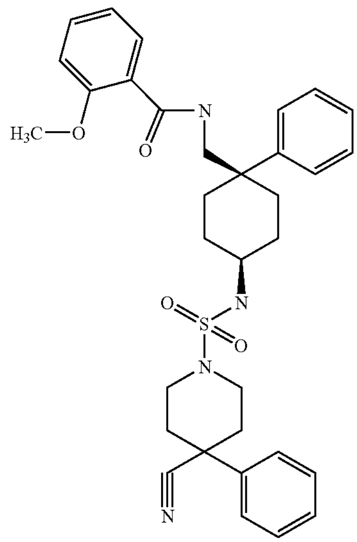 | cis-N-[4-(4-Cyano-4-phenyl-piperidine-1-sulfonylamino)-1-phenyl-cyclohexyl-methyl]-2-methoxy-benzamide | 587 |
| 86 | 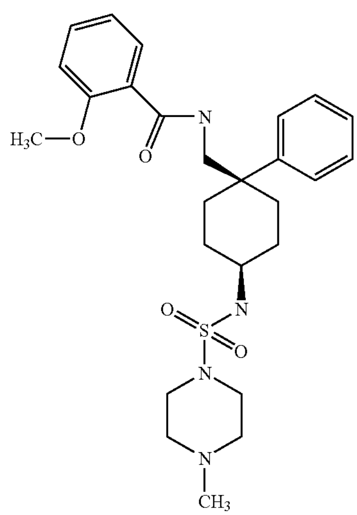 | cis-N-[4-(4-Methyl-piperidine-1-sulfonylamino)-1-phenyl-cyclohexyl-methyl]-2-methoxy-benzamide | 501 |
| 87 | 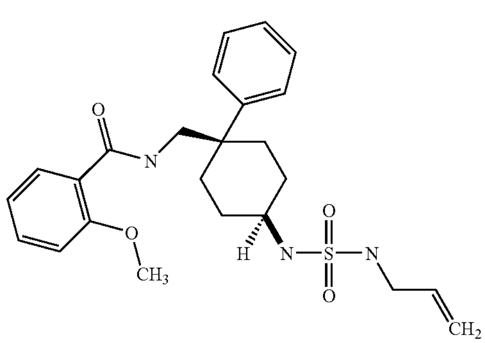 | cis-2-Methoxy-N-[4-(N-Allyl-N'-sulfenylurido)-1-phenylcyclohexyl-methyl]-benzamide | 458 |

| Ex. | Structure | Name | (M + H) |
|---|---|---|---|
| 88 | 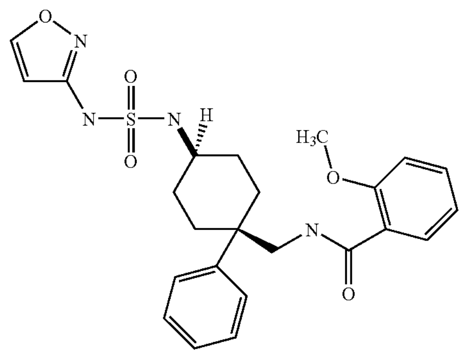 | cis-2-Methoxy-N-{4-[N-(3-isoxazol)-N'-sulfenylurido]-1-phenyl-cyclohexyl-methyl}-benzamide | 485 |
| 89 | 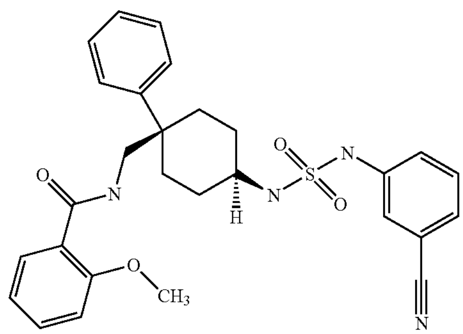 | cis-2-Methoxy-N-{4-[N-(3-cyano-phenyl)-N'-sulfenylurido]-1-phenyl-cyclohexyl-methyl}-benzamide | 519 |
| 90 | 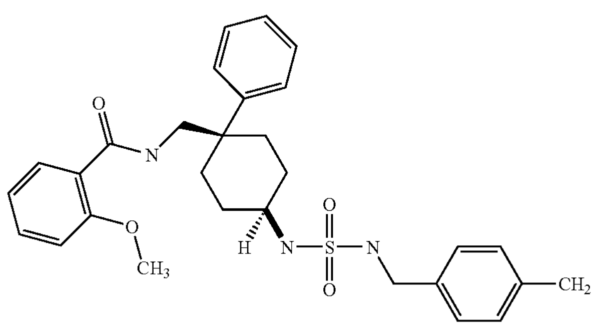 | cis-2-Methoxy-N-{4-[N-(4-methylbenzyl)-N'-sulfenylurido]-1-phenyl-cyclohexyl-methyl}-benzamide | 522 |
| 91 | 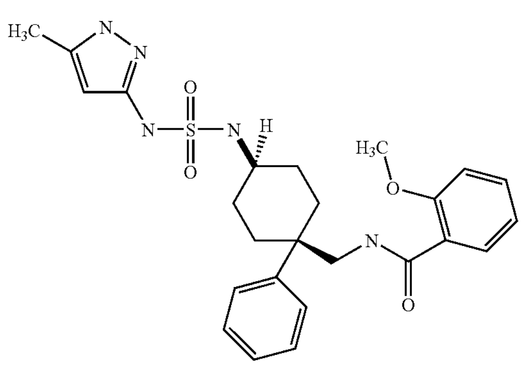 | cis-2-Methoxy-N-{4-[N-(5-methyl-1H-3-pyrazol)-N'-sulfenylurido]-1-phenyl-cyclohexyl-methyl}-benzamide | 498 |

-continued

| Ex. | Structure | Name | (M + H) |
|---|---|---|---|
| 92 | 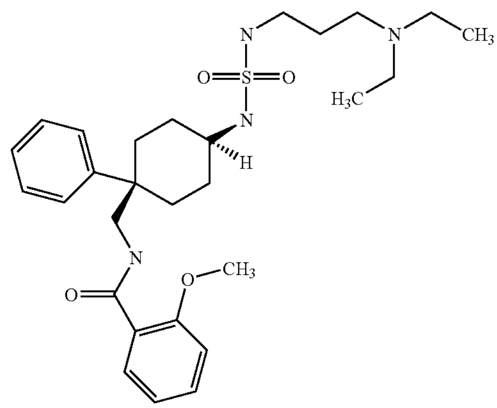 | cis-2-Methoxy-N-{4-[N-1-(3-N,N-diethyl-propyl)-N'-sulfenylurido]-1-phenyl-cyclohexyl-methyl}]-benzamide | 531 |
| 93 | 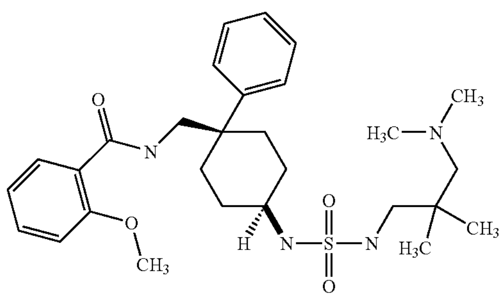 | cis-2-Methoxy-N-{4-[N-1-(3-N,N-dimethyl-2,2-dimethyl-propyl)-N'-sulfenylurido]-1-phenyl-cyclohexyl-methyl}]-benzamide | 531 |
| 94 | 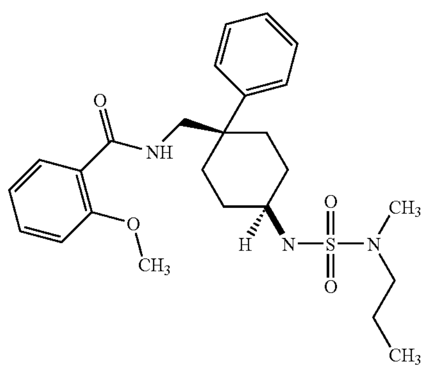 | cis-2-Methoxy-N-[4-(N-methyl-N-2-hydroxyethyl-N'-sulfenylurido)-1-phenyl-cyclohexyl-methyl]-benzamide | 476 |
| 95 | 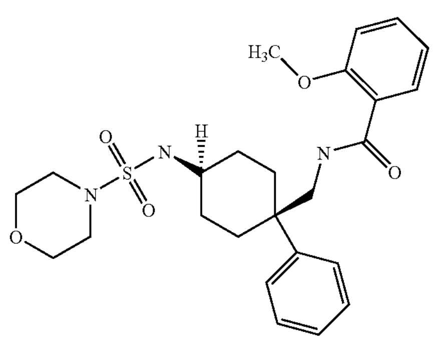 | 2-Methoxy-N-[4-(morpholine-4-sulfonylamino)-1-phenyl-cyclohexyl-methyl]-benzamide | 488 |

-continued

| Ex. | Structure | Name | (M + H) |
| --- | --- | --- | --- |
| 96 | 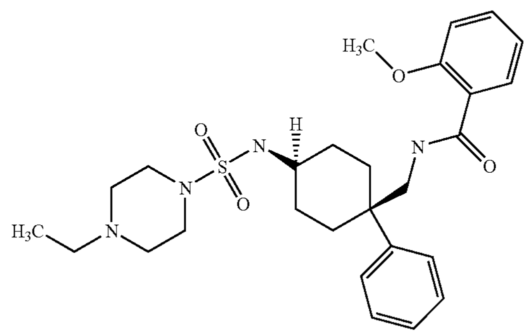 | cis-N-[4-(4-Methyl-piperidine-1-sulfonylamino)-1-phenyl-cyclohexyl-methyl]-2-methoxy-benzamide | 515 |
| 97 | 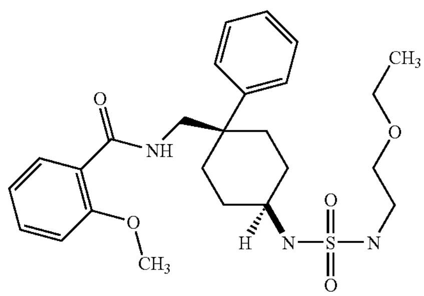 | cis-2-Methoxy-N-{4-[N-(ethoxy2-ethyl)-N'-sulfenylurido]-1-phenyl-cyclohexyl-methyl}-benzamide | 490 |
| 98 | 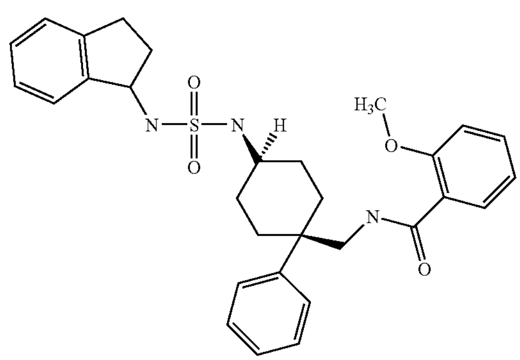 | cis-2-Methoxy-N-[4-(N-indan-1-yl-N'-sulfenylurido)-1-phenyl-cyclohexyl-methyl]-benzamide | 534 |
| 99 | 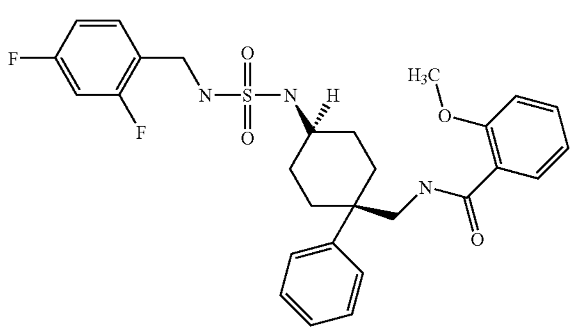 | cis-2-Methoxy-N-{4-[N-(2,4-difluoro-benzyl)-N'-sulfenylurido]-1-phenyl-cyclohexyl-methyl}-benzamide | 544 |

-continued

| Ex. | Structure | Name | (M + H) |
|---|---|---|---|
| 100 | 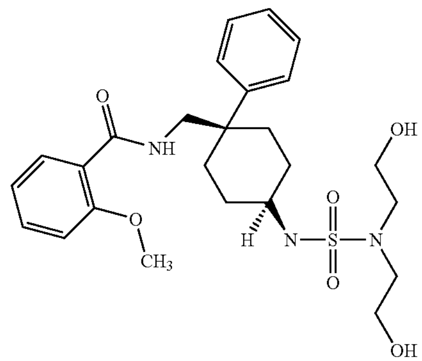 | cis-2-Methoxy-N-{4-[N,N-di(2-hydroxy-ethyl)-N'-sulfenyl-urido]-1-phenyl-cyclohexyl-methyl}-benzamide | 506 |
| 101 | 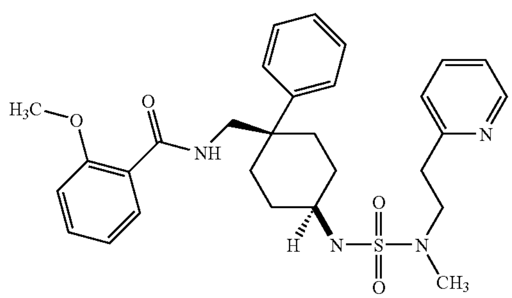 | cis-2-Methoxy-N-{4-[N-methyl-N-(pyridin-2-yl-ethyl)-N'-sulfenyl-urido]-1-phenyl-cyclohexyl-methyl}-benzamide | 537 |
| 102 | 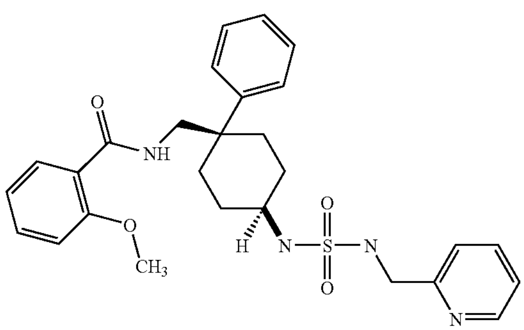 | cis-2-Methoxy-N-{4-[N-(pyridin-2-yl-methyl)-N'-sulfenyl-urido]-1-phenyl-cyclohexyl-methyl}-benzamide | 509 |
| 103 | 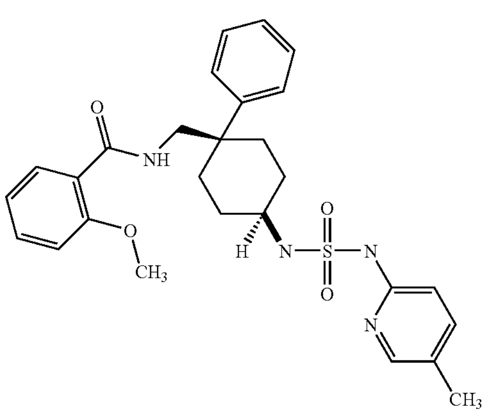 | cis-2-Methoxy-N-{4-[N-(4-methyl-pyridin-2-yl)-N'-sulfenylurido]-1-phenyl-cyclohexyl-methyl}-benzamide | 509 |

| Ex. | Structure | Name | (M + H) |
|---|---|---|---|
| 104 | 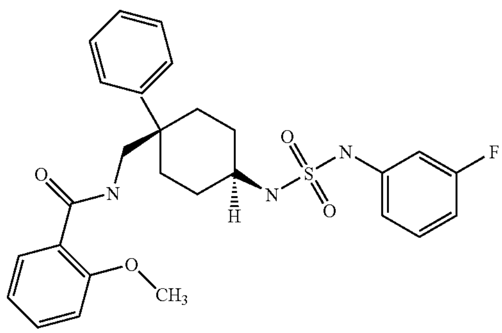 | cis-2-Methoxy-N-{4-[N-(3-fluoro-phenyl)-N'-sulfenylurido]-1-phenyl-cyclohexyl-methyl}-benzamide | 512 |
| 105 | 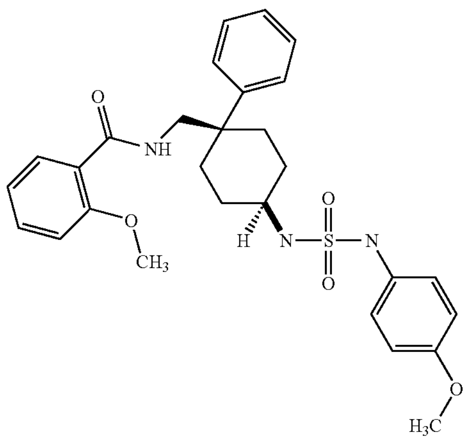 | cis-2-Methoxy-N-{4-[N-(4-anisoyl)-N'-sulfenylurido]-1-phenyl-cyclohexyl-methyl}-benzamide | 524 |
| 106 | 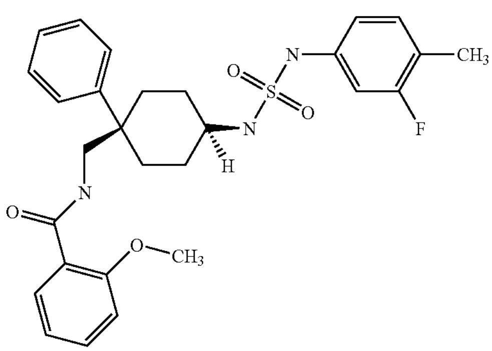 | cis-2-Methoxy-N-{4-[N-(3-fluoro-4-methyl-phenyl)-N'-sulfenylurido]-1-phenyl-cyclohexyl-methyl}-benzamide | 526 |
| 107 | 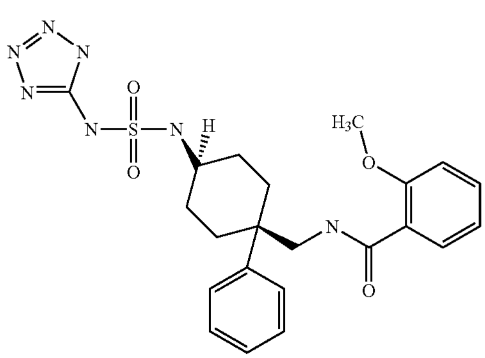 | cis-2-Methoxy-N-{4-[N-(tetrazol-5-yl)-N'-sulfenyl-urido]-1-phenyl-cyclohexyl-methyl}-benzamide | 486 |

-continued

| Ex. | Structure | Name | (M + H) |
|---|---|---|---|
| 108 | 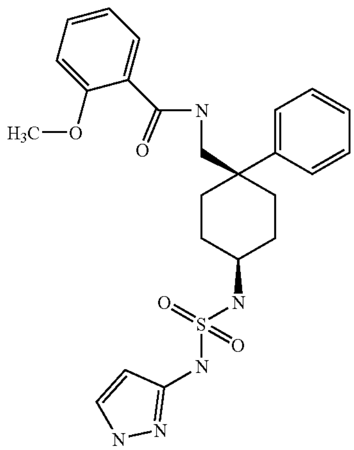 | cis-2-Methoxy-N-{4-[N-(1H-pyrazol-3-yl)-N'-sulfenyl-urido]-1-phenyl-cyclohexyl-methyl}-benzamide | 484 |
| 109 | 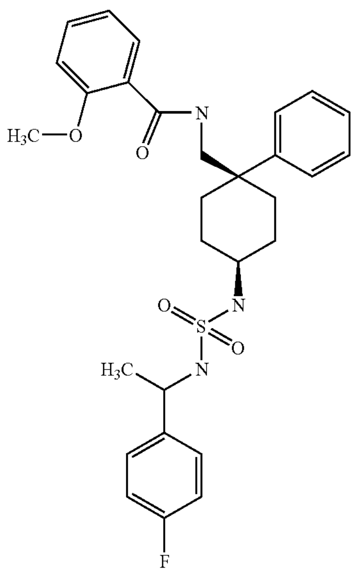 | cis-2-Methoxy-N-{4-[N-(4-fluoro-□-methyl-benzyl)-N'-sulfenyl-urido]-1-phenyl-cyclohexyl-methyl}-benzamide | 540 |
| 110 | 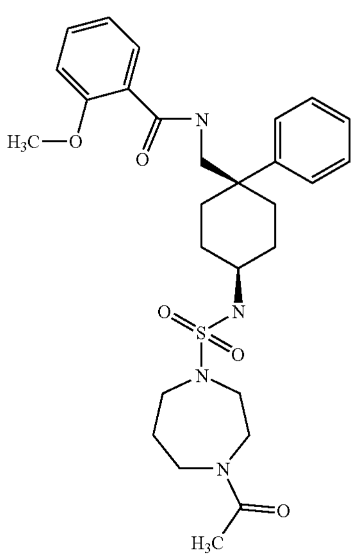 | N-[4-(4-Acetyl-[1,4]diazepane-1-sulfonylamino)-1-phenyl-cyclohexyl-methyl]-2-methoxy-benzamide | 543 |

-continued

| Ex. | Structure | Name | (M + H) |
|---|---|---|---|
| 111 | 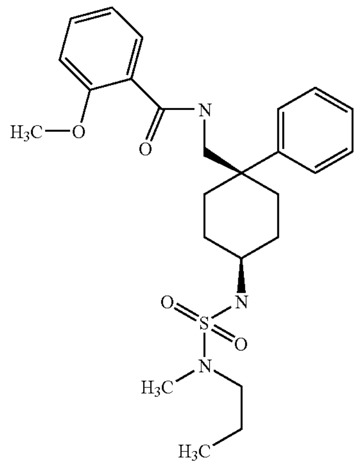 | cis-2-Methoxy-N-[4-(N-methyl-N-propyl-N'-sulfenylurido)-1-phenyl-cyclohexyl-methyl]-benzamide | 474 |
| 112 | 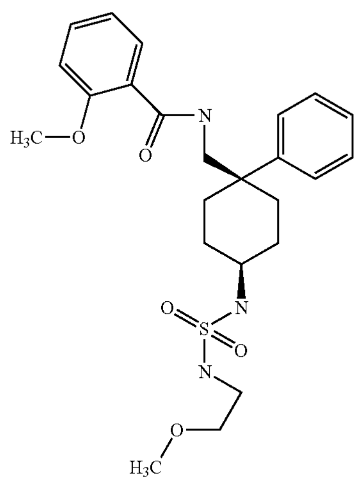 | cis-2-Methoxy-N-{4-[N-(2-methoxyethyl)-N'-sulfenylurido]-1-phenyl-cyclohexyl-methyl}-benzamide | 476 |
| 113 | 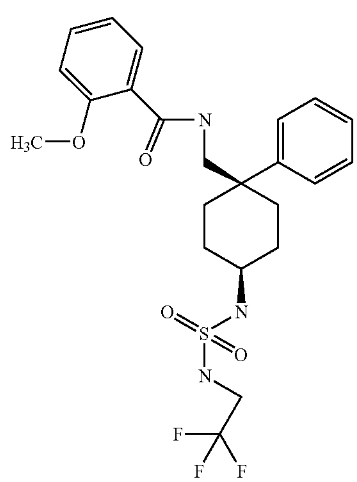 | cis-2-Methoxy-N-{4-[N-(2,2,2-trifluoroethyl)-N'-sulfenylurido]-1-phenyl-cyclohexyl-methyl}-benzamide | 500 |

| Ex. | Structure | Name | (M + H) |
|---|---|---|---|
| 114 | 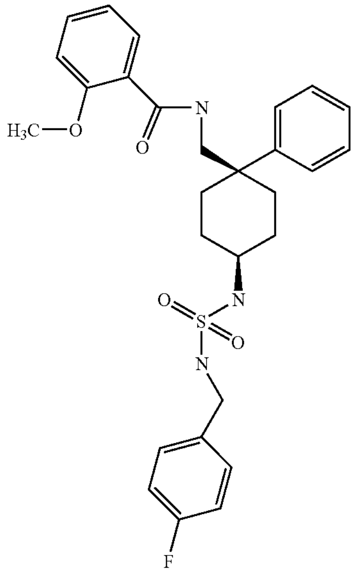 | cis-2-Methoxy-N-{4-[N-(4-fluoro-benzyl)-N'-sulfenyl-urido]-1-phenyl-cyclohexyl-methyl}-benzamide | 526 |
| 115 | 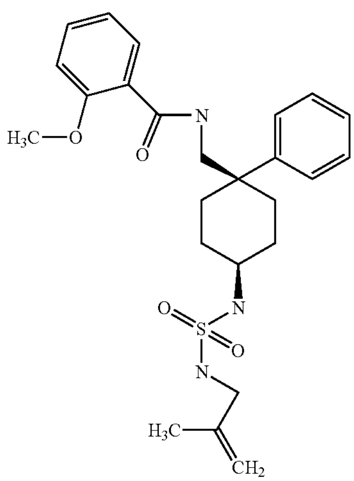 | cis-2-Methoxy-N-{4-[N-(2-methyl-2-propen-1-yl)-N'-sulfenyl-urido]-1-phenyl-cyclohexyl-methyl}-benzamide | 472 |
| 116 | 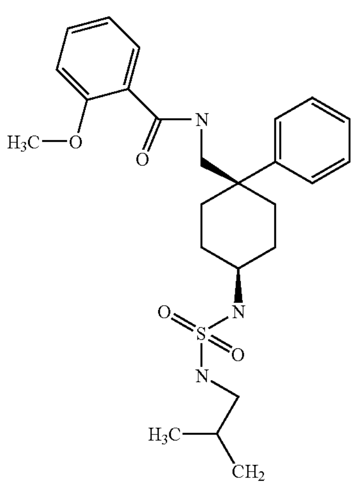 | cis-2-Methoxy-N-{4-[N-(2-methyl-1-propan-1-yl)-N'-sulfenyl-urido]-1-phenyl-cyclohexyl-methyl}-benzamide | 474 |

| Ex. | Structure | Name | (M + H) |
|---|---|---|---|
| 117 | 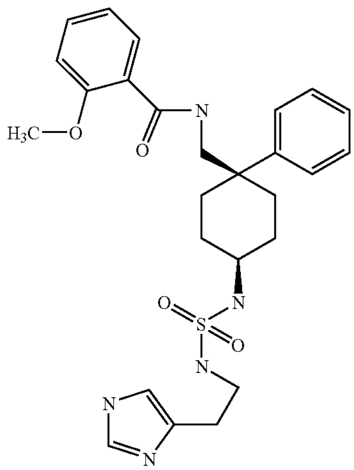 | cis-2-Methoxy-N-{4-[N-(imidazol-4-ylethyl)-N'-sulfenyl-urido]-1-phenyl-cyclohexyl-methyl}-benzamide | 512 |
| 118 | 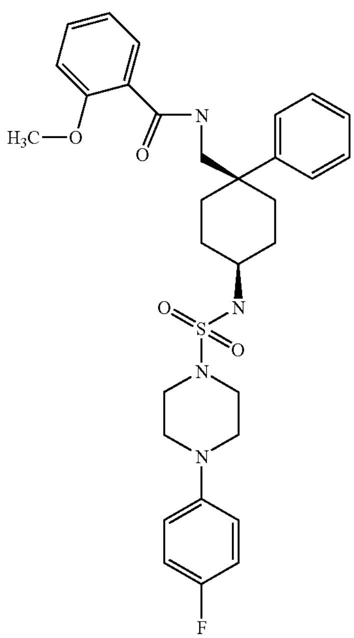 | N-{4-[4-(4-Fluoro-phenyl)-piperazine-1-sulfonylamino]-1-phenyl-cyclohexyl-methyl}-2-methoxy-benzamide | 581 |
| 119 | 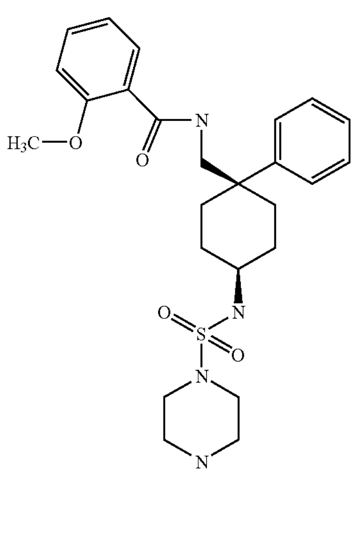 | 2-Methoxy-N-[1-phenyl-4-(piperazine-1-sulfonylamino)-cyclohexylmethyl]-benzamide | 457 |

-continued

| Ex. | Structure | Name | (M + H) |
|---|---|---|---|
| 120 | 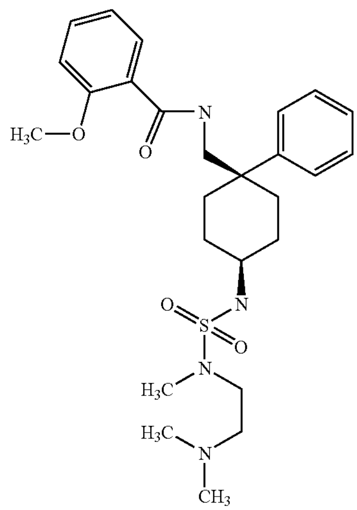 | cis-2-Methoxy-N-{4-[N-methyl-N-1-(2-N,N-dimethyl-ethyl)-N'-sulfenyl-urido]-1-phenyl-cyclohexyl-methyl}-benzamide | 503 |
| 121 | 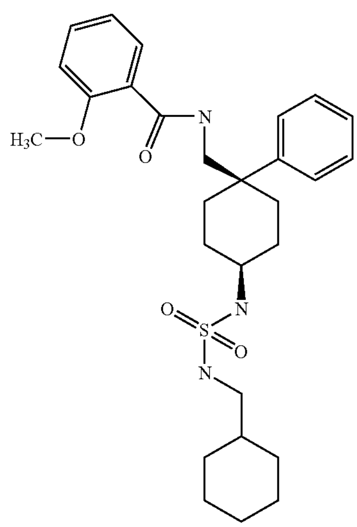 | cis-2-Methoxy-N-[4-(N-cyclohexyl-methyl-N'-sulfenyl-urido)-1-phenyl-cyclohexyl-methyl]-benzamide | 514 |
| 122 | 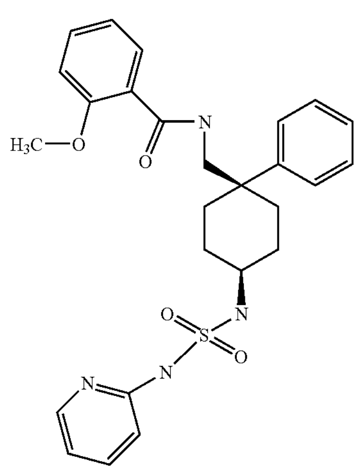 | cis-2-Methoxy-N-{4-[N-(pyridin-2-yl)-N'-sulfenyl-urido]-1-phenyl-cyclohexyl-methyl}-benzamide | 495 |

| Ex. | Structure | Name | (M + H) |
|---|---|---|---|
| 123 | 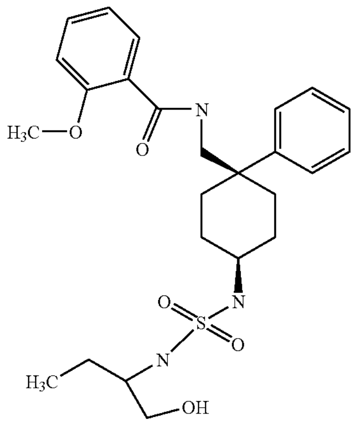 | cis-2-Methoxy-N-{4-[N-1-(2-hydroxymethyl-propyl)-N'-sulfenyl-urido]-1-phenyl-cyclohexyl-methyl}-benzamide | 490 |
| 124 | 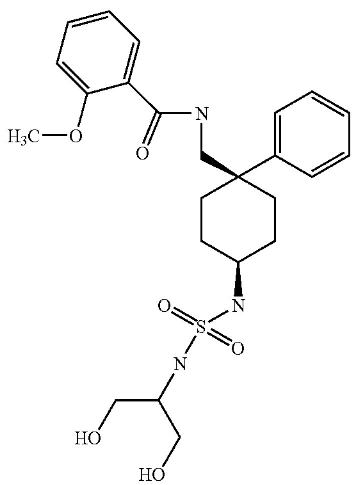 | cis-2-Methoxy-N-{4-[N-(bis-hydroxymethyl-methyl)-N'-sulfenyl-urido]-1-phenyl-cyclohexyl-methyl}-benzamide | 492 |
| 125 | 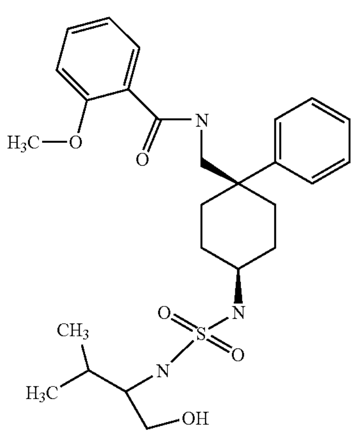 | cis-2-Methoxy-N-{4-[N-1-(2-hydroxymethyl-3-methyl-propyl)-N'-sulfenyl-urido]-1-phenyl-cyclohexyl-methyl}-benzamide | 504 |

| Ex. | Structure | Name | (M + H) |
|---|---|---|---|
| 126 | 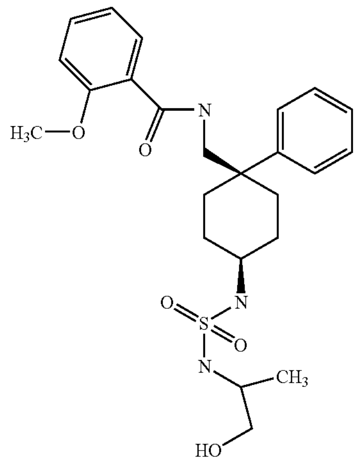 | cis-2-Methoxy-N-{4-[N-1-(1-hydroxymethyl-ethyl)-N'-sulfenyl-urido]-1-phenyl-cyclohexyl-methyl}-benzamide | 476 |
| 127 | Chiral | N-[4-((R)3-Hydroxy-pyrrolidine-1-sulfonylamino)-1-phenyl-cyclohexylmethyl]-2-methoxy-benzamide | 488 |
| 128 | Chiral | cis-2-Methoxy-N-{4-[N-1-(2-hydroxy-propyl)-N'-sulfenyl-urido]-1-phenyl-cyclohexyl-methyl}-benzamide | 476 |

| Ex. | Structure | Name | (M + H) |
|---|---|---|---|
| 129 | 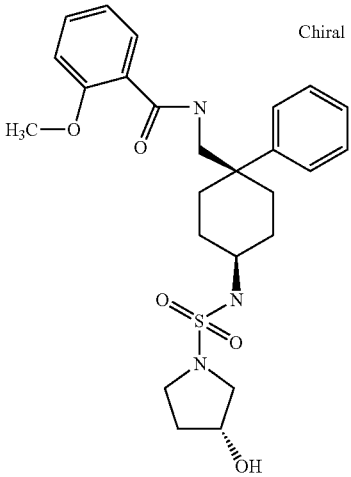 Chiral | N-[4-((S)-3-Hydroxy-pyrrolidine-1-sulfonylamino)-1-phenyl-cyclohexylmethyl]-2-methoxy-benzamide | 488 |
| 130 | 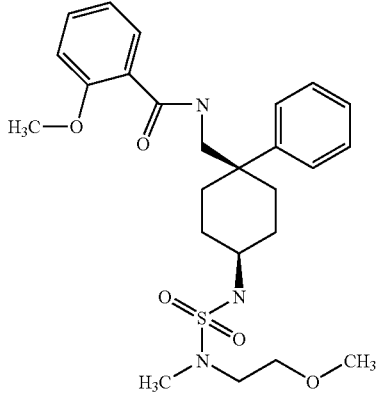 | cis-2-Methoxy-N-{4-[N-methyl-N-1-(2-methoxy-ethyl)-N'-sulfenyl-urido]-1-phenyl-cyclohexyl-methyl}-benzamide | 490 |
| 131 | 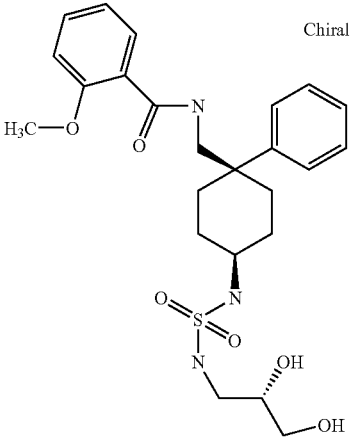 Chiral | cis-2-Methoxy-N-{4-[N-1-((S)-2,3-dihydroxy-propyl)-N'-sulfenyl-urido]-1-phenyl-cyclohexyl-methyl}-benzamide | 492 |

-continued

| Ex. | Structure | Name | (M + H) |
|---|---|---|---|
| 132 | 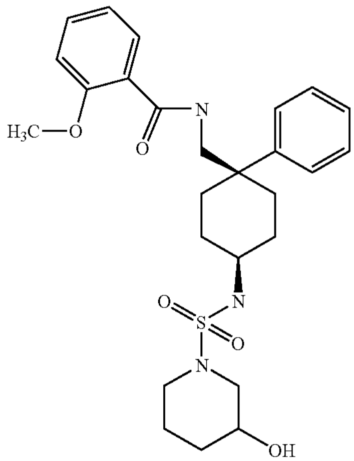 | N-[4-(3-Hydroxy-piperidine-1-sulfonylamino)-1-phenyl-cyclohexylmethyl]-2-methoxy-benzamide | 502 |
| 133 | Chiral | N-[4-((R)-2-Hydroxymethyl-pyrrolidine-1-sulfonylamino)-1-phenyl-cyclohexylmethyl]-2-methoxy-benzamide | 502 |
| 134 | Chiral | N-[4-((s)-2-Hydroxymethyl-pyrrolidine-1-sulfonylamino)-1-phenyl-cyclohexylmethyl]-2-methoxy-benzamide | 502 |

-continued

| Ex. | Structure | Name | (M + H) |
|---|---|---|---|
| 135 | 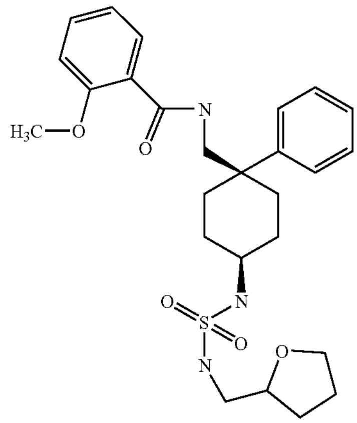 | cis-2-Methoxy-N-{4-[N-((R)-tetrahydrofuran-2-yl-methyl)-N'-sulfenyl-urido]-1-phenyl-cyclohexyl-methyl}-benzamide | 502 |
| 136 | Chiral | cis-2-Methoxy-N-{4-[N-((S)-tetrahydrofuran-2-yl-methyl)-N'-sulfenyl-urido]-1-phenyl-cyclohexyl-methyl}-benzamide | 502 |
| 137 | 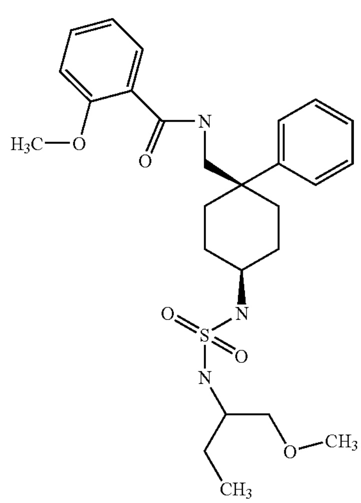 | cis-2-Methoxy-N-{4-[N-1-(1-methoxymethyl-propyl)-N'-sulfenyl-urido]-1-phenyl-cyclohexyl-methyl}-benzamide | 504 |

-continued

| Ex. | Structure | Name | (M + H) |
|---|---|---|---|
| 138 | 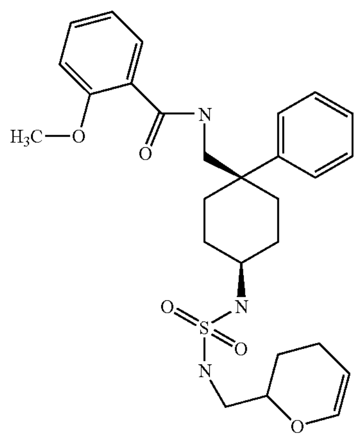 | cis-2-Methoxy-N-{4-[N-C-(3,4-dihydro-2H-pyran-2-yl)methylamino]-N'-sulfenyl-urido]-1-phenyl-cyclohexyl-methyl}-benzamide | 514 |
| 139 | 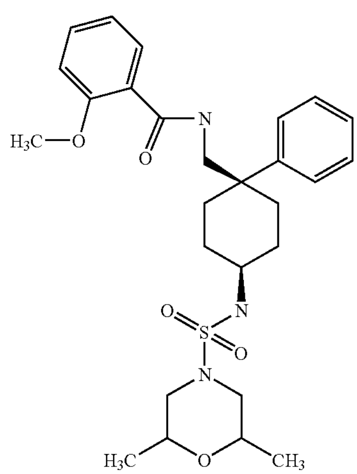 | N-[4-(2,6-Dimethyl-morpholine-4-sulfonylamino)-1-phenyl-cyclohexylmethyl]-2-methoxy-benzamide | 516 |
| 140 | Chiral | cis-2-Methoxy-N-[4-(N-α-(R)-hydroxymethyl-benzyl-N'-sulfenyl-urido)-1-phenyl-cyclohexyl-methyl]-benzamide | 538 |

| Ex. | Structure | Name | (M + H) |
|---|---|---|---|
| 141 | 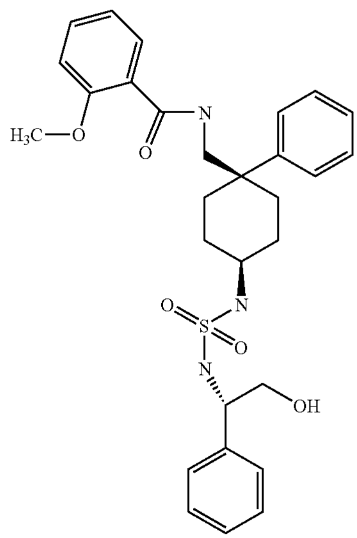 | cis-2-Methoxy-N-[4-(N-α-(S)-hydroxymethyl-benzyl-N'-sulfenyl-urido)-1-phenyl-cyclohexyl-methyl]-benzamide | 538 |
| 142 | 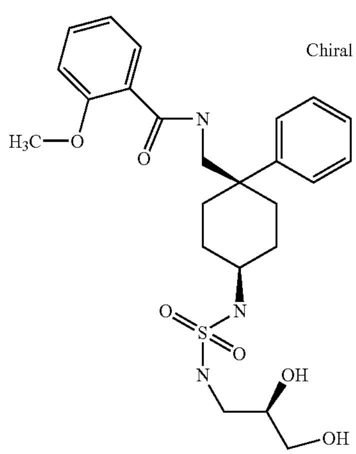 | cis-2-Methoxy-N-{4-[N-1-((R)-2,3-dihydroxy-propyl)-N'-sulfenyl-urido]-1-phenyl-cyclohexyl-methyl}-benzamide | 492 |
| 143 | 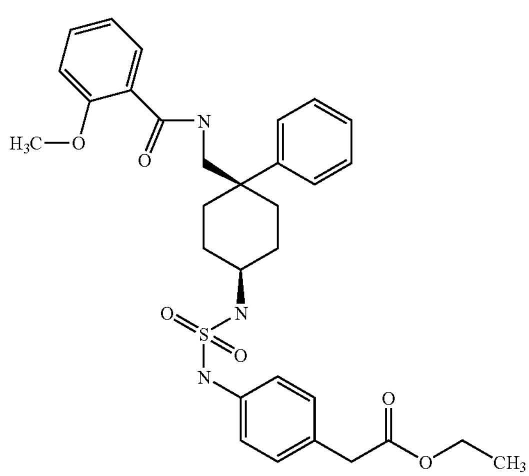 | cis-2-Methoxy-{N-[4-(N-4-ethylacetylphenyl-N'-sulfenyl-urido]-1-phenyl-cyclohexyl-methyl}-benzamide | 580 |

| Ex. | Structure | Name | (M + H) |
|---|---|---|---|
| 144 | 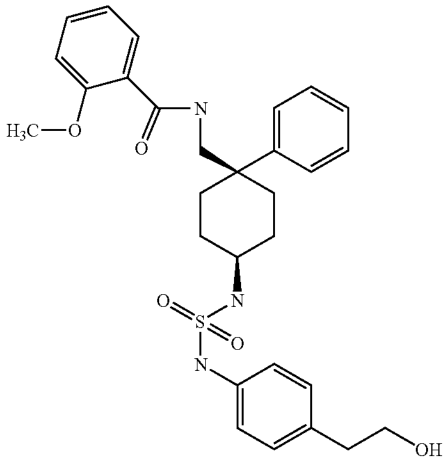 | cis-2-Methoxy-{N-[4-(N-4-(2-hydroxyethyl)phenyl)-N'-sulfenyl-urido]-1-phenyl-cyclohexyl-methyl}-benzamide | 538 |
| 145 | 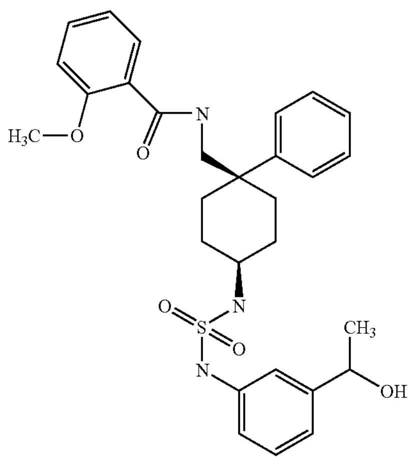 | cis-2-Methoxy-{N-[4-(N-4-(1-hydroxyethyl)phenyl)-N'-sulfenyl-urido]-1-phenyl-cyclohexyl-methyl}-benzamide | 538 |
| 146 | 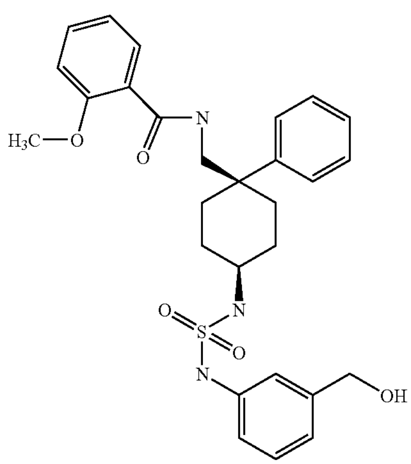 | cis-2-Methoxy-{N-[4-(N-4-hydroxymethylphenyl)-N'-sulfenyl-urido-1-phenyl]-cyclohexyl-methyl}-benzamide | 524 |

| Ex. | Structure | Name | (M + H) |
|---|---|---|---|
| 147 | 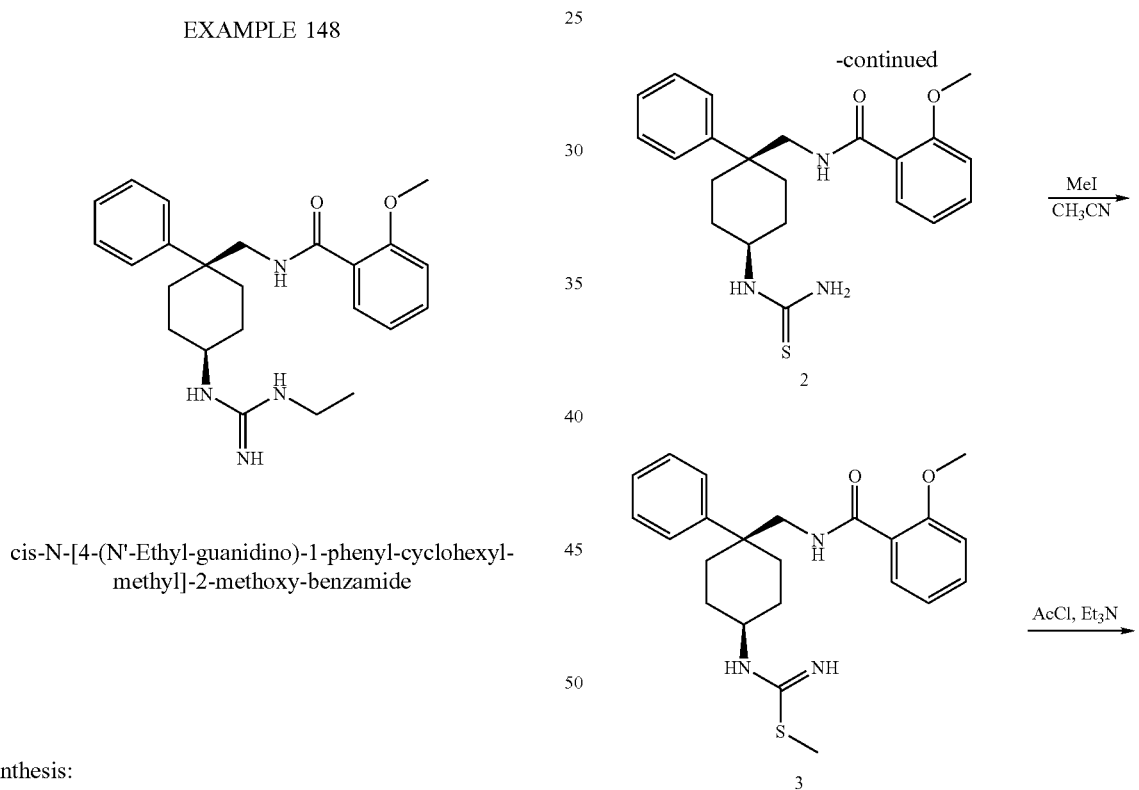 | cis-2-Methoxy-{N-[4-(N-2-hydroxy-indan-1-yl)-N'-sulfenyl-urido-1-phenyl]-cyclohexyl-methyl}-benzamide | 550 |
EXAMPLE 148
cis-N-[4-(N'-Ethyl-guanidino)-1-phenyl-cyclohexyl-methyl]-2-methoxy-benzamide
Synthesis:
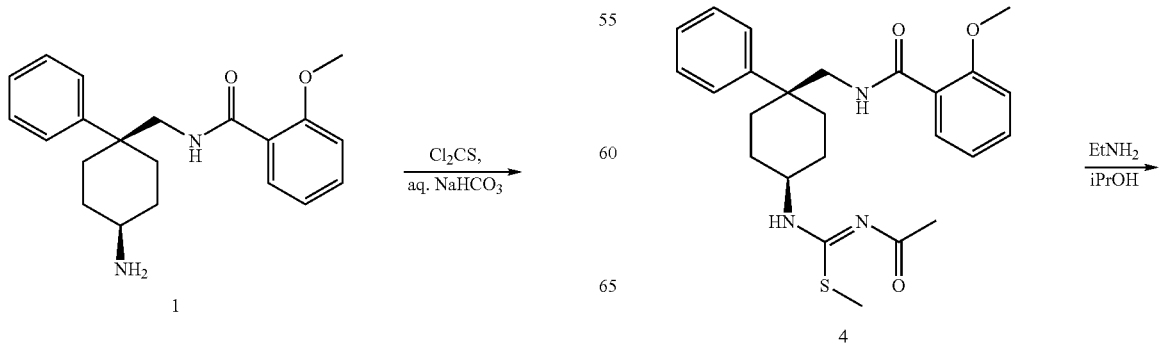

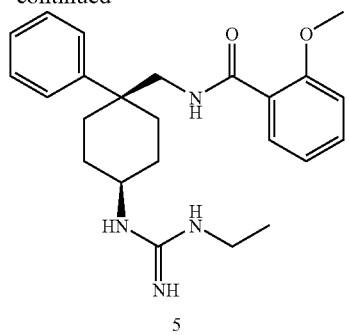

Compound 1: The synthesis of compound 1 was described in Example 31.

Compound 2: To a solution of the amine 1 (0.35 g, 1.0 mmol) in 10 ml of dichloromethane and 5 ml of aq. NaHCO₃ was added thiophosgene (0.3 ml, 4.0 mmol) in one portion. The reaction mixture stirred for 2 h at 25° C. The organic layer was then separated and concentrated in vacuo to provide an oil (0.34 g, 89%). The oil was dissolved in 10 ml of 7N NH₃/MeOH and stirred for 12 h at 25° C. The reaction mixture was concentrated in vacuo to provide 2 as an oil which was used in the following reaction without further purification.

Compound 3: To a solution of 2 in 10 ml of CH₃CN was added MeI (0.5 ml) and the resulting solution was stirred for 12 h at 25° C. The reaction mixture was concentrated in vacuo to provide a white solid which was partitioned between EtOAc (50 ml) and brine (20 ml). The organic layer was dried over MgSO₄ and concentrated in vacuo to yield 350 mg (>95%) of 3 as an oil which was subjected to the following reaction without further purification.

Compound 4: To a solution of 3 (0.17 g, 0.45 mmol) in 10 ml of dichloromethane was added triethylamine (0.2 ml) and acetyl chloride (0.2 ml, 2.8 mmol) and the resulting solution was stirred for 1 h at 0° C. The reaction mixture was diluted with EtOAc (50 ml) and washed with brine (10 ml×2). The organic layer was dried over MgSO₄ and concentrated in vacuo to yield 4 as a dark oil which was subjected to the following reaction without further purification.

Compound 5: A solution of 4 (35 mg, 0.077 mmol) and ethylamine (1 mmol, 0.5 ml of 2M NH₃ in THF) in 1 ml of 2-propanol was stirred for 12 h at 70° C. in a sealed tube. The reaction mixture was then subjected to prearative HPLC purification (described in a synthesis of Example 31) to yield 17.9 mg (40%) of the desired product 5 as a colorless oil. Mass Spec [M+H]⁺=409.

EXAMPLES 149–152

Examples 149 to 152 were synthesized using methodology described in Example 148.

| Ex. | Structure | Name | (M + H) |
|---|---|---|---|
| 149 | 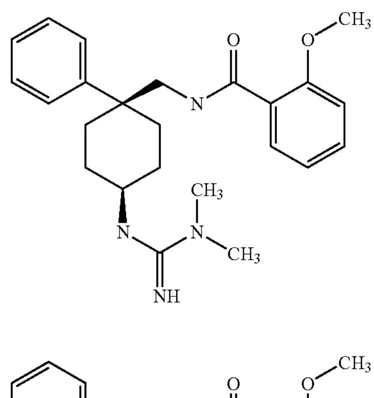 | cis-N-[4-(N',N'-dimethyl-guanidino)-1-phenyl-cyclohexyl-methyl]-2-methoxy-benzamide | 409 |
| 150 | 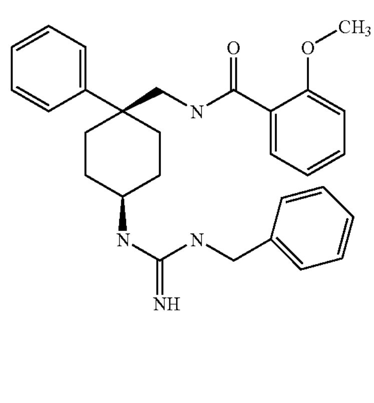 | cis-N-[4-(N'-benzyl-guanidino)-1-phenyl-cyclohexyl-methyl]-2-methoxy-benzamide | 471 |

| Ex. | Structure | Name | (M + H) |
|---|---|---|---|
| 151 | 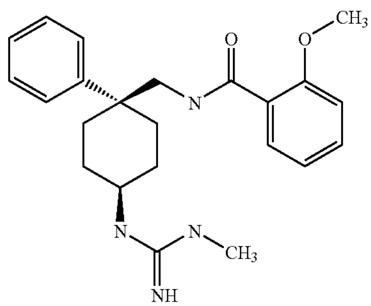 | cis-N-[4-(N'-methyl-guanidino)-1-phenyl-cyclohexyl-methyl]-2-methoxy-benzamide | 395 |
| 152 | 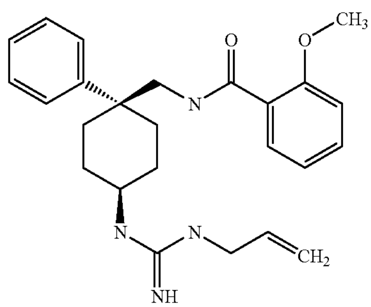 | cis-N-[4-(N'-allyl-guanidino)-1-phenyl-cyclohexyl-methyl]-2-methoxy-benzamide | 421 |
EXAMPLE 153
cis-2,4-Dimethoxy-N-[4-(N-methyl-N'-cyanoguanidino)-1-phenyl-cyclohexylmethyl]-benzamide
Synthesis:
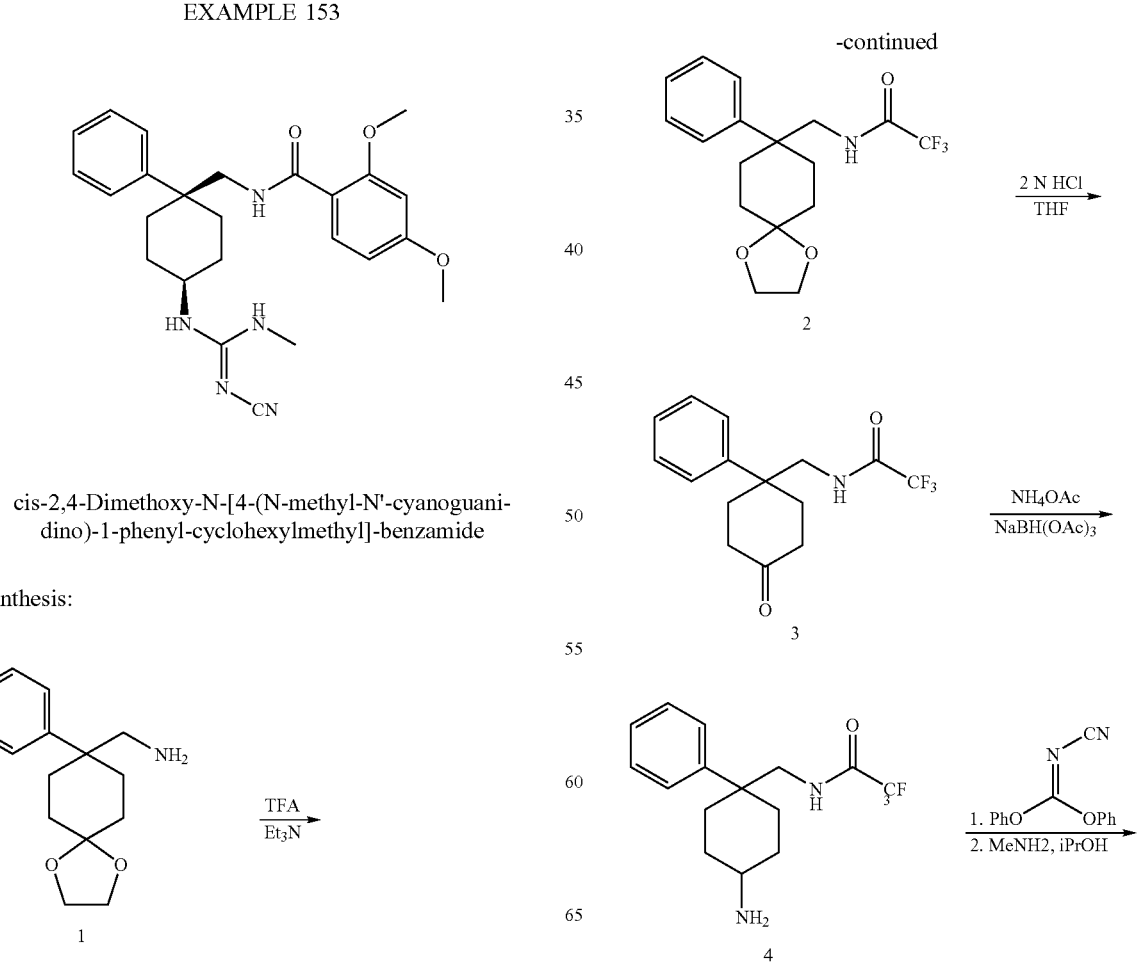

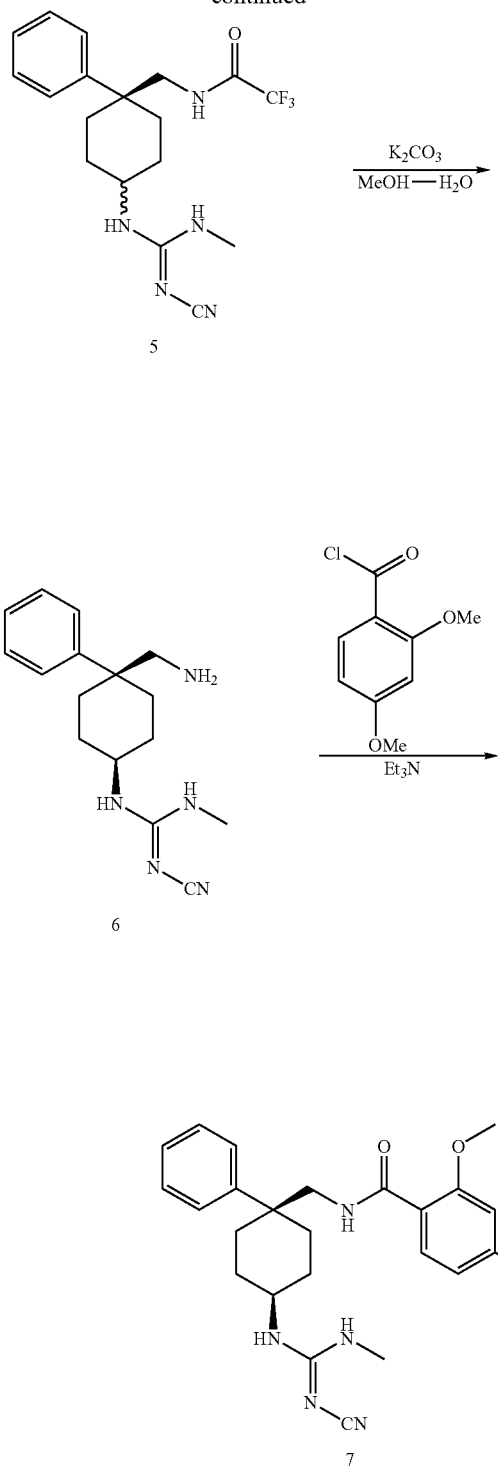

Compound 1 The synthesis of 1 was described in Example 31.

Compound 2: To a solution of the amine 1 (1.0 g, 4.0 mmol) and triethylamine (0.67 ml, 4.8 mmol) in 10 ml of dichloromethane was added trifluoroacetic anhydride (1.0 ml, 4.8 mmol) dropwise and the resulting solution was stirred at −78° C. for 2 h. The reaction mixture was concentrated in vacuo to provide an oily residue which was partitioned between EtOAc (100 ml) and brine (20 ml×2). The organic layer was dried over MgSO$_4$ and concentrated in vacuo to provide the desired product 2 (1.3 g, 0.38 mmol, >95%) as a colorless oil. It was subjected to the following reaction without further purification.

Compound 3: The intermediate 2 (1.3 g) was dissolved in THF (50 ml). Into the solution was added 30 ml of 2N HCl and the resulting solution was stirred for 12 h at 25° C. The HPLC analysis showed the complete disappearance of the starting material and formation of a new product. The reaction mixture was diluted with EtOAc (100 ml) and washed with aq. NaHCO$_3$ (30 ml×2). The organic layer was dried over MgSO$_4$ and concentrated in vacuo to provide 1.2 g (>95%) of 3 as an oil.

Compound 4: To the solution of the ketone 3 (1.2 g, 4 mmol) in MeOH (60 ml) was added NH$_4$OAc (2.5 g, 31 mmol) followed by addition of NaBH(OAc)$_3$ (1.4 g, 5.2 mmol) in one portion. The resulting solution was stirred for 3 h at 25° C. The reaction mixture was concentrated and the resulting solid was redissolved in EtOAc (100 ml) and washed with aq. NaOH (1M, 30 ml×2). The organic layer was dried over MgSO$_4$ and concentrated in vacuo to provide an oil which is a 1:1 mixture of the cis and trans diastereomers of the desired amine 4.

Compound 5: To a solution of the amine 4 (0.30 g, 1 mmol) in 2-propanol (2 ml) was added diphenyl cyanocarbonidate (240 mg, 1 mmol) and the resulting solution was stirred for 3 h at 70° C. HPLC analysis indicated completion of the reaction. The reaction mixture was cooled to 25° C. and transferred into a sealed tube. To the sealed tube was added 2 ml of 2M MeNH$_2$ (4 mmol). The resulting solution was stirred for another 5 h at 70° C. The reaction mixture was concentrated to 2 ml of solution and purified on preparative HPLC (described in a synthesis of Example 31) to provide cis-isomer (retention time: 2.90 min) (70 mg) and trans-isomer (retention time: 2.65 min) (60 mg) of compound 5.

Compound 6: The cis isomer of intermediate 5 (1.1 g, 2.9 mmol) was dissolved in 40 ml of 1:1 mixture of MeOH—H$_2$O with 7% aq. K$_2$CO$_3$ and the resulting solution was stirred for 3 h at 25° C. HPLC analysis indicated completion of the reaction. The reaction mixture was concentrated in vacuo to provide a white solid, which was partitioned between EtOAc (100 ml) and brine (20 ml×2). The aqueous layer was extracted with EtOAc (50 ml). The organic layer was dried over MgSO$_4$ and concentrated in vacuo to provide 0.81 g (>95%) of 6 as an oil which was subjected to the following reaction without any further purification.

Compound 7: To a solution of the amine 6 (40 mg, 0.014 mmol) in 2 ml of dichloromethane was added 2,4-dimethoxybenzoic acid (38 mg, 0.021 mmol), EDCI (60 mg, 0.031 mmol) and diisopropylethylamine (57 μL, 0.031 mmol) sequentially. The mixture as allowed to stirred for 30 h at 35° C. The reaction mixture was purified on preparative HPLC (described in a synthesis of Example 31) to provide 6.7 mg of the desired product 7 as a colorless oil. Mass Spec [M+H]$^+$=450.

EXAMPLES 154–170

Examples 154 to 170 were synthesized using methodology described in Example 153.

| Ex. | Structure | Name | (M + H) |
|---|---|---|---|
| 154 | 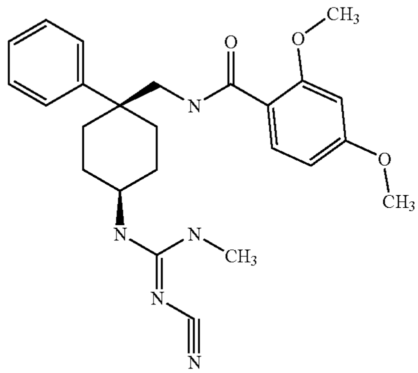 | cis-2,4-Dimethoxy-N-[4-(N-methyl-N'-cyanoguanidino)-1-phenyl-cyclohexylmethyl]-benzamide | 450 |
| 155 | 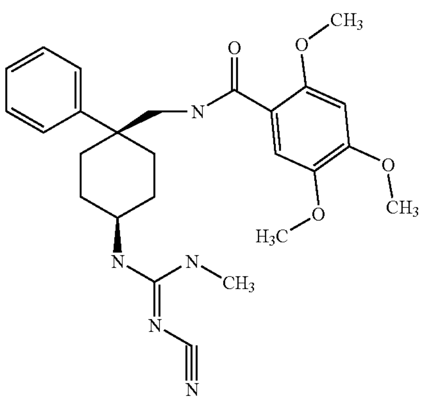 | cis-2,4,5-Trimethoxy-N-[4-(N-methyl-N'-cyanoguanidino)-1-phenyl-cyclohexylmethyl]-benzamide | 480 |
| 156 | 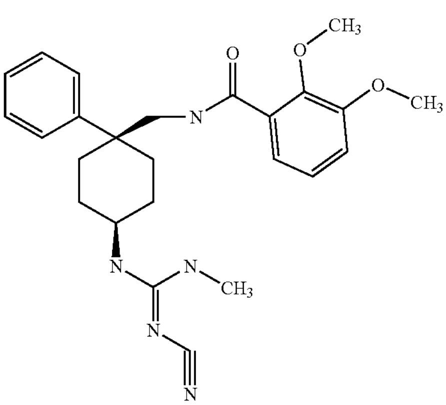 | cis-2,3-Dimethoxy-N-[4-(N-methyl-N'-cyanoguanidino)-1-phenyl-cyclohexylmethyl]-benzamide | 450 |

-continued
| Ex. | Structure | Name | (M + H) |
|---|---|---|---|
| 157 | 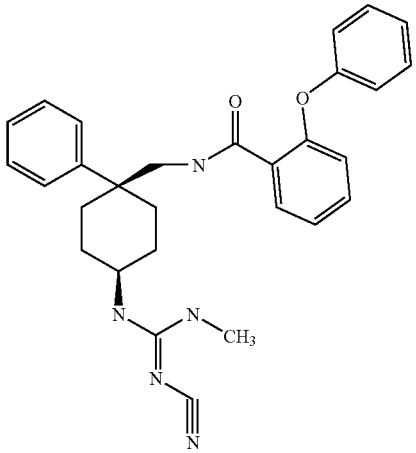 | cis-2-Phenoxy-N-[4-(N-methyl-N'-cyanoguanidino)-1-phenyl-cyclohexylmethyl]-benzamide | 482 |
| 158 | 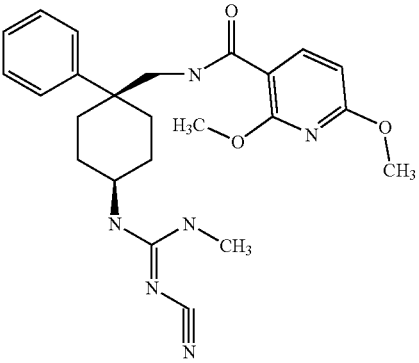 | cis-(2,4-Dimethoxy-pyridin-3-yl)-N-[4-(N-methyl-N'-cyanoguanidino)-1-phenyl-cyclohexylmethyl]-benzamide | 451 |
| 159 | 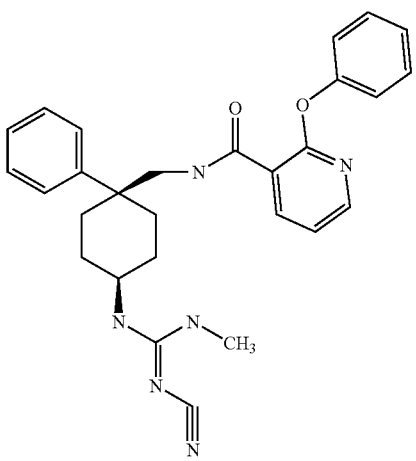 | cis-(2-Phenoxy-pyridin-3-yl)-N-[4-(N-methyl-N'-cyanoguanidino)-1-phenyl-cyclohexylmethyl]-benzamide | 483 |

-continued

| Ex. | Structure | Name | (M + H) |
|---|---|---|---|
| 160 | 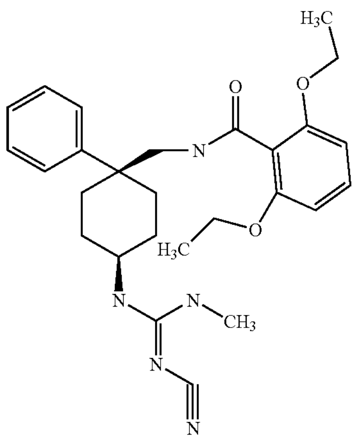 | cis-2,3-Diethoxy-N-[4-(N-methyl-N'-cyanoguanidino)-1-phenyl-cyclohexylmethyl]-benzamide | 478 |
| 161 | 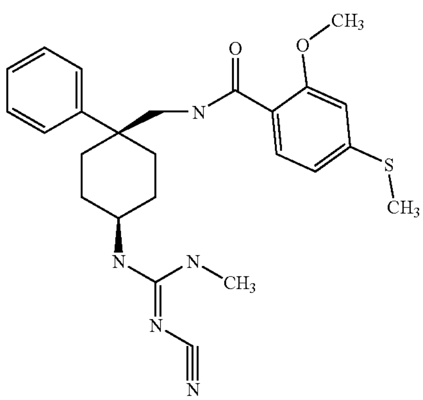 | cis-2-Methoxy-4-thiomethoxy-N-[4-(N-methyl-N'-cyanoguanidino)-1-phenyl-cyclohexylmethyl]-benzamide | 466 |
| 162 | 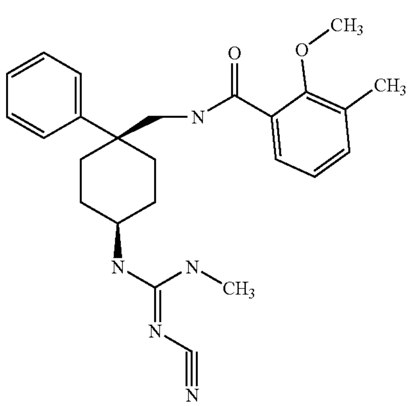 | cis-2-Methoxy-3-methyl-N-[4-(N-methyl-N'-cyanoguanidino)-1-phenyl-cyclohexylmethyl]-benzamide | 434 |

| Ex. | Structure | Name | (M + H) |
|---|---|---|---|
| 163 | 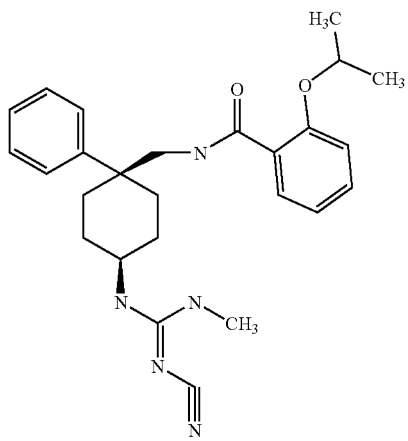 | cis-2-Isopropoxy-N-[4-(N-methyl-N'-cyanoguanidino)-1-phenyl-cyclohexylmethyl]-benzamide | 448 |
| 164 | 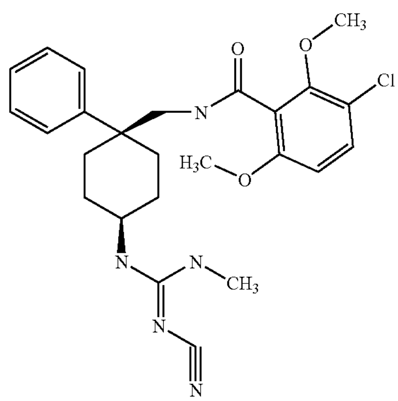 | cis-2,6-Dimethoxy-3-chloro-N-[4-(N-methyl-N'-cyanoguanidino)-1-phenyl-cyclohexylmethyl]-benzamide | 485 |
| 165 | 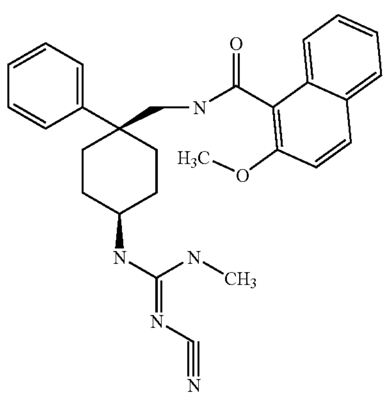 | 2-Methoxy-naphthalene-1-carboxylic acid [4-(N'-methyl-cyanoguanidino)-1-phenyl-cyclohexylmethyl]-amide | 470 |
| 166 | 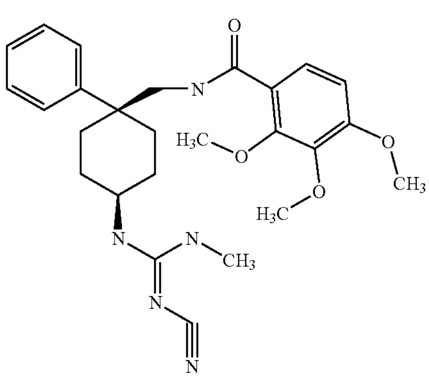 | cis-2,3,4-Triethoxy-N-[4-(N-methyl-N'-cyanoguanidino)-1-phenyl-cyclohexylmethyl]-benzamide | 480 |

| Ex. | Structure | Name | (M + H) |
|---|---|---|---|
| 167 | 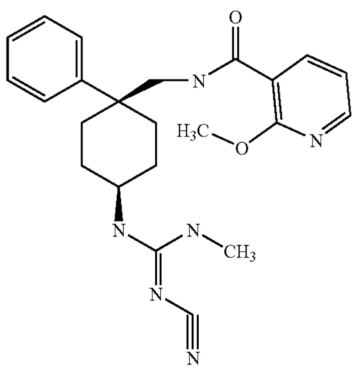 | cis-(2-Methoxy-pyridin-3-yl)-N-[4-(N-methyl-N'-cyanoguanidino)-1-phenyl-cyclohexylmethyl]-benzamide | 421 |
| 168 | 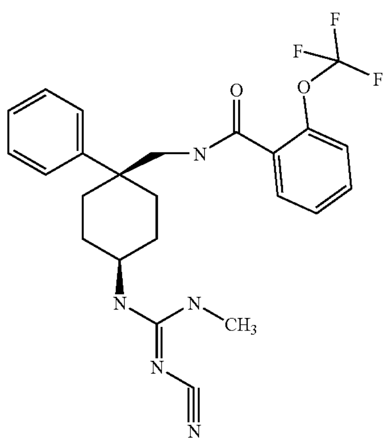 | N-[4-(N'-Methyl-cyanoguanidino)-1-phenyl-cyclohexylmethyl]-2-trifluoromethoxy-benzamide | 474 |
| 169 | 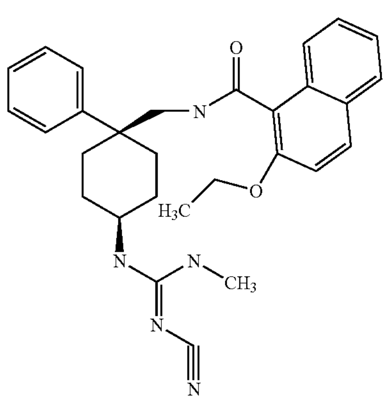 | 2-Ethoxy-naphthalene-1-carboxylic acid [4-(N'-methyl-cyanoguanidino)-1-phenyl-cyclohexylmethyl]-amide | 484 |

| Ex. | Structure | Name | (M + H) |
|---|---|---|---|
| 170 | 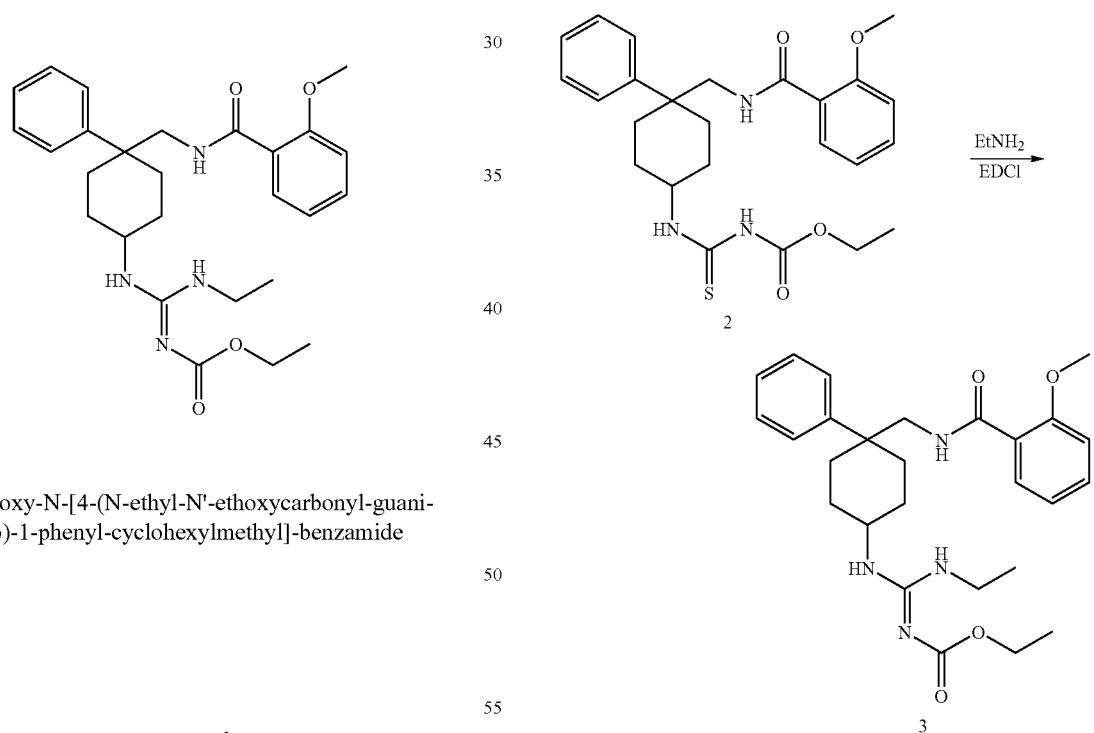 | 2-Benzyloxy-N-[4-(N'-methyl-cyanoguanidino)-1-phenyl-cyclohexylmethyl]-benzamide | 496 |

EXAMPLE 171

2-Methoxy-N-[4-(N-ethyl-N'-ethoxycarbonyl-guanidino)-1-phenyl-cyclohexylmethyl]-benzamide Synthesis:

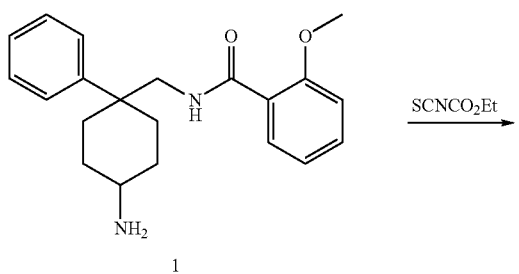

Compound 1: The synthesis of 1 was described in Example 31.

Compound 2: To a solution of the amine 1 (mixture of cis and trans isomers, 0.34 g, 1.0 mmol) in 15 ml of dichloromethane was added 0.12 ml of ethyl isothiocyanatoformate (0.12 ml, 1.0 mmol) at 0° C. The mixture was stirred for 0.5 h at 0° C. and 3 h at 25° C. The reaction mixture was diluted with 100 ml of dichloromethane and washed with 1N HCl (20 ml) and brine (20 ml). The organic solution was dried over MgSO$_4$ and concentrated in vacuo to provide 0.43 g (95%) of the desired product 2 as a colorless oil which was subjected to the following reaction without further purification.

Compound 3: To a solution of the intermediate 2 (50 mg, 0.11 mmol) in 5 ml of dichloromethane was added ethylamine (0.1 ml of 2N in THF, 0.2 mmol), EDCI (42 mg, 0.22 mmol) and diisopropylethylamine (0.02 ml, 0.11 mmol) sequentially. The reaction mixture was stirred for 12 h at 25° C. The reaction mixture was purified by preparative HPLC (described in a synthesis of Example 31) to yield 22.2 mg (42%) of the desired product 3 (1:1 mixture of cis- and trans-isomers) as a colorless oil. Mass Spec [M+H]$^+$=481.

EXAMPLES 172–178

Examples 172 to 178 were synthesized using methodology described in Example 171.

| Ex. | Structure | Name | (M + H) |
|---|---|---|---|
| 172 | 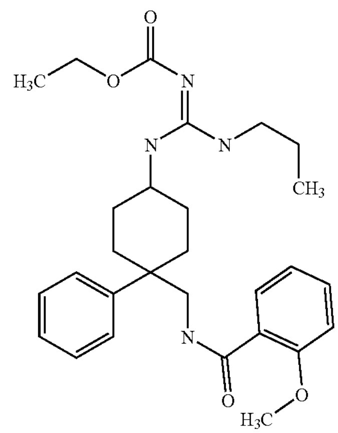 | 2-Methoxy-N-[4-(N-ethyl-N'-ethoxycarbonyl-guanidino)-1-phenyl-cyclohexylmethyl]-benzamide | 495 |
| 173 | 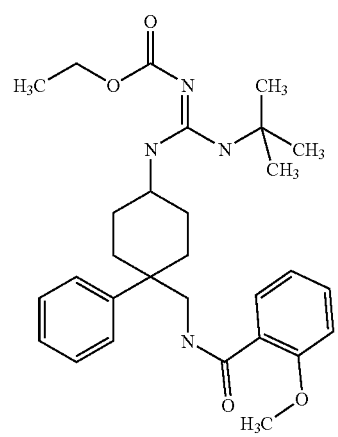 | 2-Methoxy-N-[4-(N-tert-butyl-N'-ethoxycarbonyl-guanidino)-1-phenyl-cyclohexylmethyl]-benzamide | 509 |
| 174 | 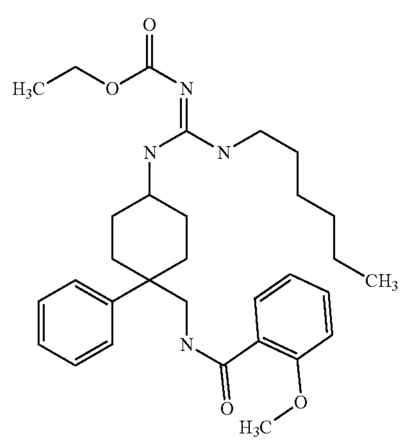 | 2-Methoxy-N-[4-(N-n-hexyl-N'-ethoxycarbonyl-guanidino)-1-phenyl-cyclohexylmethyl]-benzamide | 537 |

| Ex. | Structure | Name | (M + H) |
| --- | --- | --- | --- |
| 175 | 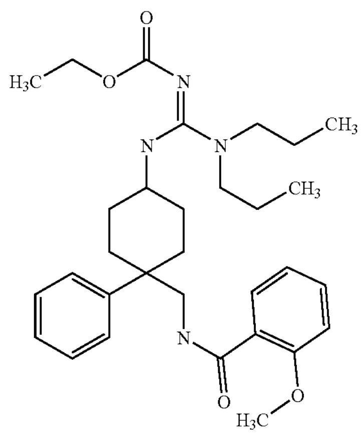 | 2-Methoxy-N-[4-(N,N-dipropyl-N'-ethoxycarbonyl-guanidino)-1-phenyl-cyclohexylmethyl]-benzamide | 537 |
| 176 | 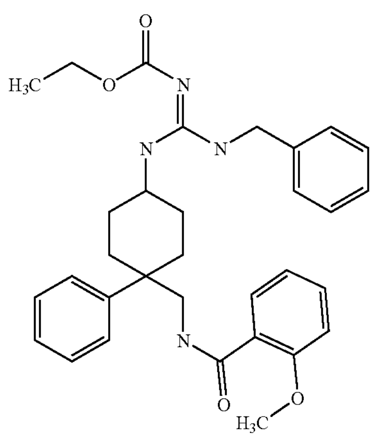 | 2-Methoxy-N-[4-(N-benzyl-N'-ethoxycarbonyl-guanidino)-1-phenyl-cyclohexylmethyl]-benzamide | 543 |
| 177 | 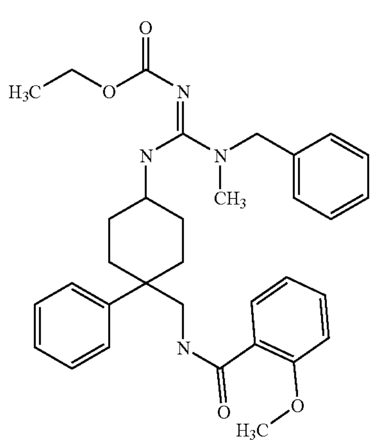 | 2-Methoxy-N-[4-(N-methyl-N-benzyl-N'-ethoxycarbonyl-guanidino)-1-phenyl-cyclohexylmethyl]-benzamide | 557 |

| Ex. | Structure | Name | (M + H) |
|---|---|---|---|
| 178 | 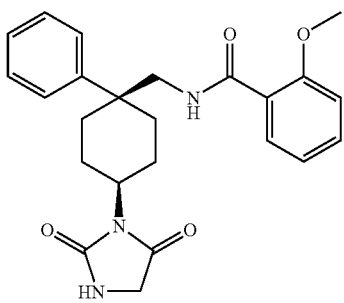 | 2-Methoxy-N-[4-(N-ethoxycarbonyl-guanidino)-1-phenyl-cyclohexylmethyl]-benzamide | 453 |

EXAMPLE 179 cis-N-[4-(2,5-Dioxo-imidazolin-1-yl)-1-phenyl-cyclohexylmethyl]-2-methoxy-benzamide Synthesis:

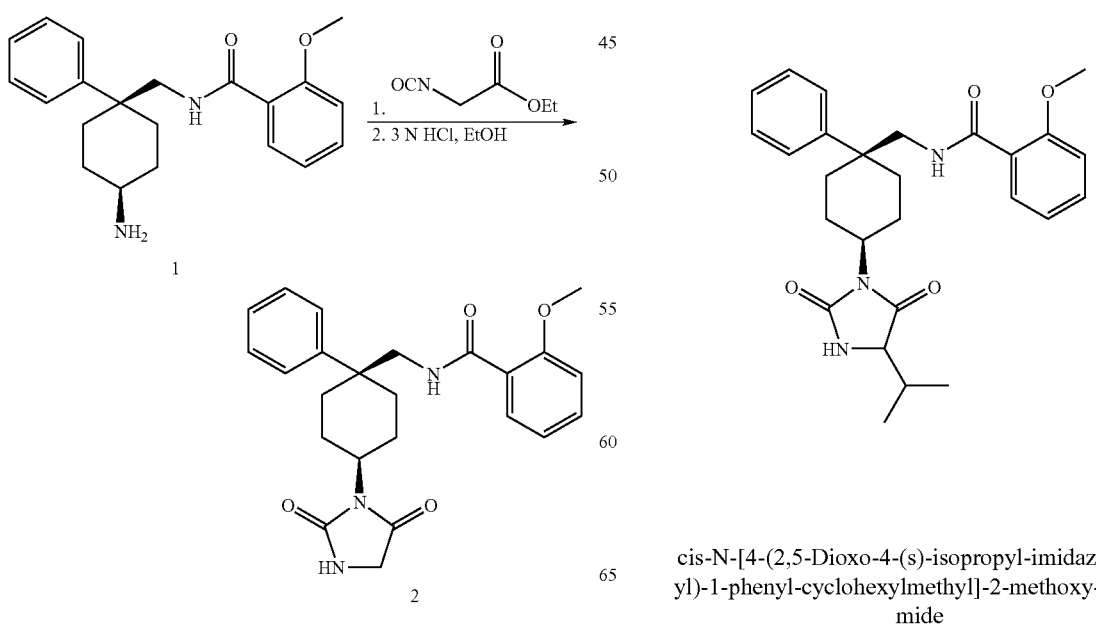

Compound 1: The synthesis of compound 1 was described in Example 31.

Compound 2: To a solution of the cis-amine (50 mg, 0.15 mmol) in 5 ml of dichloromethane was added ethyl isocyanatoacetate (30 mg, 0.16 mmol) in one portion and the reaction mixture was stirred for 5 h at 25° C. The reaction mixture was then concentrated in vacuo yielding an oily residue, which was dissolved in 1 ml of EtOH-3N aq.HCl (1:1 mixture). The mixture was stirred for 12 h at 45° C. The reaction mixture was purified on preparative HPLC to yield 23.4 mg (37%) of the desired product 2 as a white solid. Mass Spec [M+H]⁺=422.

EXAMPLE 180 cis-N-[4-(2,5-Dioxo-4-(s)-isopropyl-imidazolin-1-yl)-1-phenyl-cyclohexylmethyl]-2-methoxy-benzamide Synthesis:

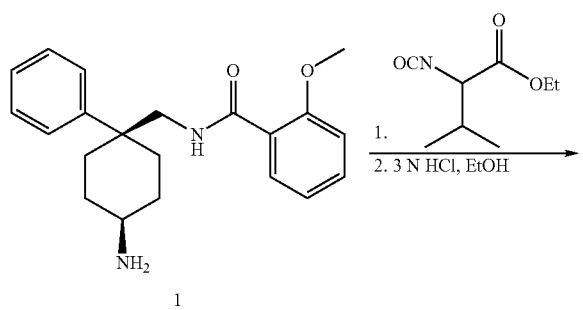

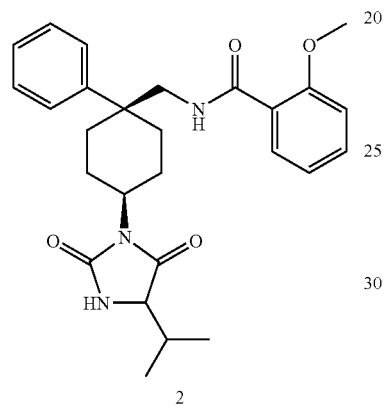

Compound 1; The synthesis of 1 was described in Example 31.

Compound 2: The reaction was carried out in a same procedure as described in Example 179 starting with the cis-amine 1 (50 mg, 0.15 mmol) and methyl (S)-(−)-2-isocyanato-3-methylbutyrate (35 mg, 0.23 mmol) to provide 16.7 mg (0.036 mmol, 24%) of the desired product as a white solid. Mass Spec [M+H]$^+$=464.

EXAMPLE 181

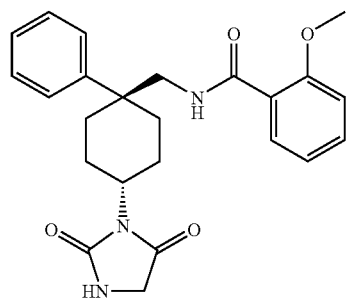

trans-N-[4-(2,5-Dioxo-imidazolin-1-yl)-1-phenyl-cyclohexylmethyl]-2-methoxy-benzamide Synthesis:

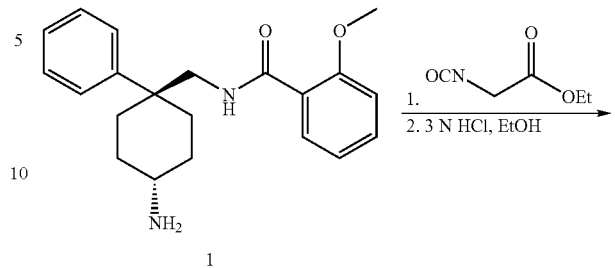

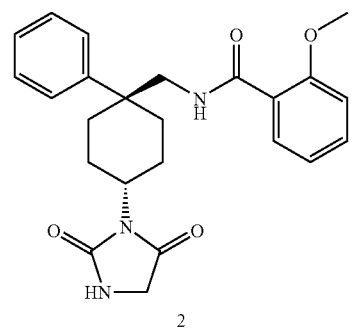

Compound 1: The synthesis of 1 was described in Example 31.

Compound 2: The reaction was carried out in a same procedure as described in Example 179 starting with the trans-amine (50 mg, 0.15 mmol) ethyl isocyanatoacetate (30 mg, 0.16 mmol) to provide 6.4 mg (0.015 mmol, 10%) of the desired product as a white solid. Mass Spec [M+H]$^+$=422.

EXAMPLE 182

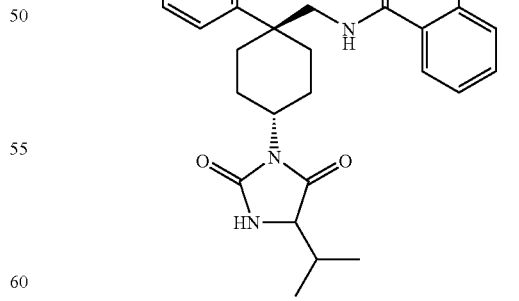

trans-N-[4-(2,5-Dioxo-4-(s)-isopropyl-imidazolin-1-yl)-1-phenyl-cyclohexylmethyl]-2-methoxy-benzamide Synthesis:

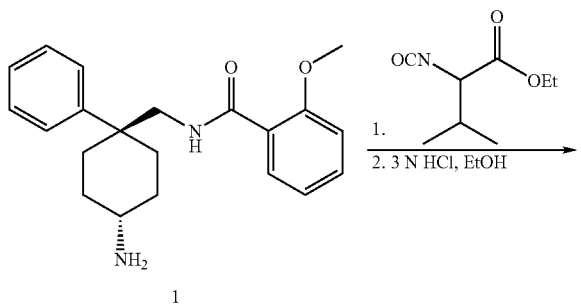

Compound 1: The synthesis of 1 was described in Example 31.

Compound 2: The reaction was carried out in a same procedure as described in Example 180 starting with the trans-amine (50 mg, 0.15 mmol) and methyl (S)-(−)-2-isocyanato-3-methylbutyrate (35 mg, 0.23 mmol) to provide 23.4 mg (0.051 mmol, 33%) of the desired product as a white solid. Mass Spec [M+H]$^+$=464.

EXAMPLE 183

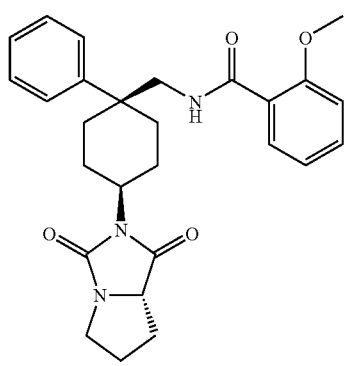

cis-N-[4-(2,5-Dioxo-4-(s)-tetrahydro-pyrrolo[1,2-C]imidazol-2-yl)-1-phenyl-cyclohexylmethyl]-2-methoxy-benzamide Synthesis:

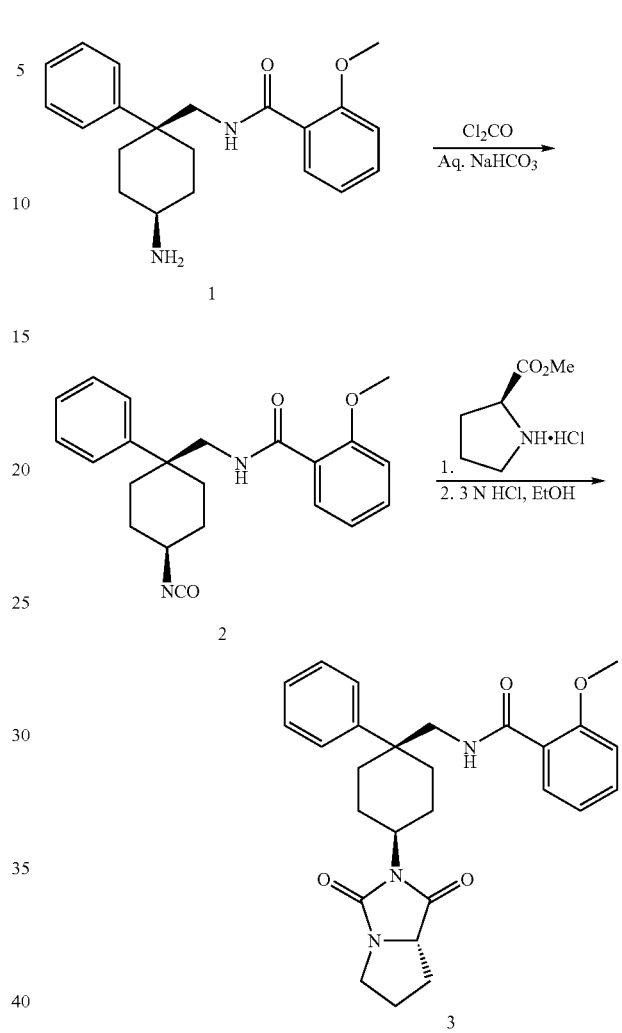

Compound 1: The synthesis of 1 was described in Example 31.

Compound 2: To a solution of the cis-amine 1 (200 mg, 0.59 mmol) in 10 ml of dichloromethane was added 10 ml of aq. NaHCO$_3$. To the heterogeneous solution was added 1 ml of phosgene (20% in toluene) dropwise and the resulting mixture was stirred for 5 h at 25° C. The organic layer was separated. The aqueous layer was extracted with dichloromethane (20 ml). The combined organic layer was dried over MgSO$_4$ and concentrated in vacuo to provide an oil, which was identified as the desired product 2 and subjected to the following reaction without further purification.

Compound 3: To a solution of the isocyanate 2 (1/10 of 2 produced in the previous step) in 1 ml of 2-propanol was added 0.1 ml of triethylamine and L-proline methyl ester-.HCl (100 mg, 0.61 mmol) and the resulting solution was stirred for 12 h at 25° C. The reaction mixture was mixed with 1 ml of 3N aq. HCl and the resulting solution was stirred for 12 h at 70° C. It was cooled to 25° C. and purified by preparative HPLC (described in a synthesis of Example 31) to provide 14.6 mg (53%) of the desired product 3 as a colorless oil. Mass Spec [M+H]$^+$=462.

EXAMPLES 184–192

Examples 184 to 192 were synthesized using methodology described in Example 183.

| Ex. | Structure | Name | (M + H) |
|---|---|---|---|
| 184 | 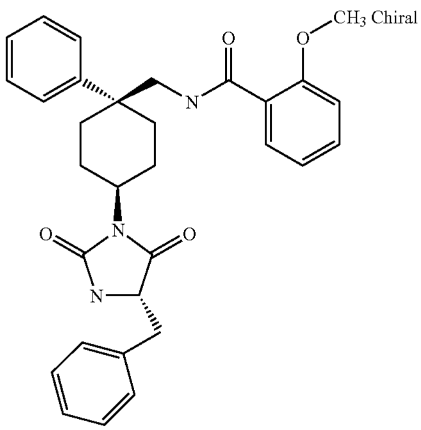 | cis-N-[4-(2,5-Dioxo-4-(s)-benzyl-imidazolin-1-yl)-1-phenyl-cyclohexylmethyl]-2-methoxy-benzamide | 512 |
| 185 | 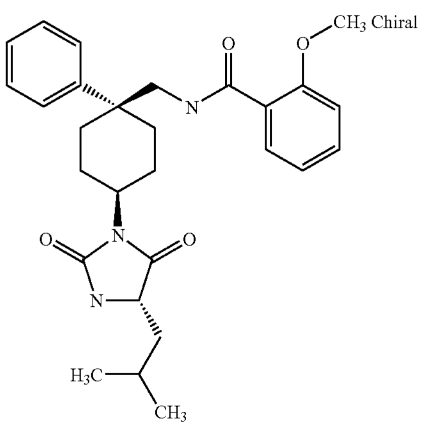 | cis-N-[4-(2,5-Dioxo-4-(s)-isobutyl-imidazolin-1-yl)-1-phenyl-cyclohexylmethyl]-2-methoxy-benzamide | 478 |
| 186 | 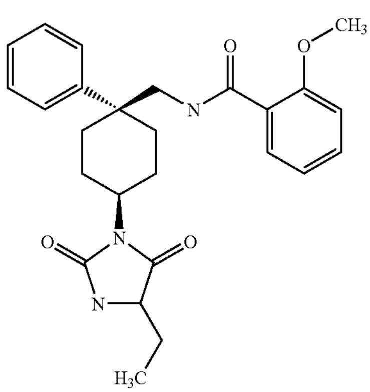 | cis-N-[4-(2,5-Dioxo-4-(s)-ethyl-imidazolin-1-yl)-1-phenyl-cyclohexylmethyl]-2-methoxy-benzamide | 450 |

-continued

| Ex. | Structure | Name | (M + H) |
|---|---|---|---|
| 187 | 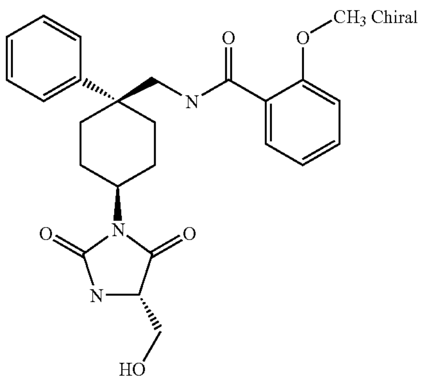 | cis-N-[4-(2,5-Dioxo-4-(s)-hydroxymethyl-imidazolin-1-yl)-1-phenyl-cyclohexylmethyl]-2-methoxy-benzamide | 451 |
| 188 | 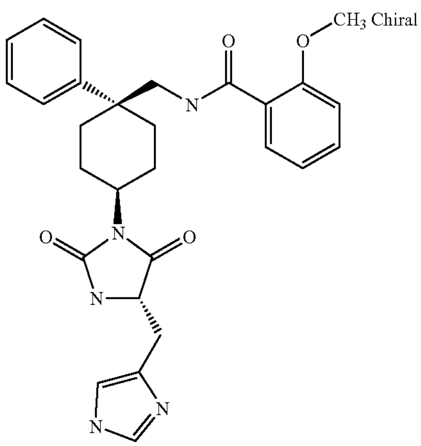 | cis-N-{4-[2,5-Dioxo-4-(s)-(imidazo-4-yl)methyl-imidazolin-1-yl]-1-phenyl-cyclohexylmethyl}-2-methoxy-benzamide | 502 |
| 189 | 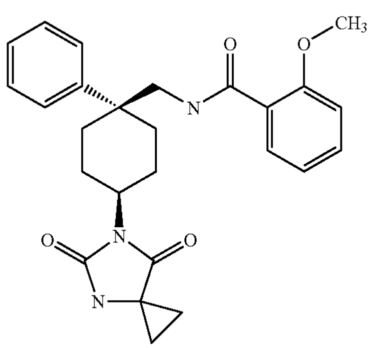 | cis-N-[4-(5,7-Dioxo-4,6-diaza-spiro-[2.4]hept-6-yl)--1-phenyl-cyclohexyl-methyl]-2-methoxy-benzamide | 448 |
| 190 | 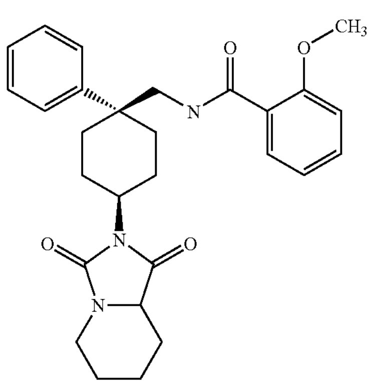 | cis-N-[4-(1,3-Dioxo-4-(s)-tetrahydro-imidazo[1,5-a]-pyridin-2-yl)-1-phenyl-cyclohexyl-methyl]-2-methoxy-benzamide | 76 |

-continued
| Ex. | Structure | Name | (M + H) |
|---|---|---|---|
| 191 | 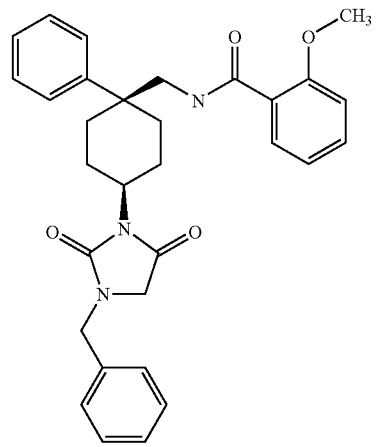 | cis-N-[4-(3-Benzyl-2,5-dioxo-imidazolidin-1-yl)-1-phenyl-cyclohexyl-methyl]-2-methoxy-benzamide | 512 |
| 192 | 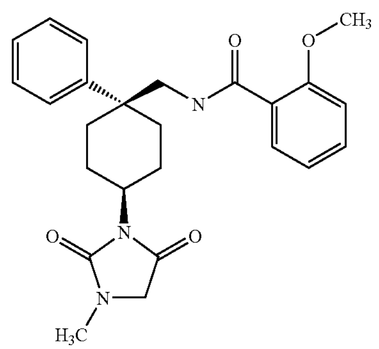 | cis-N-[4-(3-Methyl-2,5-dioxo-imidazolidin-1-yl)-1-phenyl-cyclohexyl-methyl]-2-methoxy-benzamide | 436 |
EXAMPLE 193
Synthesis
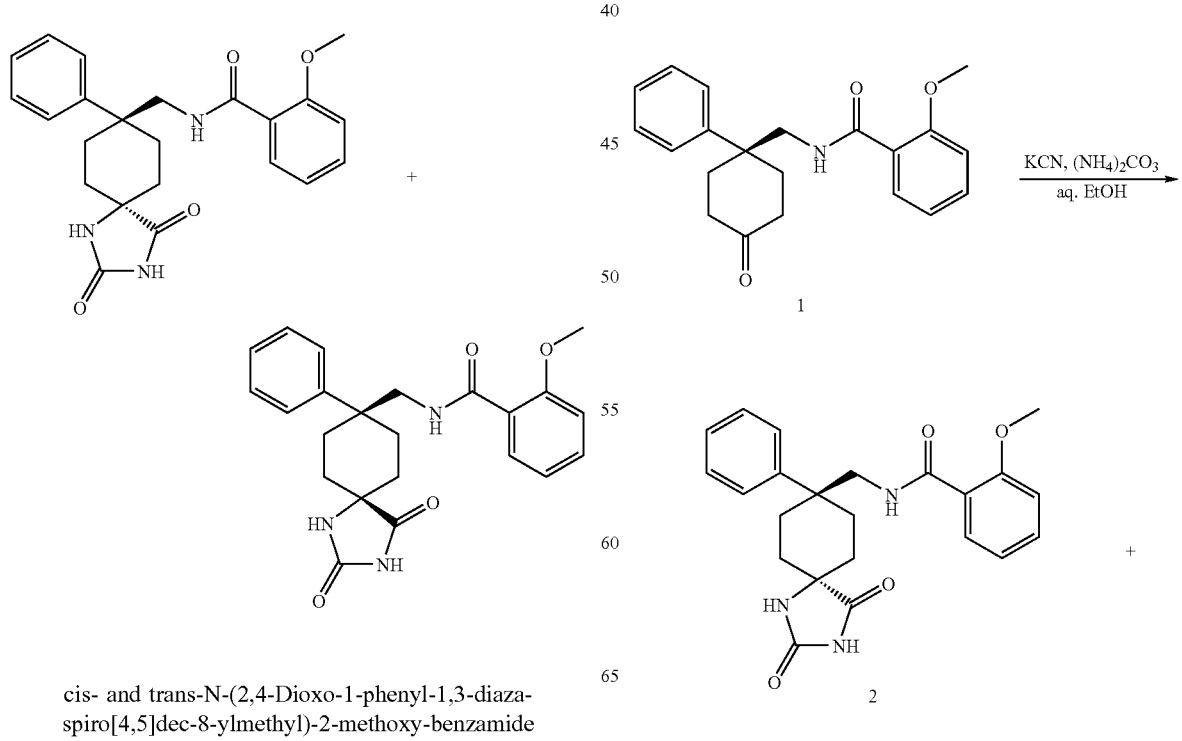
cis- and trans-N-(2,4-Dioxo-1-phenyl-1,3-diaza-spiro[4,5]dec-8-ylmethyl)-2-methoxy-benzamide

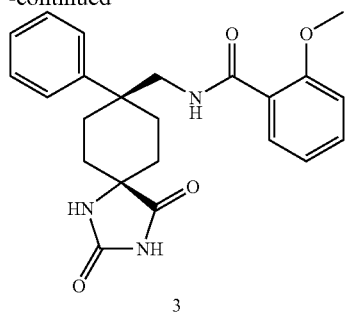

3

Compound 1 The synthesis of 1 was described in Example 31.

Compounds 2 and 3: To a solution of the ketone (0.48 g, 1.42 mmol) in 20 ml of 50% aq. EtOH was added KCN (0.11 g, 1.70 mmol) and $(NH_4)_2CO_3$ (0.68 g, 7.10 mmol) in one portion, respectively and the resulting solution was stirred for 12 h at 55° C. The mixture was concentrated in vacuo yielding an aqueous solution, which was extracted with EtOAc (100 ml×3). The organic layer was dried over $MgSO_4$ and concentrated in vacuo yielding a colorless oil. Upon dissolving the oil in dichloromethane a white solid precipitated out. The white solid (230 mg) was comprised of two diastereoisomers in a 1:1 ratio. The mother liquor was concentrated in vacuo to provide an oil, which was purified on prep-HPLC (described in a synthesis of Example 31) to yield 16.1 mg of one isomer (retention time: 2.82 min). The white solid was dissolved in 30 ml of hot EtOH and stored for 5 days at 25° C. to provide 55.7 mg a white solid precipitate of the other isomer. Mass Spec for both compounds $[M+H]^+=408$.

EXAMPLE 194

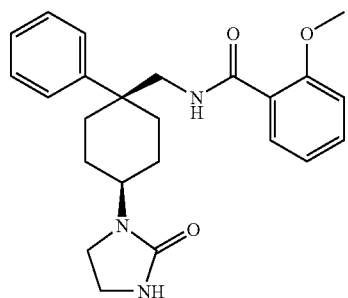

cis-2-Methoxy-N-[4-(2-oxo-imidazolidin-1-yl)-1-phenyl-cyclohexylmethyl]-benzamide Synthesis:

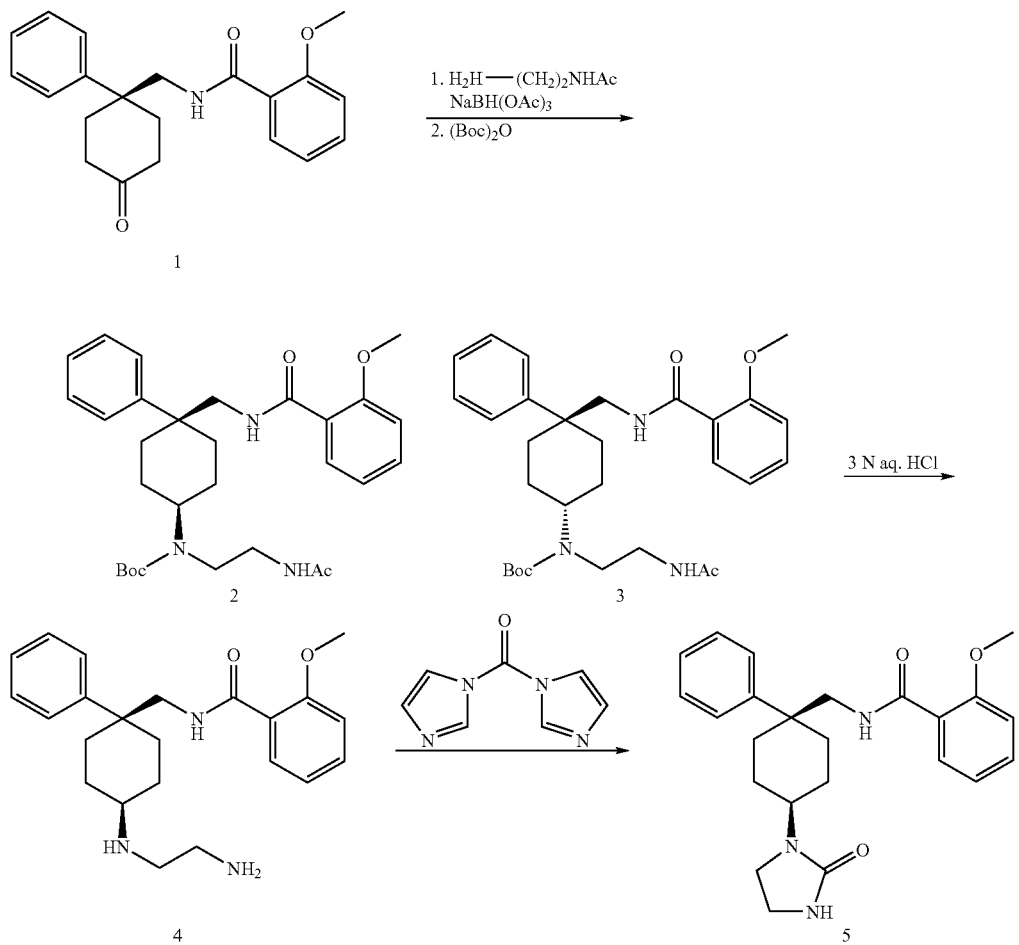

Compound 1: The synthesis of compound 1 was described in Example 31.

Compounds 2 and 3: To a solution of the ketone 1 (0.5 g, 1.5 mmol) in 10 ml of dichloroethane was added N-acetyl-ethylenediamine (0.34 ml, 3.0 mmol) and NaBH(OAc)₃ (0.64 g, 3.0 mmol) in a portion, respectively and the resulting solution was stirred for 12 h at 25° C. It was diluted with dichloromethane (50 ml) and washed with 1N aq. NaOH. Organic layer was separated and concentrated in vacuo to provide oily residue. The residue was dissolved in 20 ml of dichloromethane and stirred with 1.0 g (4.5 mmol) of di-tert-butyl dicarbonate for 1 h at 25° C. The reaction mixture was concentrated in vacuo yielding an oily residue which was purified on preparative HPLC (described in the synthesis of Example 31) to provide both cis-2 (retention time: 2.42 min) and trans-3 (retention time: 2.57 min) isomers.

Compound 4: Compound 2 was dissolved in 20 ml of 3N aq. HCl and stirred for 12 h at 25° C. The reaction was cooled to 0° C., basified with 20% aq. NaOH and extracted with dichloromethane (50 ml×3). The organic layer was dried over MgSO₄ and concentrated in vacuo to provide 157 mg of 4.

Compound 5: The cis-amine 4 (100 mg, 0.26 mmol) was dissolved in 5 ml of dichloromethane and stirred with carbonyldiimdazole (100 mg, 0.61 mmol) for 12 h at 25° C. The reaction mixture was concentrated and subjected to preparative HPLC (described in the synthesis of Example 31) to yield 14.6 mg of the desired product as a white solid. Mass Spec [M+H]⁺=408.

EXAMPLE 195

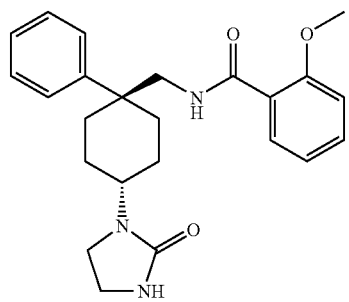

trans-2-Methoxy-N-[4-(2-oxo-imidazolidin-1-yl)-1-phenyl-cyclohexylmethyl]-benzamide Synthesis:

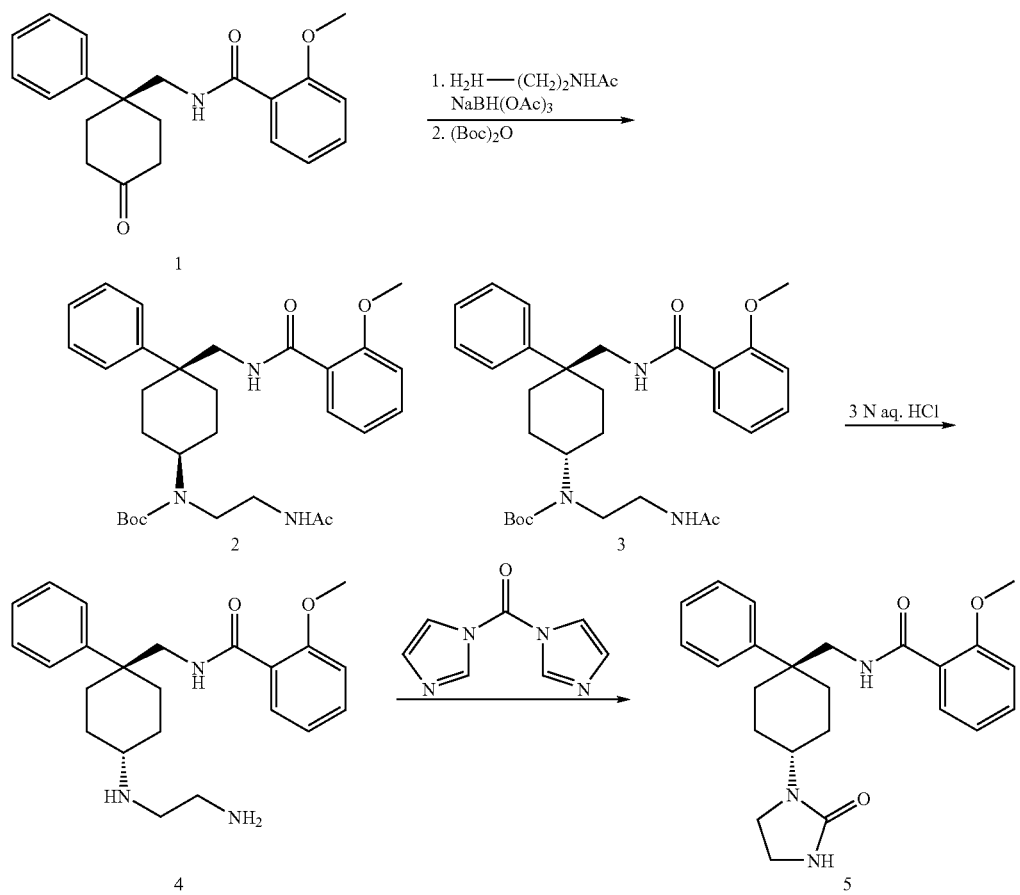

Compound 1: The synthesis of compound 1 was described in Example 31.

Compounds 2 and 3: The synthesis of compounds 2 and 3 is described in Example 194.

Compound 4: Compound 3 was dissolved in 20 ml of 3N aq. HCl and stirred for 12 h at 25° C. The reaction was cooled to 0° C., basified with 20% aq. NaOH and extracted with dichloromethane (50 ml×3). The organic layer was dried over MgSO$_4$ and concentrated in vacuo to provide 135 mg of 4.

Compound 5: The trans-amine 4 (100 mg, 0.26 mmol) was dissolved in 5 ml of dichloromethane and stirred with carbonyldiimdazole (100 mg, 0.61 mmol) for 12 h at 25° C. The reaction mixture was concentrated and subjected to preparative HPLC (described in the synthesis of Example 31) to yield 15.8 mg of the desired product as a white solid. Mass Spec [M+H]$^+$=408.

EXAMPLE 196

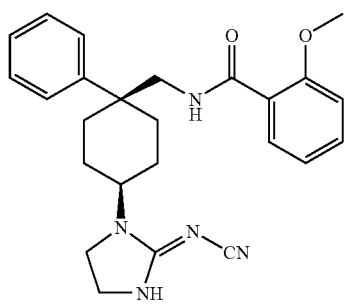

cis-N-[4-(2-Cyanoimino-imidazolin-1-yl)-1-phenyl-cyclohexylmethyl]-2-methoxy-benzamide Synthesis:

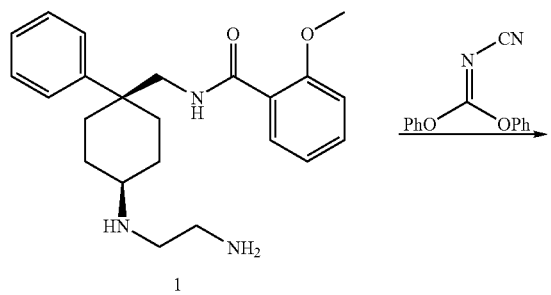

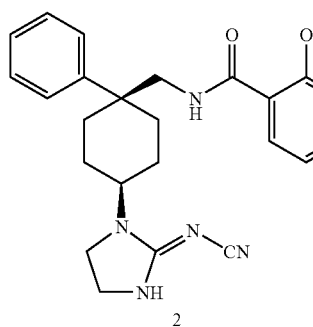

Compound 1: The synthesis of 1 was described in Example 194.

Compound 2; A solution of the cis-amine (75 mg, 0.20 mmol) and diphenyl cyanocarbonidate (75 mg, 0.32 mmol) in 3 ml of 2-propanol was stirred for 4 h at 70° C. The reaction mixture was purified on preparative HPLC (described in Example 31) to provide 32.0 mg (37%) of the desired product 2 as a colorless oil. Mass Spec [M+H]$^+$=432.

EXAMPLE 197

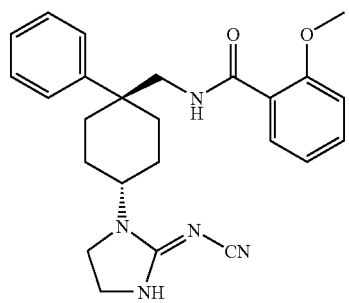

trans-N-[4-(2-Cyanoimino-imidazolin-1-yl)-1-phenyl-cyclohexylmethyl]-2-methoxy-benzamide Synthesis:

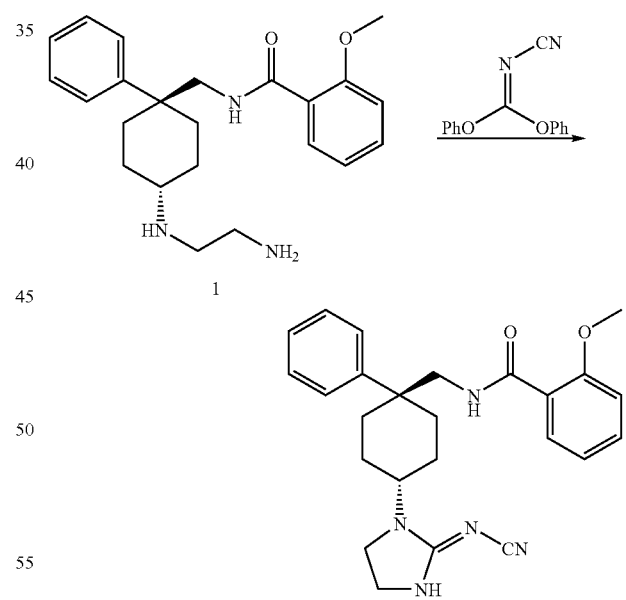

Compound 1: The synthesis of 1 was described in Example 194.

Compound 2 The reaction was carried out in a same procedure described in Example 196, starting with 75 mg (0.20 mmol) of the trans-amine and diphenyl cyanocarbonidate (75 mg, 0.32 mmol) to provide 47.6 mg (0.11 mmol, 55%) of the desired product 2 as a white solid. Mass Spec [M+H]$^+$=432.

EXAMPLE 198

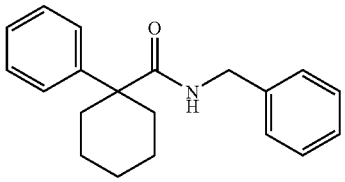

1-Phenyl-cyclohexanecarboxylic acid benzylamide

Synthesis:

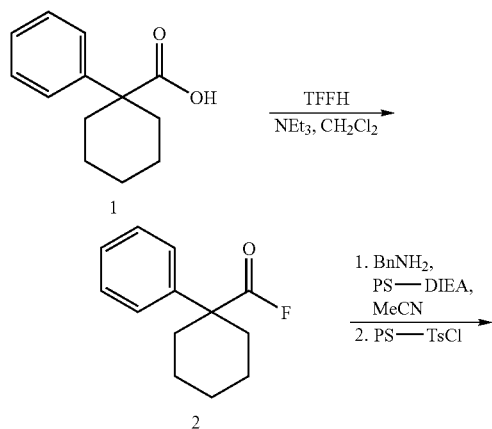

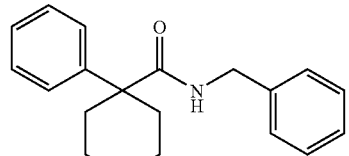

Compound 1: Compound 1 is commercially available.

Compound 2 A suspension of 1-phenyl-cyclohexanecarboxylic acid 1 (0.010 g; 0.049 mmol) in methylene chloride (1 mL) was cooled to 0° C. and treated with triethylamine (0.010 mL; 0.072 mmol) followed by tetramethylfluoroformamidinium hexafluorophosphate (0.014g; 0.053 mmol). After warming to room temperature (approximately 1 h), the solvent was removed and the residue was used in the subsequent reaction.

Compound 3: Compound 2 was dissolved in acetonitrile (1 mL). PS-DIEA (polystrene-diisopropylethylamine resin; 0.2 g) was added and the resulting suspension was treated with benzyl amine (0.006 mg; 0.056 mmol) and shaken at room temperature. After 12 h, PS-TsCl (polystrene-tosyl chloride, high loading resin; 0.2 g) was added and the reaction mixture is allowed to shake an additional 12 h. The reaction mixture was filtered and concentrated to give 0.011 g (79%) of compound 3. LCMS m/z=294.4 (M+H)$^+$

EXAMPLES 199–289

Examples 199 to 289 were synthesized using methodology described in Example 198. In some cases, further purification was accomplished using reverse phase HPLC.

| Ex. | Structure | Name | M + H |
|---|---|---|---|
| 199 | 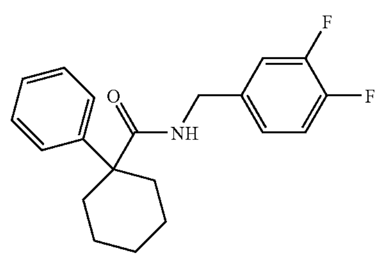 | 1-Phenyl-cyclohexanecarboxylic acid 3,4-difluoro-benzylamide | 330.4 |
| 200 | 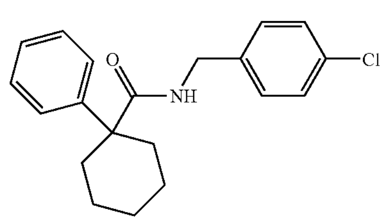 | 1-Phenyl-cyclohexanecarboxylic acid 4-chloro-benzylamide | 328.9 |

-continued

| Ex. | Structure | Name | M + H |
|---|---|---|---|
| 201 | 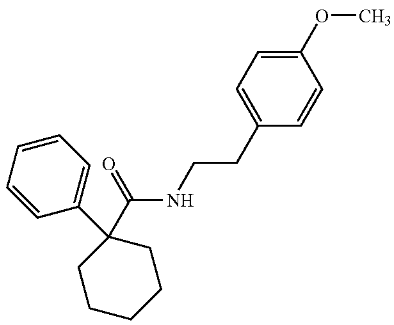 | 1-Phenyl-cyclohexanecarboxylic acid [2-(4-methoxy-phenyl)-ethyl]-amide | 338.5 |
| 202 | 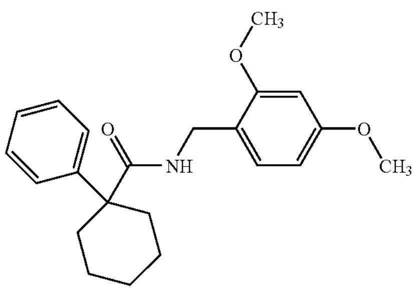 | 1-Phenyl-cyclohexanecarboxylic acid 2,4-dimethoxy-benzylamide | 354.5 |
| 203 | 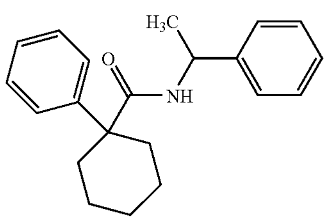 | 1-Phenyl-cyclohexanecarboxylic acid (1-phenyl-ethyl)-amide | 308.4 |
| 204 | 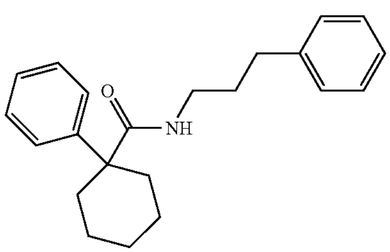 | 1-Phenyl-cyclohexanecarboxylic acid (3-phenyl-propyl)-amide | 322.5 |
| 205 | 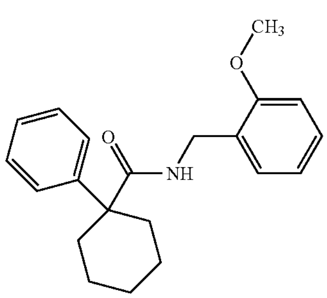 | 1-Phenyl-cyclohexanecarboxylic acid 2-methoxy-benzylamide | 324.4 |

-continued

| Ex. | Structure | Name | M + H |
|---|---|---|---|
| 206 | 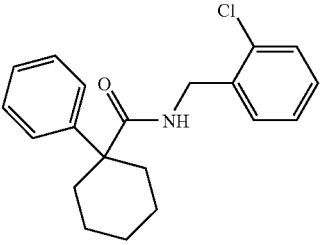 | 1-Phenyl-cyclohexanecarboxylic acid 2-chloro-benzylamide | 328.9 |
| 207 | 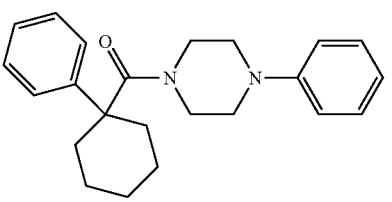 | (1-Phenyl-cyclohexyl)-(4-phenyl-piperazin-1-yl)-methanone | 349.5 |
| 208 | 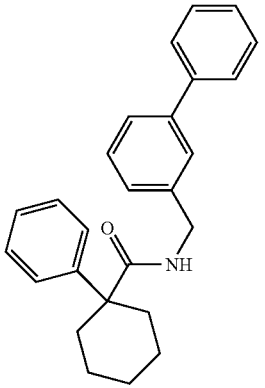 | 1-Phenyl-cyclohexanecarboxylic acid (biphenyl-3-ylmethyl)-amide | 370.5 |
| 209 | 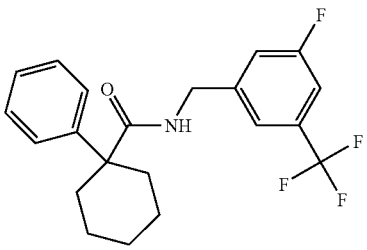 | 1-Phenyl-cyclohexanecarboxylic acid 3-fluoro-5-trifluoromethyl-benzylamide | 380.4 |
| 210 | 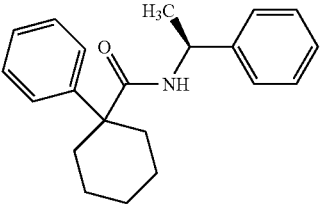 | 1-Phenyl-cyclohexanecarboxylic acid (1-phenyl-ethyl)-amide | 308.4 |
| 211 | 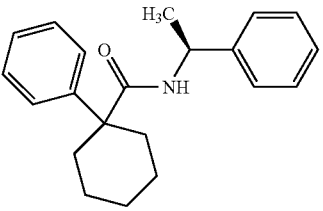 | 1-Phenyl-cyclohexanecarboxylic acid (1-phenyl-ethyl)-amide | 308.4 |

-continued

| Ex. | Structure | Name | M + H |
|---|---|---|---|
| 212 | 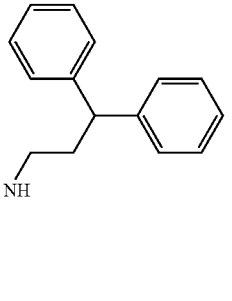 | 1-Phenyl-cyclohexanecarboxylic acid (3,3-diphenyl-propyl)-amide | 398.6 |
| 213 | 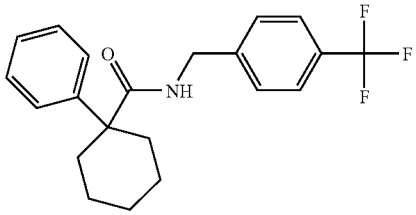 | 1-Phenyl-cyclohexanecarboxylic acid 4-trifluoromethyl-benzylamide | 362.4 |
| 214 | 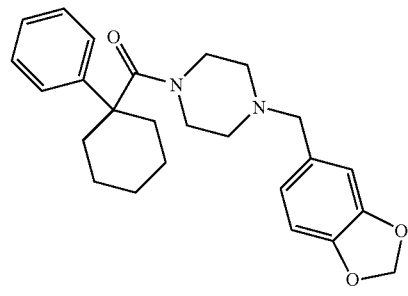 | (4-Benzo[1,3]dioxol-5-ylmethyl-piperazin-1-yl)-(1-phenyl-cyclohexyl)-methanone | 407.5 |
| 215 | 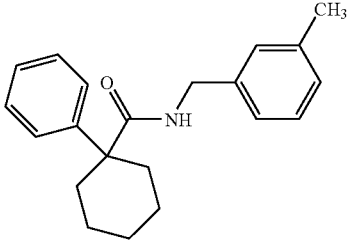 | 1-Phenyl-cyclohexanecarboxylic acid 3-methyl-benzylamide | 308.4 |
| 216 | 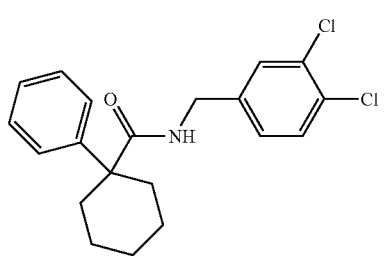 | 1-Phenyl-cyclohexanecarboxylic acid 3,4-dichloro-benzylamide | 363.3 |
| 217 | 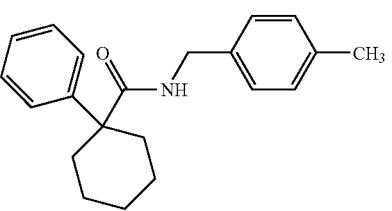 | 1-Phenyl-cyclohexanecarboxylic acid 4-methyl-benzylamide | 308.4 |

-continued

| Ex. | Structure | Name | M + H |
|---|---|---|---|
| 218 | 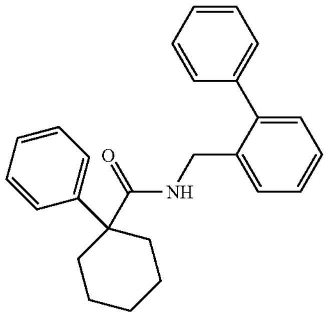 | 1-Phenyl-cyclohexanecarboxylic acid (biphenyl-2-ylmethyl)-amide | 370.5 |
| 219 | 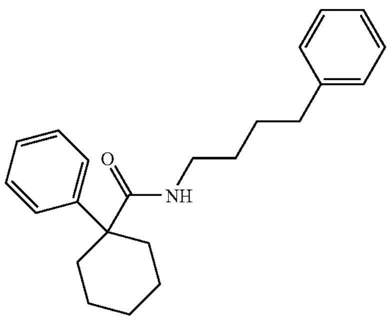 | 1-Phenyl-cyclohexanecarboxylic acid (4-phenyl-butyl)-amide | 336.5 |
| 220 | 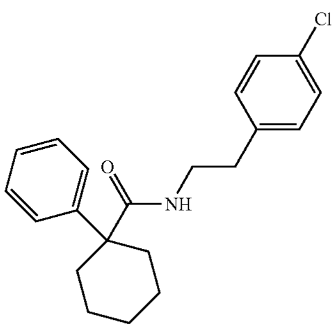 | 1-Phenyl-cyclohexanecarboxylic acid [2-(4-chloro-phenyl)-ethyl]-amide | 342.9 |
| 221 | 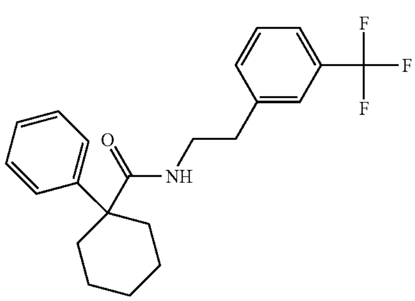 | 1-Phenyl-cyclohexanecarboxylic acid [2-(3-trifluoromethyl-phenyl)-ethyl]-amide | 376.4 |
| 222 | 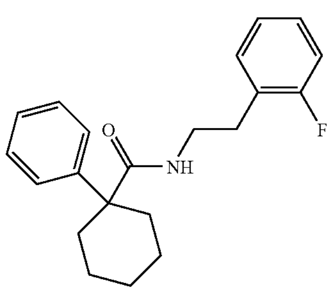 | 1-Phenyl-cyclohexanecarboxylic acid [2-(2-fluoro-phenyl)-ethyl]-amide | 326.4 |

| Ex. | Structure | Name | M + H |
|---|---|---|---|
| 223 | 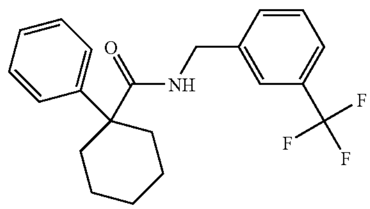 | 1-Phenyl-cyclohexanecarboxylic acid 3-trifluoromethyl-benzylamide | 362.4 |
| 224 | 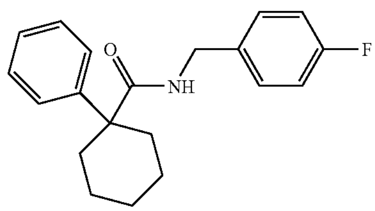 | 1-Phenyl-cyclohexanecarboxylic acid 4-fluoro-benzylamide | 312.4 |
| 225 | 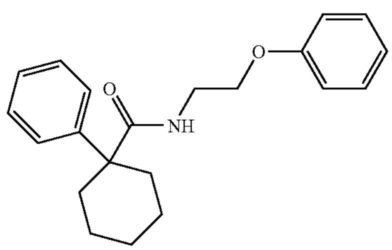 | 1-Phenyl-cyclohexanecarboxylic acid (2-phenoxy-ethyl)-amide | 324.4 |
| 226 | 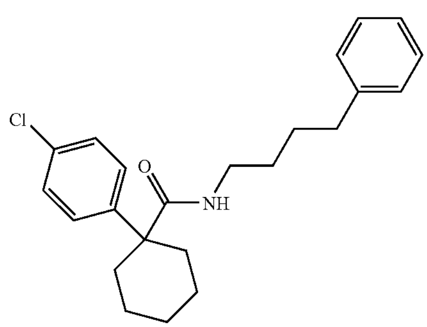 | 1-(4-Chloro-phenyl)-cyclohexanecarboxylic acid (4-phenyl-butyl)-amide | 370.9 |
| 227 | 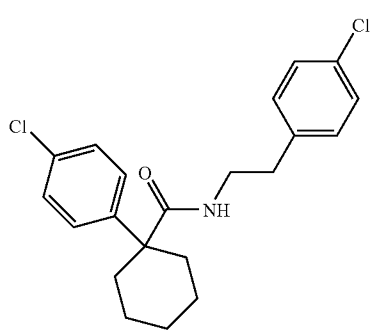 | 1-(4-Chloro-phenyl)-cyclohexanecarboxylic acid [2-(4-chloro-phenyl)-ethyl]-amide | 377.3 |

-continued

| Ex. | Structure | Name | M + H |
|---|---|---|---|
| 228 | 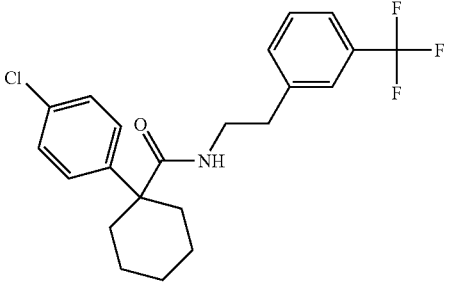 | 1-(4-Chloro-phenyl)-cyclohexanecarboxylic acid [2-(3-trifluoromethyl-phenyl)-ethyl]-amide | 410.9 |
| 229 | 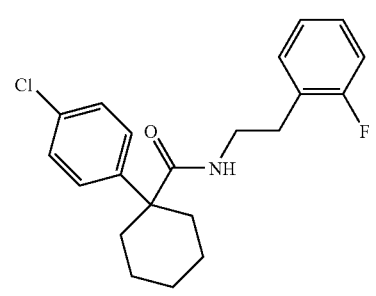 | 1-(4-Chloro-phenyl)-cyclohexanecarboxylic acid [2-(2-fluoro-phenyl)-ethyl]-amide | 360.9 |
| 230 | 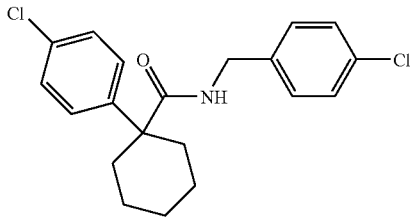 | 1-(4-Chloro-phenyl)-cyclohexanecarboxylic acid 4-chloro-benzylamide | 363.3 |
| 231 | 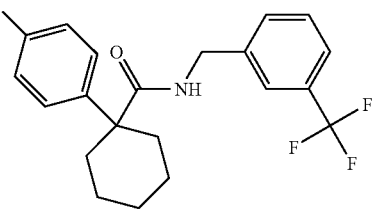 | 1-(4-Chloro-phenyl)-cyclohexanecarboxylic acid 3-trifluoromethyl-benzylamide | 396.9 |
| 232 | 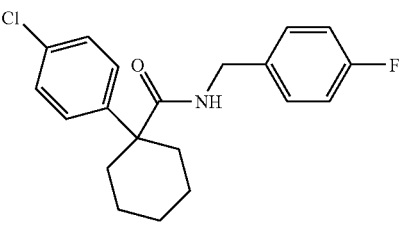 | 1-(4-Chloro-phenyl)-cyclohexanecarboxylic acid 4-fluoro-benzylamide | 346.8 |

-continued

| Ex. | Structure | Name | M + H |
|---|---|---|---|
| 233 | 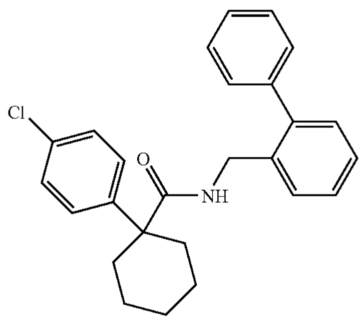 | 1-(4-Chloro-phenyl)-cyclohexanecarboxylic acid (biphenyl-2-ylmethyl)-amide | 405.0 |
| 234 | 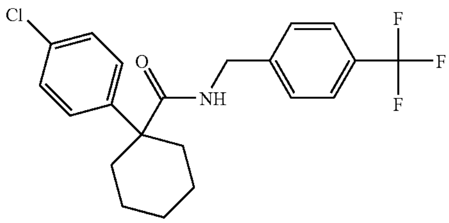 | 1-(4-Chloro-phenyl)-cyclohexanecarboxylic acid 4-trifluoromethyl-benzylamide | 396.9 |
| 235 | 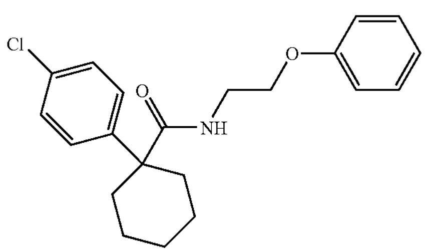 | 1-(4-Chloro-phenyl)-cyclohexanecarboxylic acid (2-phenoxy-ethyl)-amide | 358.9 |
| 236 | 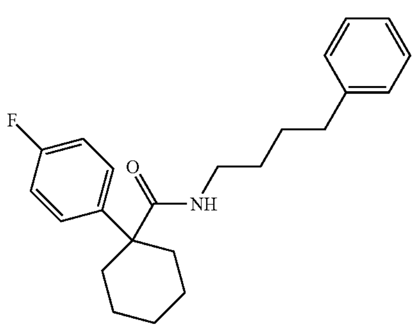 | 1-(4-Fluoro-phenyl)-cyclohexanecarboxylic acid (4-phenyl-butyl)-amide | 354.5 |
| 237 | 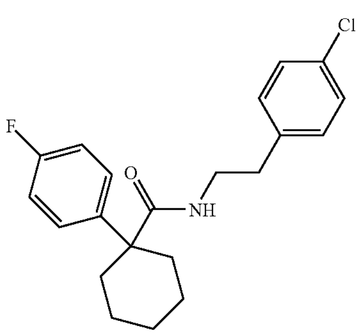 | 1-(4-Fluoro-phenyl)-cyclohexanecarboxylic acid [2-(4-chloro-phenyl)-ethyl]-amide | 360.9 |

| Ex. | Structure | Name | M + H |
|---|---|---|---|
| 238 | 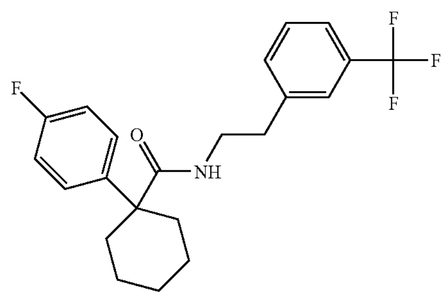 | 1-(4-Fluoro-phenyl)-cyclohexanecarboxylic acid [2-(3-trifluoromethyl-phenyl)-ethyl]-amide | 394.4 |
| 239 | 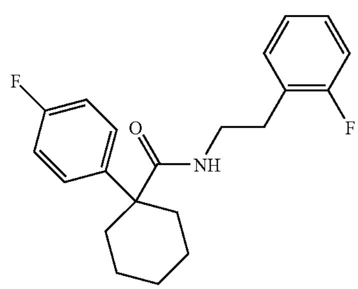 | 1-(4-Fluoro-phenyl)-cyclohexanecarboxylic acid [2-(2-fluoro-phenyl)-ethyl]-amide | 344.4 |
| 240 | 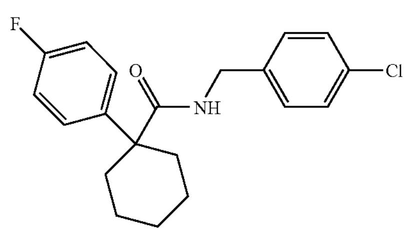 | 1-(4-Fluoro-phenyl)-cyclohexanecarboxylic acid 4-chloro-benzylamide | 346.8 |
| 241 | 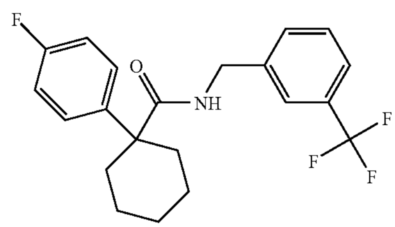 | 1-(4-Fluoro-phenyl)-cyclohexanecarboxylic acid 3-trifluoromethyl-benzylamide | 380.4 |
| 242 | 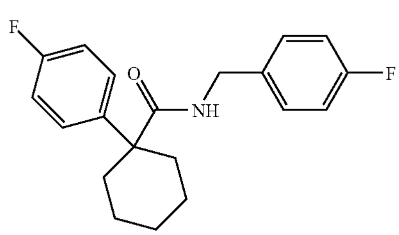 | 1-(4-Fluoro-phenyl)-cyclohexanecarboxylic acid 4-fluoro-benzylamide | 330.4 |

| Ex. | Structure | Name | M + H |
|---|---|---|---|
| 243 | 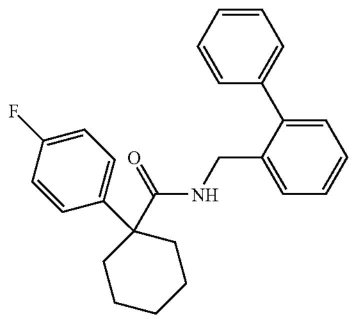 | 1-(4-Fluoro-phenyl)-cyclohexanecarboxylic acid (biphenyl-2-ylmethyl)-amide | 387.5 |
| 244 | 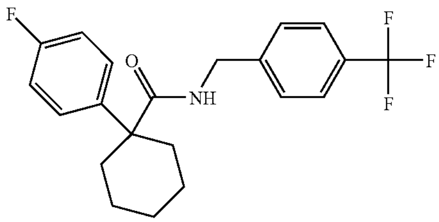 | 1-(4-Fluoro-phenyl)-cyclohexanecarboxylic acid 4-trifluoromethyl-benzylamide | 380.4 |
| 245 | 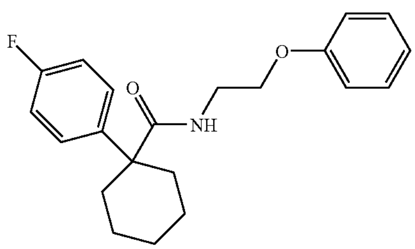 | 1-(4-Fluoro-phenyl)-cyclohexanecarboxylic acid (2-phenoxy-ethyl)-amide | 342.4 |
| 246 | 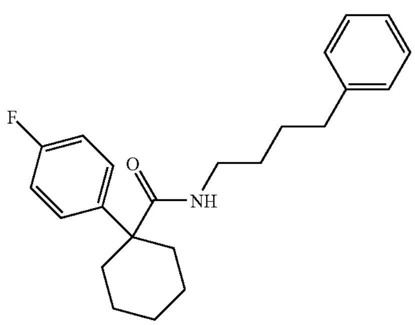 | 1-(3-Fluoro-phenyl)-cyclohexanecarboxylic acid (4-phenyl-butyl)-amide | 354.5 |
| 247 | 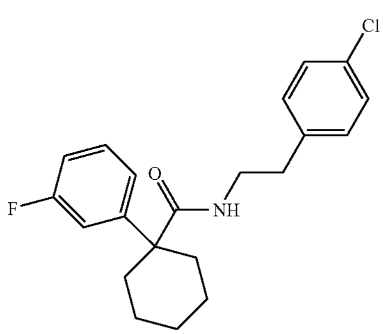 | 1-(3-Fluoro-phenyl)-cyclohexanecarboxylic acid [2-(4-chloro-phenyl)-ethyl]-amide | 360.9 |

-continued

| Ex. | Structure | Name | M + H |
|---|---|---|---|
| 248 | 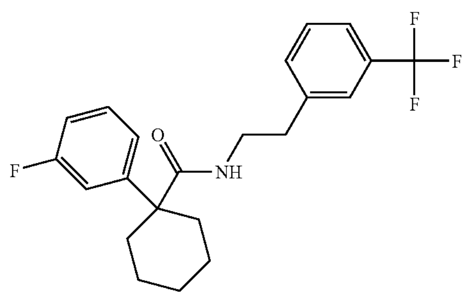 | 1-(3-Fluoro-phenyl)-cyclohexanecarboxylic acid [2-(3-trifluoromethyl-phenyl)-ethyl]-amide | 394.4 |
| 249 | 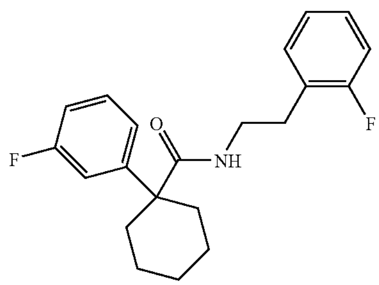 | 1-(3-Fluoro-phenyl)-cyclohexanecarboxylic acid [2-(2-fluoro-phenyl)-ethyl]-amide | 344.4 |
| 250 | 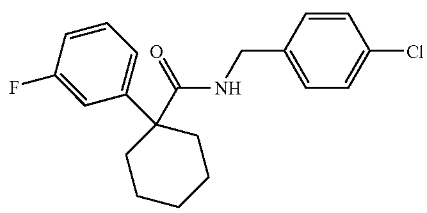 | 1-(3-Fluoro-phenyl)-cyclohexanecarboxylic acid 4-chloro-benzylamide | 346.8 |
| 251 | 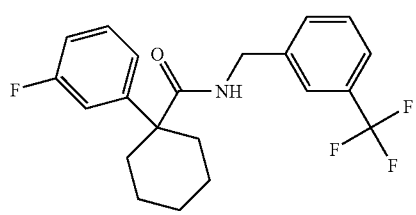 | 1-(3-Fluoro-phenyl)-cyclohexanecarboxylic acid 3-trifluoromethyl-benzylamide | 380.4 |
| 252 | 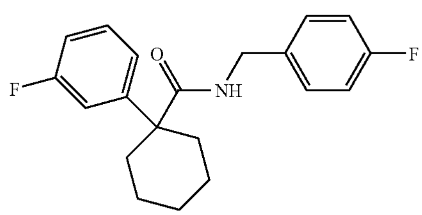 | 1-(3-Fluoro-phenyl)-cyclohexanecarboxylic acid 4-fluoro-benzylamide | 330.4 |
| 253 | 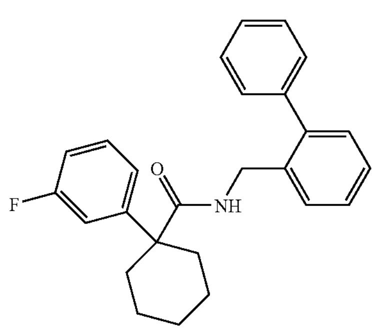 | 1-(3-Fluoro-phenyl)-cyclohexanecarboxylic acid (biphenyl-2-ylmethyl)-amide | 388.5 |

-continued

| Ex. | Structure | Name | M + H |
|---|---|---|---|
| 254 | 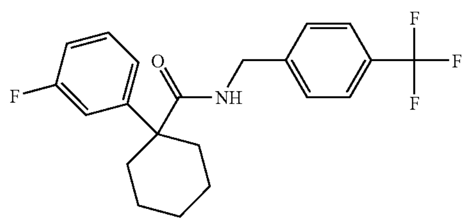 | 1-(3-Fluoro-phenyl)-cyclohexanecarboxylic acid 4-trifluoromethyl-benzylamide | 380.4 |
| 255 | 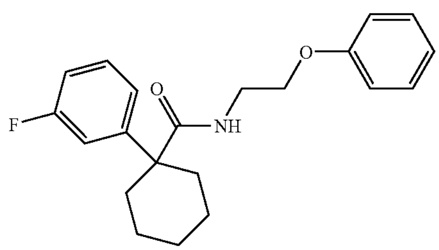 | 1-(3-Fluoro-phenyl)-cyclohexanecarboxylic acid (2-phenoxy-ethyl)-amide | 341.4 |
| 256 | 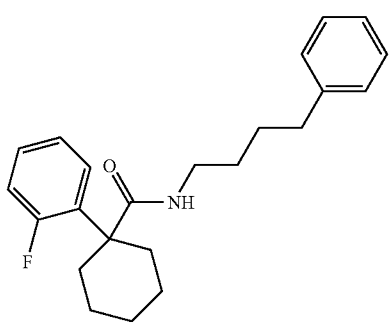 | 1-(2-Fluoro-phenyl)-cyclohexanecarboxylic acid (4-phenyl-butyl)-amide | 354.5 |
| 257 | 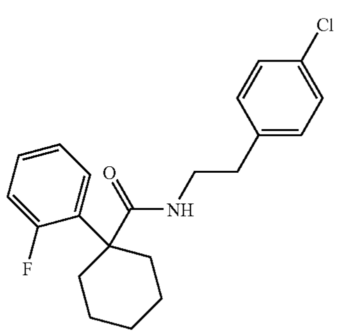 | 1-(2-Fluoro-phenyl)-cyclohexanecarboxylic acid [2-(4-chloro-phenyl)-ethyl]-amide | 360.9 |
| 258 | 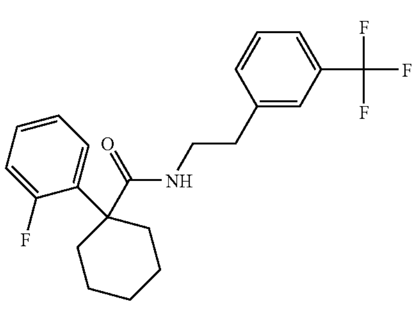 | 1-(2-Fluoro-phenyl)-cyclohexanecarboxylic acid [2-(3-trifluoromethyl-phenyl)-ethyl]-amide | 384.4 |

-continued

| Ex. | Structure | Name | M + H |
|---|---|---|---|
| 259 | 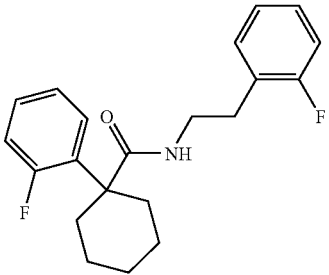 | 1-(2-Fluoro-phenyl)-cyclohexanecarboxylic acid [2-(2-fluoro-phenyl)-ethyl]-amide | 344.4 |
| 260 | 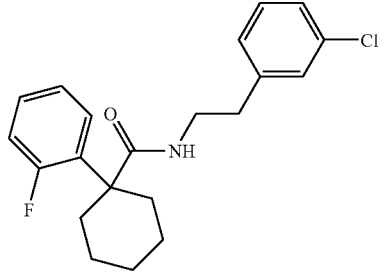 | 1-(2-Fluoro-phenyl)-cyclohexanecarboxylic acid 4-chloro-benzylamide | 346.8 |
| 261 | 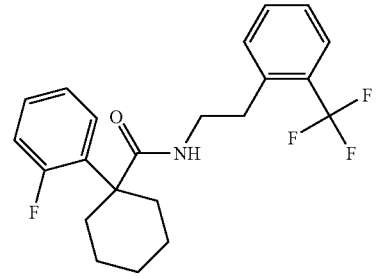 | 1-(2-Fluoro-phenyl)-cyclohexanecarboxylic acid 3-trifluoromethyl-benzylamide | 380.4 |
| 262 | 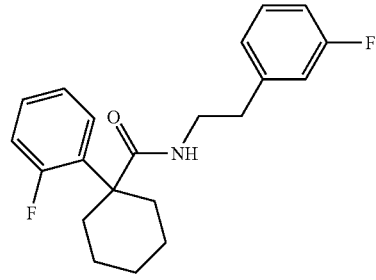 | 1-(2-Fluoro-phenyl)-cyclohexanecarboxylic acid 4-fluoro-benzylamide | 330.4 |
| 263 | 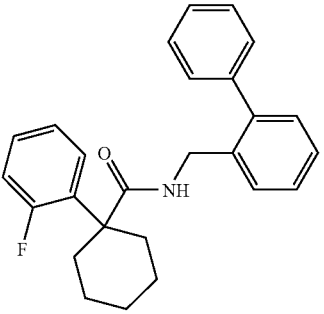 | 1-(2-Fluoro-phenyl)-cyclohexanecarboxylic acid (biphenyl-2-ylmethyl)-amide | 387.5 |

-continued

| Ex. | Structure | Name | M + H |
|---|---|---|---|
| 264 | 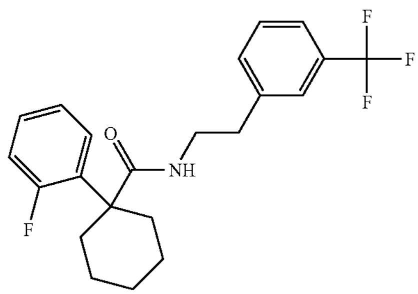 | 1-(2-Fluoro-phenyl)-cyclohexanecarboxylic acid 4-trifluoromethyl-benzylamide | 380.4 |
| 265 | 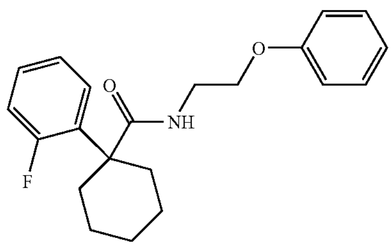 | 1-(2-Fluoro-phenyl)-cyclohexanecarboxylic acid (2-phenoxy-ethyl)-amide | 342.4 |
| 266 | 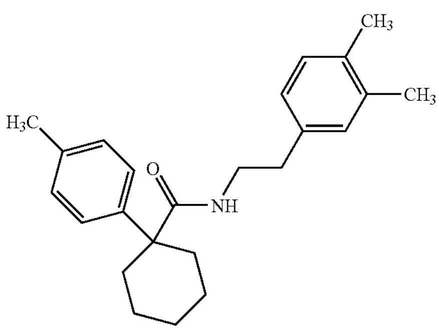 | 1-p-Tolyl-cyclohexanecarboxylic acid [2-(3,4-dimethyl-phenyl)-ethyl]-amide | 350.5 |
| 267 | 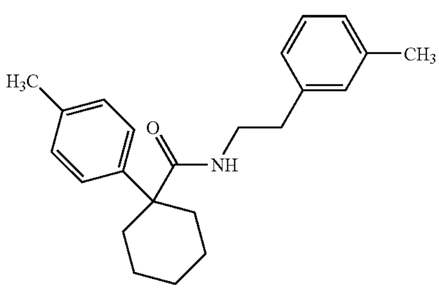 | 1-p-Tolyl-cyclohexanecarboxylic acid (2-m-tolyl-ethyl)-amide | 336.5 |
| 268 | 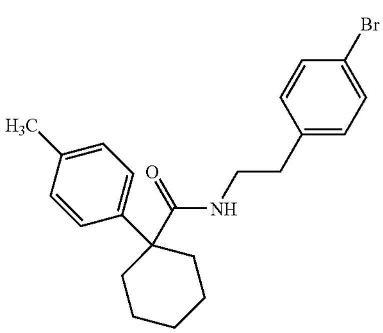 | 1-p-Tolyl-cyclohexanecarboxylic acid [2-(4-bromo-phenyl)-ethyl]-amide | 401.4 |

| Ex. | Structure | Name | M + H |
|---|---|---|---|
| 269 | 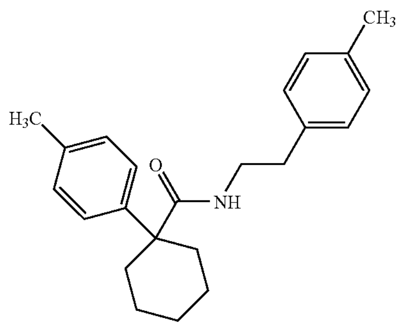 | 1-p-Tolyl-cyclohexanecarboxylic acid (2-p-tolyl-ethyl)-amide | 336.5 |
| 270 | 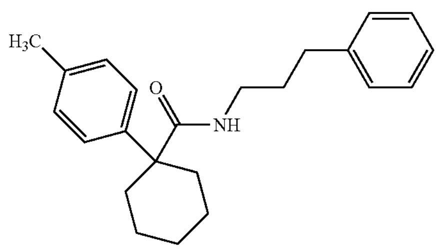 | 1-p-Tolyl-cyclohexanecarboxylic acid (3-phenyl-propyl)-amide | 336.5 |
| 271 | 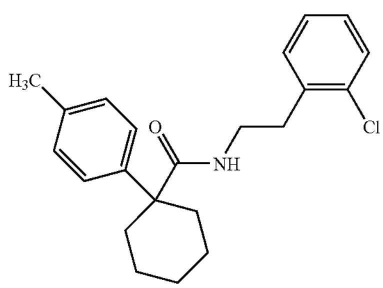 | 1-p-Tolyl-cyclohexanecarboxylic acid [2-(2-chloro-phenyl)-ethyl]-amide | 356.9 |
| 272 | 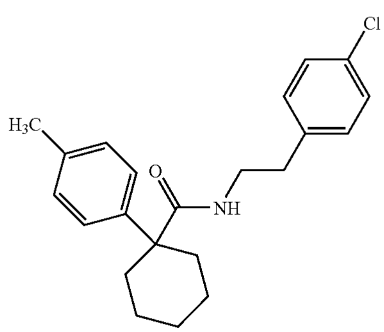 | 1-p-Tolyl-cyclohexanecarboxylic acid [2-(4-chloro-phenyl)-ethyl]-amide | 356.9 |
| 273 | 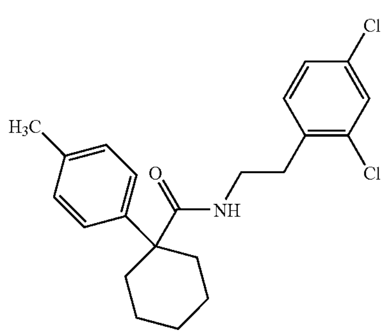 | 1-p-Tolyl-cyclohexanecarboxylic acid [2-(2,4-dichloro-phenyl)-ethyl]-amide | 391.4 |

-continued
| Ex. | Structure | Name | M + H |
|---|---|---|---|
| 274 | 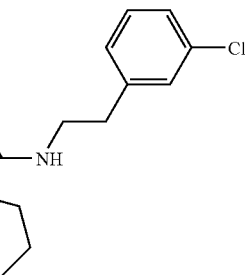 | 1-p-Tolyl-cyclohexanecarboxylic acid [2-(3-chloro-phenyl)-ethyl]-amide | 356.9 |
| 275 | 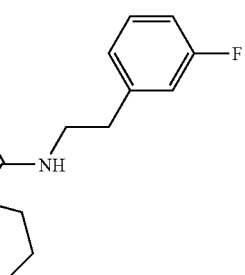 | 1-p-Tolyl-cyclohexanecarboxylic acid 4-fluoro-benzylamide | 326.4 |
| 276 | 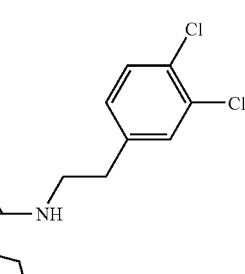 | 1-p-Tolyl-cyclohexanecarboxylic acid [2-(3,4-dichloro-phenyl)-ethyl]-amide | 391.4 |
| 277 | 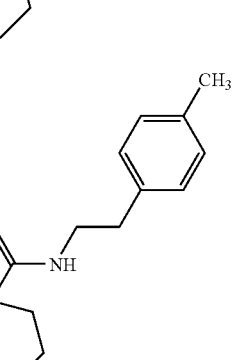 | 1-p-Tolyl-cyclohexanecarboxylic acid 3-methyl-benzylamide | 322.5 |
| 278 | 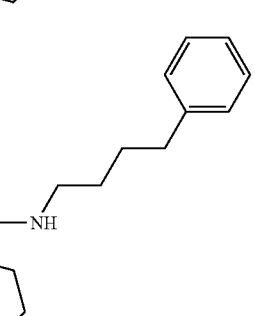 | 1-p-Tolyl-cyclohexanecarboxylic acid (4-phenyl-butyl)-amide | 350.5 |

| Ex. | Structure | Name | M + H |
|---|---|---|---|
| 279 | 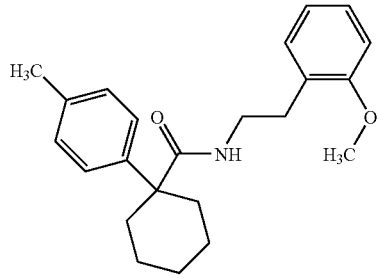 | 1-p-Tolyl-cyclohexanecarboxylic acid [2-(2-methoxy-phenyl)-ethyl]-amide | 352.5 |
| 280 | 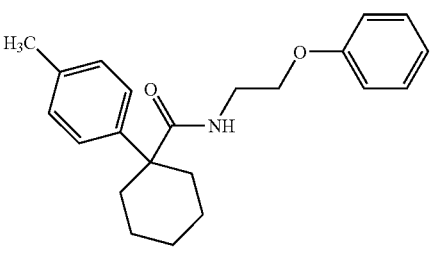 | 1-p-Tolyl-acid (2-phenoxy-ethyl)-amide | 338.5 |
| 281 | 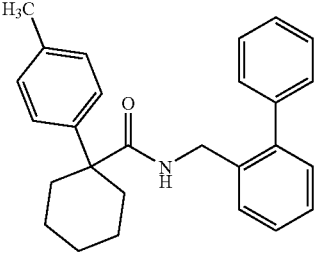 | 1-p-Tolyl-cyclohexanecarboxylic acid (biphenyl-2-ylmethyl)-amide | 384.5 |
| 282 | 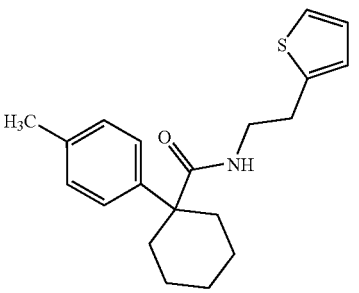 | 1-p-Tolyl-cyclohexanecarboxylic acid (2-thiophen-2-yl-ethyl)-amide | 328.5 |
| 283 | 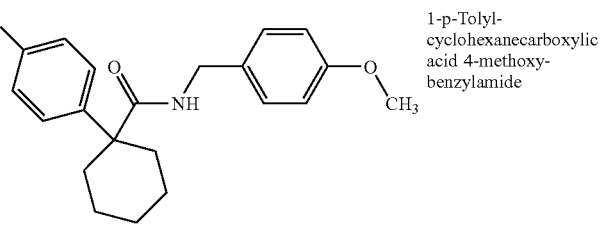 | 1-p-Tolyl-cyclohexanecarboxylic acid 4-methoxy-benzylamide | 338.5 |

-continued

| Ex. | Structure | Name | M + H |
|---|---|---|---|
| 284 | 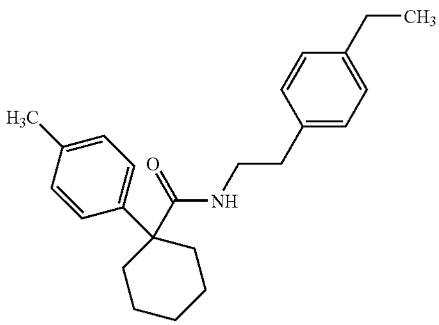 | 1-p-Tolyl-cyclohexanecarboxylic acid [2-(4-ethyl-phenyl)-ethyl]-amide | 350.5 |
| 285 | 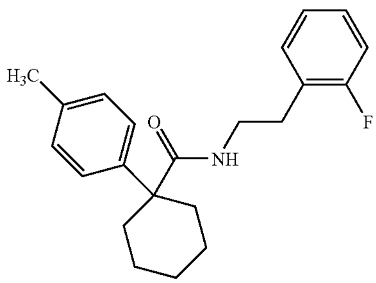 | 1-p-Tolyl-cyclohexanecarboxylic acid [2-(2-fluoro-phenyl)-ethyl]-amide | 340.5 |
| 286 | 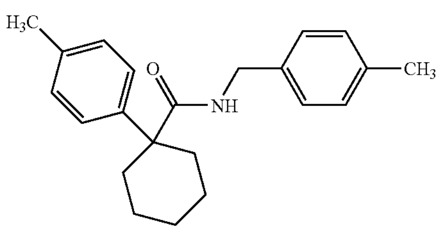 | 1-p-Tolyl-cyclohexanecarboxylic acid 4-methyl-benzylamide | 322.5 |
| 287 | 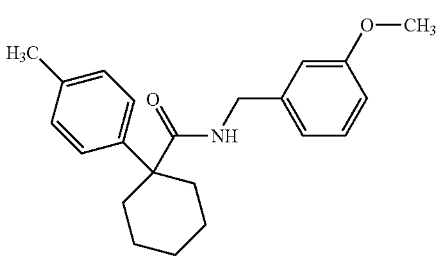 | 1-p-Tolyl-cyclohexanecarboxylic acid 3-methoxy-benzylamide | 338.5 |
| 288 | 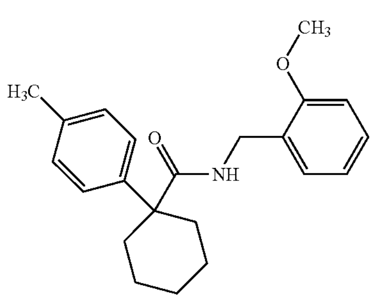 | 1-p-Tolyl-cyclohexanecarboxylic acid 2-methoxy-benzylamide | 338.5 |

| Ex. | Structure | Name | M + H |
|---|---|---|---|
| 289 | 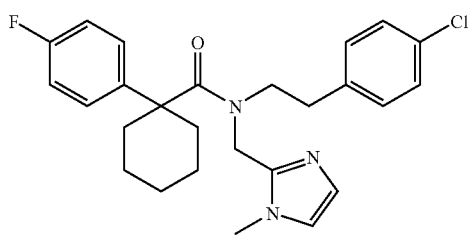 | 1-p-Tolyl-cyclohexanecarboxylic acid (1-phenyl-ethyl)-amide | 322.5 |

EXAMPLE 290

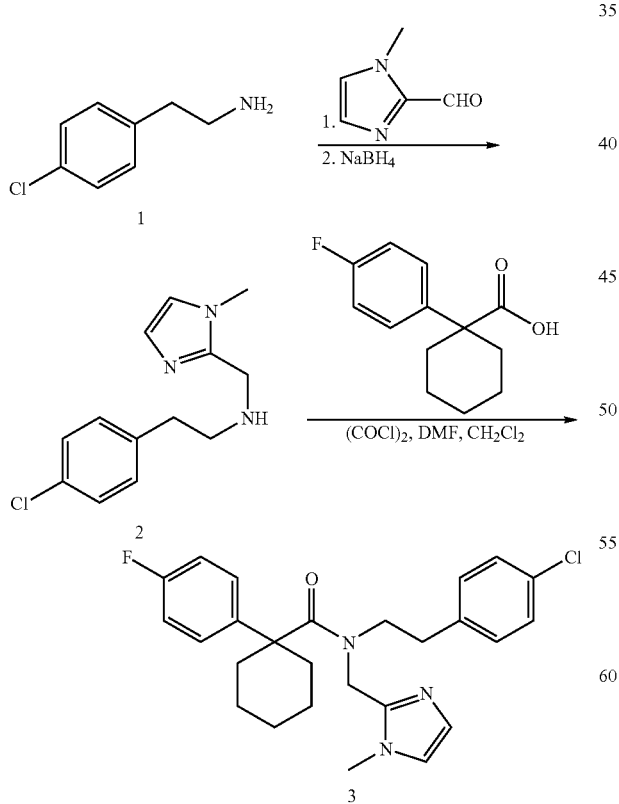

1-(4-fluoro-phenyl)-cyclohexanecarboxylic acid [2-(4-chloro-phenyl)-ethyl]-(1-methyl-1H-imidazol-2-ylmethyl)-amide Synthesis:

Compound 1: Compound 1 is commercially available.

Compound 2: A suspension 2-(4-chlorophenyl)ethylamine (2.25 mL; 16.1 mmol) and sodium sulfate (10.0 g; 70.4 mmol) in methanol (20 mL) was treated with 1-methyl-1H-imidazole-2-carbaldehyde (1.80 g; 16.3 mmol) and heated to 40° C. After 24 h, the reaction mixture was cooled to 0° C., treated with sodium borohydride (0.73 g; 19.3 mmol) and allowed to slowly warm to room temperature. After 3 h, the solvent was removed and the crude residue was partitioned between ethyl acetate and saturated aqueous sodium bicarbonate. The organic layer was separated, washed with saturated aqueous sodium chloride, dried (magnesium sulfate) and concentrated. The oily residue was dissolved in tetrahydrofuran and treated with a solution of 1N HCl in diethyl ether (35 mL). A white precipitate formed immediately and was collected to give 5g (96%) of [2-(4-chloro-phenyl)-ethyl]-(1-methyl-1H-imidazol-2-ylmethyl)-amine. 2HCl. LCMS m/z=250.7 (M+H)$^+$ Compound 3: A suspension of 1-(4-fluoro-phenyl)-cyclohexanecarboxylic acid (0.106 mg; 0.48 mmol) in methylene chloride (10 mL) was treated with oxalyl chloride (0.042 mL; 0.48 mmol) and 1 drop of N,N-dimethylformamide. The reaction mixture was allowed to stir at room temperature for 15 min at which time triethylamine (0.28 mL; 2.0 mmol) and [2-(4-Chloro-phenyl)-ethyl]-(1-methyl-1H-imidazol-2-ylmethyl)-amine. 2HCl (0.16 g; 0.50 mmol) was added. After an addition 30 min of stirring the solvent was removed and the residue was purified using reverse phase HPLC to give 0.114 g (52%) of 3 as a white solid. LCMS m/z=455.0 (M+H)$^+$.

EXAMPLE 291

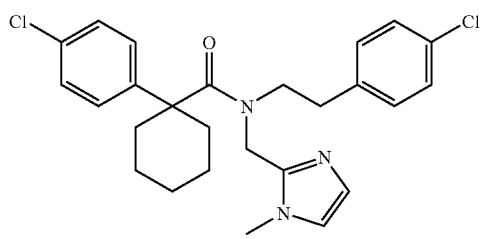

1-(4-Chloro-phenyl)-cyclohexanecarboxylic acid [2-(4-chloro-phenyl) ethyl]-(1-methyl-1H-imidazol-2-ylmethyl)-amide.

Synthesis:
The titled compound was prepared using methodology described in Example 290. LCMS m/z=471.5 (M+H)⁺.

EXAMPLE 292

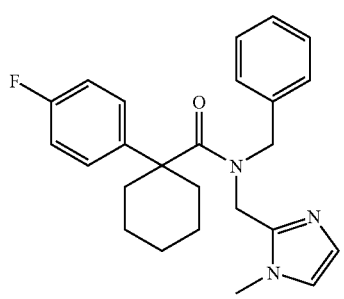

1-(4-fluoro-phenyl)-cyclohexanecarboxylic acid benzyl-(1-methyl-1H-imidazol-2-ylmethyl)-amide The titled compound was prepared using methodology described in Example 290. LCMS m/z=406.5 (M+H)⁺

EXAMPLE 293

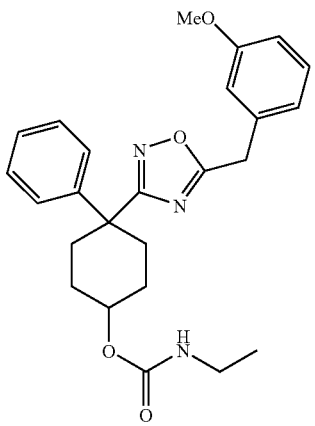

Ethyl-carbamic acid 4-[5-(3-methoxy-benzyl)-[1,2,4]oxadiazol-3-yl]-4-phenyl-cyclohexyl ester Synthesis:

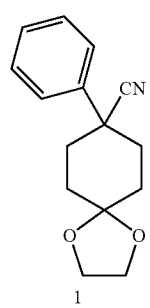

-continued

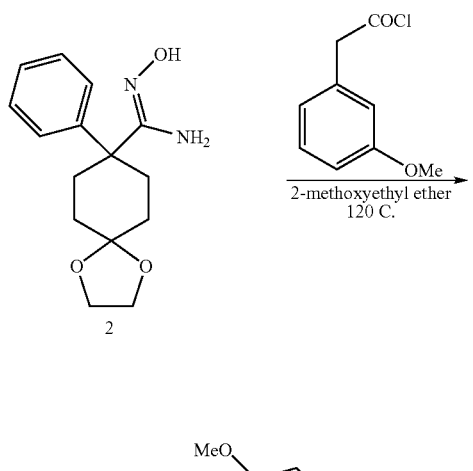

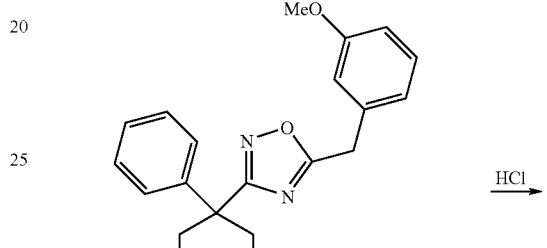

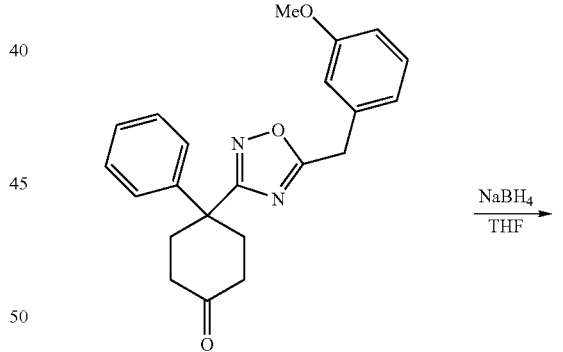

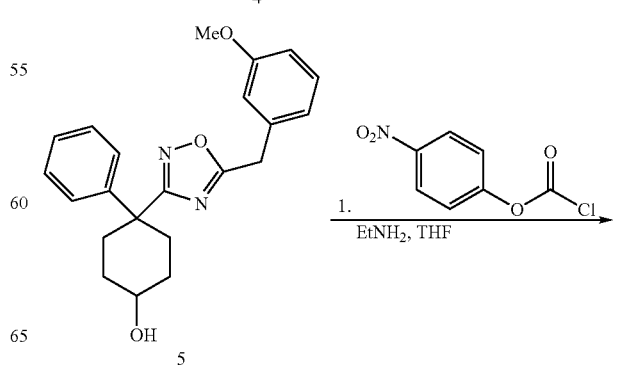

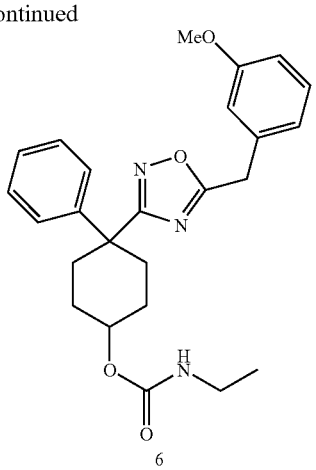

6

Compound 1: the synthesis of Compound 1 is described in Example 31.

Compound 2: A solution of compound 1 (5.8 g; 23.8 mmol), hydroxylamine hydrochloride (4.21 g; 60.6 mmol) and sodium methoxide (3.27 g; 60.6 mmol) in n-propanol (100 mL) was heated at 98° C. overnight. The reaction mixture was concentrated under reduced pressure, diluted with EtOAc (100 mL), washed with H$_2$O and dried over anhydrous sodium sulfate. Purification by flash chromatography (1:1; Hexanes:ethyl acetate) gave 2 (4.6 g; 71%) as a white solid. LCMS m/z=277.1 (M+H)$^+$ Compound 3: To a solution of Compound 2 (0.100 g, 0.36 mmol) in 2-methoxyethyl ether (5 mL) was added potassium carbonate (0.72 mmol) followed by 3-methoxyphenyl acetyl chloride (0.067 g, 0.36 mmol). The reaction mixture was stirred at room temperature for 30 min. then heated at 120° C. for 3 h. After cooling to room temperature, the reaction mixture was diluted with water, extracted with ethyl acetate and dried over anhydrous sodium sulfate. Purification by column chromatography on silica gel (7:3 hexanes:ethyl acetate) gave 3 (0.085 g; 58%) as an oil. $^1$H NMR (CDCl$_3$, 300 MHz): δ (ppm) 1.65–1.80 (4H, m), 2.25–2.40 (2H, m), 2.60–2.70 (2H, m), 3.74 (3H, s), 3.94 (4H, s), 4.14 (2H, s), 6.75–6.90 (3H, m), 7.15–7.45 (6H, m); LCMS m/z=407.2 (M+H)$^+$.

Compound 4: A solution of Compound 3 (80 mg, 0.20 mmol) in tetrahydrofuran (1.25 mL) was treated with 2 N HCl (0.4 mL) and heated at 40° C. for 6 h. Saturated aqueous sodium bicarbonate was added. The aqueous phase was extracted with ethyl acetate and the organic phase dried over anhydrous sodium sulfate. Purification by column chromatography on silica gel (7:3 hexanes:ethyl acetate) gave 4 (40 mg; 60%) as an oil. LCMS m/z=363.2 (M+H)$^+$.

Compound 5: A solution of 4 (1.2 g, 3.31 mmol) in tetrahydrofuran ( 20 mL) at 0° C. was treated with sodium borohydride (250 mg, 6.62 mmol). After stirring from 0° C. to room temperature overnight, the reaction mixture was quenched with saturated aqueous sodium carbonate and extracted with ethyl acetate. The organic layer was washed with saturated aqueous sodium chloride and dried over anhydrous sodium sulfate. Purification by column chromatography on silica gel (7:3 hexanes:ethyl acetate) gave 5 (1.12 g, 93%). LCMS m/z=365.5 (M+H)$^+$.

Compound 6: $^1$H NMR (CDCl$_3$, 300 MHz): δ (ppm) 1.11 (3H, t, J=7.1 Hz), 1.50–1.70 (2H, m), 1.90–2.18 (4H, bd, J=9.7 Hz), 2.88 (2H, bd, J=13.6 Hz), 3.10–3.25 (2H, m), 3.74 (3H, s), 4.14 (2H, s), 4.60–4.80 (2H, m), 6.70–6.90 (3H, m), 7.08–7.40 (6H, m). LCMS m/z=436.2 (M+H)$^+$.

EXAMPLES 294–322

Examples 294 to 322 were synthesized using methodology described in Example 293. In some cases, further purification was accomplished using reverse phase HPLC.

| Ex. | Structure | Name | M + H |
|---|---|---|---|
| 295 | 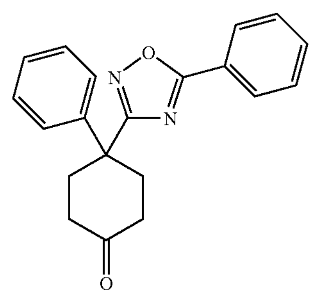 | 4-Phenyl-4-(5-phenyl-[1,2,4]oxadiazol-3-yl)-cyclohexanone | 319.4 |

| Ex. | Structure | Name | M + H |
|---|---|---|---|
| 296 | 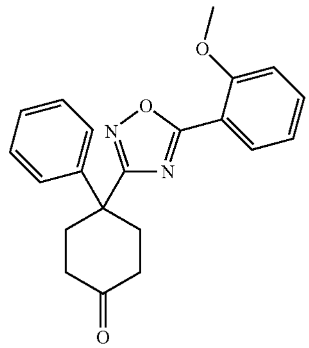 | 4-[5-(2-Methoxy-phenyl)-[1,2,4]oxadiazol-3-yl]-4-phenyl-cyclohexanone | 349.4 |
| 297 | 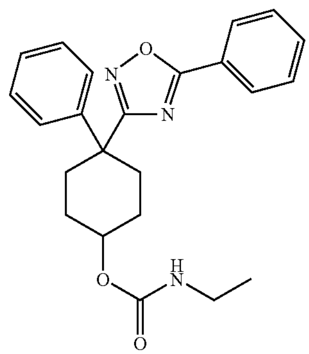 | Ethyl-carbamic acid 4-phenyl-4-(5-phenyl-[1,2,4]oxadiazol-3-yl)-cyclohexyl ester | 392.5 |
| 298 | 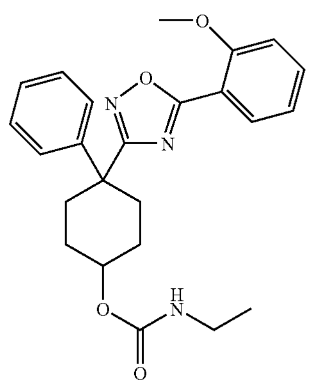 | Ethyl-carbamic acid 4-[5-(2-methoxy-phenyl)-[1,2,4]oxadiazol-3-yl]-4-phenyl-cyclohexyl ester | 422.5 |
| 299 | 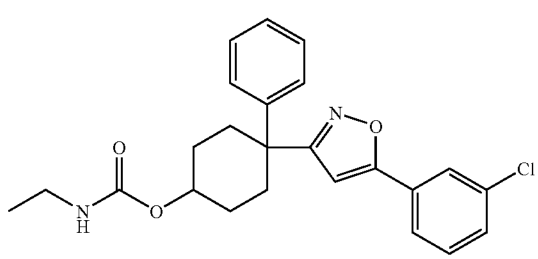 | Ethyl-carbamic acid 4-[5-(3-chloro-phenyl)-[1,2,4]oxadiazol-3-yl]-4-phenyl-cyclohexyl ester | 426.9 |

-continued

| Ex. | Structure | Name | M + H |
|---|---|---|---|
| 300 | 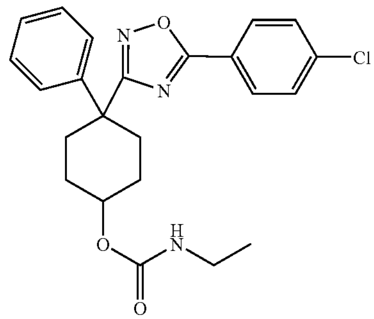 | Ethyl-carbamic acid 4-[5-(4-chloro-phenyl)-[1,2,4]oxadiazol-3-yl]-4-phenyl-cyclohexyl ester | 426.9 |
| 301 | 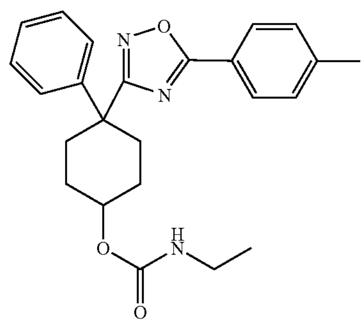 | Ethyl-carbamic acid 4-phenyl-4-(5-p-tolyl-[1,2,4]oxadiazol-3-yl)-cyclohexyl ester | 406.5 |
| 302 | 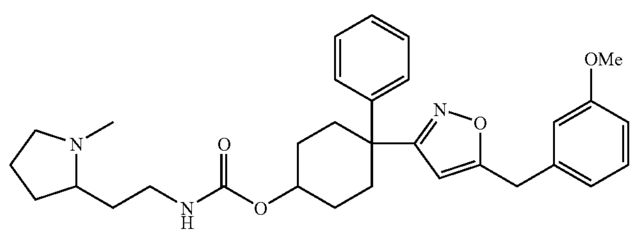 | [2-(1-Methyl-pyrrolidin-2-yl)-ethyl]-carbamic acid 4-[5-(3-methoxy-benzyl)-[1,2,4]oxadiazol-3-yl]-4-phenyl-cyclohexyl ester | 519.7 |
| 303 | 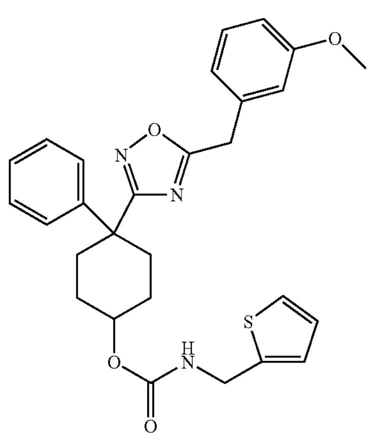 | Thiophen-2-ylmethyl-carbamic acid 4-[5-(3-methoxy-benzyl)-[1,2,4]oxadiazol-3-yl]-4-phenyl-cyclohexyl ester | 504.6 |

| Ex. | Structure | Name | M + H |
|---|---|---|---|
| 304 | 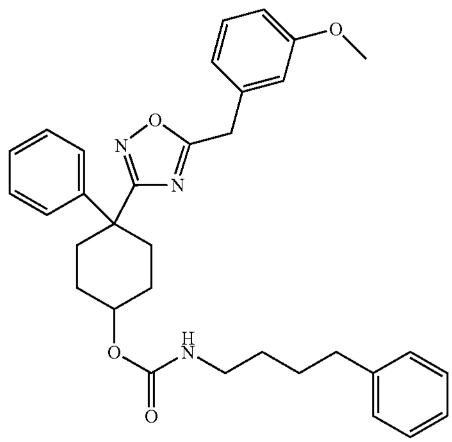 | 4-Phenyl-butyl)-carbamic acid 4-[5-(3-methoxy-benzyl)-[1,2,4]oxadiazol-3-yl]-4-phenyl-cyclohexyl ester | 540.7 |
| 305 | 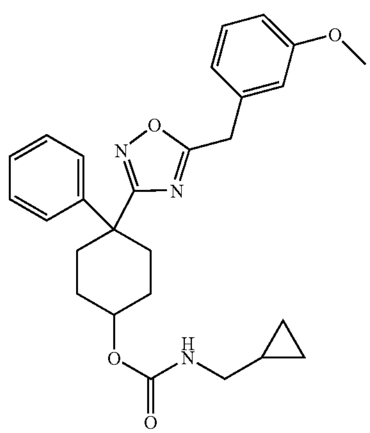 | Cyclopropylmethyl-carbamic acid 4-[5-(3-methoxy-benzyl)-[1,2,4]oxadiazol-3-yl]-4-phenyl-cyclohexyl ester | 462.6 |
| 306 | 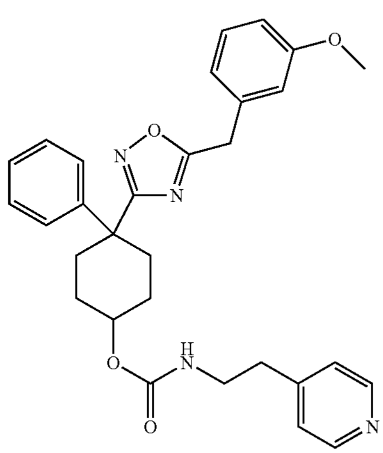 | (2-Pyridin-4-yl-ethyl)-carbamic acid 4-[5-(3-methoxy-benzyl)-[1,2,4]oxadiazol-3-yl]-4-phenyl cyclohexyl ester | 513.6 |

-continued

| Ex. | Structure | Name | M + H |
|---|---|---|---|
| 307 | 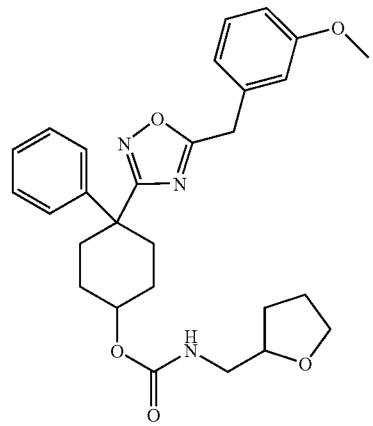 | (Tetrahydro-furan-2-ylmethyl)-carbamic acid 4-[5-(3-methoxy-benzyl)-[1,2,4]oxadiazol-3-yl]-4-phenyl-cyclohexyl ester | 492.6 |
| 308 | 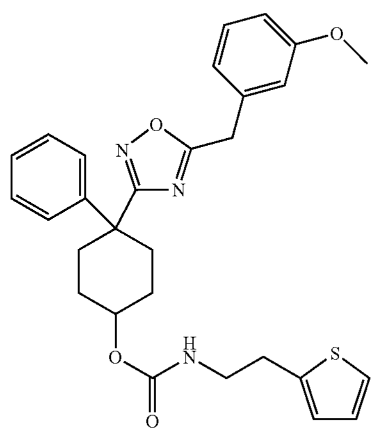 | 2-Thiophen-2-yl-ethyl)-carbamic acid 4-[5-(3-methoxy-benzyl)-[1,2,4]oxadiazol-3-yl]-4-phenyl-cyclohexyl ester | 518.6 |
| 309 | 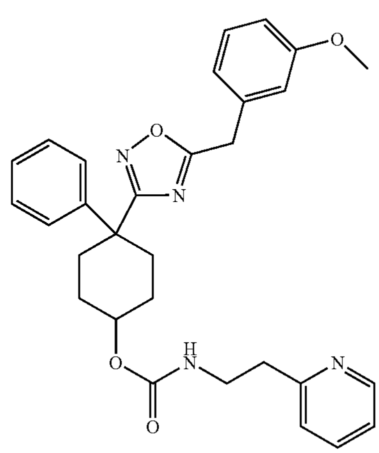 | (2-Pyridin-2-yl-ethyl)-carbamic acid 4-[5-(3-methoxy-benzyl)-[1,2,4]oxadiazol-3-yl]-4-phenyl-cyclohexyl ester | 513.6 |

| Ex. | Structure | Name | M + H |
|---|---|---|---|
| 310 | 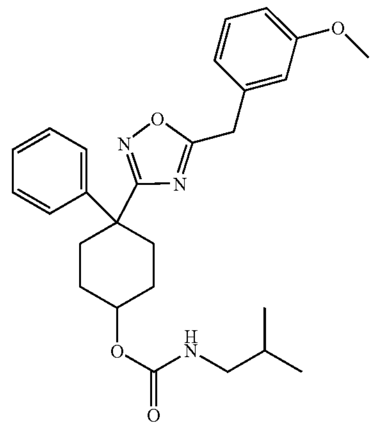 | Isobutyl-carbamic acid 4-[5-(3-methoxy-benzyl)-[1,2,4]oxadiazol-3-yl]-4-phenyl-cyclohexyl ester | 464.6 |
| 311 | 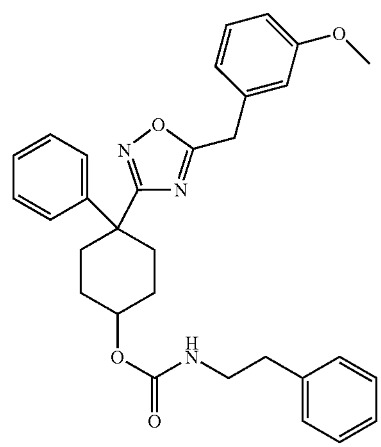 | Phenethyl-carbamic acid 4-[5-(3-methoxy-benzyl)-[1,2,4]oxadiazol-3-yl]-4-phenyl-cyclohexyl ester | 512.6 |
| 312 | 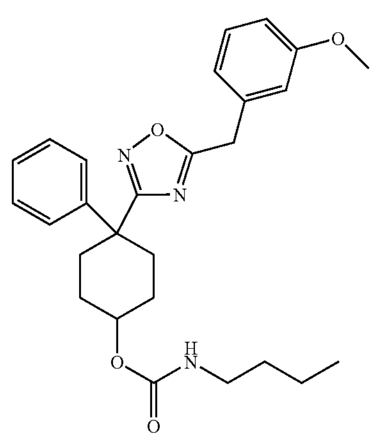 | Butyl-carbamic acid 4-[5-(3-methoxy-benzyl)-[1,2,4]oxadiazol-3-yl]-4-phenyl-cyclohexyl ester | 464.6 |

-continued

| Ex. | Structure | Name | M + H |
|---|---|---|---|
| 313 | 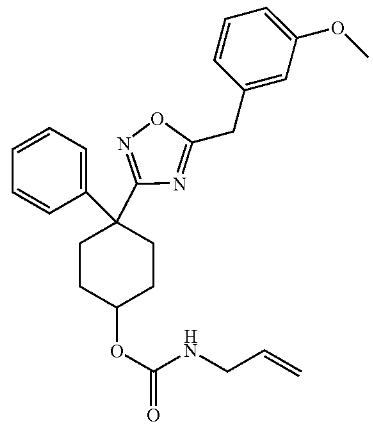 | Allyl-carbamic acid 4-[5-(3-methoxy-benzyl)-[1,2,4]oxadiazol-3-yl]-4-phenyl-cyclohexyl ester | 448.5 |
| 314 | 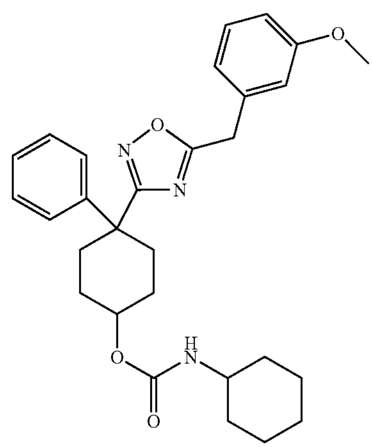 | Cyclohexyl-carbamic acid 4-[5-(3-methoxy-benzyl)-[1,2,4]oxadiazol-3-yl]-4-phenyl-cyclohexyl ester | 490.6 |
| 315 | 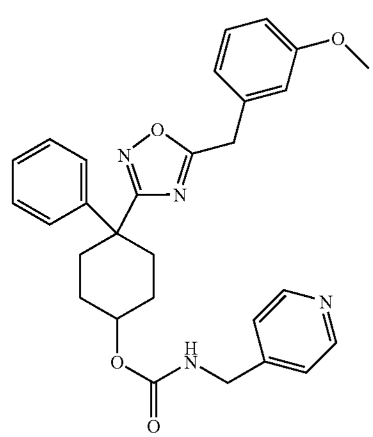 | Pyridin-4-ylmethyl-carbamic acid 4-[5-(3-methoxy-benzyl)-[1,2,4]oxadiazol-3-yl]-4-phenyl-cyclohexyl ester | 499.6 |

| Ex. | Structure | Name | M + H |
|---|---|---|---|
| 316 | 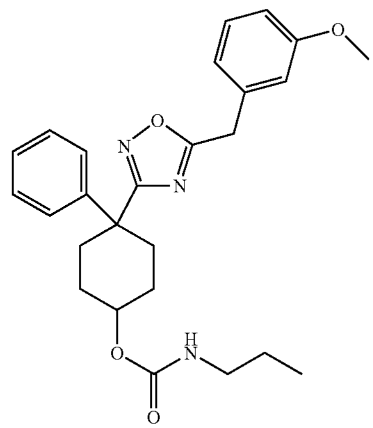 | Propyl-carbamic acid 4-[5-(3-methoxy-benzyl)-[1,2,4]oxadiazol-3-yl]-4-phenyl-cyclohexyl ester | 450.5 |
| 317 | 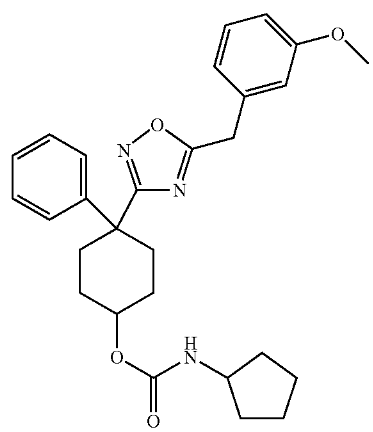 | Cyclopentyl-carbamic acid 4-[5-(3-methoxy-benzyl)-[1,2,4]oxadiazol-3-yl]-4-phenyl-cyclohexyl ester | 476.6 |
| 318 | 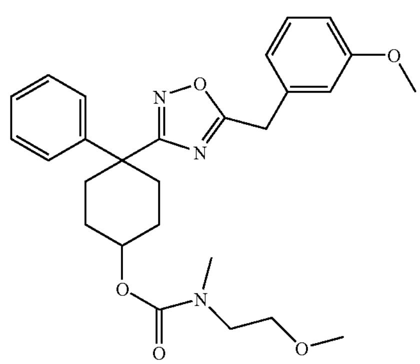 | (2-Methoxy-ethyl)-methyl-carbamic acid 4-[5-(3-methoxy-benzyl)-[1,2,4]oxadiazol-3-yl]-4-phenyl-cyclohexyl ester | 480.6 |

| Ex. | Structure | Name | M + H |
|---|---|---|---|
| 319 | 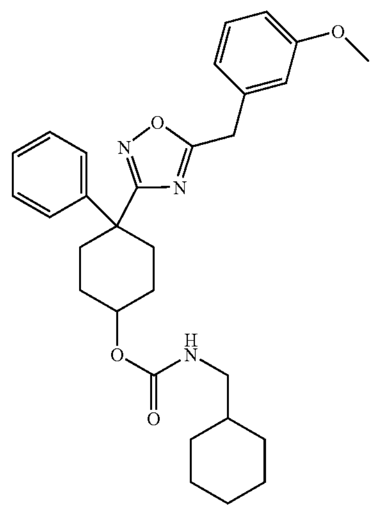 | Cyclohexylmethyl-carbamic acid 4-[5-(3-methoxy-benzyl)-[1,2,4]oxadiazol-3-yl]-4-phenyl-cyclohexyl ester | 504.6 |
| 320 | 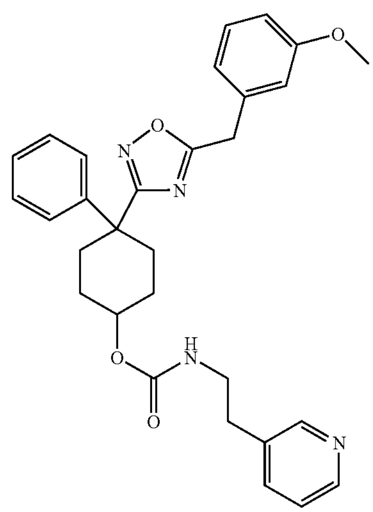 | (2-Pyridin-3-yl-ethyl)-carbamic acid 4-[5-(3-methoxy-benzyl)-[1,2,4]oxadiazol-3-yl]-4-phenyl-cyclohexyl ester | 513.6 |
| 321 | 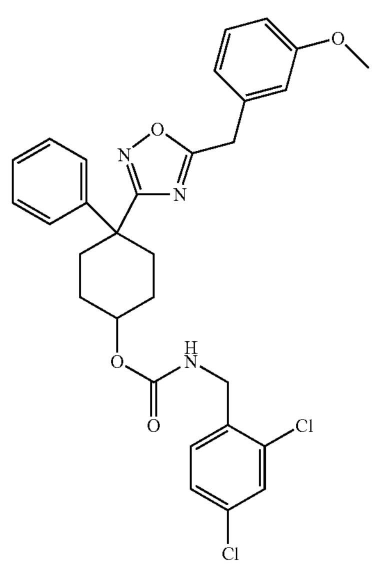 | (2,4-Dichloro-benzyl)-carbamic acid 4-[5-(3-methoxy-benzyl)-[1,2,4]oxadiazol-3-yl]-4-phenyl-cyclohexyl ester | 567.5 |

-continued
| Ex. | Structure | Name | M + H |
|---|---|---|---|
| 322 | 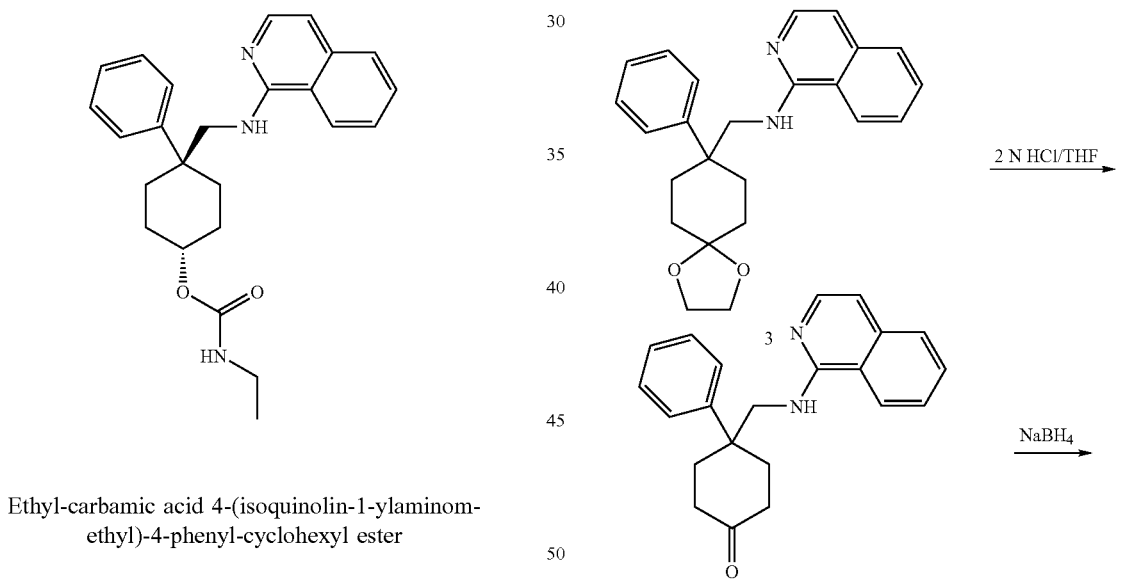 | Benzyl-methyl-carbamic acid 4-[5-(3-methoxy-benzyl)-[1,2,4]oxadiazol-3-yl]-4-phenyl-cyclohexyl ester | 512.6 |
EXAMPLE 323
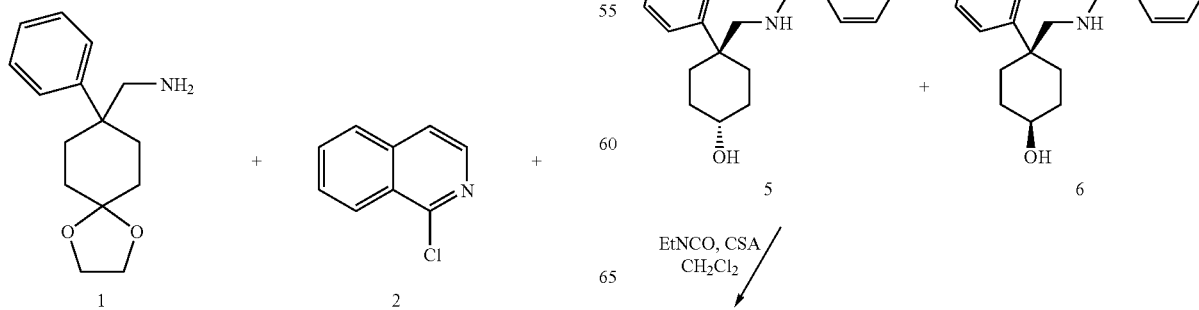
Ethyl-carbamic acid 4-(isoquinolin-1-ylaminomethyl)-4-phenyl-cyclohexyl ester
Synthesis:

-continued

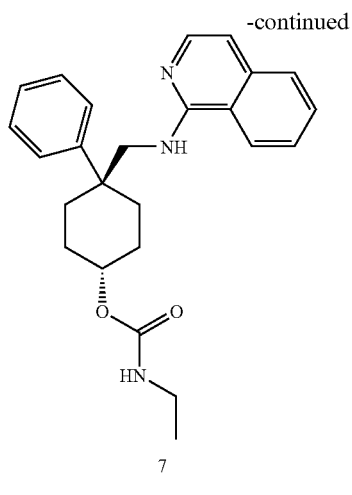

7

Compound 1: Synthesis of compound 1 is described in Example 31

Compound 2: is commercially available

Compound 3: A mixture of compound 1 (2.0 g, 8.09 mmol), 2 (1.1 g, 6.75 mmol), sodium-t-butoxide (908 mg, 9.75 mmol), palladium acetate (75.7 mg, 0.34 mmol) and 2-(di-t-butylphosphino)biphenyl (100.7 mg, 0.3374 mmol) in toluene (20 mL) was heated at 110° C. for 20 h. The insolubles were filtered off through CELITE, the solvent was removed under reduced pressure and the residue was purified by flash chromatography through silica eluting with 40% ethyl acetate-hexane providing the title compound (1.5 g, 50% yield) as a yellow oil.

Compound 4: Dioxolane 3 (1.5 g) was dissolved in THF, diluted with 2N HCl and stirred overnight. The solution was added to a mixture of ethyl acetate and saturated sodium bicarbonate. The organic solution was washed with an additional two portions of bicarbonate solution followed by brine. The solution was dried over sodium sulfate and the solvent removed under reduced pressure providing 1.25 g (94%) of Compound 4 as an orange syrup which was used without further purification.

Compounds 5 and 6: Sodium borohydride (215 mg, 5.82 mmol) was added to a solution of ketone 4 (1.25 g, 3.79 mmol) in THF (10 mL) and the mixture was stirred overnight. The reaction was partitioned between ethyl acetate and dilute HCl. The aqueous layer was basified with saturated sodium bicarbonate. The product was extracted into ethyl acetate which was dried over sodium sulfate and the solvent removed under reduced pressure. Flash chromatography through silica with ethyl acetate as eluent provided 5 (isomer A, 469 mg) and 6 (isomer B, 170 mg).

Compound 7: Camphorsulphonic acid (160.1 mg, 0.689 mmol) was added to a stirred solution of 5 (114 mg, 0.344 mmol) in dichloromethane (10 mL). After 5 min. ethyl isocyanate (32.7 µL, 0.414 mmol) was added and stirring continued for 2 h. The reaction was quenched with a methanolic solution of ammonia, the solvent was removed under reduced pressure and the residue was flash chromatographed through silica eluting with 60% ethyl acetate-hexane, then 5% methanol-dichloromethane affording 10.2 mg of the title compound, [M+H] 404.

EXAMPLE 324

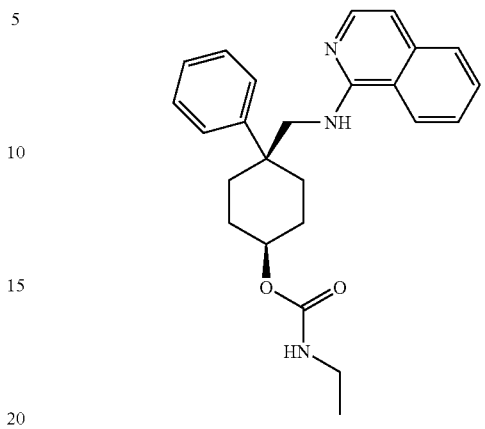

Ethyl-carbamic acid 4-(isoquinolin-1-ylaminomethyl)-4-phenyl-cyclohexyl ester

Synthesis:

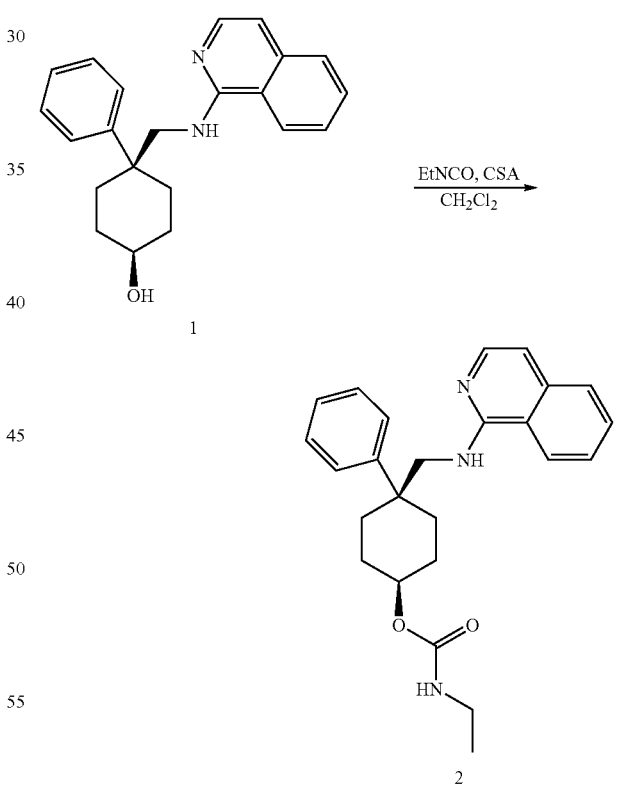

Compound 1: Synthesis of compound 1 is described in Example 323.

Compound 2: In a reaction similar to that described in example 323, Compound 1 (76.3 mg, 0.230 mmol), camphorsulfonic acid (106.8 mg, 0.460 mmol) and ethyl isocyanate (21.8 µL, 0.276 mmol) in dichloromethane (10 mL) produced 16.3 mg of Compound 2, [M+H] 403.

EXAMPLE 325

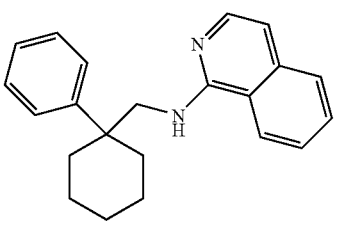

Isoquinolin-1-yl-(1-phenyl-cyclohexylmethyl)-amine

Synthesis:

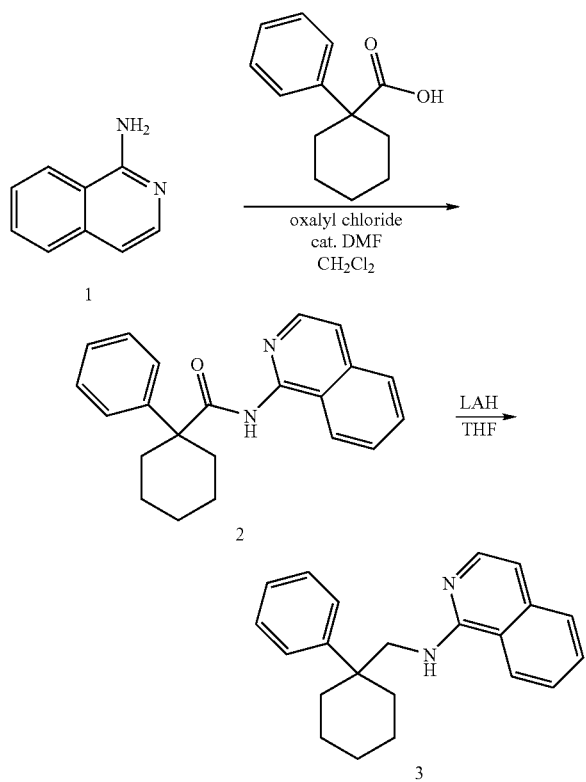

Compound 1: Compound 1 is commercially available

Compound 2: A suspension of 1-phenyl-1-cyclohexane carboxylic acid (0.484 g; 2.37 mmol) in methylene chloride (30 ml) was treated with oxalyl chloride (0.23 mL; 2.64 mmol) and 1 drop of N,N-dimethylformamide. The reaction mixture was allowed to stir at room temperature for 30 minutes at which time triethylamine (1 mL; 7.2 mmol) and 1-aminoisoquinoline (0.36 g; 2.50 mmol). After an additional 15 minutes of stirring the reaction mixture was washed with water and saturated aqueous sodium chloride, dried (magnesium sulfate) and concentrated. The crude residue was purified by column chromatography on silicia gel using 3:1:1 hexane:ethyl acetate:dichloromethane as the eluent to give 0.605 g of 1-phenyl-cyclohexanecarboxylic acid isoquinolin-1-ylamide as a white foam. LCMS m/z=331.2 (M+H)$^+$ Compound 3: A solution of 1-phenyl-cyclohexanecarboxylic acid isoquinolin-1-ylamide (0.117 g; 0.35 mmol) in tetrahydrofuran (10 mL) was cooled to 0° C. and treated with lithium aluminum hydride (0.040 g; 1.05 mmol). The reaction mixture was allowed to slowly warm to room temperature. After 18 h at room temperature additional lithium aluminum hydride was added (0.04 g; 1.05 mmol) and the reaction mixture was heated at 40° C. for 2 h. The reaction mixture was cooled back to 0° C. and carefully quenched by the dropwise addition of water. The tetrahydrofuran was removed by evaporation and the crude residue was diluted with ethyl acetate and saturated aqueous sodium bicarbonate. The organic layer was separated, washed with saturated aqueous sodium chloride, dried (magnesium sulfate), filtered and concentrated. Column chromatography on silicia gel using 7:3 hexane:ethyl acetate as the eluent gave 0.042 g of isoquinolin-1-yl-(1-phenyl-cyclohexylmethyl)-amine as a light yellow oil. LCMS m/z=317.2 (M+H)$^+$; $^1$H NMR (CDCl$_3$, 300 MHz) δ (ppm) 7.96 (1H, d, J=6.0 Hz), 7.54–7.26 (9H, m), 6.61 (1H, d, J=6.0 Hz), 4.80 (1H, broad S), 3.76 (2H, d, J=5.4 hz), 2.26–2.20 (2H, m), 1.84–1.77 (2H, m), 1.66–1.61 (2H, m), 1.55–1.43 (4H, m); $^{13}$C NMR (CDCl$_3$, 75 MHz) 155.4, 144.9, 141.4, 137.1, 129.5, 128.9 (two carbons), 127.1, 127.0 (two carbons), 126.4, 125.8, 121.0, 118.1, 110.5, 52.2, 42.6, 34.3 (two carbons), 26.6, 22.2 (two carbons).

EXAMPLES 326–329

Examples 326 to 329 were synthesized using methodology described in Example 325.

| Example | Structure | Name | M + H |
|---|---|---|---|
| 326 | 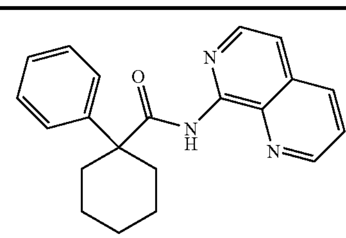 | 1-Phenyl-cyclohexanecarboxylic acid [1,7]naphthyridin-8-ylamide | 332.2 |

-continued

| Example | Structure | Name | M + H |
|---|---|---|---|
| 327 | 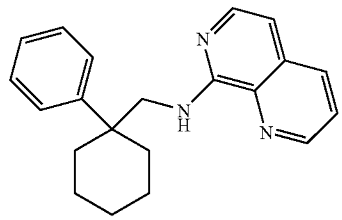 | [1,7]Naphthyridin-8-yl-(1-phenyl-cyclohexylmethyl)-amine | 318.2 |
| 328 | 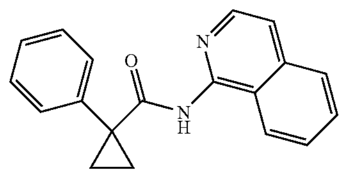 | 1-Phenyl-cyclopropanecarboxylic acid isoquinolin-1-ylamide | 289.1 |
| 329 | 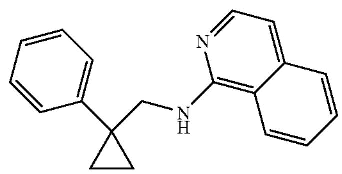 | Isoquinolin-1-yl-(1-phenyl-cyclopropylmethyl)-amine | 275.2 |

EXAMPLE 330

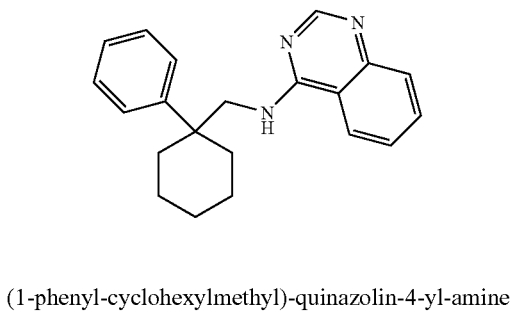

(1-phenyl-cyclohexylmethyl)-quinazolin-4-yl-amine

Synthesis:

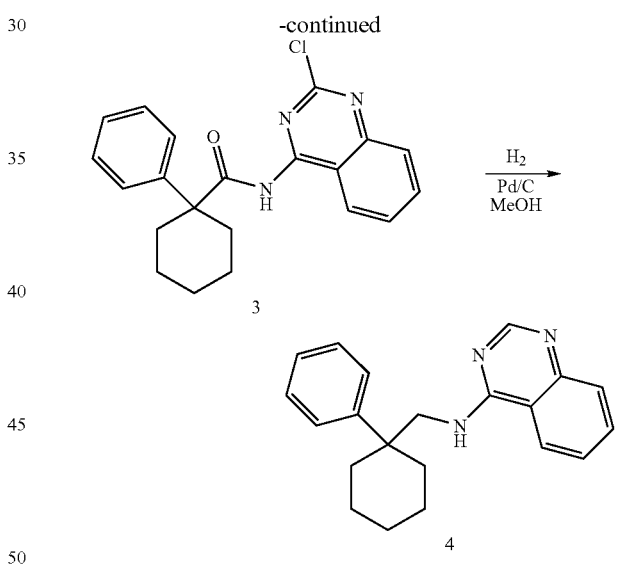

Compound 1: Compound 1 is commercially available.

Compound 2: A solution of 1-phenyl-cyclohexanecarbonitrile (11.0 g; 59 mmol) in tetrahydrifuran (100 mL) was cooled to 0° C. and treated with lithium aluminum hydride (11 g, 289 mmol) in several portions over the course of 0.5 h. When the addition of lithium aluminum hydride was complete the cooling bath was removed and the reaction mixture was allowed to stir at room temperature for 12 h. The reaction mixture was cooled back to 0° C. and carefully quenched by dropwise addition of 2 N NaOH (approximately 20 mL), diluted with ethyl ether, filtered through a celite plug and dried (magnesium sulfate). C-(1-Phenyl-cyclohexyl)-methylamine was obtained as a colorless oil which was used without further purification. LCMS m/z=190.2 (M+H)$^+$ Compound 3: A solution of C-(1-phenyl-cyclohexyl)-methylamine (0.28 g; 1.48 mmol) in tetrahydrofuran (10 mL) at room temperature was treated with triethylamine (0.3 mL; 2.2 mmol) and 2,4-dichloro-quinazoline (0.32 g; 1.62 mmol). The reaction was stirred at room temperature 12 h at which time the solvent was removed by rotary evaporation. The crude residue was portioned between ethyl acetate and 10% aqueous HCl. The organic layer was separated, washed with saturated aqueous sodium chloride, dried (magnesium sulfate), filtered and concentrated. The product was recrystallized from methylene chloride to give (2-chloro-quinazolin-4-yl)-(1-phenyl-cyclohexylmethyl)-amine as a white solid. LCMS m/z=352.2 (M+H)$^+$ Compound 4: A solution of (2-chloro-quinazolin-4-yl)-(1-phenyl-cyclohexylmethyl)-amine (0.065 g; 0.18 mmol) in anhydrous methanol (2 mL) was treated with 10% palladium on carbon (200 mg) and placed under an atmosphere of hydrogen (45 psi). The reaction mixture was shaken at room temperature for 3 h. The reaction mixture was filtered through celite and evaporated. The crude residue was purified by column chromatography on silicia gel using 9:1 ethyl acetate:hexane as the eluent to give 0.052 g (1-phenyl-cyclohexylmethyl)-quinazolin-4-yl-amine as a white foam. LCMS m/z=318.2 (M+H)$^+$

EXAMPLE 331

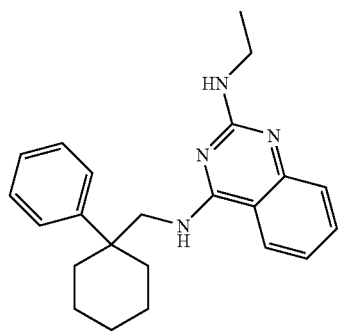

$N^2$-ethyl-$N^4$-(1-phenyl-cyclohexylmethyl)-quinazoline-2,4-diamine

Synthesis:

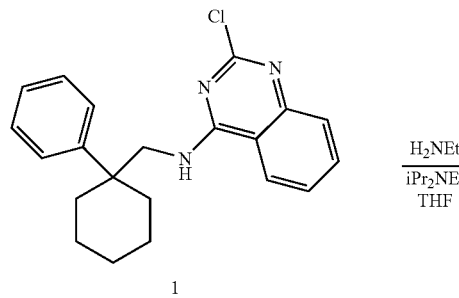

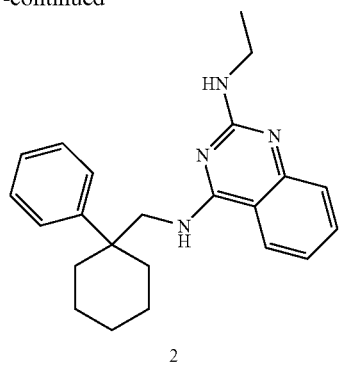

2

Compound 1: Compound 1 is prepared as described above.

Compound 2: (2-chloro-quinazolin-4-yl)-(1-phenyl-cyclohexylmethyl)-amine (0.052 g; 0.15 mmol) was treated with 1 mL of a 2 M solution of ethylamine in tetrahydrofuran. The reaction vessel was tightly sealed and the reaction mixture was heated at 60° C. for 24 h. The volatile components were removed under vacuum and the crude residue was purified directly be preparative HPLC to give 0.020 g of $N^2$-ethyl-$N^4$-(1-phenyl-cyclohexylmethyl)-quinazoline-2,4-diamine as a white solid. LCMS m/z=361.2 (M+H)$^+$

EXAMPLE 332

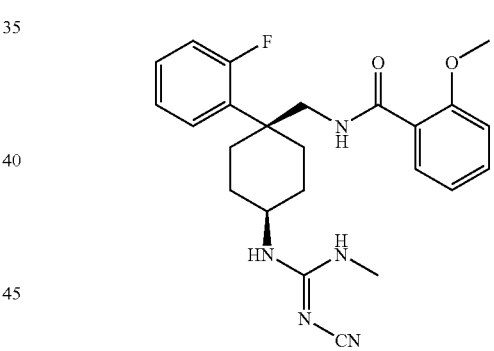

Synthesis:

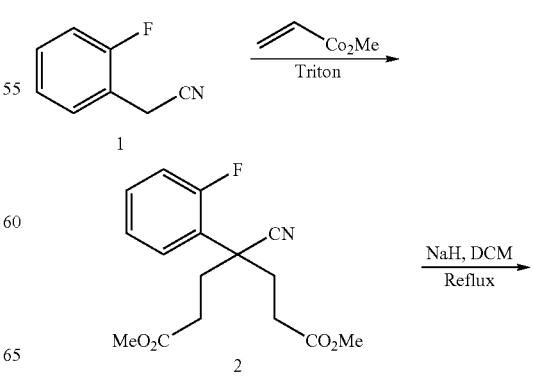

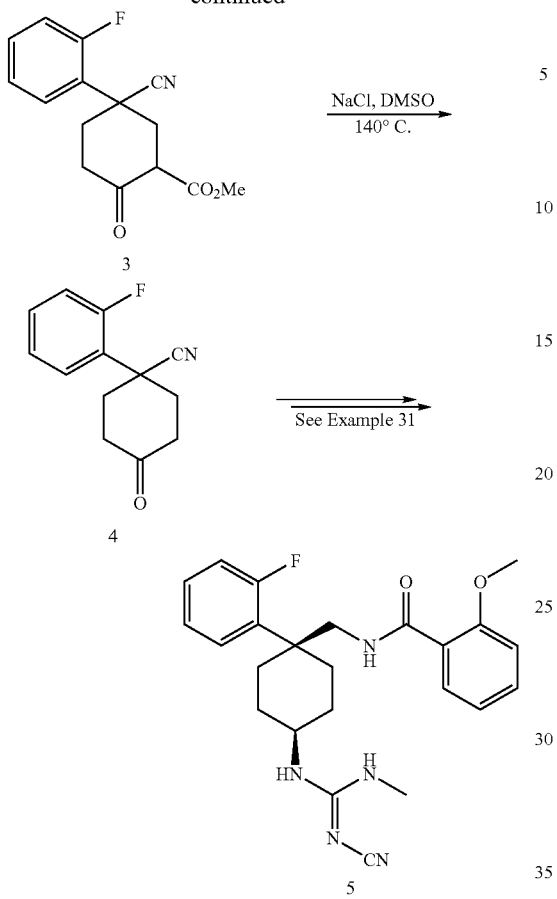

Compound 1: Compound 1 is commercially available.

Compound 2: To a refluxing solution of 2-flourophenylacetonitrile (5 ml, 41 mmol) in 100 ml of acetonitrile was added dropwise methyl acrylate (36 ml, 400 mmol) in 100 ml of acetonitrile for 3 h period. The resulting solution was stirred for additional 6 h at reflux. Reaction mixture was concentrated in vacuo, yielding oily residue, which was purified on column chromatography (40% EtOAc/Hexane) to produce compound 2 (11.2 g, 89%) as a colorless oil.

Compound 3: To a solution of compound 2 in 200 ml of DCM was added NaH (2.5 g, 108 mmol) in a portion and the resulting solution was stirred at reflux for 12 h. Reaction mixture was cooled to −78° C. and quenched by adding ice. The mixture was diluted with EtOAc (150 ml) and organic layer was filtered out. The concentration of organic layer provided an oil (8.8 g, 89%), which corresponds to the desired product in NMR analysis and was subjected to the following reaction without further purification.

Compound 4: Compound 3 was dissolved in 80 ml of DMSO and 4 ml of $H_2O$. The mixture was stirred at 140° C. for 15 h. The reaction mixture was cooled down, diluted with EtOAc (400 ml) and washed with 10% aqueous LiCl (30 ml×3). The aqueous layer was extracted with EtOAc (50 ml×2). The combined organic layer was dried over $MgSO_4$ and concentrated in vacuo to provide oily residue, which was purified on column chromatography (25–50% EtOAc/hexane) to provide the desired product (5.5 g, 65%).

Compound 5: Synthesis of compound 5 was carried out in an exactly same reaction sequence as in a synthesis of Example 31, where the compound 1 in example 31 was substituted compound 4 in this example. [M+H]=438.

EXAMPLES 333–334

Examples 333 to 334 were synthesized using methodology described in Example 332.

| Example | Structure | [M + H] |
|---|---|---|
| 333 | 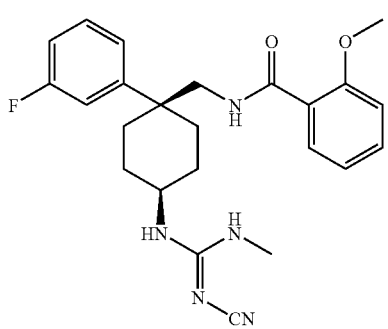 | 452 |
| 334 | 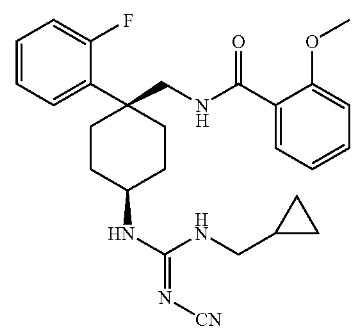 | 478 |

EXAMPLE 335

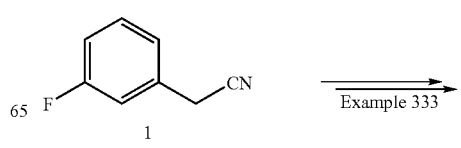

Synthesis:

-continued

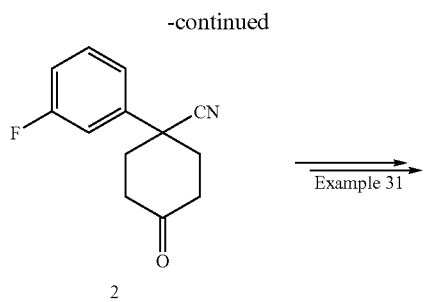

2

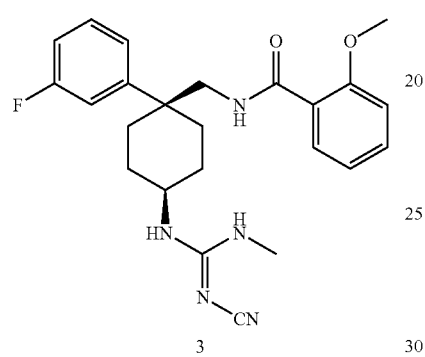

3

Compound 1: Compound 1 is commercially available.

Compound 2: Compound 2 is prepared in an exact same procedure as described in synthesis of Example 333 where 3-fluorophenylacetonitrile replaced 2-fluorophenylacetonitrile in synthesis of Example 335.

Compound 3: Compound 3 was prepared in a sequence described in synthesis of Example 31, where 4-(3-fluorophenyl)-4-cyanocyclohexanone 2 was used instead of compound 1 in example 31. [M+H]=438.

Examples 336 to 341 were synthesized using methodology described in Example 335.

-continued

| Example | Structure | [M + H] |
|---|---|---|
| 336 | 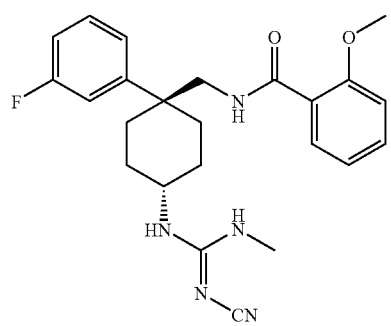 | 438 |
| 337 | 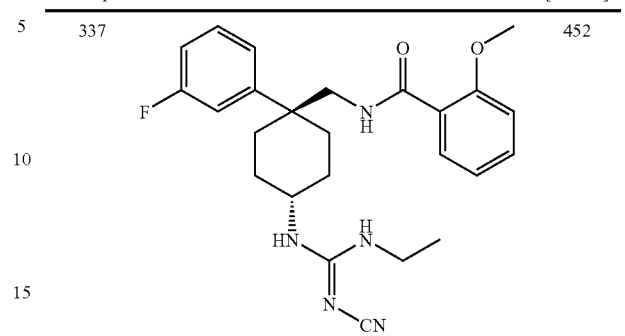 | 452 |
| 338 | 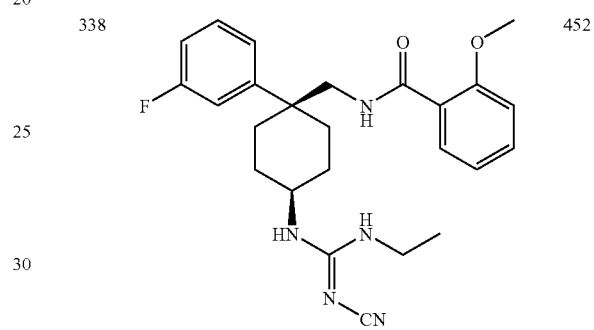 | 452 |
| 339 | 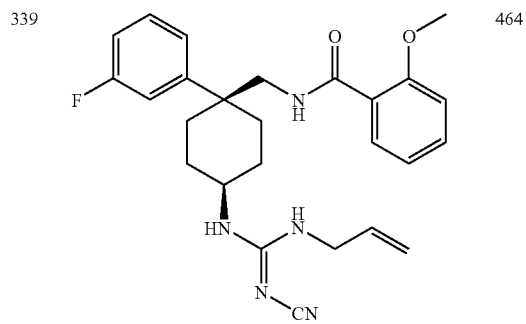 | 464 |
| 340 | 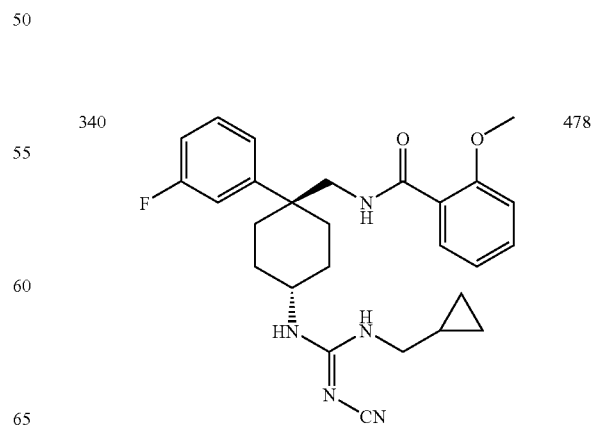 | 478 |

| Example | Structure | [M + H] |
|---|---|---|
| 341 | 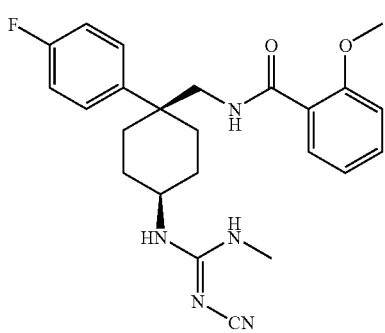 | 478 |

EXAMPLE 342

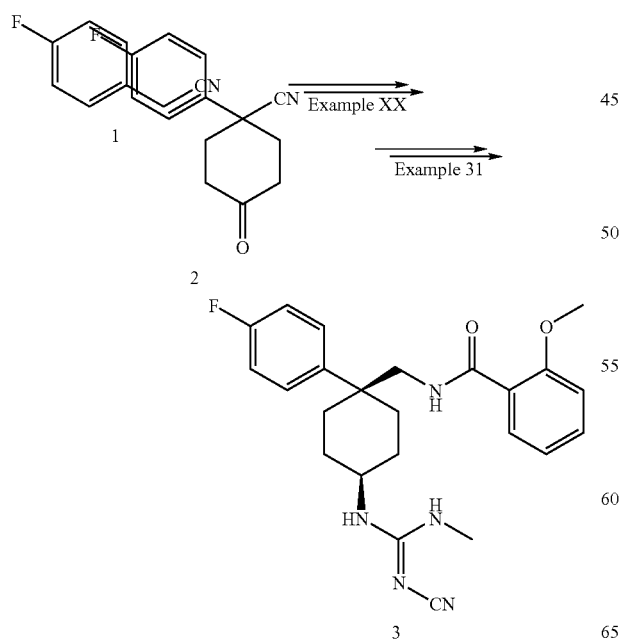

Synthesis:

Compound 1: Compound 1 is commercially available.

Compound 2: Compound 2 is prepared in an exact same procedure as described in synthesis of Example 332 where 4-fluorophenylacetonitrile replaced the 2-fluorophenylacetonitrile.

Compound 3: Compound 3 was prepared in a sequence described in synthesis of Example 31, where compound 2 was used instead of compound 1 in example 31. [M+H] =438.

EXAMPLES 343–348

Examples 343 to 348 were synthesized using methodology described in Example 342.

| Example | Structure | [M + H] |
|---|---|---|
| 343 | 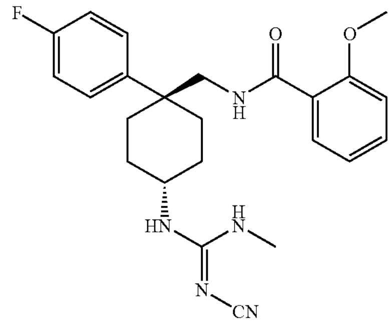 | 438 |
| 344 | 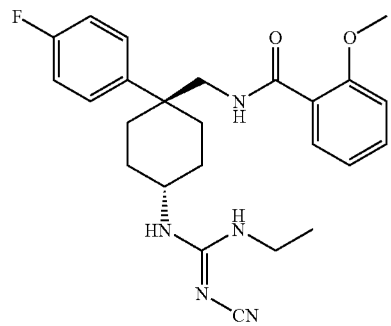 | 452 |
| 345 | 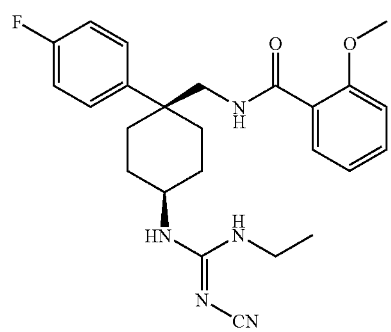 | 452 |

-continued

| Example | Structure | [M + H] |
|---------|-----------|---------|
| 346 | 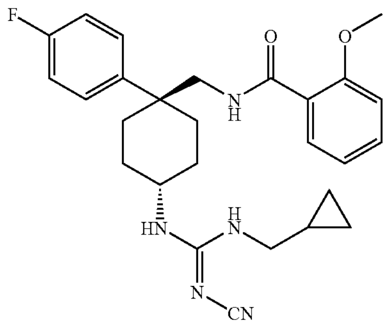 | 478 |
| 347 | 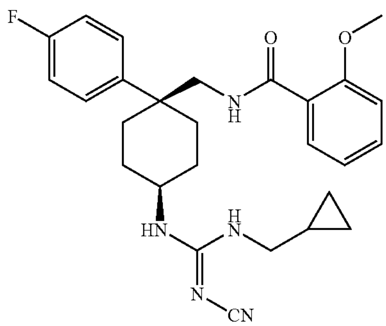 | 478 |
| 348 | 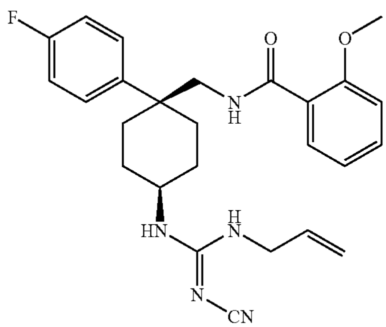 | 464 |

EXAMPLE 349

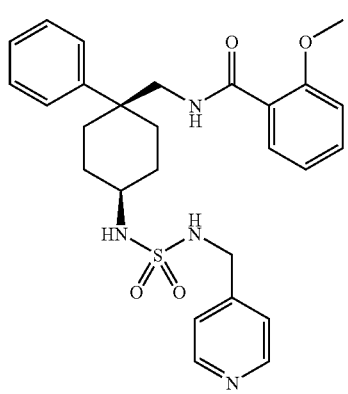

Synthesis:

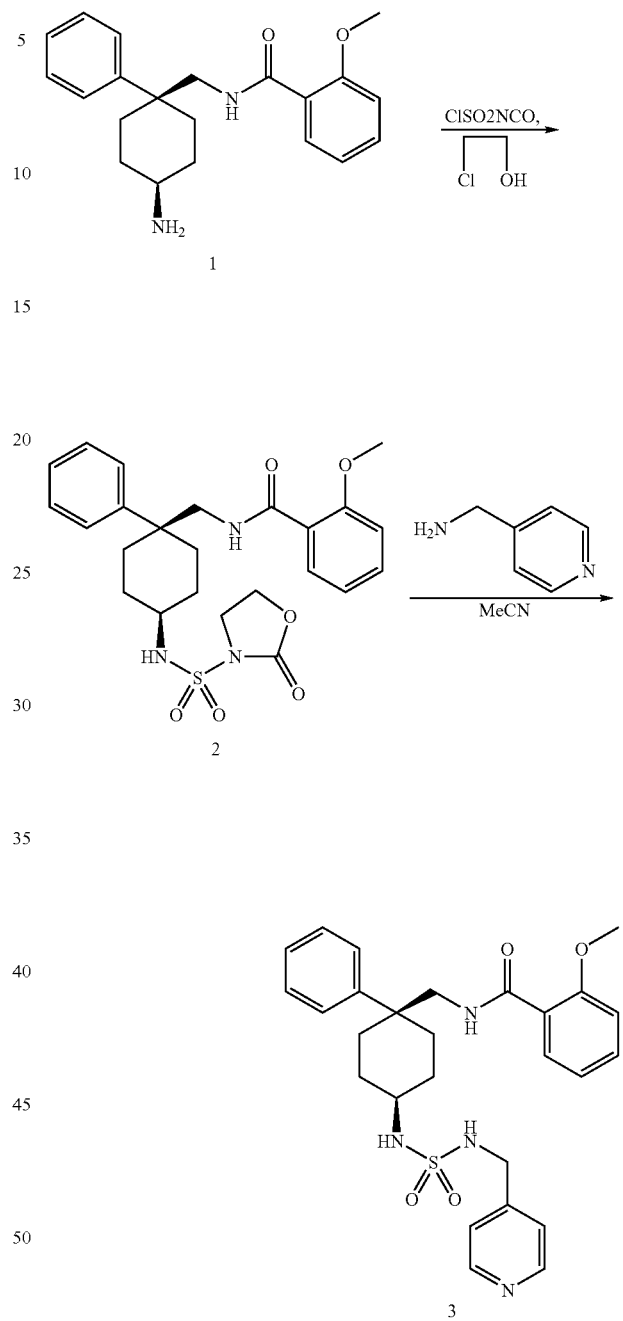

Compound 1: The synthesis of 1 was described in Example 31.

Compound 2: The synthesis of 2 was described in Example 73.

Compound 3: A solution of 2 (20 mg, 0.041 mmol), 4-(aminomethyl)pyridine (10 mg, 0.10 mmol) in 1 ml of $CH_3CN$ was stirred for 2 h at 65° C. The reaction mixture was purified by preparative HPLC (described in a synthesis of Example 31) to yield 11.2 mg of the 3 as a colorless oil. Mass Spec [M+H]=509.

EXAMPLES 350–396
Examples 350 to 396 were synthesized using methodology described in Example 349.
| Example | Structure | [M + H] |
|---|---|---|
| 350 | 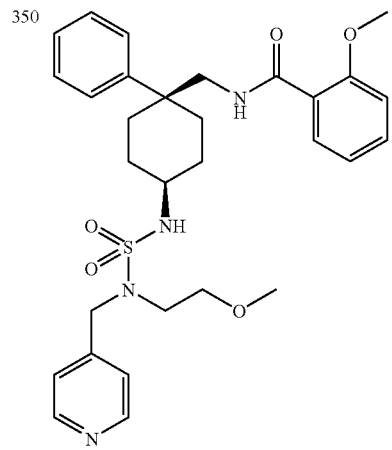 | 567 |
| 351 | 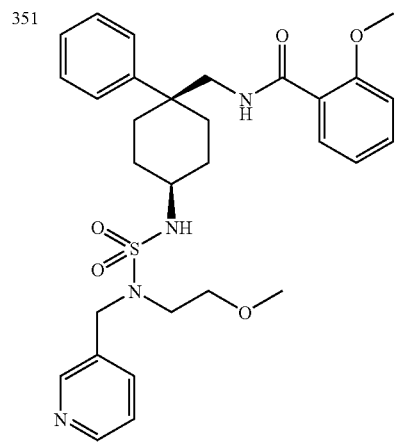 | 567 |
| 352 | 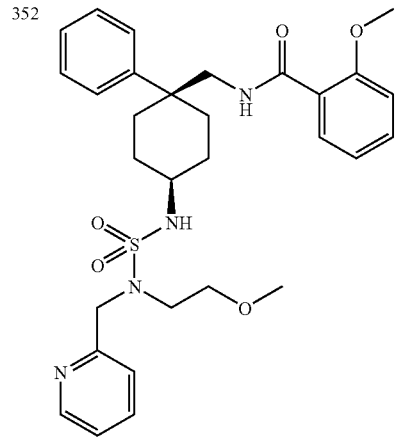 | 567 |
-continued
| Example | Structure | [M + H] |
|---|---|---|
| 353 | 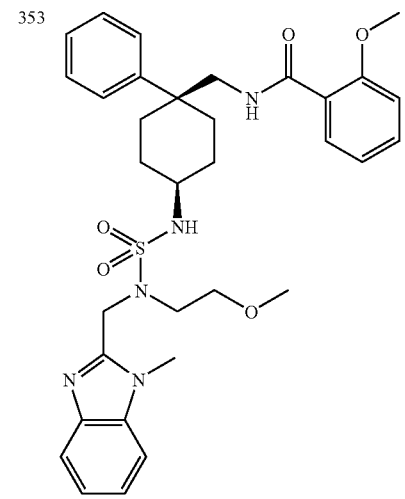 | 620 |
| 354 | 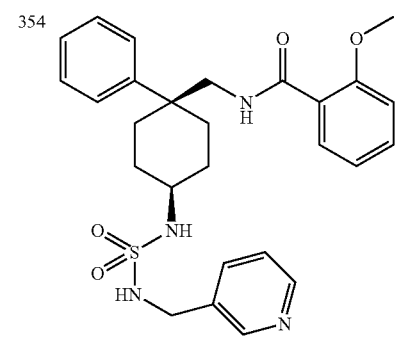 | 509 |
| 355 | 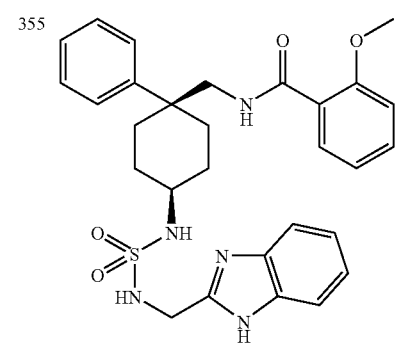 | 548 |
| 356 | 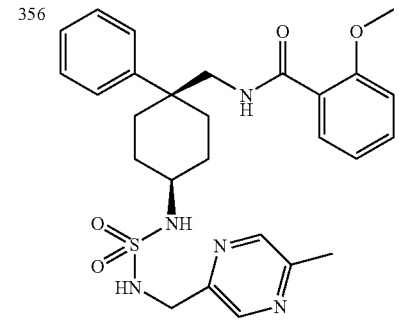 | 524 |

| Example | Structure | [M+H] |
|---|---|---|
| 357 | 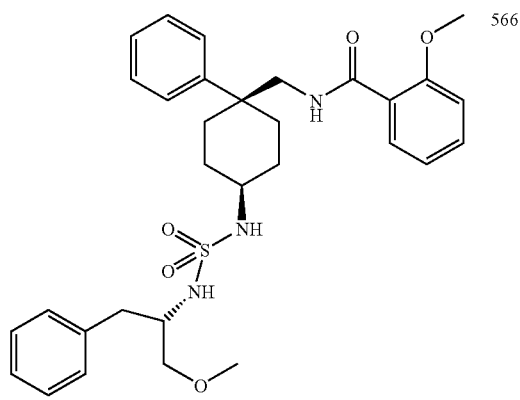 | 566 |
| 358 | 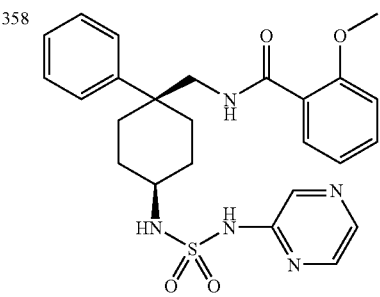 | 496 |
| 359 | 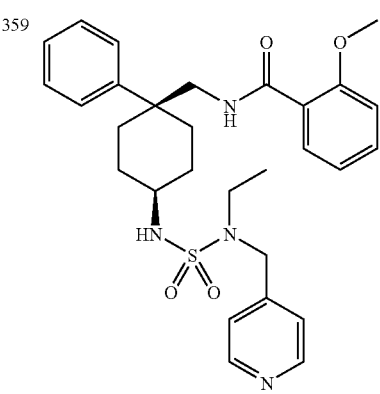 | 537 |
| 360 | 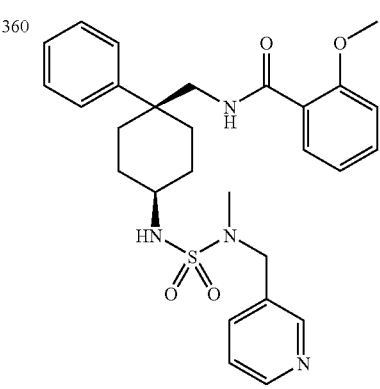 | 537 |
| Example | Structure | [M+H] |
|---|---|---|
| 361 | 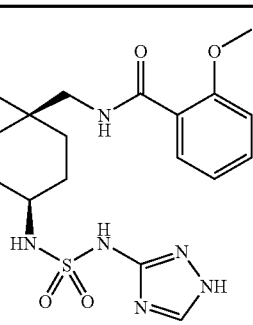 | 485 |
| 362 | 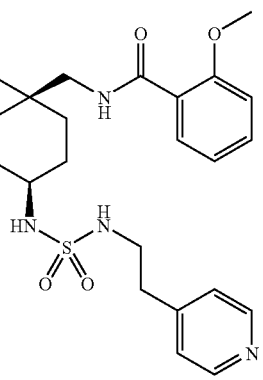 | 523 |
| 363 | 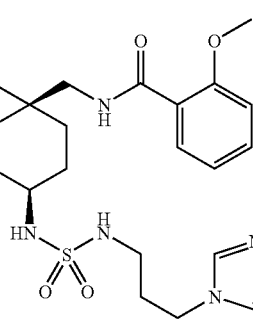 | 527 |
| 364 | 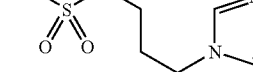 | 529 |

-continued
| Example | Structure | [M + H] |
|---|---|---|
| 365 | 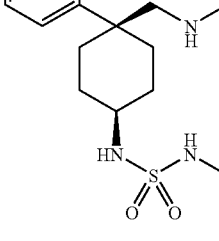 | 537 |
| 366 | 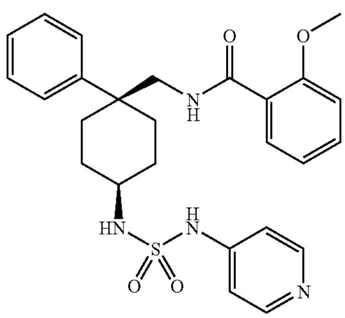 | 495 |
| 367 | 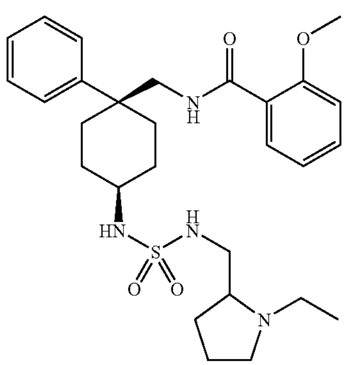 | 529 |
| 368 | 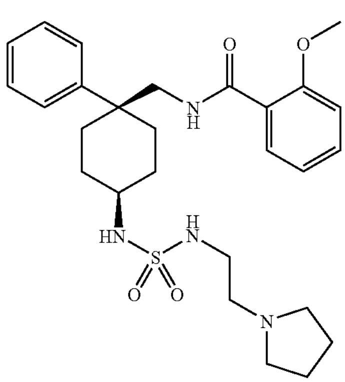 | 515 |
-continued
| Example | Structure | [M + H] |
|---|---|---|
| 369 | 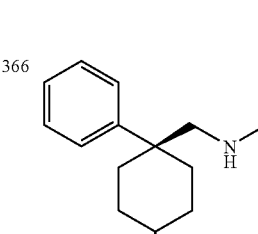 | 539 |
| 370 | 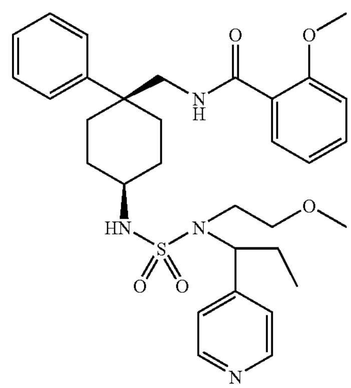 | 595 |
| 371 | 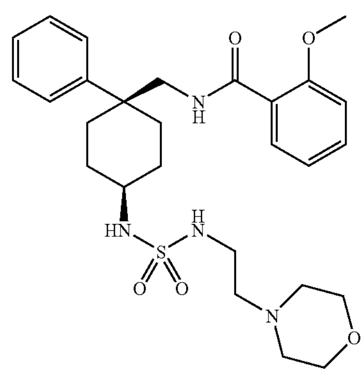 | 531 |
| 372 | 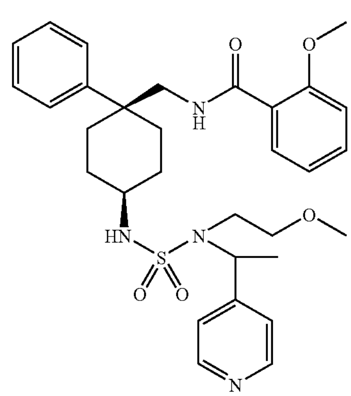 | 581 |

| Example | Structure | [M + H] |
|---|---|---|
| 373 | 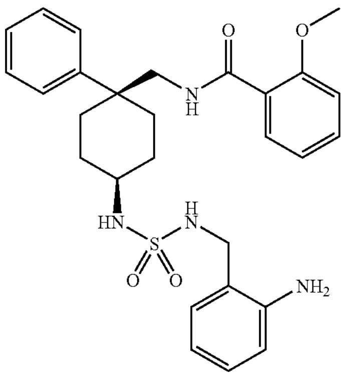 | 523 |
| 374 | 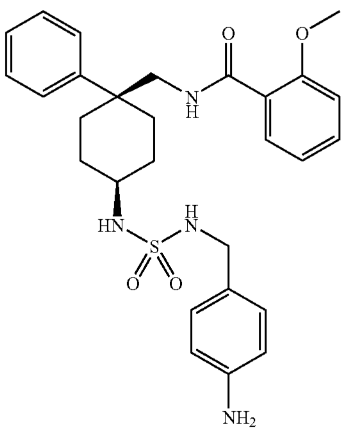 | 523 |
| 375 | 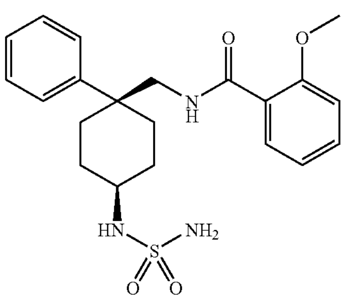 | 418 |
| 376 | 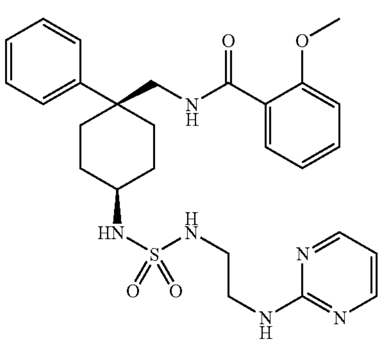 | 539 |
| 377 | | 567 |
| 378 | | 538 |
| 379 | | 632 |
| 380 | | 607 |

-continued
| Example | Structure | [M + H] |
|---|---|---|
| 381 | 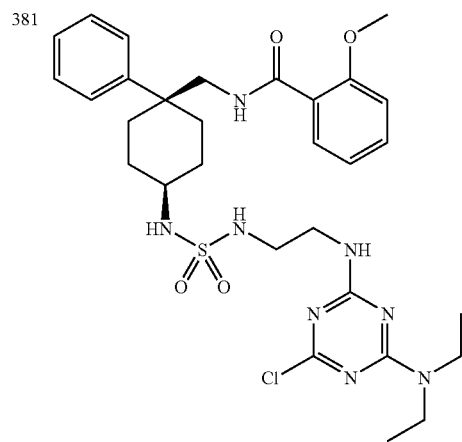 | 646 |
| 382 | 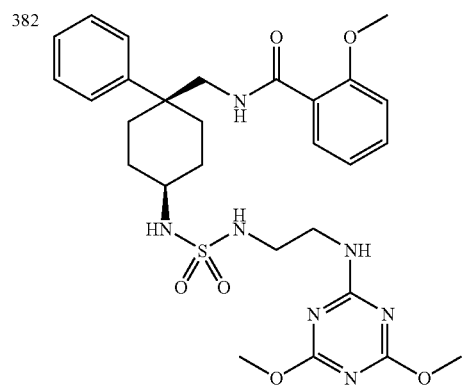 | 600 |
| 383 | 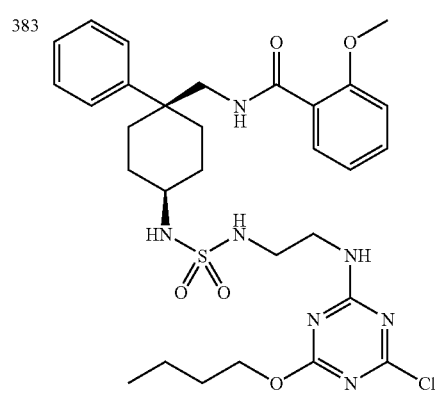 | 647 |
-continued
| Example | Structure | [M + H] |
|---|---|---|
| 384 | 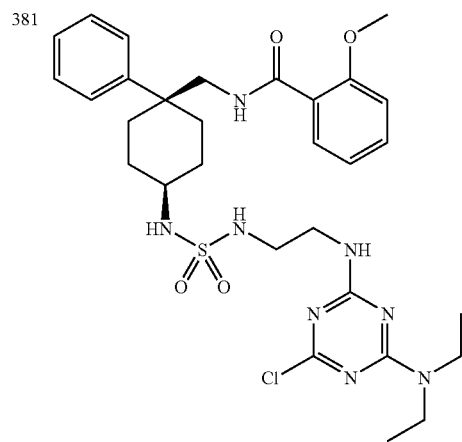 | 588 |
| 385 | 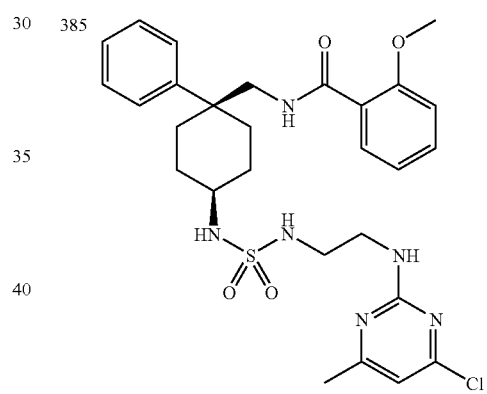 | 588 |
| 386 | 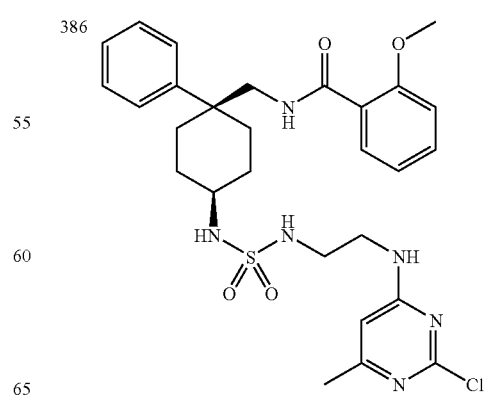 | 588 |

-continued
| Example | Structure | [M + H] |
|---|---|---|
| 387 | 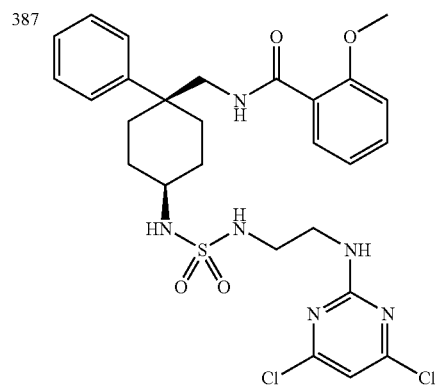 | 608 |
| 388 | 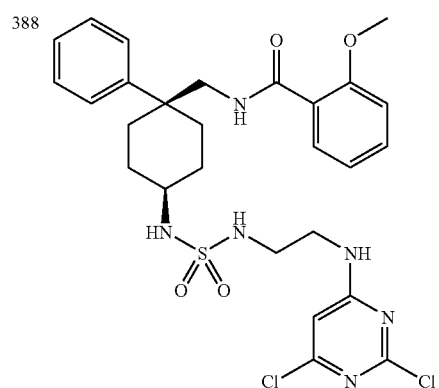 | 608 |
| 389 | 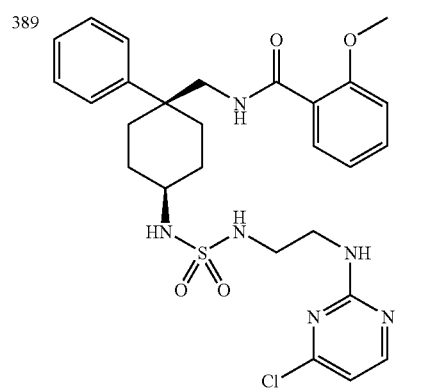 | 574 |
| 390 | 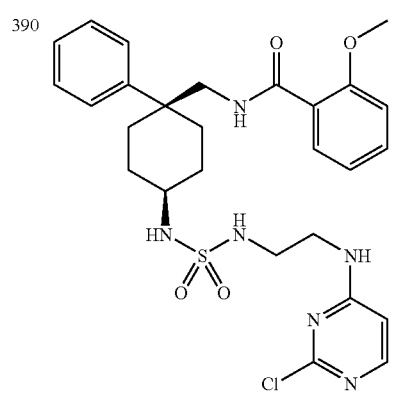 | 574 |
-continued
| Example | Structure | [M + H] |
|---|---|---|
| 391 | 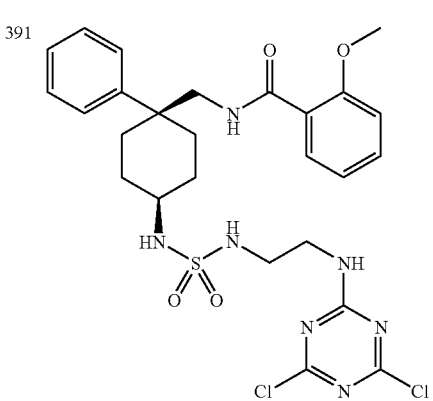 | 609 |
| 392 | 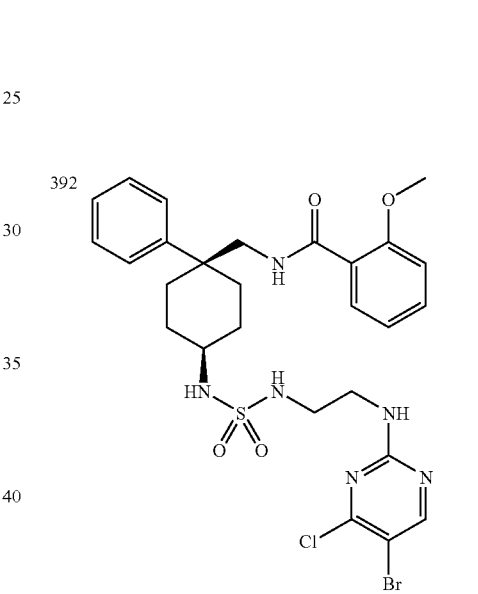 | 653 |
| 393 | 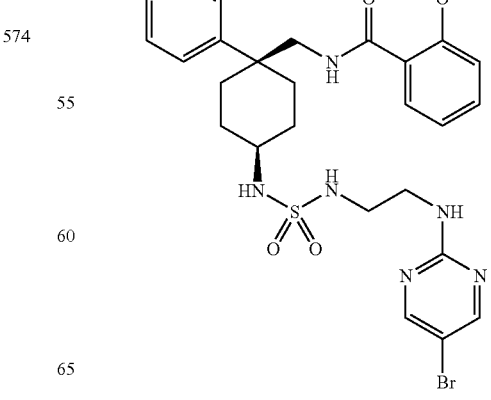 | 618 |

EXAMPLE 397

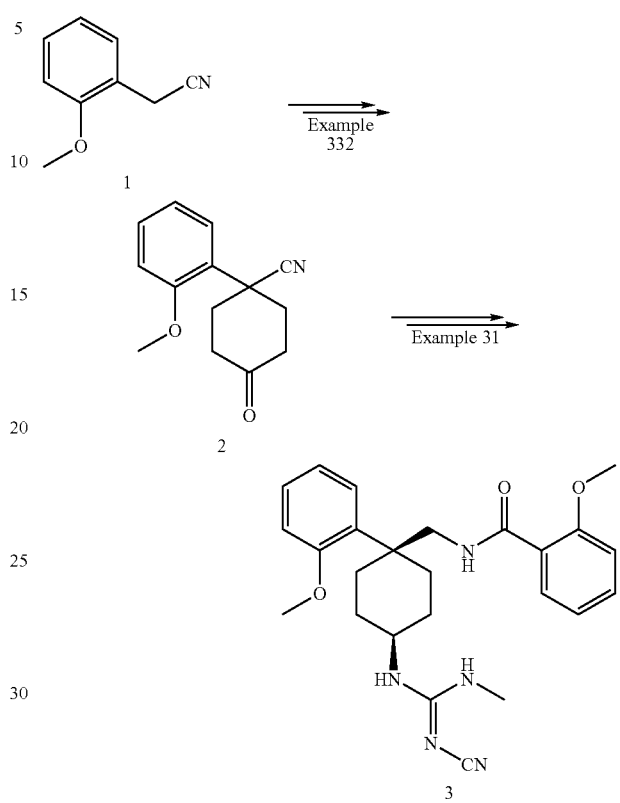

| Ex- ample | Structure | [M + H] |
|---|---|---|
| 394 | 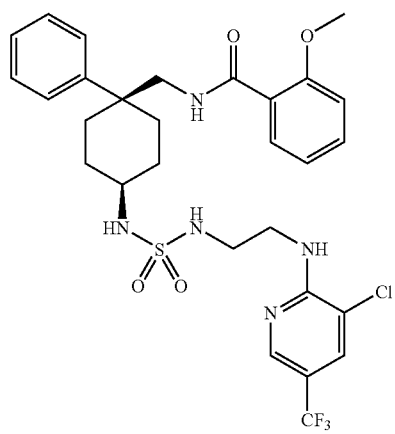 | 628 |
| 395 | 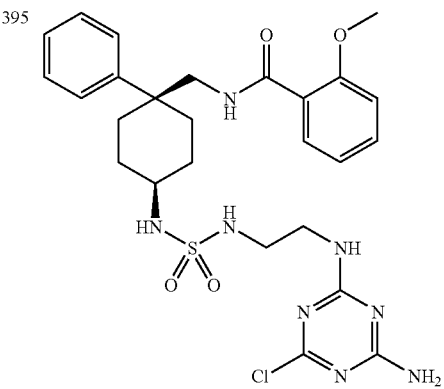 | 590 |
| 396 | 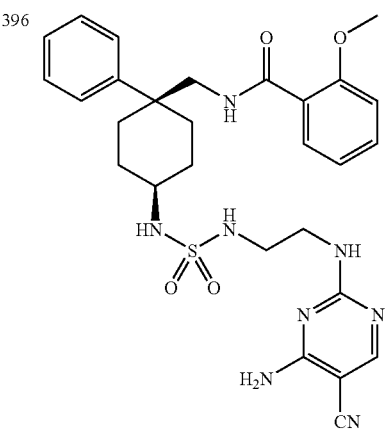 | 579 |

Compound 1: Compound 1 is commercially available.

Compound 2: Compound 2 is prepared in an exact same procedure as described in synthesis of Example 332 where 2-methoxyphenylacetonitrile replaced the 2-fluorophenylacetonitrile in synthesis of Example 332.

Compound 3: Compound 3 was prepared in a sequence described in synthesis of Example 31, where 4-(2-methoxyphenyl)-4-cyanocyclohexanone 2 was used instead of compound 1 in example 31. [M+H]=450.

EXAMPLES 398–404

Examples 398 to 404 were synthesized using methodology described in Example 397.

| Example | Structure | [M + H] |
|---|---|---|
| 398 | 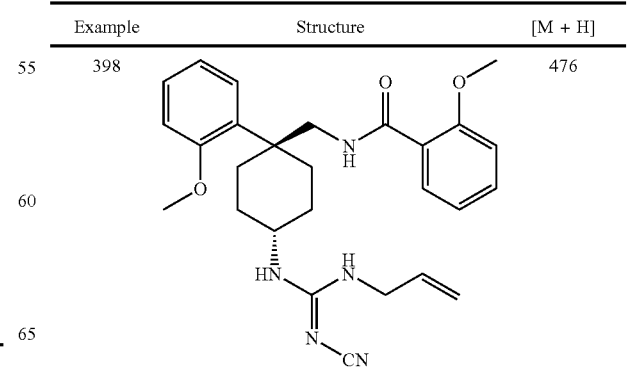 | 476 |

-continued
| Example | Structure | [M + H] |
|---------|-----------|---------|
| 399 | 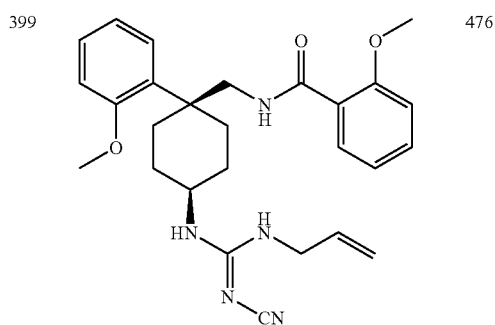 | 476 |
| 400 | 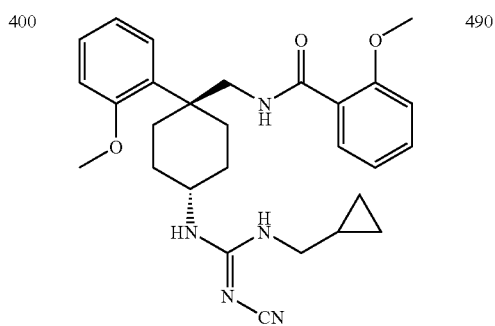 | 490 |
| 401 | 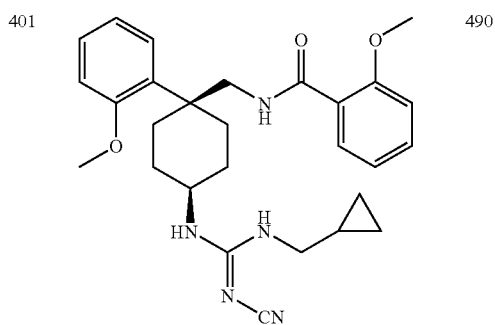 | 490 |
| 402 | 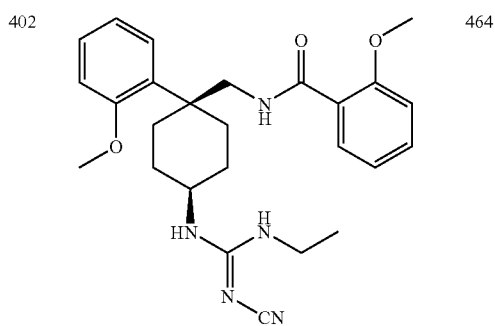 | 464 |
-continued
| Example | Structure | [M + H] |
|---------|-----------|---------|
| 403 | 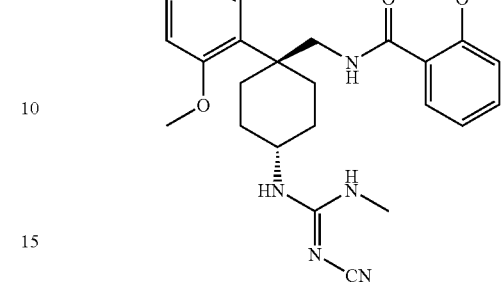 | 450 |
| 404 | 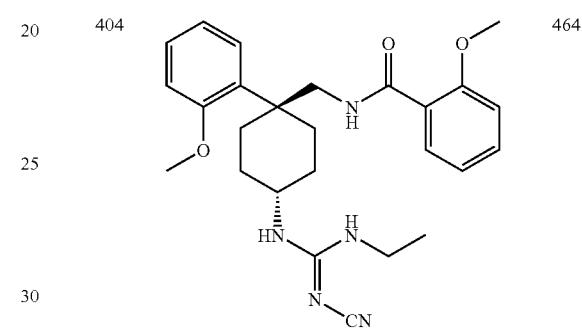 | 464 |
EXAMPLE 405
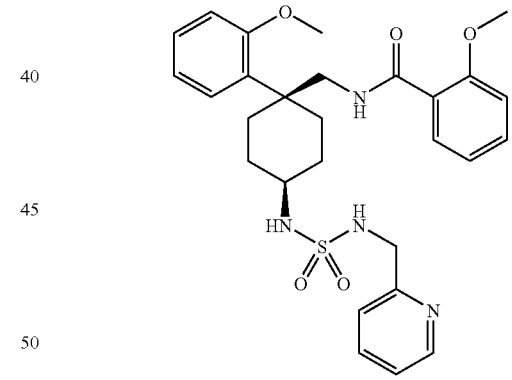
Synthesis:
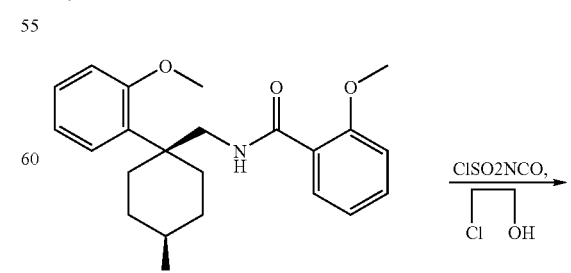

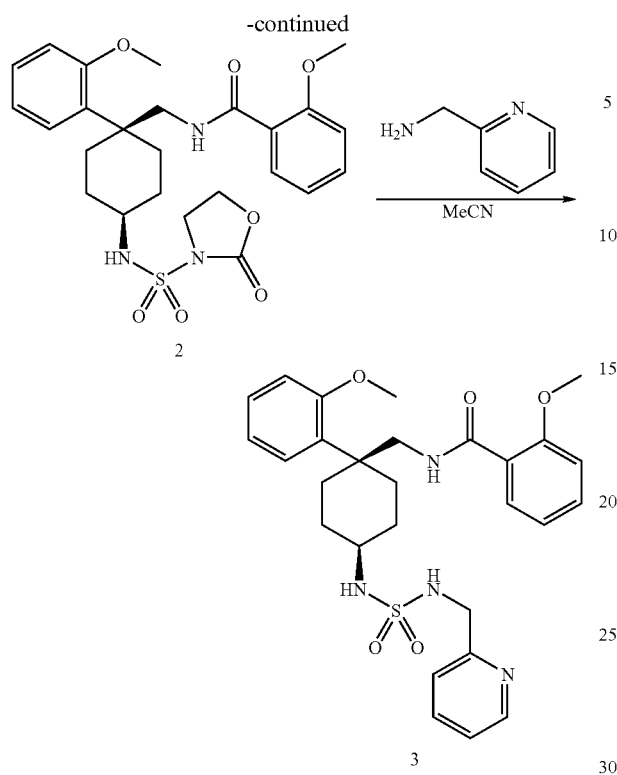

Compound 1: The synthesis of 1 was described in Example 388.

Compound 2: The synthesis of 2 was proceeded in a same procedure described in Example 73.

Compound 3: A solution of 2 (40 mg, 0.083 mmol), 4-(aminomethyl)pyridine (20 mg, 0.20 mmol) in 1 ml of CH₃CN was stirred for 2 h at 65° C. The reaction mixture was purified by preparative HPLC (described in a synthesis of Example 31) to yield 8.9 mg of the 3 as a colorless oil. Mass Spec [M+H]=539.

EXAMPLES 406–410

Examples 406 to 410 were synthesized using methodology described in Example 405.

| Example | Structure | [M + H] |
|---|---|---|
| 406 | 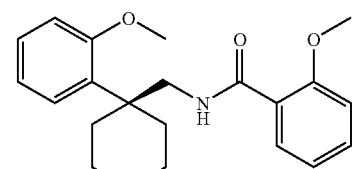 | 596 |
| 407 | 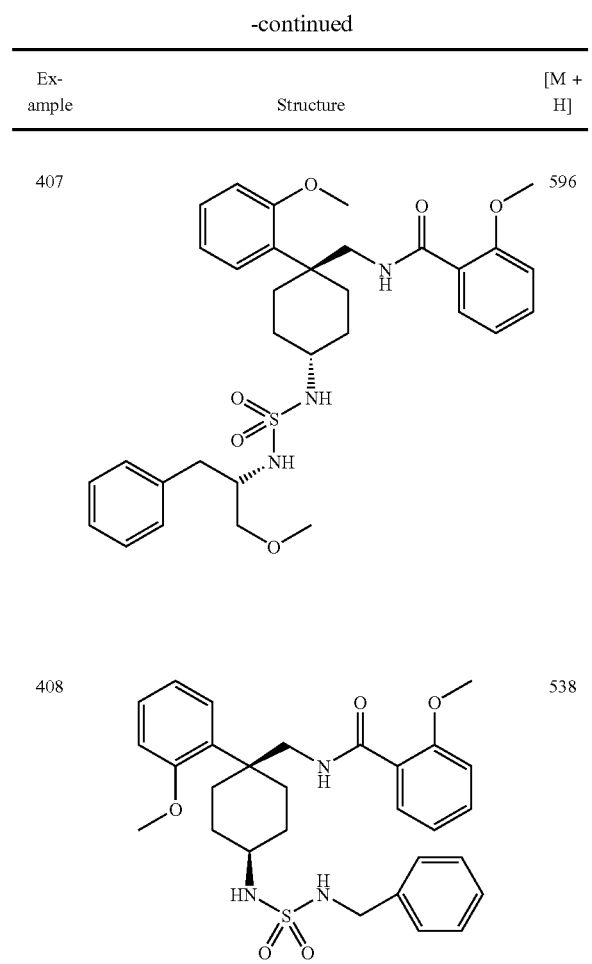 | 596 |
| 408 | 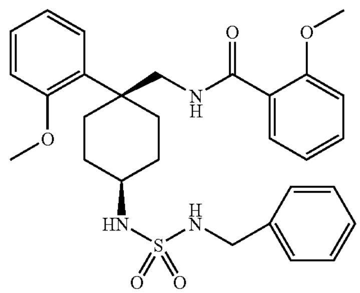 | 538 |
| 409 | 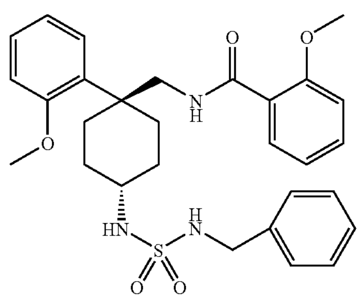 | 538 |
| 410 | 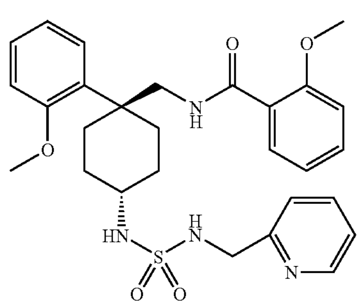 | 539 |

EXAMPLES 411 and 412
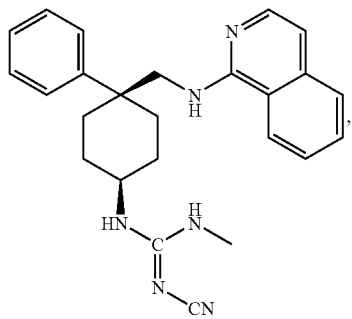
Ex. 411
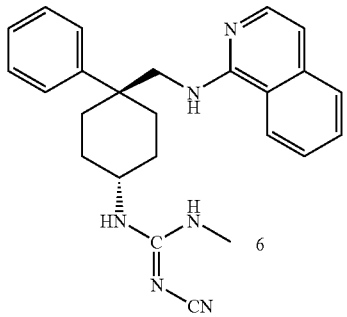
Ex. 412
Synthesis:
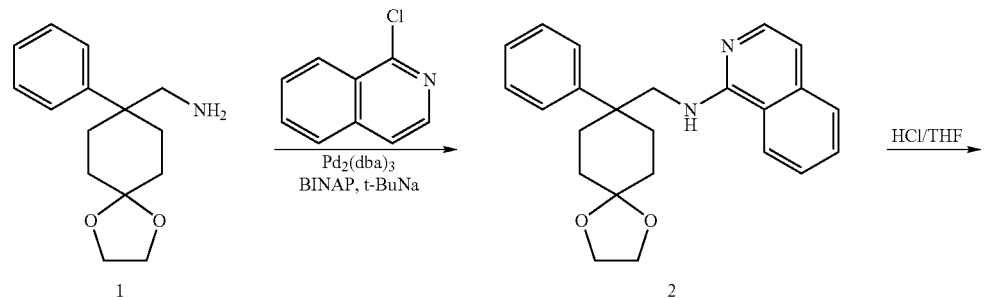
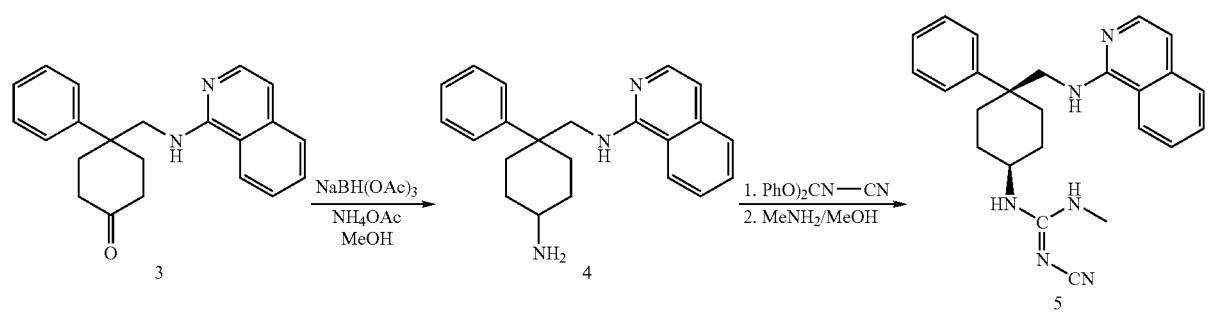
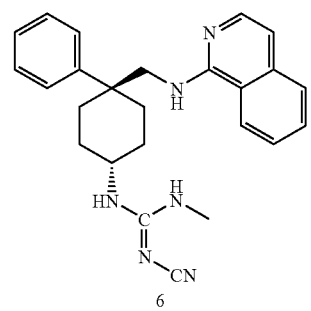

Compound 1: Synthesis of compound 1 is described in Example 31.

Compound 2: To a specially designed vial for microwave reactor was added compound 1 (0.57 g, 2.3 mmol), Pd$_2$(dba)$_3$ (42 mg, 0.046 mmol), BINAP (79 mg, 0.13 mmol) and t-BuONa (0.38 g, 2.3 mmol) in a portion. The reaction vial was placed under vacuum to remove air. Toward the mixture was, then, added 22 ml of degassed THF and the reaction vial was capped. The reaction mixture was placed in microwave reactor and heated for 20 min at 180° C. The reaction mixture was cooled down and placed on column chromatography (20–50 % EtOAc/Hexane) to yield 0.62 g (72%) of the desired product as oily solid.

Compound 3: Compound 2 (3.0 g, 8.0 mmol) was dissolved in THF (60 ml) and aq. HCl (10 ml), and the resulting solution was stirred for 4 h at 35° C. THF was evaporated from the reaction mixture and the remaining aqueous solution was extracted with EtOAc (100 ml×2). The organic layer was dried over MgSO4 and concentrated in vacuo to provide an oil (2.4 g, >95%), which was identified as the desired product (1:1 mixture of two isomers) and subjected to the following reaction without any further purification (>95% pure).

Compound 4: To a solution of compound 3 (1.2 g, 3.6 mmol) in 50 ml of MeOH was added NH$_4$OAc (2.2 g, 27 mmol) and NaBH(OAc)$_3$ (0.98 g, 4.6 mmol) in a portion and the resulting solution was stirred at room temperature for 12 h. The reaction mixture was concentrated in vacuo, yielding oily residue, which was partitioned between EtOAc (200 ml) and brine (50 ml). The aqueous layer was further extracted with EtOAc (50 ml×2). The combined organic solution was dried over MgSO4 and concentrated in vacuo to yield an oil (1.2 g, >95%), which was identified as the desired product and subjected to following reactions without further purification (>90% pure).

Compound 5 and 6: Synthesis of compound 4 was carried out in an exact same procedure as in synthesis of Example 31 using compound 4 (0.13 g, 0.39 mmol), diphenyl cyanocarbonimidate (94 mg, 0.39 mmol) and 5 ml of 2 N MeNH$_2$ in MeOH to produce 20.9 mg of compound 5 and 12.3 mg of compound 6.

EXAMPLES 413–418

Examples 413 to 418 were synthesized using methodology described in Example 411.

| Example | Structure | [M + H] |
|---------|-----------|---------|
| 413 | | 427 |
| 414 | 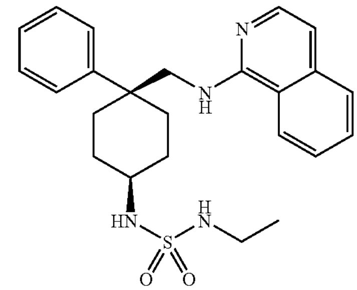 | 427 |
| 415 | 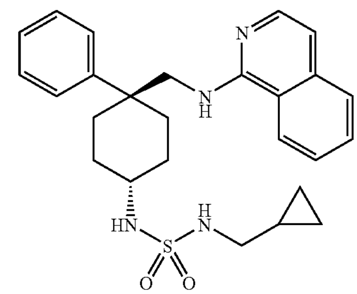 | 453 |
| 416 | 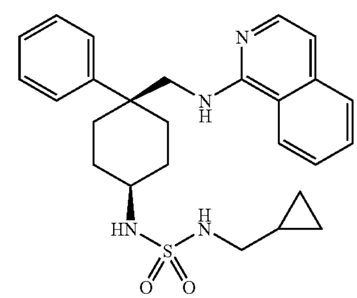 | 453 |
| 417 | 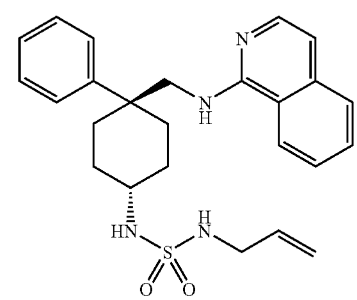 | 439 |
| 418 | 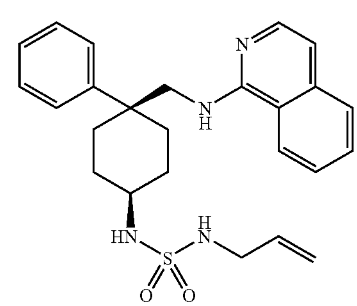 | 439 |

EXAMPLE 419

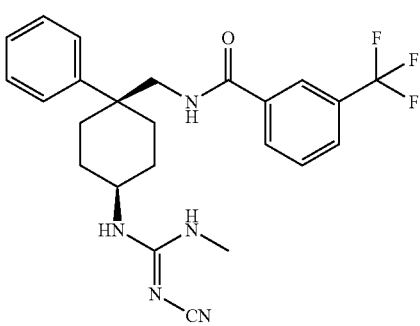

Synthesis:

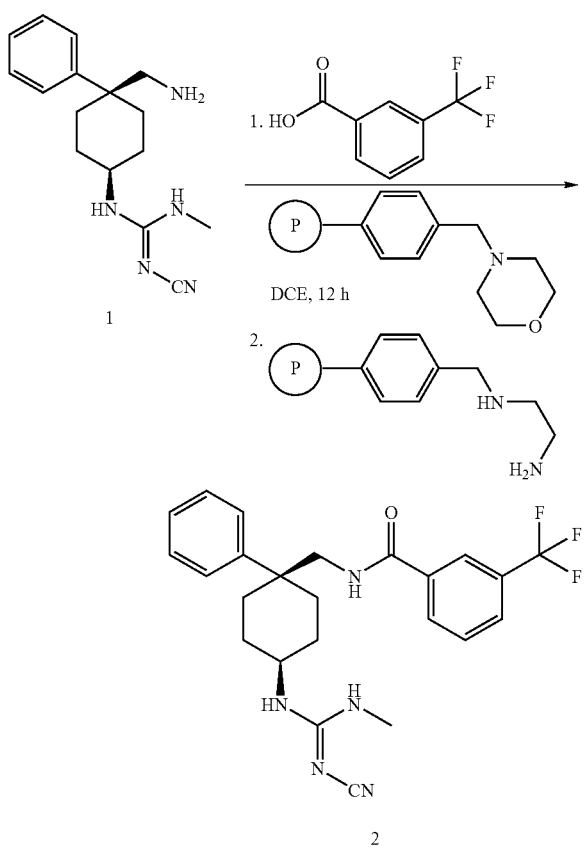

Compound 1: Synthesis of compound 1 is described in Example 153.

Compound 2: Compound 2 was prepared as a part of the library synthesis. The general procedure is following:

To a solution of the compound 1 (8.3 mg, 0.03 mmol) in 1 ml of 1,2-dichloroethane was added 3-(trifluoromethyl) benzoyl chloride (20 µL, 0.14 mmol) and 20 mg polymer-bound amine (PL-MPH resin, Polymer Laboratories) in a portion and the resulting mixture was swirled for 12 h. Toward the reaction mixture was added polymer-bound resin PL-EDA (50 mg, Polymer Laboratories) and the resulting mixture was swirled for additional 5 h. The reaction mixture was then filtered and concentrated in speed-vac to yield 8.0 mg (0.020 mmol, 67%) of the desired product as a colorless oil. [M+H]=458.

EXAMPLES 420–449

Examples 420 to 449 were synthesized using methodology described in Example 419.

| Example | Structure | [M + H] |
|---|---|---|
| 420 | 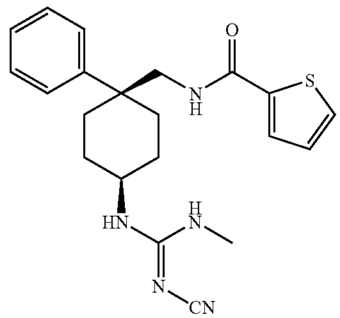 | 396 |
| 421 | 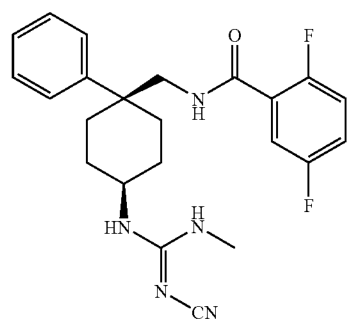 | 426 |
| 422 | 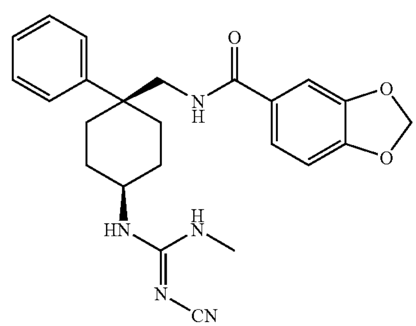 | 434 |
| 423 | 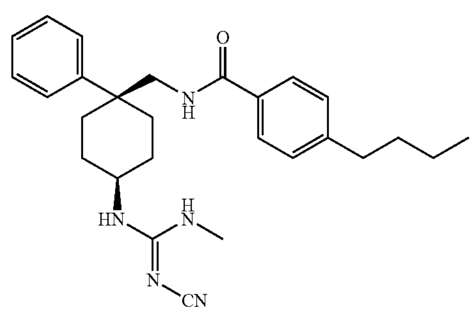 | 446 |

-continued
| Example | Structure | [M + H] |
|---|---|---|
| 424 | 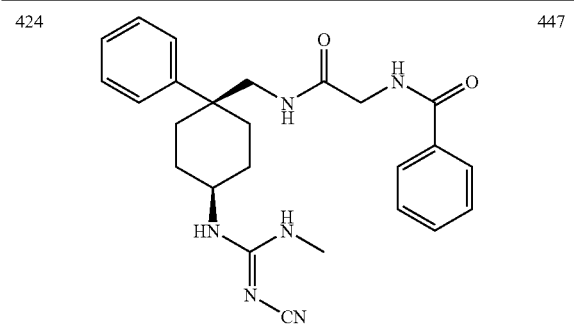 | 447 |
| 425 | 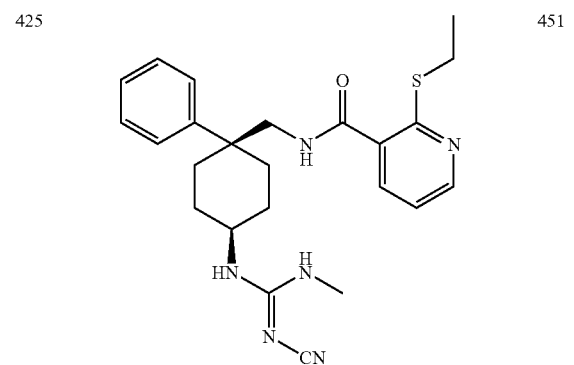 | 451 |
| 426 | 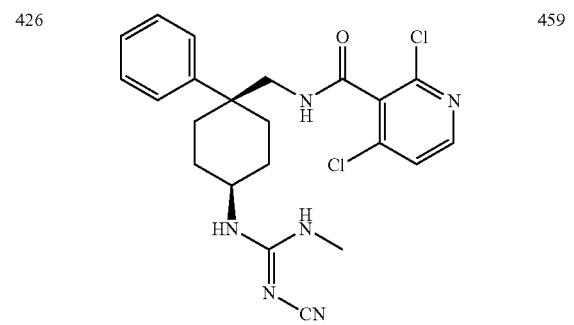 | 459 |
| 427 | 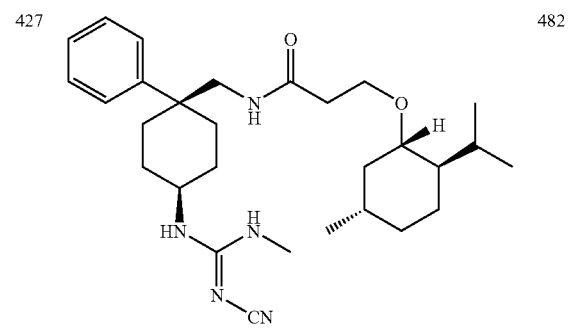 | 482 |
-continued
| Example | Structure | [M + H] |
|---|---|---|
| 428 | 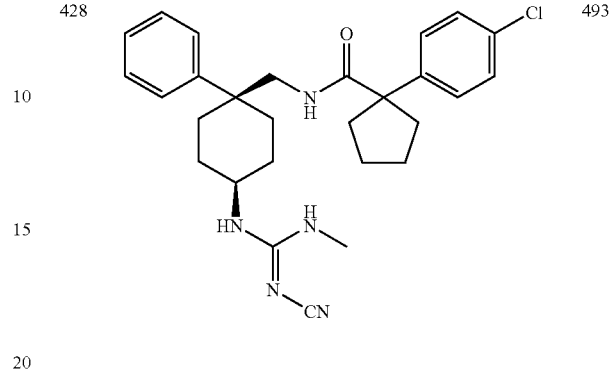 | 493 |
| 429 | 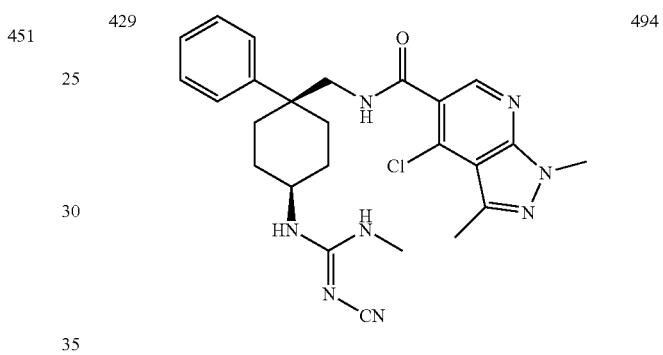 | 494 |
| 430 | 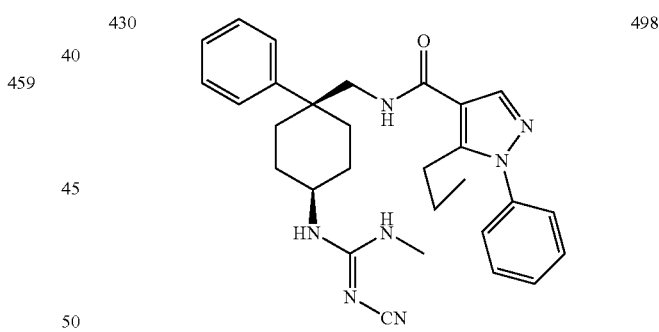 | 498 |
| 431 | 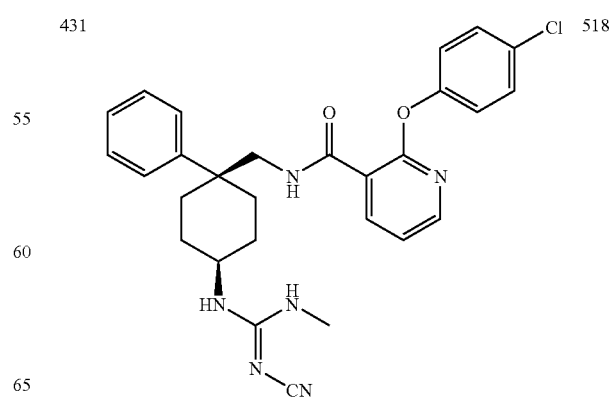 | 518 |

| Example | Structure | [M + H] |
|---------|-----------|---------|
| 432 | 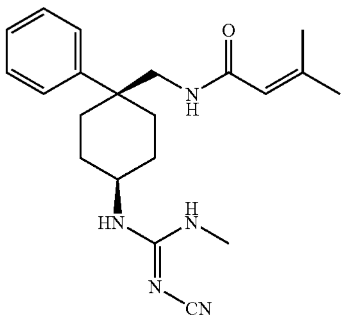 | 368 |
| 433 | 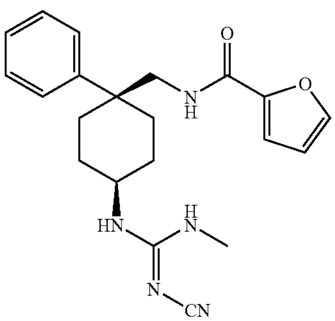 | 380 |
| 434 | 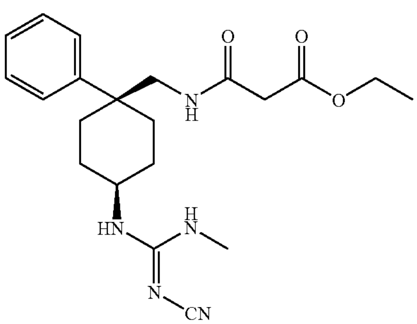 | 400 |
| 435 | 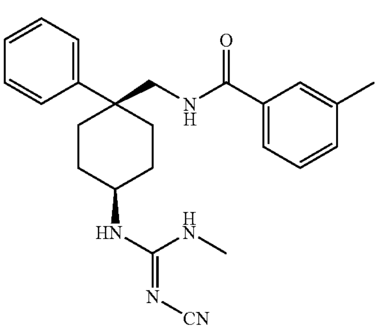 | 404 |

| Example | Structure | [M + H] |
|---------|-----------|---------|
| 436 | 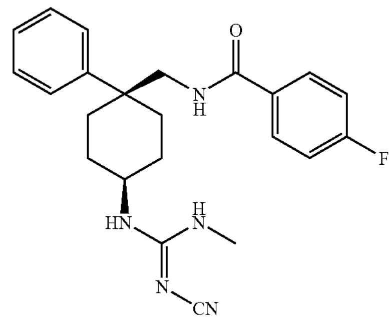 | 408 |
| 437 | 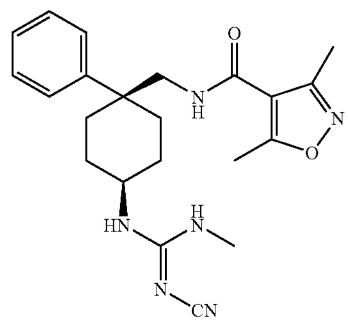 | 409 |
| 438 | 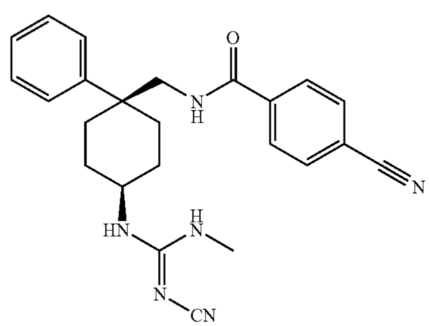 | 415 |
| 439 | 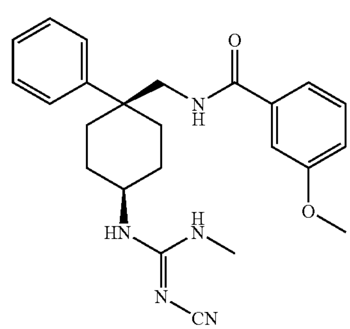 | 420 |

-continued

| Example | Structure | [M + H] |
|---|---|---|
| 440 | 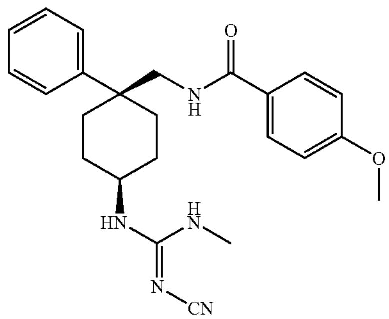 | 420 |
| 441 | 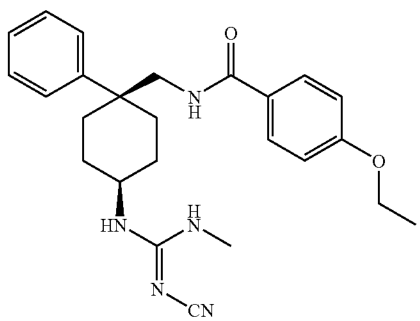 | 434 |
| 442 | 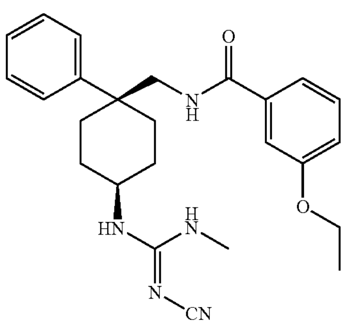 | 434 |
| 443 | 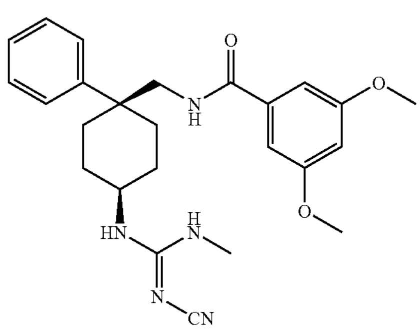 | 450 |

-continued

| Example | Structure | [M + H] |
|---|---|---|
| 444 | 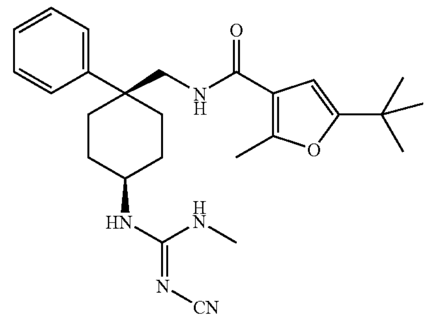 | 450 |
| 445 | 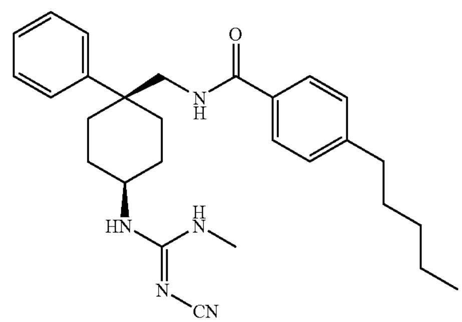 | 460 |
| 446 | 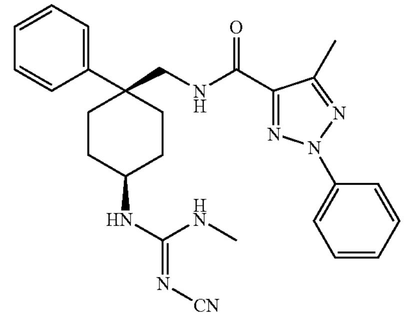 | 471 |
| 447 | 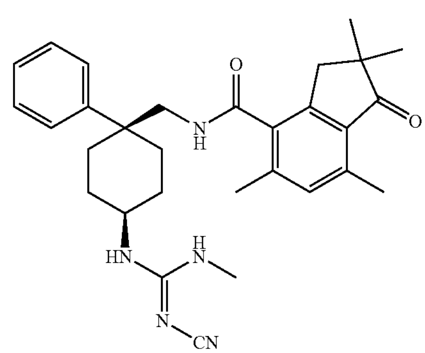 | 500 |

-continued

| Example | Structure | [M+H] |
|---|---|---|
| 448 | 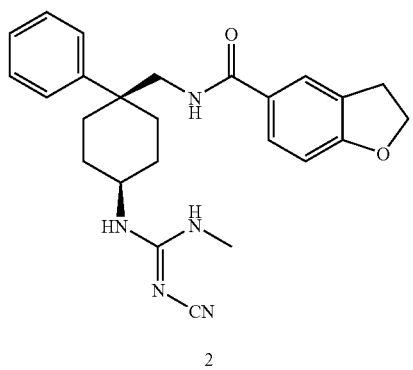 | 506 |
| 449 | 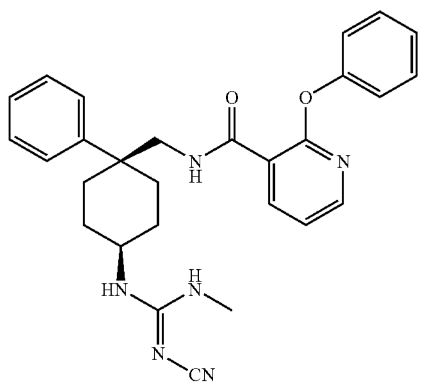 | 483 |

EXAMPLE 450

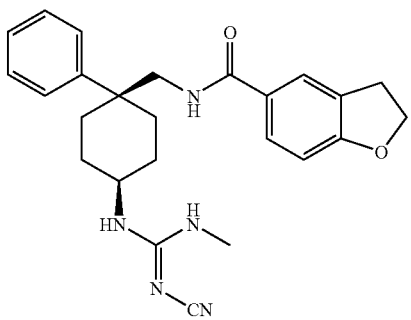

Synthesis:

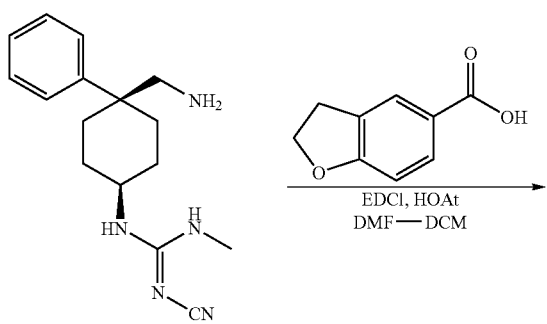

Compound 1: Synthesis of compound 1 is described in Example 153.

Compound 2: Compound 2 was prepared as a part of the library synthesis. The general procedure is following:

To a solution of the acid (10 mg, 0.06 mmol) in 1 ml of DCM and 0.3 ml of DMF was added EDCl (11.5 mg, 0.06 mmol), and HOAt (8.2 mg, 0.06 mmol). Toward the solution was added the compound 1 (11 mg, 0.04 mmol) in 1.2 ml of DCE-DMF (2:1). The reaction mixture was allowed to stir for 12 h at 25° C. The reaction mixture was purified on prep-HPLC (see Example 31) and concentrated in speed-vac to yield 10.8 mg (0.021 mmol, 41%) of the desired product as a colorless oil.

EXAMPLES 451–562

Examples 451 to 562 were synthesized using methodology described in Example 450.

| Example | Structure | [M+H] |
|---|---|---|
| 451 | 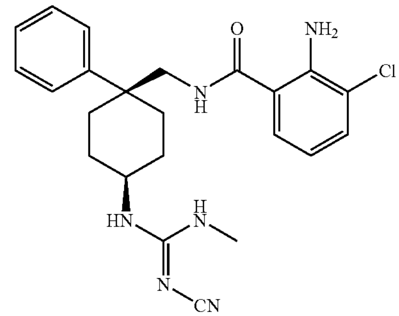 | 440 |

-continued
| Example | Structure | [M + H] |
|---|---|---|
| 452 | 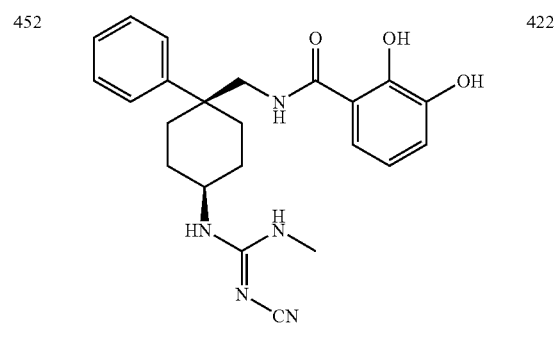 | 422 |
| 453 | 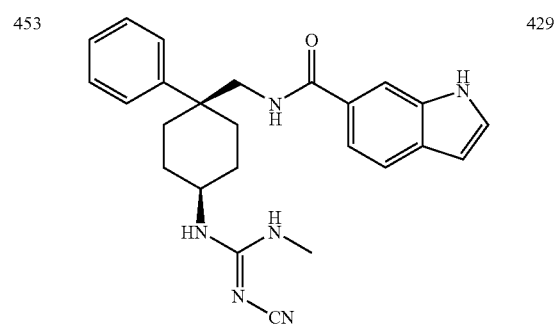 | 429 |
| 454 | 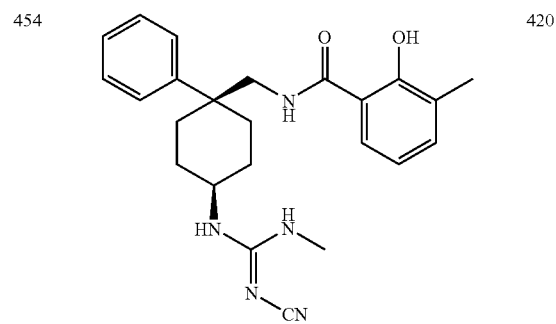 | 420 |
| 455 | 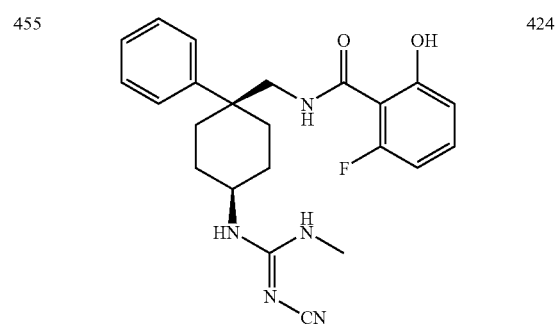 | 424 |
-continued
| Example | Structure | [M + H] |
|---|---|---|
| 456 | 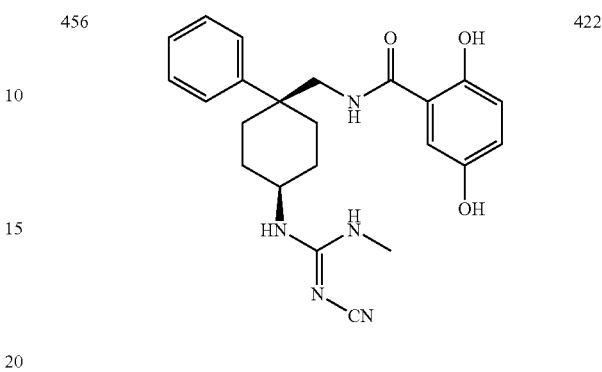 | 422 |
| 457 | 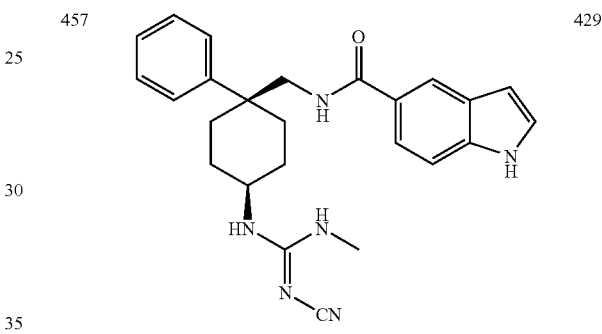 | 429 |
| 458 | 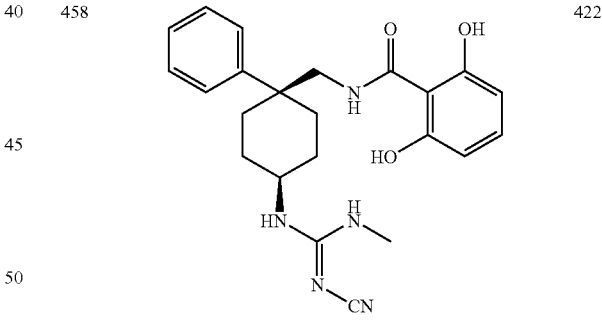 | 422 |
| 459 | 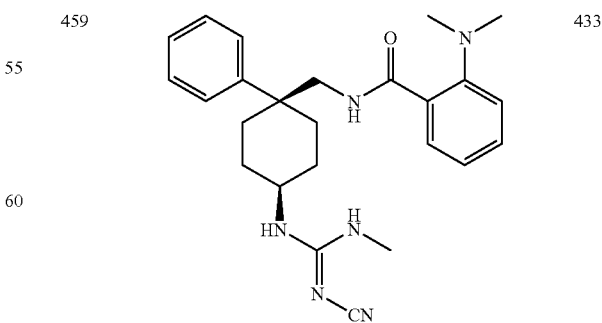 | 433 |

-continued
| Example | Structure | [M + H] |
|---|---|---|
| 460 | 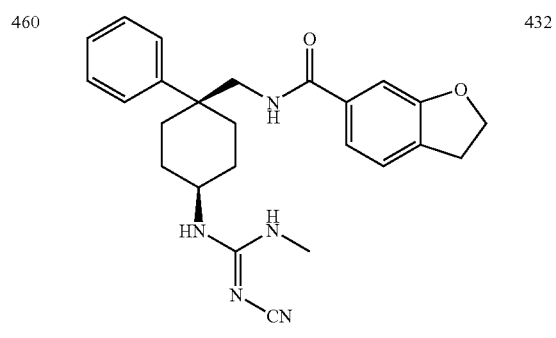 | 432 |
| 461 | 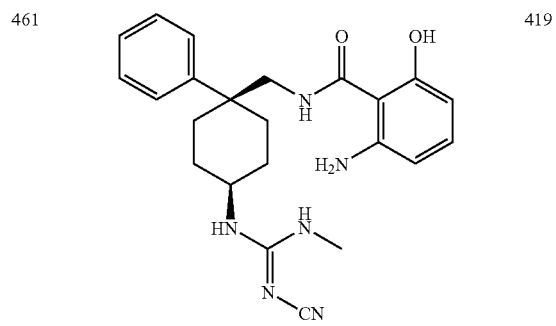 | 419 |
| 462 | 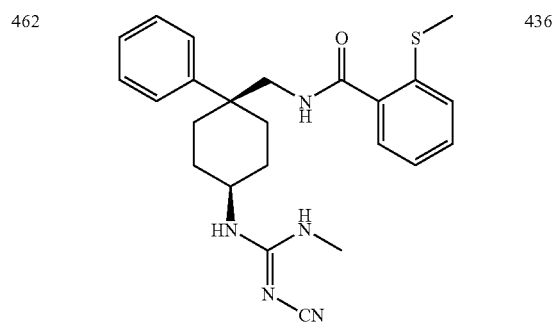 | 436 |
| 463 | 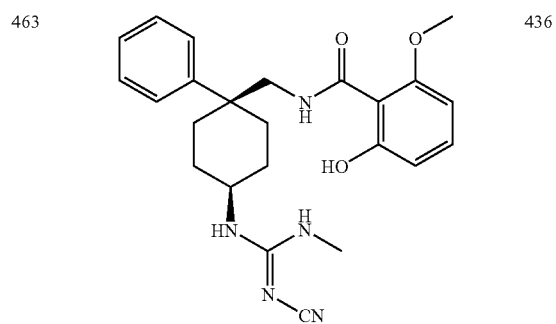 | 436 |
-continued
| Example | Structure | [M + H] |
|---|---|---|
| 464 | 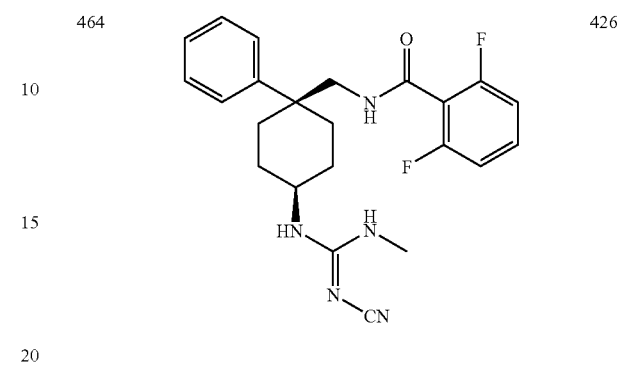 | 426 |
| 465 | 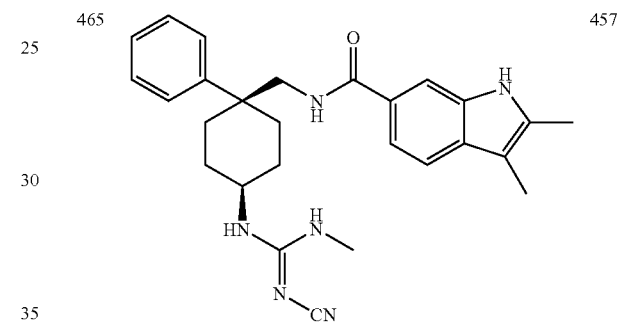 | 457 |
| 466 | 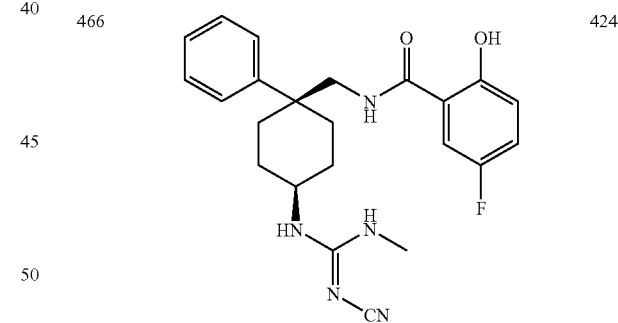 | 424 |
| 467 | 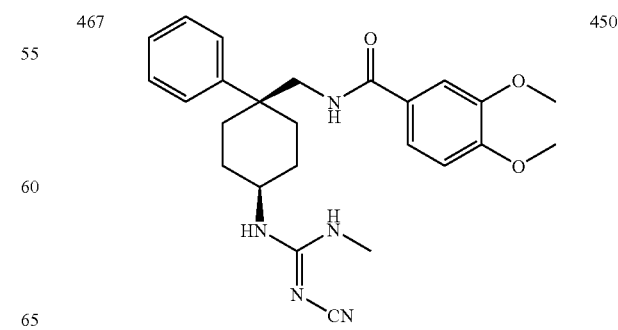 | 450 |

-continued

| Example | Structure | [M + H] |
|---|---|---|
| 468 | 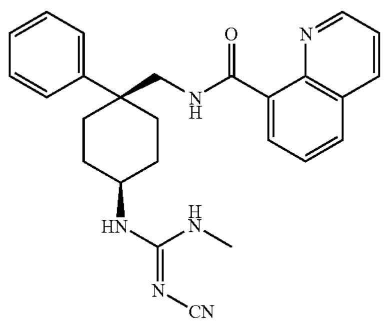 | 441 |
| 469 | 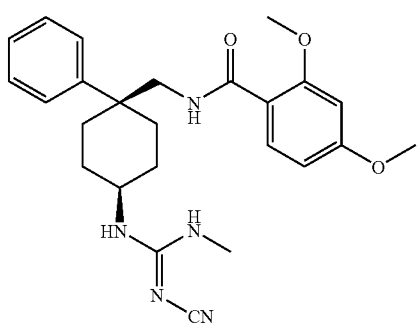 | 450 |
| 470 | 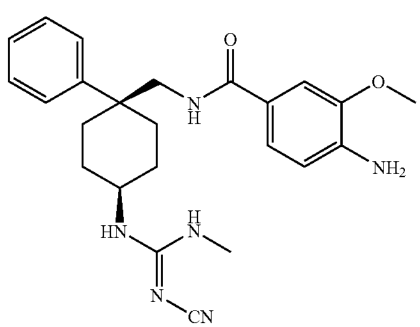 | 435 |
| 471 | 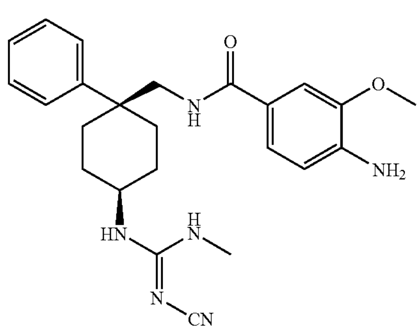 | 440 |

-continued

| Example | Structure | [M + H] |
|---|---|---|
| 472 | 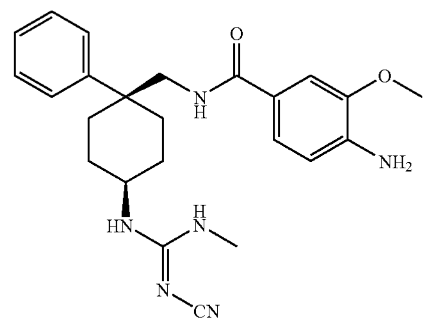 | 423 |
| 473 | 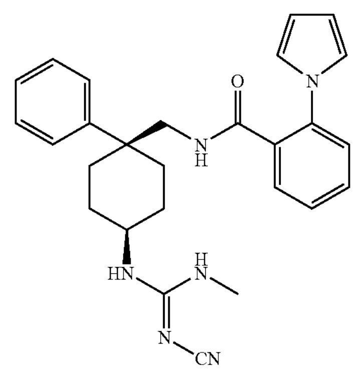 | 455 |
| 474 | 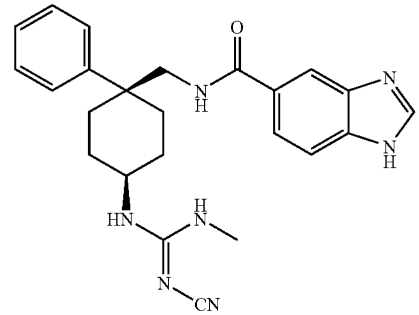 | 430 |
| 475 | 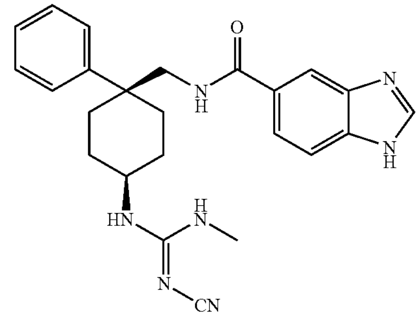 | 456 |

-continued
| Example | Structure | [M + H] |
|---|---|---|
| 476 | 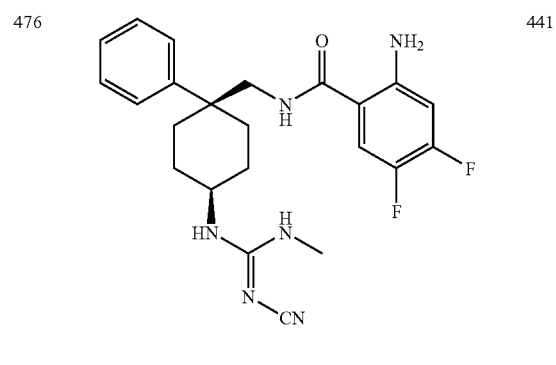 | 441 |
| 477 | 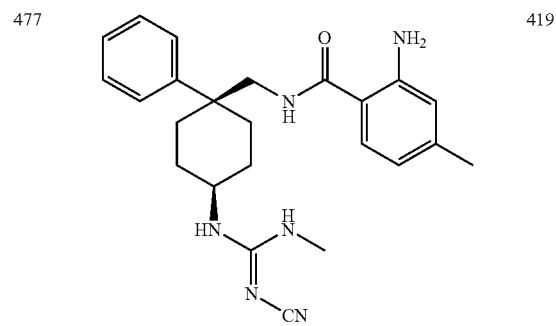 | 419 |
| 478 | 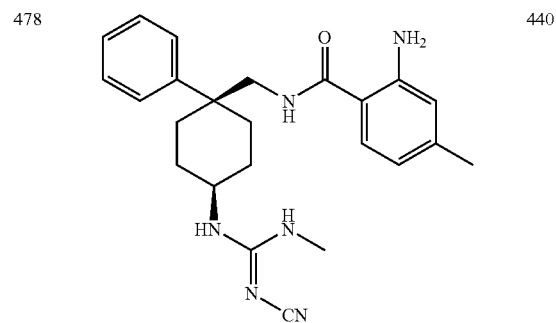 | 440 |
| 479 | 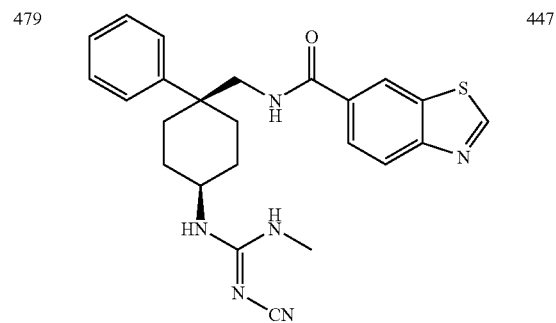 | 447 |
-continued
| Example | Structure | [M + H] |
|---|---|---|
| 480 | 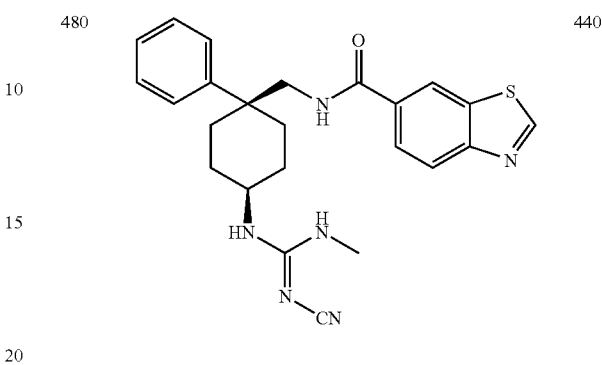 | 440 |
| 481 | 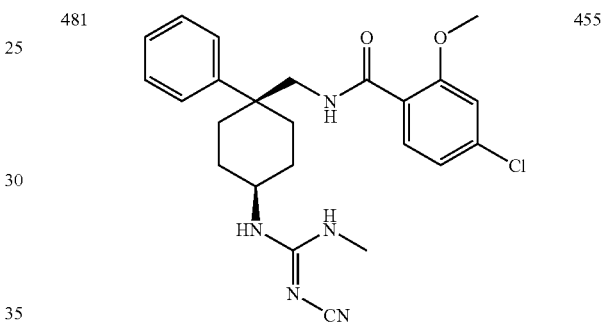 | 455 |
| 482 | 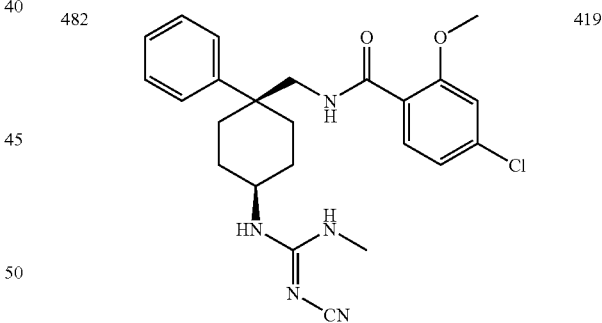 | 419 |
| 483 | 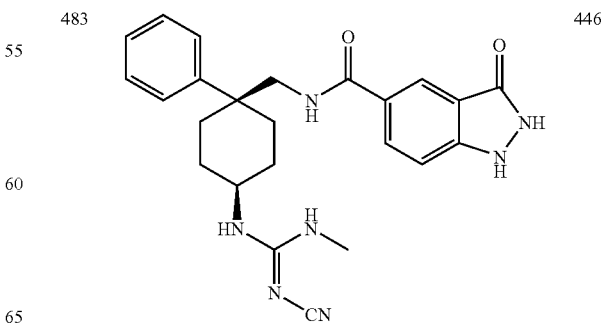 | 446 |

-continued

| Example | Structure | [M+H] |
|---|---|---|
| 484 | 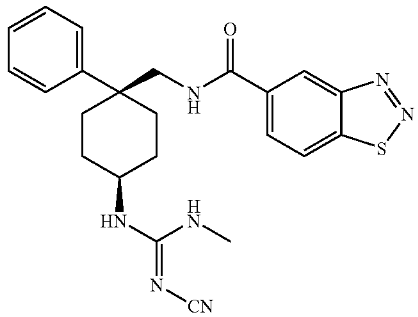 | 448 |
| 485 | 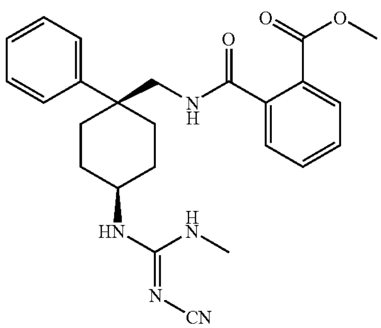 | 448 |
| 486 | 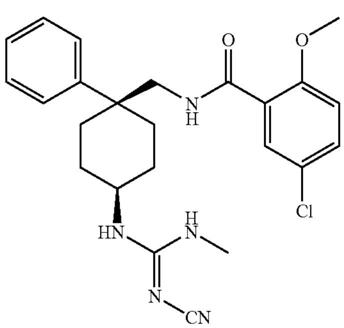 | 455 |
| 487 | 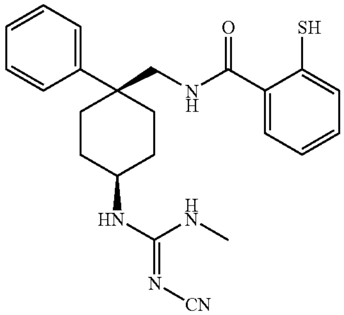 | 422 |

-continued

| Example | Structure | [M+H] |
|---|---|---|
| 488 | 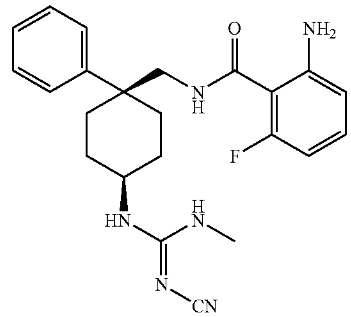 | 423 |
| 489 | 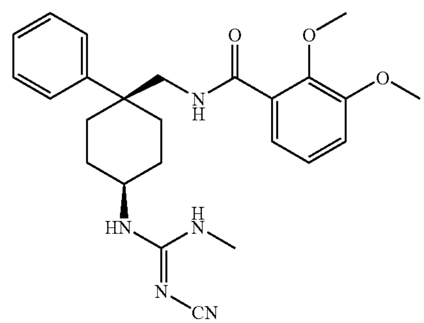 | 450 |
| 490 | 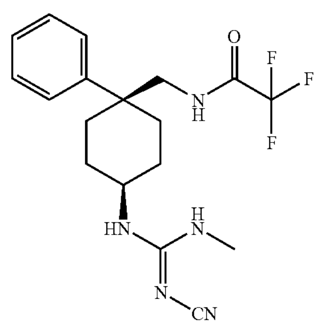 | 382 |
| 491 | 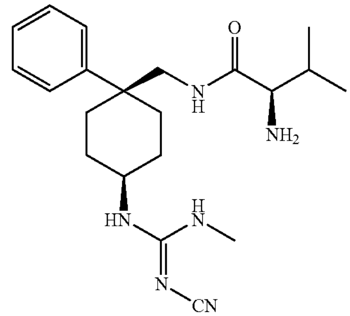 | 385 |

-continued
| Example | Structure | [M + H] |
|---|---|---|
| 492 | 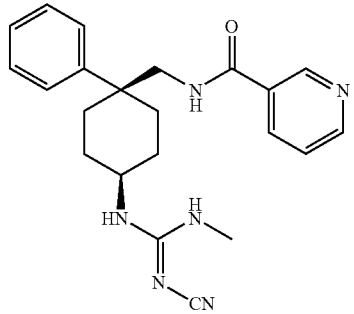 | 391 |
| 493 | 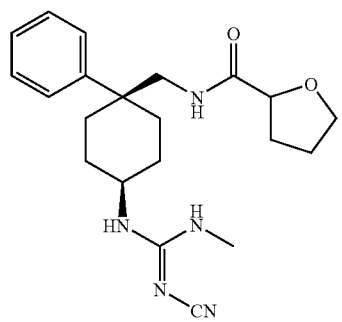 | 384 |
| 494 | 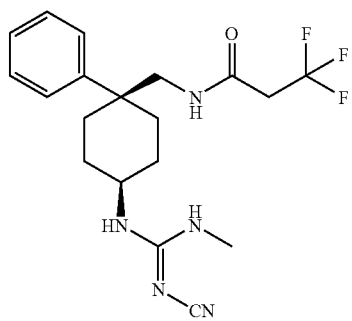 | 386 |
| 495 | 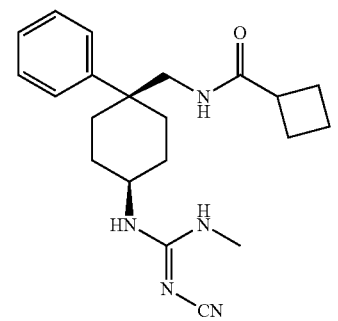 | 368 |
-continued
| Example | Structure | [M + H] |
|---|---|---|
| 496 | 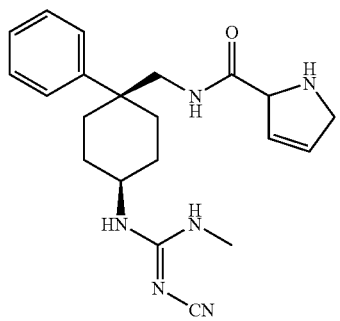 | 381 |
| 497 | 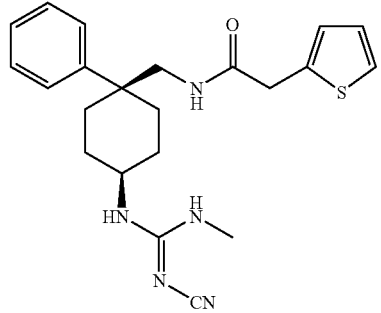 | 410 |
| 498 | 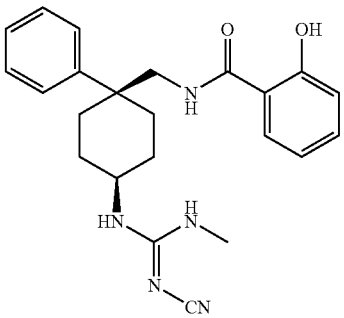 | 406 |
| 499 | 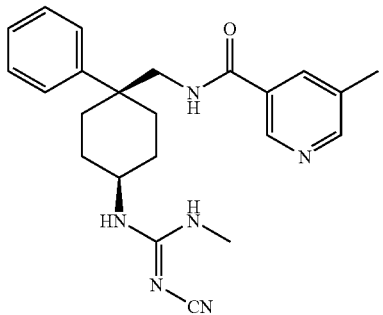 | 405 |

301
-continued
| Example | Structure | [M + H] |
|---|---|---|
| 500 | 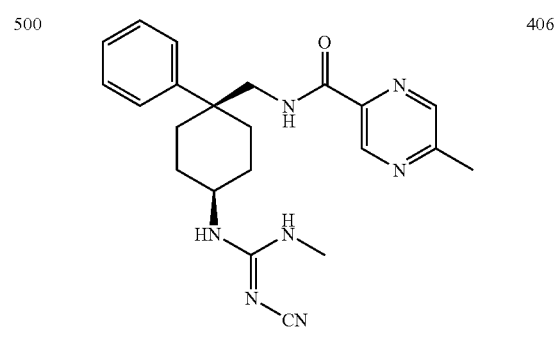 | 406 |
| 501 | 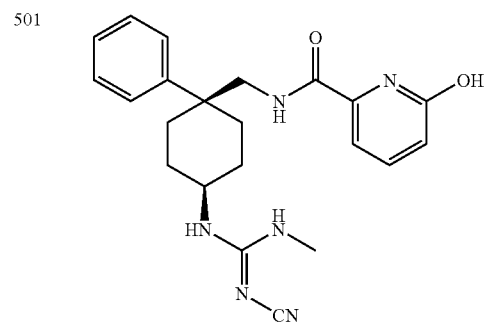 | 407 |
| 502 | 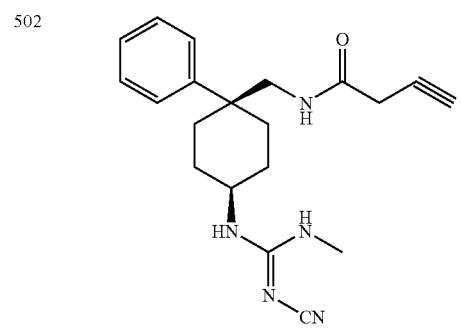 | 366 |
| 503 | 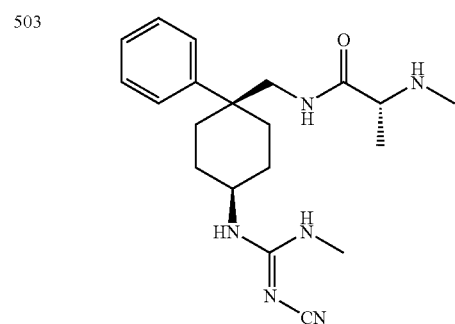 | 371 |
302
-continued
| Example | Structure | [M + H] |
|---|---|---|
| 504 | 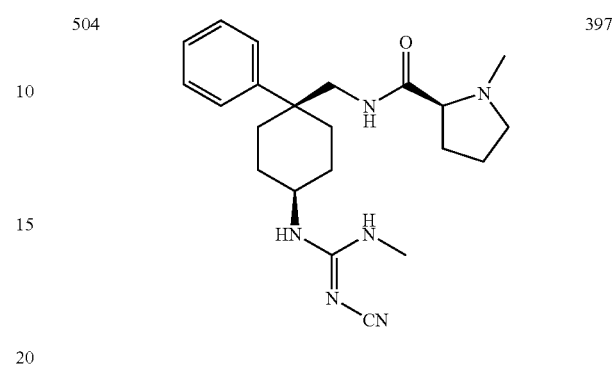 | 397 |
| 505 | 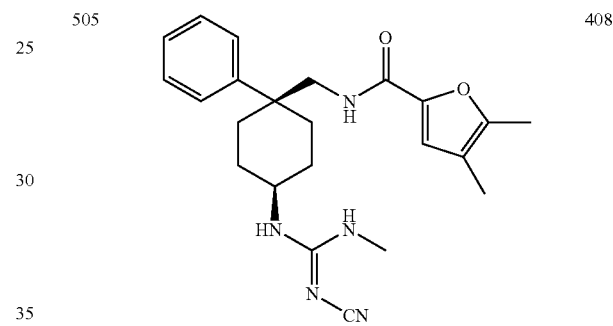 | 408 |
| 506 | 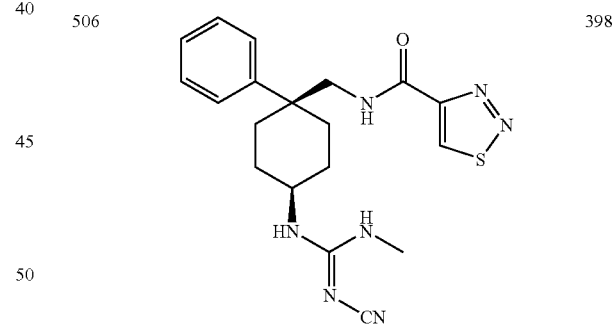 | 398 |
| 507 | 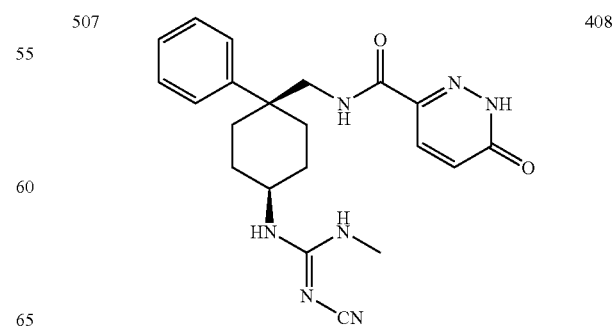 | 408 |

| Example | Structure | [M+H] |
|---|---|---|
| 508 | 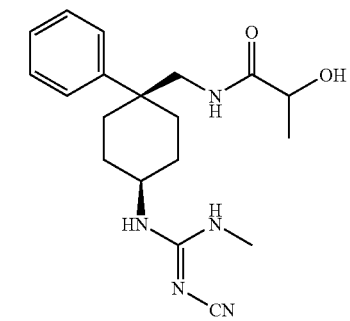 | 358 |
| 509 | | 414 |
| 510 | 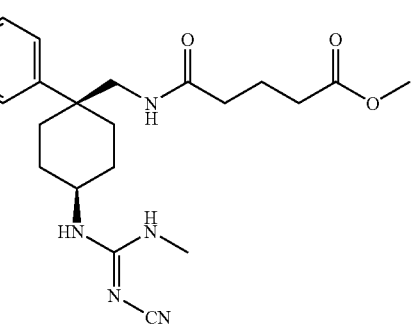 | 392 |
| 511 | 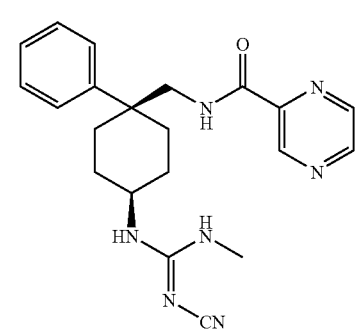 | 407 |
| Example | Structure | [M+H] |
|---|---|---|
| 512 | 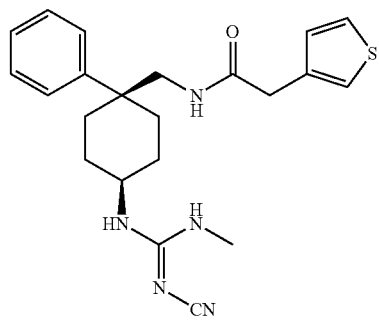 | 410 |
| 513 | | 372 |
| 514 | | 385 |
| 515 | | 405 |

-continued
| Example | Structure | [M + H] |
|---|---|---|
| 516 | 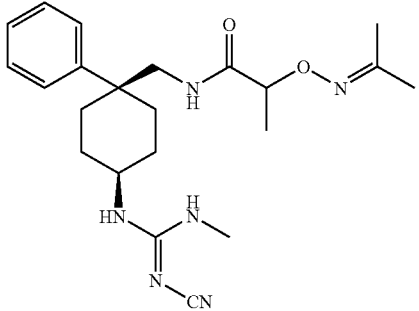 | 398 |
| 517 | 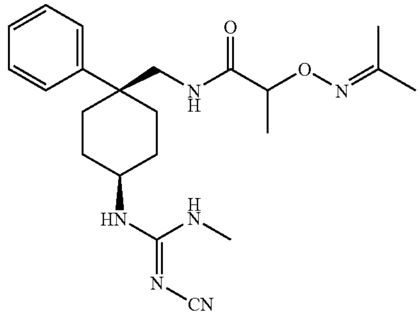 | 413 |
| 518 | 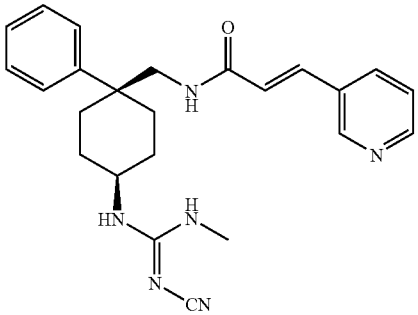 | 417 |
| 519 | 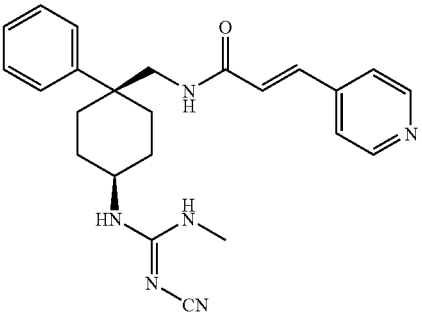 | 417 |
-continued
| Example | Structure | [M + H] |
|---|---|---|
| 520 | 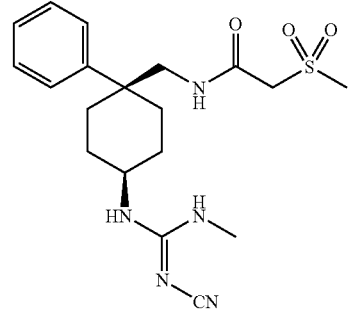 | 371 |
| 521 | 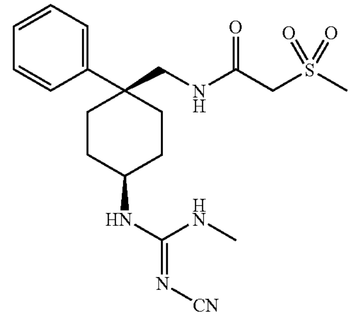 | 406 |
| 522 | 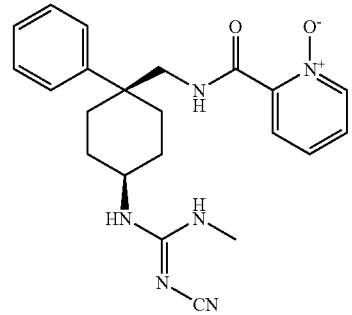 | 407 |
| 523 | 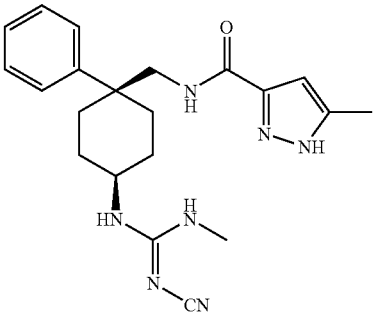 | 394 |

-continued
| Example | Structure | [M + H] |
|---|---|---|
| 524 | 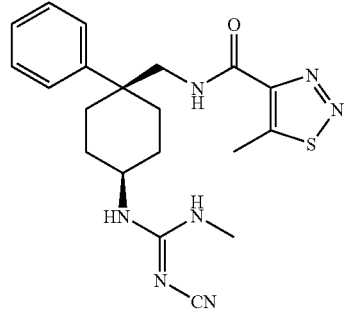 | 412 |
| 525 | 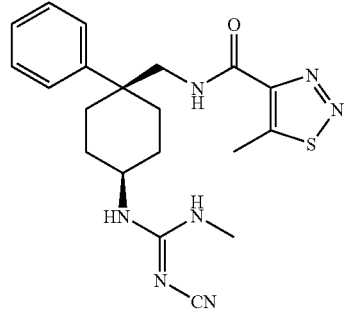 | 408 |
| 526 | 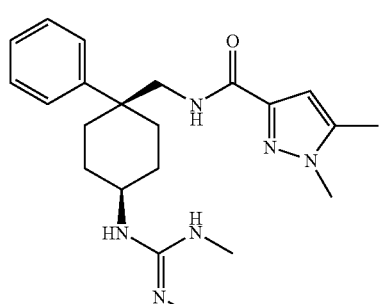 | 398 |
| 527 | 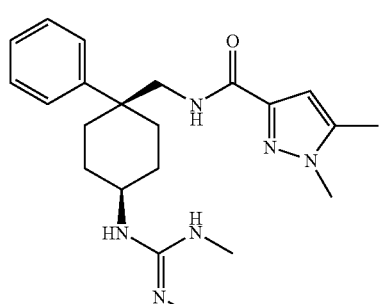 | 380 |
-continued
| Example | Structure | [M + H] |
|---|---|---|
| 528 | 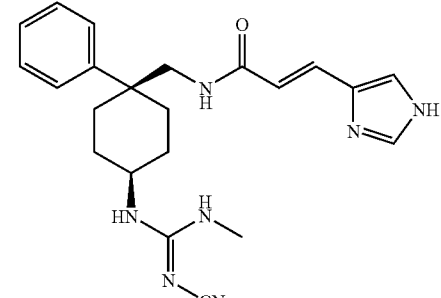 | 406 |
| 529 | 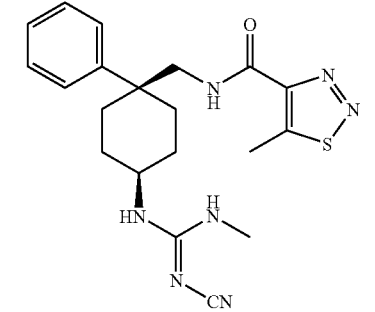 | 404 |
| 530 | 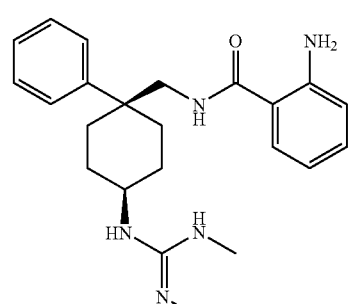 | 406 |
| 531 | 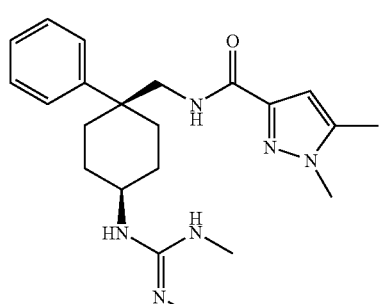 | 408 |

-continued

| Example | Structure | [M+H] |
|---|---|---|
| 532 | 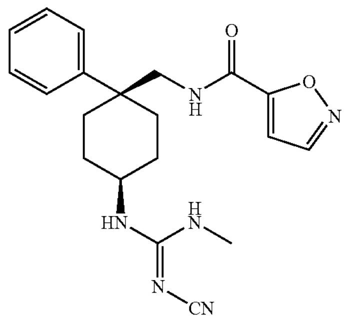 | 381 |
| 533 | 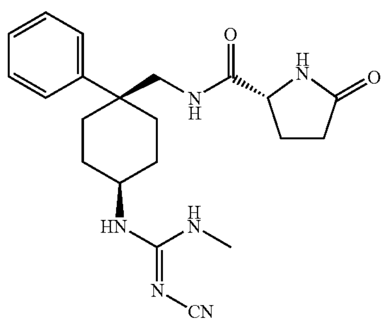 | 397 |
| 534 | 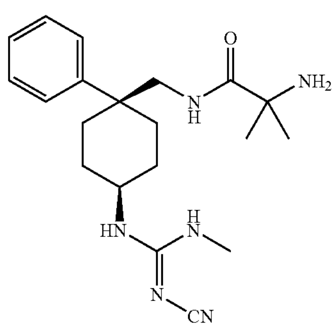 | 371 |
| 535 | 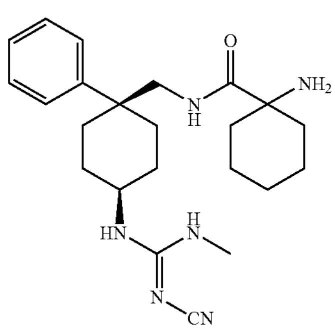 | 411 |

-continued

| Example | Structure | [M+H] |
|---|---|---|
| 536 | 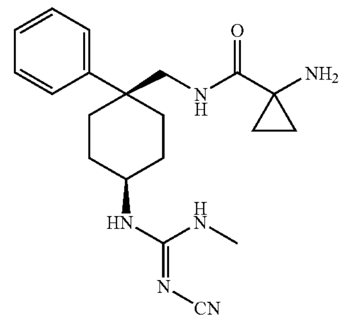 | 369 |
| 537 | 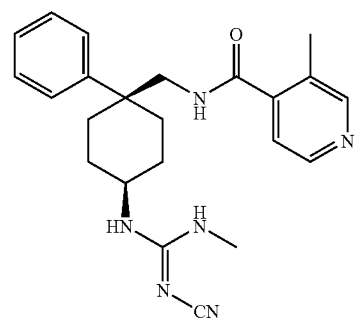 | 406 |
| 538 | 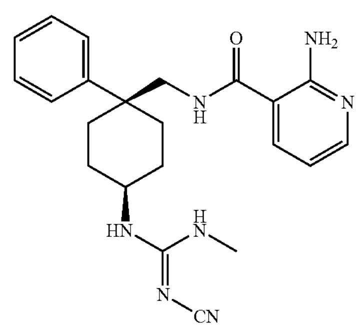 | 406 |
| 539 | 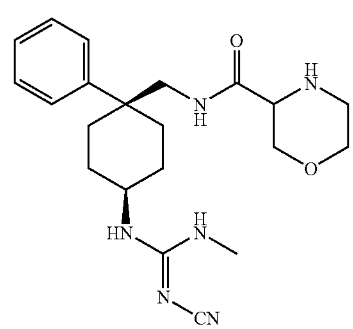 | 399 |

| Example | Structure | [M + H] |
|---|---|---|
| 540 | 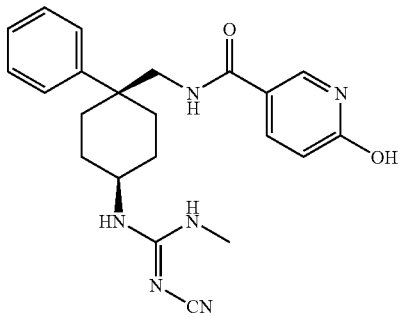 | 408 |
| 541 | 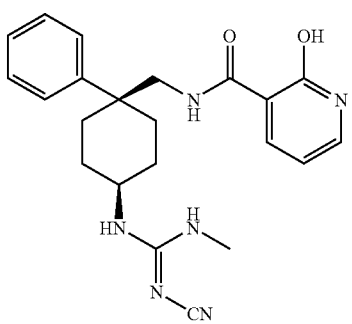 | 407 |
| 542 | 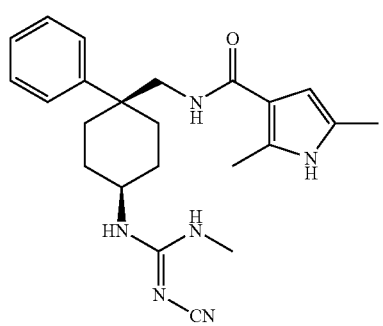 | 407 |
| 543 | | 406 |
| Example | Structure | [M + H] |
|---|---|---|
| 544 | 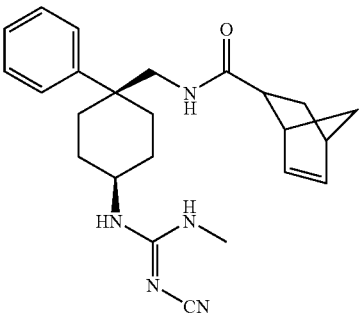 | 368 |
| 545 | 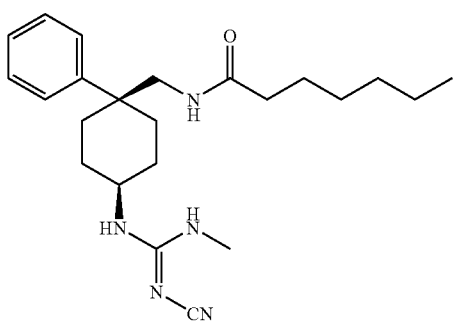 | 407 |
| 546 | 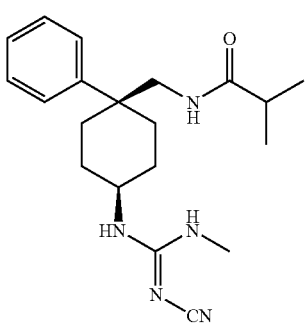 | 398 |
| 547 | | 356 |

-continued
| Example | Structure | [M + H] |
|---|---|---|
| 548 | 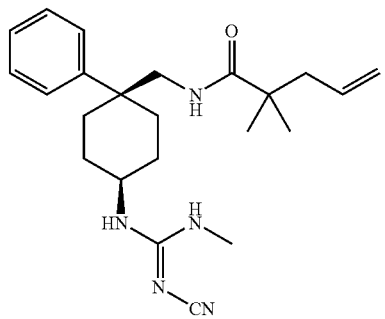 | 396 |
| 549 | 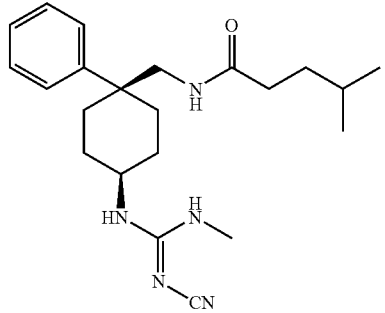 | 384 |
| 550 | 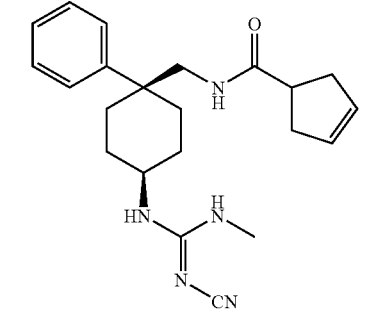 | 380 |
| 551 | 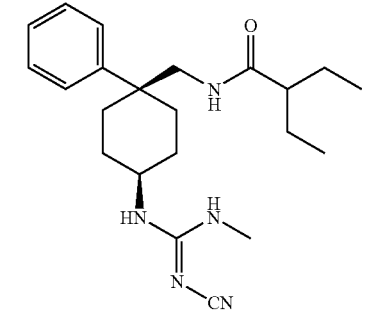 | 384 |
-continued
| Example | Structure | [M + H] |
|---|---|---|
| 552 | 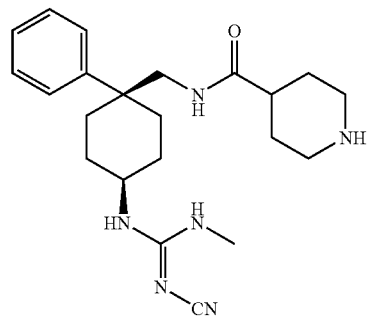 | 397 |
| 553 | 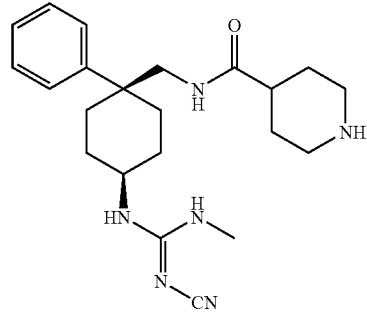 | 380 |
| 554 | 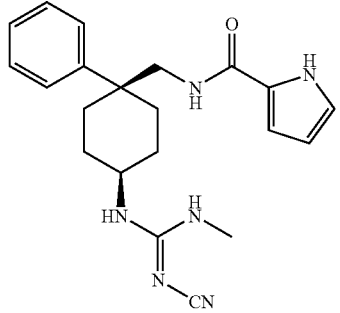 | 379 |
| 555 | 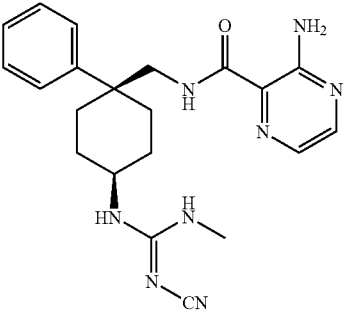 | 407 |

-continued
| Example | Structure | [M + H] |
|---|---|---|
| 556 | 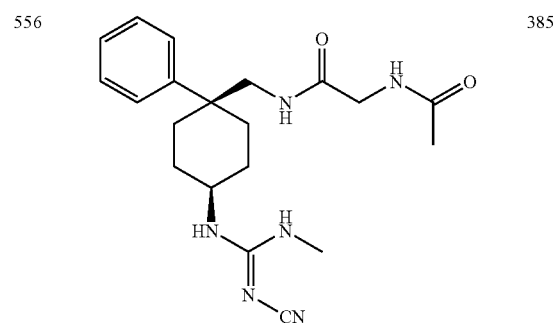 | 385 |
| 557 | 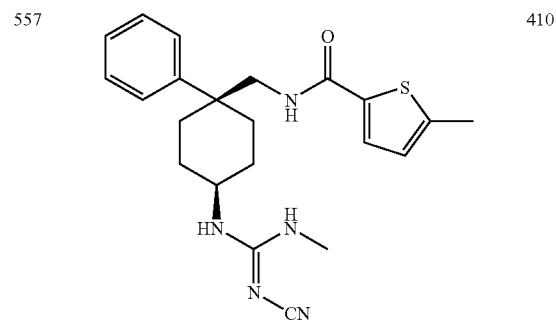 | 410 |
| 558 | 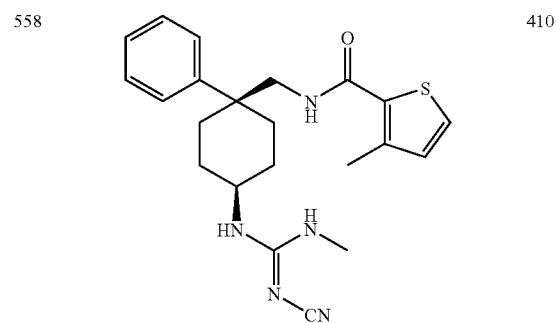 | 410 |
| 559 | 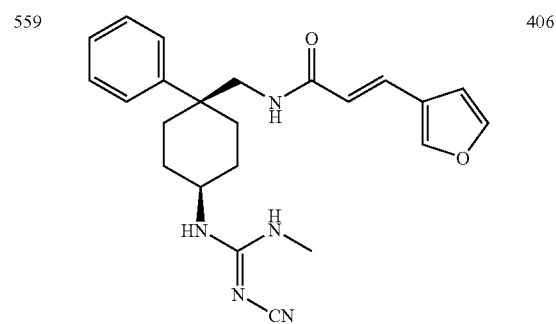 | 406 |
-continued
| Example | Structure | [M + H] |
|---|---|---|
| 560 | 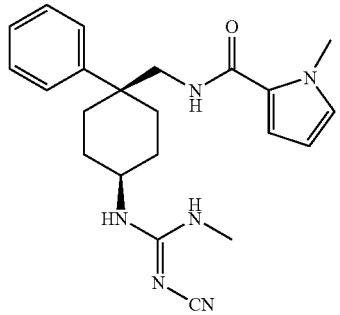 | 393 |
| 561 | 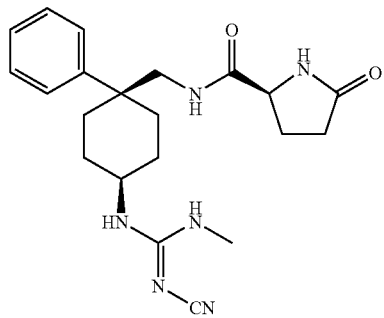 | 397 |
| 562 | 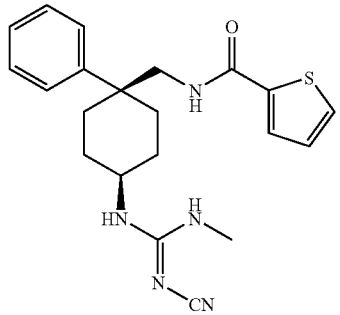 | 396 |
EXAMPLE 563
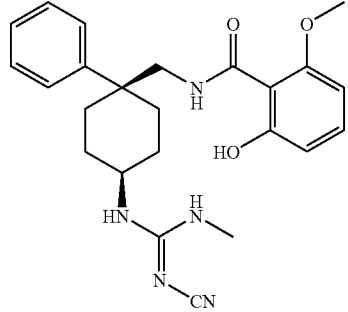

Synthesis:

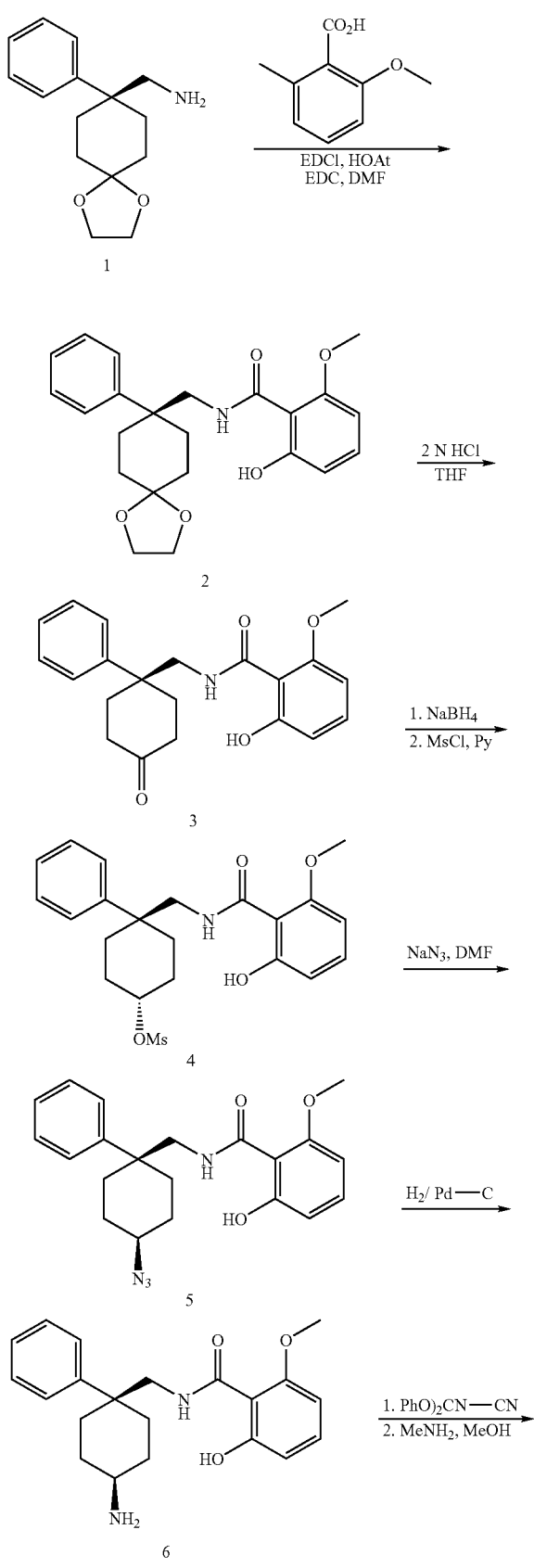

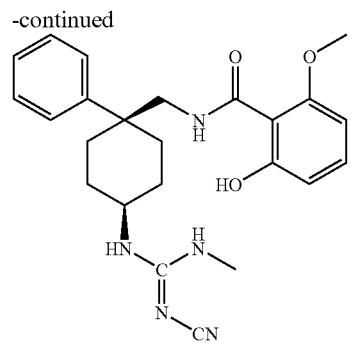

Compound 1: Synthesis of compound 1 is described in Example 31.

Compound 2: To a solution of 6-methoxysalicyclic acid (4.2 g, 25 mmol) in DCM (15 ml) and DMF (5 ml) was added EDCl (3.8 g, 1.3 25 mmol) and HOAt (33.4 g, 25 mmol) in a portion, respectively and the resulting solution was stirred for 0.5 h. The mixture was added dropwise into a solution of compound 1 (4.7 g, 19 mmol) in 15 ml of DCM. The resulting solution was stirred for 12 h at 25° C. The reaction mixture was evaporated in vacuo to yield oily residue, which was purified on column chromatography (20–50% EtOAc/Hexane) to provide the compound 2 (5.8 g, 77%) as a colorless oil.

Compound 3: Compound 2 (5.8 g, 14.6 mmol) was dissolved in THF (80 ml) and 2N HCl—MeOH (40 ml). The mixture was allowed to stirr for 5 h at 50° C. The reaction mixture was then poured into EtOAc (300 ml) and the organic layer was separated. The aqueous layer was extracted with EtOAc (50 ml×2). The combined organic layer was washed with aq. $NaHCO_3$, dried over $Na_2SO_4$ and concentrated in vacuo to provide the desired product (4.0 g, 80%), which was pure (>95%) and subjected to following reactions without any further purification.

Compound 4: The compound 3 (4.0 g, 11.3 mmol) was dissolved in MeOH (100 ml) and stirred with $NaBH_4$ (0.50 g, 13 mmol) for 3 h at −78° C. HPLC analysis showed the reaction was completed. The mixture was concentrated in vacuo to produce a white solid mixture, which was partitioned between EtOAc (200 ml) and brine (50 ml). The organic layer was dried over $Na_2SO_4$ and concentrated in vacuo to provide the alcohol (4.0 g, >95%) as an oil. The alcohol was dissolved in 30 ml of DCM and added pyridine (10 ml) and methanesulfonyl chloride (1.1 ml, 13.6 mmol) at 0° C. The resulting solution was stirred for 12 h at 25° C. The reaction was quenched by adding water. Aqueous layer was further extracted with DCM (20 mL×2). The combined organic solution was washed with 1N aq. HCl (30 ml×2) and dried over $Na_2SO_4$. Concentration of the organic solution provided the desired product (5.2 g, 85% pure) as an oil, which was subjected to following reaction without any further purification.

Compound 5: The compound 4 from above was dissolved in 20 ml of DMF and was added $NaN_3$ (1.2 g, 15 mmol). The mixture was allowed to stir at 80° C. for 12 h. The reaction mixture was concentrated in vacuo to remove DMF and partitioned between EtOAc (100 ml) and brine (30 ml). The aqueous layer was extracted with EtOAc (50 ml×2). The combined organic solution was purified on CombiFlash (0 to 20% EtOAc/hexane) to yield the desired product (2.0 g, 5.3 mmol, 53% for two steps) as a mixture of cis- and trans-isomers (4:1) ratio.

Compound 6: The compound 5 was dissolved in 30 ml of MeOH and was added catalytic amount of 10% Pd/C. The mixture was placed under H$_2$ and stirred for 2 h at 25° C. The reaction mixture was filtered through celite assisted funnel. The filterate was concentrated in vacuo to provide the desired product (1.4 g, 75%) as a colorless oil.

Compound 7: To a solution of the compound 6 (0.36 g, 1 mmol) in 10 ml of isopropanol was added diphenyl cyanocarbonimidate (0.24 g, 1 mmol) and the resulting solution was stirred for 5 h at 60° C. The reaction mixture was then concentrated in vacuo to provide oily residue, which was dissolved in 10 ml of MeNH2-MeOH solution and stirred for 5 h at 80° C. in a sealed tube. The reaction mixture was concentrated and purified on CombiFlash (20–100% EtOAc/Hexane) to yield the desired product (0.34 g, 78%). [M+H] =436.

EXAMPLES 564–571

Examples 564 to 571 were synthesized using methodology described in Example 563.

| Example | Structure | [M + H] |
|---------|-----------|---------|
| 564 | | 422 |
| 565 | | 422 |
| 566 | | 450 |
| 567 | 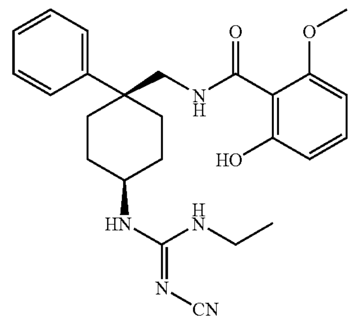 | 450 |
| 568 | 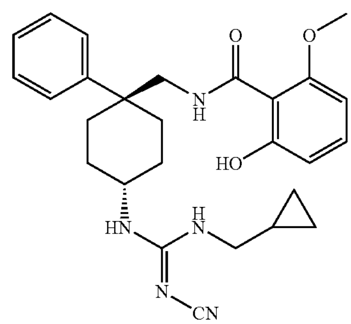 | 476 |
| 569 | 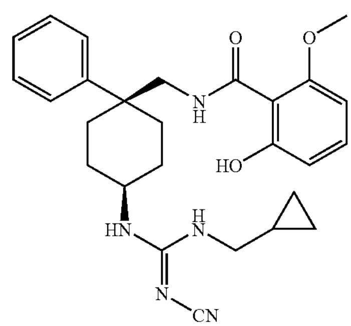 | 476 |
| 570 | 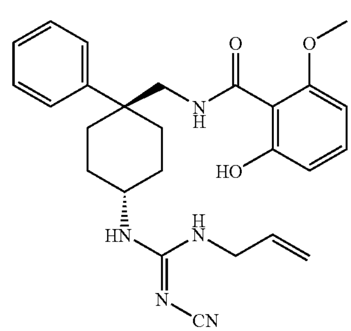 | 462 |

-continued

| Example | Structure | [M + H] |
|---|---|---|
| 571 | 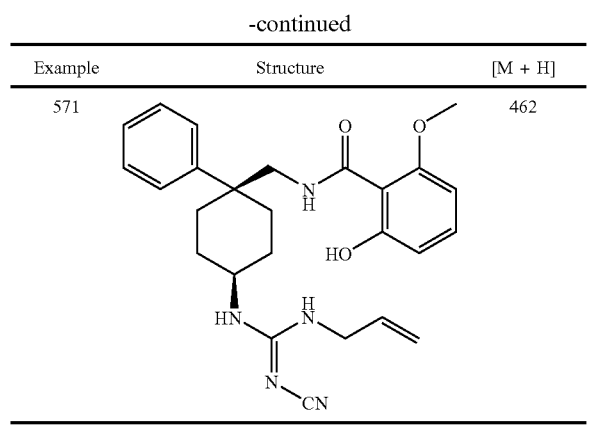 | 462 |

EXAMPLE 572 AND EXAMPLE 573

Ex. 572

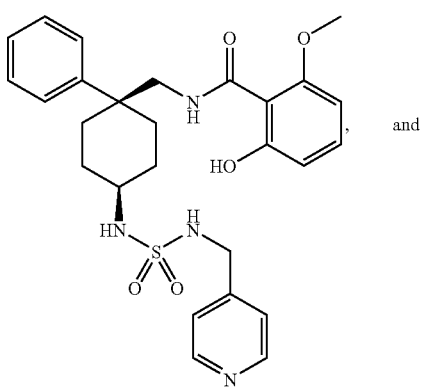, and

Ex. 573

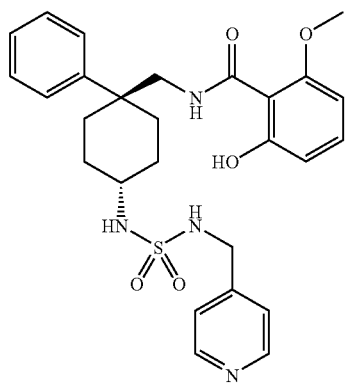

Synthesis:

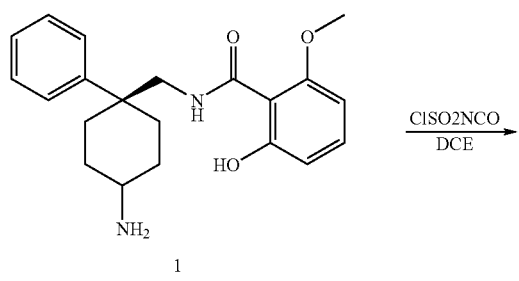

-continued

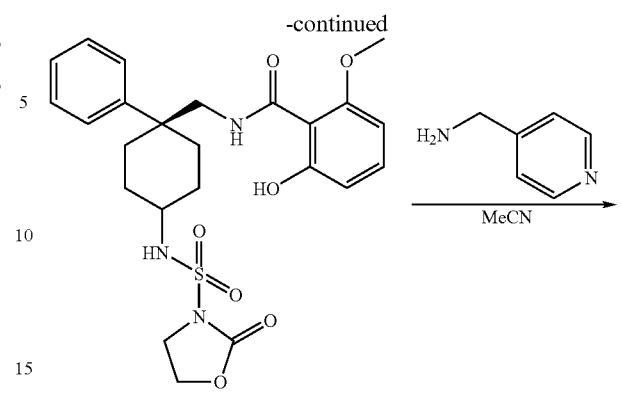

Compound 1: Synthesis of compound 1 is described in Example 554.

Compound 2: To a solution of chloro sulfonylisocyanate (22 μl, 0.25 mmol) in 1 ml of DCM was added chloroethanol (17 μl, 0.25 mmol) at 0° C. The reaction was then allowed to stir for additional 4 h 25° C. The reaction mixture was cooled down to 0° C. again and added 90 mg (0.25 mmol) of compound 1 in 2 ml of DCM. The reaction mixture was stirred for additional 12 h at 25° C. The reaction mixture was then diluted with 10 ml of DCM and washed with 1N aq. HCl. Organic solution was dried over $Na_2SO_4$ and concentrated in vacuo to provide 130 mg of the desired product, which was subjected to the following reaction without any further purification.

Compound 3 and 4: Compound 2 (30 mg, 0.07 mmol) and 4-(aminomethyl)pyridine (16 mL, 0.14 mmol) was diluted in 1 ml of CH₃CN and stirred for 12 h at 60° C. The reaction mixture was purified on preparative HPLC (see Example 31) to provide 12.7 mg of Example 572 and 3.3 mg of Example 573.

EXAMPLES 574–579

Examples 574 to 579 were synthesized using methodology described in Example 572.

| Example | Structure | [M + H] |
|---------|-----------|---------|
| 574 | 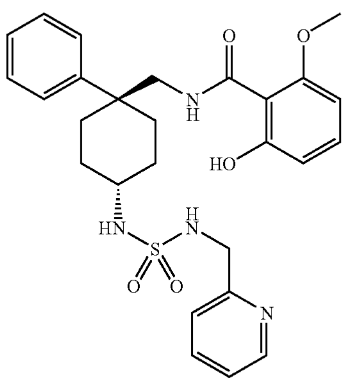 | 525 |
| 575 | 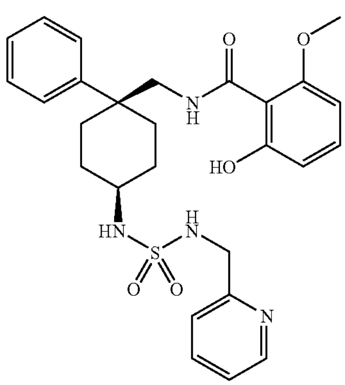 | 525 |
| 576 | 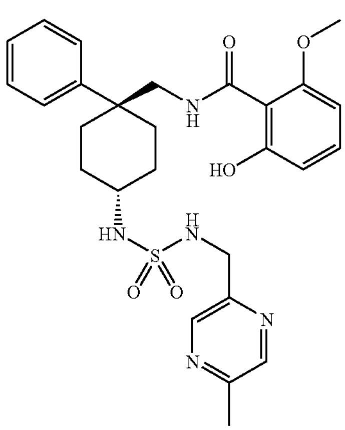 | 540 |
| 577 | | 540 |
| 578 | | 506 |
| 579 | | 506 |

EXAMPLE 580

Synthesis:

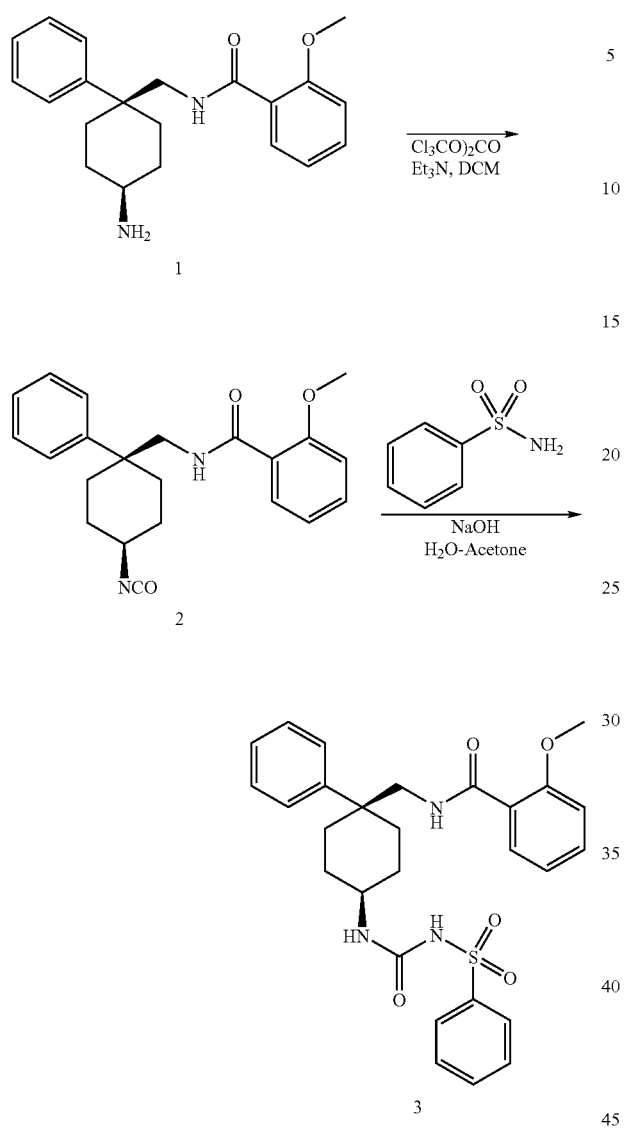

Compound 1: Synthesis of compound 1 is described in Example 31.

Compound 2: To a solution of compound 1 (0.20 g, 0.60 mmol) and Et₃N (0.5 ml) in 5 ml of DCM was added triphosgene (0.20 g, 0.67 mmol) in a portion and the resulting solution was stirred for 1 h at 25° C. The reaction mixture was concentrated in vacuo to provide oily residue, which was purified on column chromatography (50% EtOAc/Hexane) to yield 213 mg (0.58 g, >95%) of the desired product as an oil.

Compound 3: To a solution of the compound 2 (20 mg, 0.055 mmol) and benzenesulfonamide (20 mg, 0.13 mmol) in 2 ml of acetone was added 0.2 ml of 1N aq. NaOH in a portion and the resulting solution was stirred for 1 h at 25° C. The solution was neutralized by adding 0.2 ml of aq. HCl and subjected to preparative HPLC see Example 31) to provide 10.1 mg (0.019 mmol, 30%) of the desired product as a white solid after concentration in speed-vac. [M+H]= 522

EXAMPLES 581–590

Examples 581 to 590 were synthesized using methodology described in Example 580.

| Example | Structure | [M + H] |
|---------|-----------|---------|
| 581 | 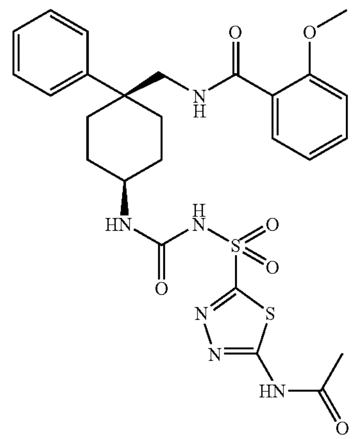 | 587 |
| 582 | 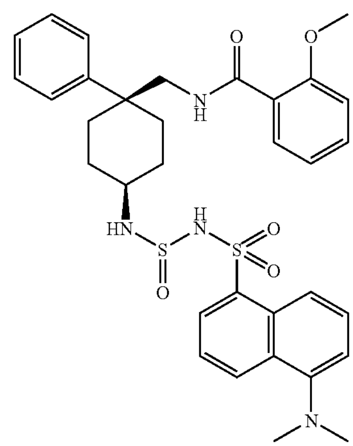 | 615 |
| 583 | 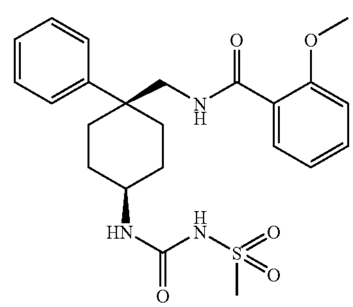 | 460 |

-continued
| Example | Structure | [M + H] |
|---|---|---|
| 584 | 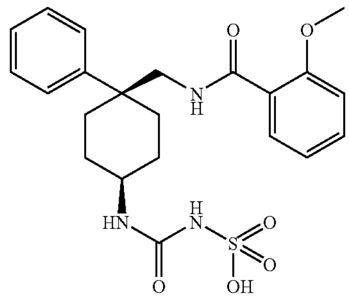 | 462 |
| 585 | 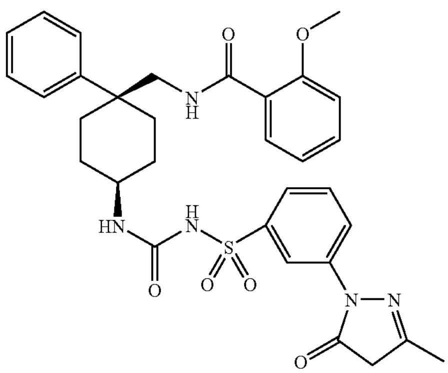 | 618 |
| 586 | 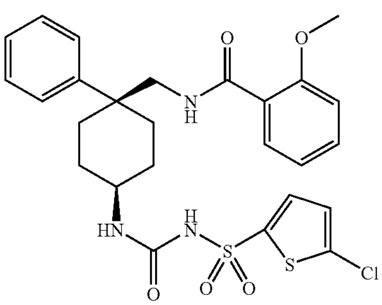 | 563 |
| 587 | 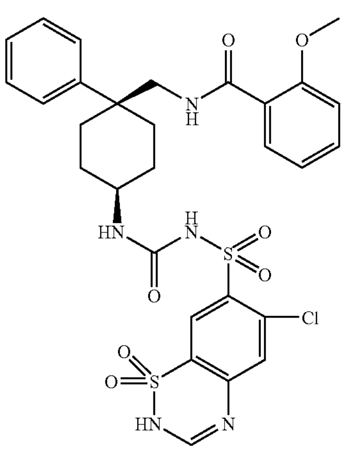 | 661 |
-continued
| Example | Structure | [M + H] |
|---|---|---|
| 588 | 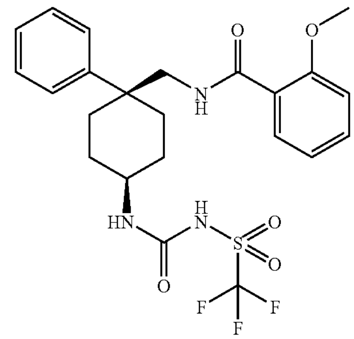 | 514 |
| 589 | 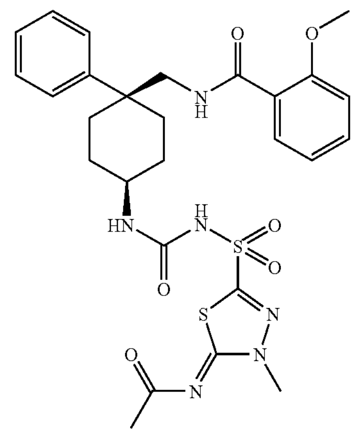 | 601 |
| 590 | 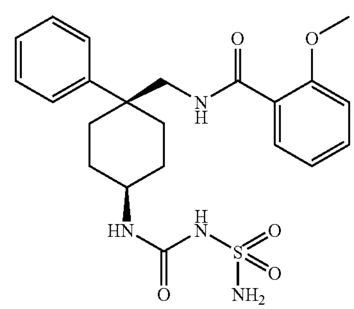 | 461 |
EXAMPLE 591
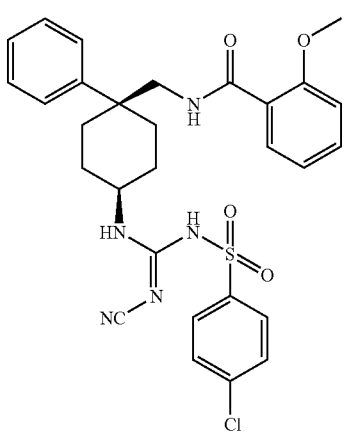

Synthesis:

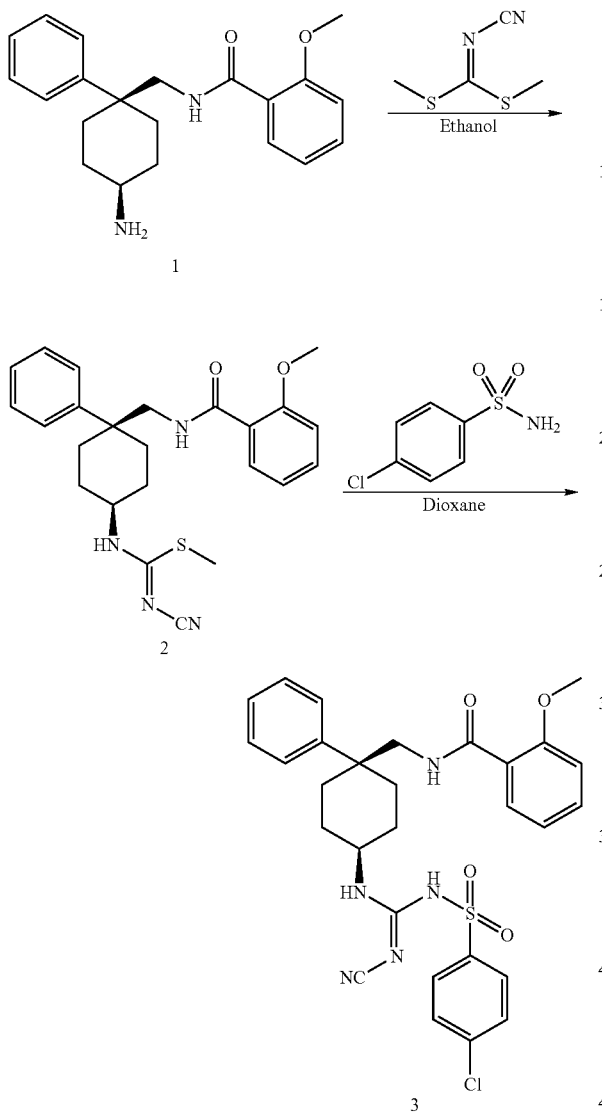

Compound 1: Synthesis of compound 1 is described in Example 31.

Compound 2: To a solution of compound 1 (338 mg, 1.0 mmol) in 10 ml of ethanol was added dimethyl N-cyanodithioiminocarbonate (147 mg, 1.0 mmol) in a portion and the resulting solution was stirred for 2 h at 70° C. HPLC and LC-MS analysis showed a completion of the reaction. Reaction mixture was concentrated in vacuo to provide an oil, which was subjected to the following reaction without any further purification.

Compound 3: Compound 2 (40 mg, 0.09 mmol), NaOH (3.7 μg, 0.09 mmol) and 4-chlorobenzenesulfonamide (34 mg, 0.18 mmol) were dissolved in 1 ml of dioxane. The resulting solution was stirred for 15 min at 230° C. in microwave reactor. The reaction mixture was then cooled down and purified in preparative HPLC (see Example 31) to yield 6.2 mg, (0.011 mmol, 11%) of the deised product as a light gray solid upon concentration of the elute. [M+H]=581.

EXAMPLES 592 AND 593

Examples 592 and 593 were synthesized using methodology described in Example 591.

| Example | Structure | [M + H] |
|---|---|---|
| 592 | 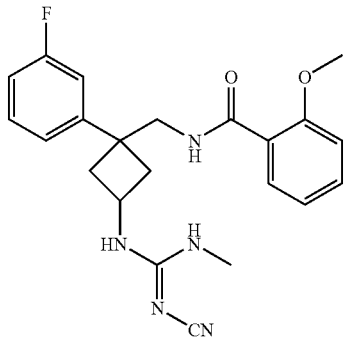 | 546 |
| 593 | 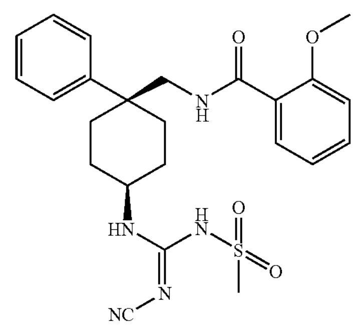 | 484 |

EXAMPLE 594

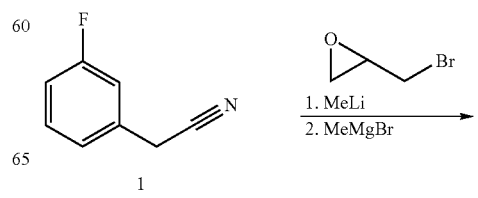

Synthesis:

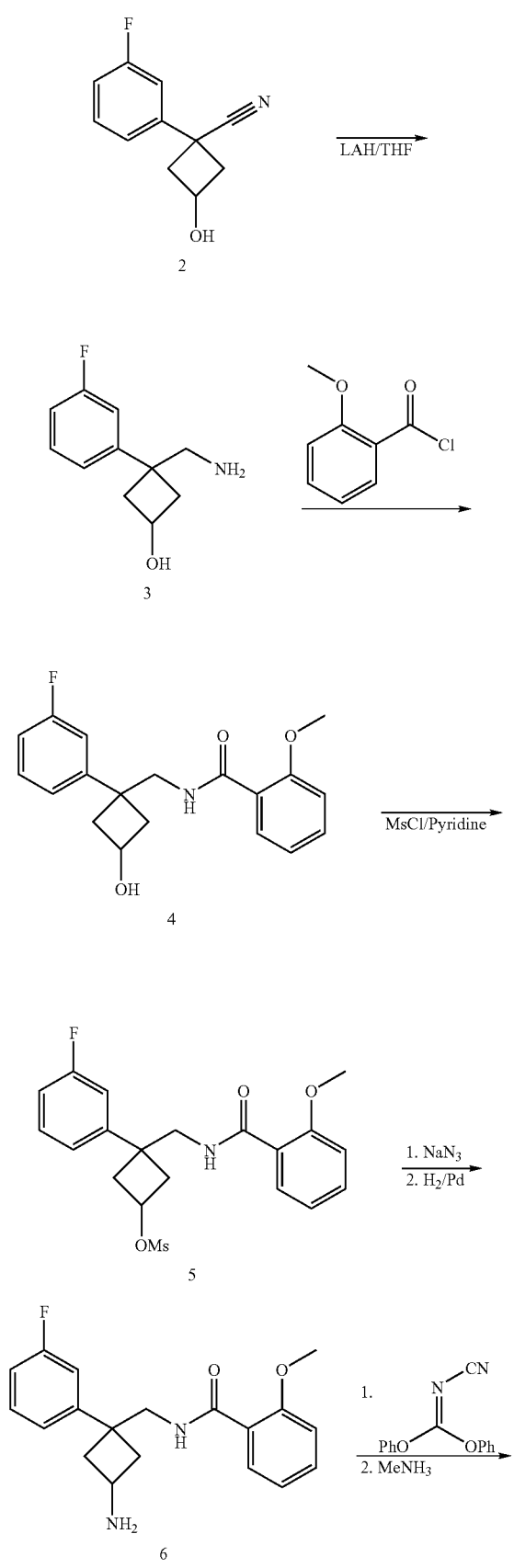

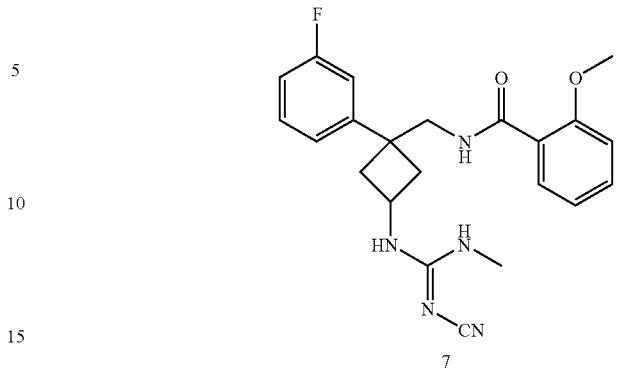

Compound 1: Compound 1 is commercially available.

Compound 2: To a solution of compound 1 (4.6 ml, 40 mmol) in 100 ml of dry THF was added MeLi (2N in THF, 40 mmol) dropwise and the resulting solution was stirred for 1 h at −78° C. Toward the solution was added bromoepihydrin (3.4 ml, 40 mmol) in 50 ml of THF dropwise for 30 min period and the reaction mixture was stirred for another 1 h at −78° C. MeMgBr (3M in THF, 40 mmol) was added into the reaction mixture. The reaction mixture was stirred for additional 12 h at ambient temperature. Reaction mixture was, then, diluted with EtOAc (250 mL) and washed with brine (50 ml×3). Organic layer was dried over MgSO4 and concentrated in vacuo to provide oily residue, which was purified on CombiFlash (0 to 100% EtOAc/Hexane) to provide 5.6 g, (29 mmol, 73%) of the desired product as a mixture of cis and trans isomers (4:1).

Compound 3: Toward solution of compound 2 (1.6 g, 9.0 mmol) in 30 ml of THF was added LAH (1.0 M in THF, 10 mmol) and the resulting solution was stirred for 4 h at 70° C. The reaction was quenched by adding pieces of ice and mixture was filtered through celite. Concentration of filterate provided an oil (1.5 g, >95%), which was subjected to following reaction without any further purification.

Compound 4: To a solution of the compound 3 (1.5 g, 9.0 mmol) in 50 ml of THF and Et$_3$N (2.0 ml) was added anisoyl chloride (1.3 ml, 9.0 mmol) dropwise and the resulting solution was stirred for 1 h at 25° C. Reaction mixture was then diluted with EtOAc (100 ml) and washed with brine. Organic solution was dried over MgSO$_4$ and concentrated in vacuo to provide an oil, which was identified as bis-acylated product. The product was dissolved in 30% aq. THF (20 ml) and LiOH (300 mg) was added into it. The resulting mixture was stirred for 12 h at 70° C. The mixture was diluted with EtOAc (50 ml) and washed with brine (30 ml). Concentration of the organic layer after drying over MgSO$_4$ provided oily residue, which was purified on CombiFlash to provide 1.5 g, (4.5 mmol, 50% for two steps) of the desired product as a colorless oil.

Compound 5: Compound 4 was dissolved in 10 ml of DCM and 2 ml of pyridine. Toward the solution was added methanesulfonyl chloride (1 ml, 13 mmol) and the resulting solution was stirred for 2 h at 25° C. The reaction mixture was diluted with EtOAc (200 ml) and washed with brine (30 ml×2). The organic layer was dried over MgSO$_4$ and concentrated in vacuo to provide an oil, which was subjected to following reaction without any further purification.

Compound 6: Compound 5 and NaN$_3$ (1.3 g, 8.9 mmol) were dissolved in 10 ml of DMF and the mixture was stirred for 5 h at 120° C. The reaction mixture was diluted with EtOAc (100 ml) and washed with brine (20 ml×3). The organic solution was dried over Na₂SO₄ and concentrated in vacuo to provide an oil, which was purified CombiFlash (0–30% EtOAc/hexane) to provide 1.1 g of the azide. The azide was dissolved in 20 ml of MeOH and catalytic amount of 10% Pd—C was added into the solution. The reaction mixture was stirred under H₂ for 2 h. Reaction mixture was filtered through funnel (Whatman, 0.45 μm NYL) and concentrated in vacuo to provide the desired product (1.1 g, 79% from compound 4) as a colorless oil.

Compound 7: To a solution of compound 6 (180 mg, 0.58 mmol) in 5 ml of isopropanol was added diphenyl cyanocarbonimidate (150 mg, 0.64 mmol) and the resulting solution was stirred for 2 h at 80° C. The reaction mixture was then concentrated in vacuo to provide oily residue It was redissolved in 5 ml of 2N MeNH₂ in methanol and stirred for 5 h at 80° C. in a sealed tube. Progress of the reaction was monitored by HPLC. The reaction mixture was concentrated in vacuo to yield oily residue, which was purified on CombiFlash (0–100% EtOAc/hexane) to provide 0.12 g (0.29 mmol, 50%) of the desired product as a mixture of cis and trans isomers. [M+H]=410.

EXAMPLES 595–597

Examples 595 to 597 were synthesized using methodology described in Example 594.

| Example | Structure | [M + H] |
|---|---|---|
| 595 | 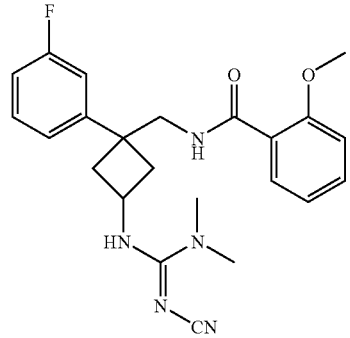 | 424 |
| 596 | 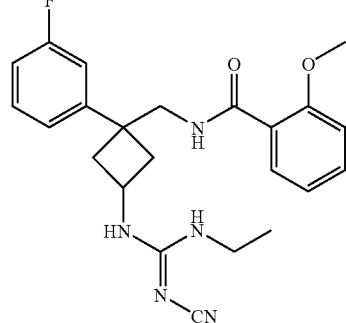 | 424 |
| 597 | | 396 |
| 598 | | 436 |

EXAMPLE 599 cis-N-{4-[N'-Cyano-N''-ethyl-N-(2-methoxy-ethyl)-guanidino]-1-phenyl-cyclohexylmethyl}-2-methoxy-benzamide Synthesis:

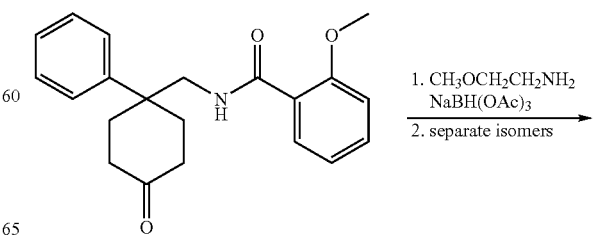

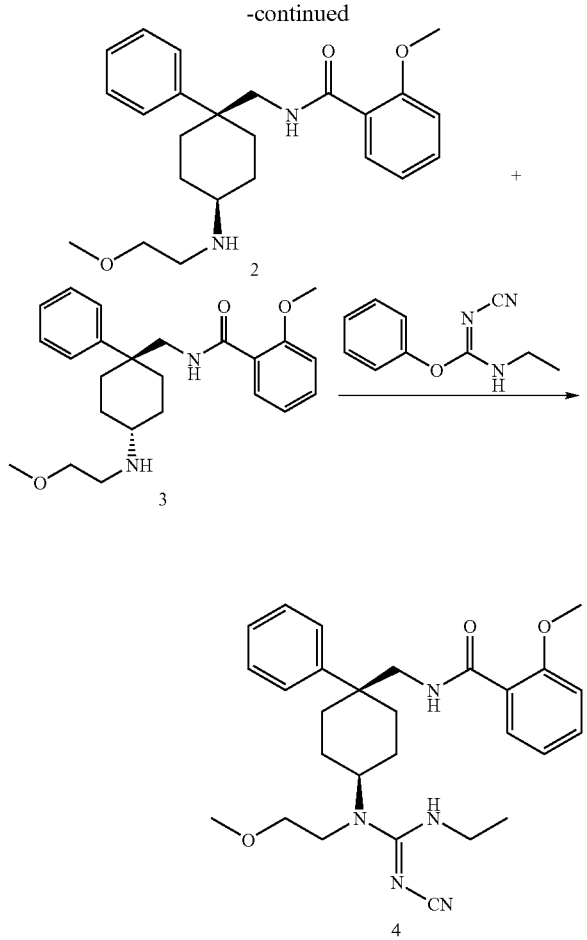

Compound 1: The synthesis of 1 has been previously described.

Compounds 2 and 3: To a solution of 1 (185 mg, 0.55 mmol) in 1,2-dichloroethane (2 mL) was added 2-methoxy-ethylamine (0.048 mL, 0.55 mmol) followed by sodium triacetoxyborohydride (163 mg, 0.77 mmol) and acetic acid (0.031 mL, 0.55 mmol), then the reaction stirred for 1.5 hours. The reaction was quenched by addition of 1N NaOH (2 mL) then extracted with $Et_2O$ (3×4 mL). The combined organic extracts were washed with brine (2 mL), dried ($MgSO_4$) filtered and concentrated in vacuo. The residue was chromatographed on silica, gradiently eluted using 1:1:98 to 1:5:94 $NH_4OH/MeOH/CHCl_3$, to give 2 (80 mg, 37% yield, HPLC Rt 1.50 min using Phenomenex 30×4.6 5 u column over 2 min gradient using flow rate of 5 mL/min. 0 to 100% Solvent B. Solvent A=10/90/0.1% MeOH/H2O/TFA. Solvent B=90/10/0.1%. M+H=397.3) and 3 (66 mg, 30% yield, HPLC Rt 1.43 min using Phenomenex 30×4.6 5 u column over 2 min gradient using flow rate of 5 ml/min. 0 to 100% Solvent B. Solvent A=10/90/0.1% MeOH/H2O/TFA. Solvent B=90/10/0.1%. M+H=397.3) as white solids.

Compound 4: To a solution of the cis-isomer of the amine 2 (15 mg, 0.038 mmol) in 2-propanol (1 mL) was added 1-cyano-3-ethyl-2-phenyl-isourea (36 mg, 0.19 mmol) then the reaction mixture was heated in a 75° C. oil-bath for 5 days. The solvent was removed under a stream of nitrogen then the residue purified by prep TLC eluted with 5:20:75 MeOH/EtOAc/hexanes to give 4 (9.5 mg, 51% yield, HPLC Rt 1.88 min using Phenomenex 30×4.6 5 u column over 2 min gradient using flow rate of 5 mL/min. 0 to 100% Solvent B. Solvent A=10/90/0.1% MeOH/H2O/TFA. Solvent B=90/10/0.1%. M+H=492.3) as a white solid.

EXAMPLES 600–604

Examples 600 to 604 were prepared using methodology described in Example 599.

| Ex. | Structure | Name | [M + 1] |
|---|---|---|---|
| 600 | 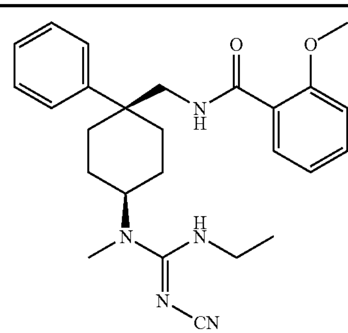 | Cis-N-[4-(N'-Cyano-N"-ethyl-N-methyl-guanidino)-1-phenyl-cyclohexylmethyl]-2-methoxy-benzamide | 448 |
| 601 | 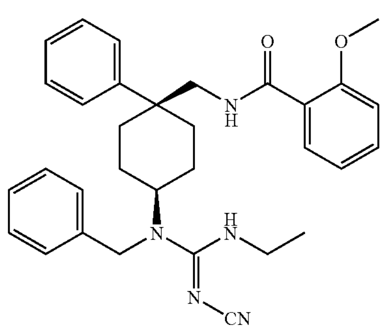 | Cis-N-[4-(N-Benzyl-N'-cyano-N"-ethyl-guanidino)-1-phenyl-cyclohexylmethyl]-2-methoxy-benzamide | 524 |

| Ex. | Structure | Name | [M + 1] |
|---|---|---|---|
| 602 | 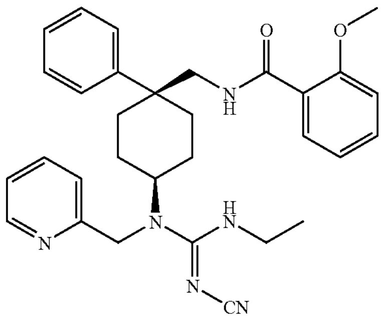 | Cis-N-[4-(N'-Cyano-N''-ethyl-N-pyridin-2-ylmethyl-guanidino)-1-phenyl-cyclohexylmethyl]-2-methoxy-benzamide | 525 |
| 603 | 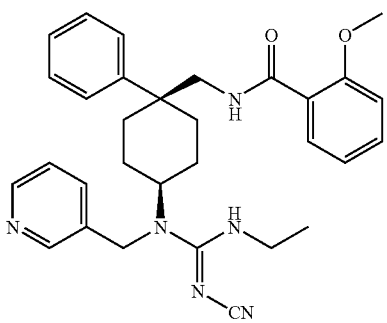 | Cis-N-[4-(N'-Cyano-N''-ethyl-N-pyridin-3-ylmethyl-guanidino)-1-phenyl-cyclohexylmethyl]-2-methoxy-benzamide | 525 |
| 604 | 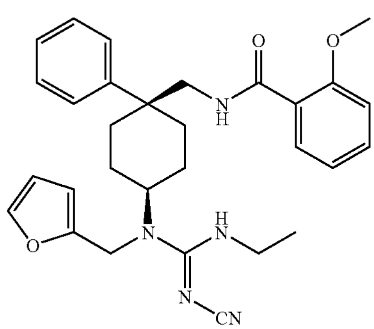 | Cis-N-[4-(N'-Cyano-N''-ethyl-N-furan-2-ylmethyl-guanidino)-1-phenyl-cyclohexylmethyl]-2-methoxy-benzamide | 514 |

EXAMPLE 605

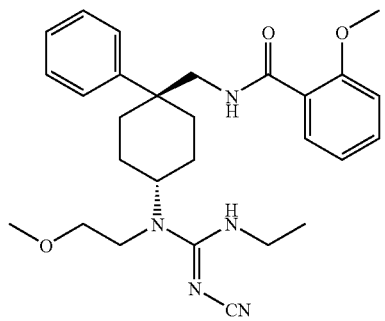

trans-N-{4-[N'-Cyano-N''-ethyl-N-(2-methoxy-ethyl)-guanidino]-1-phenyl-cyclohexylmethyl}-2-methoxy-benzamide Synthesis:

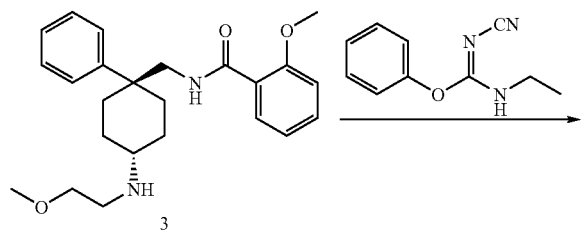

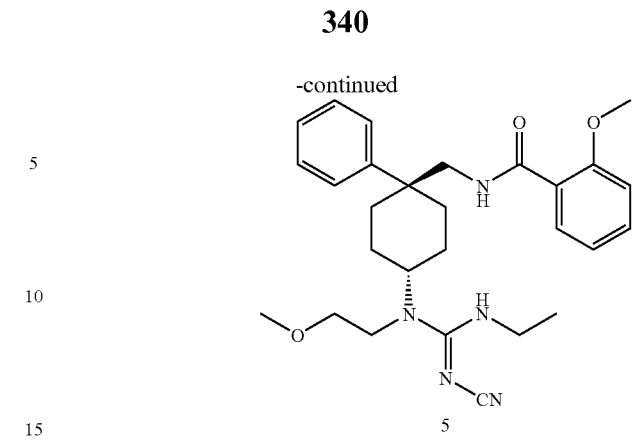

Compound 3: The synthesis of compound 3 is described in Example 599.

Compound 5: To a solution of the trans-isomer of the amine 3 (15 mg, 0.038 mmol) in 2-propanol (1 mL) was added 1-cyano-3-ethyl-2-phenyl-isourea (36 mg, 0.19 mmol) then the reaction mixture was heated in a 75° C. oil-bath for 5 days. The solvent was removed under a stream of nitrogen then the residue purified by prep TLC eluted with 5:20:75 MeOH/EtOAc/hexanes to give 5 (10.8 mg, 58% yield, HPLC Rt 1.77 min using Phenomenex 30×4.6 5 u column over 2 min gradient using flow rate of 5 min. 0 to 100% Solvent B. Solvent A=10/90/0.1% MeOH/H2O/TFA. Solvent B=90/10/0.1%. M+H=492.3) as a white solid.

EXAMPLES 606–609

Examples 606 to 609 were prepared using methodology described in Example 605.

| Ex. | Structure | Name | [M + 1] |
|---|---|---|---|
| 606 | 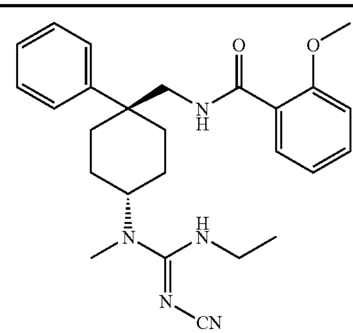 | Trans-N-[4-(N'-Cyano-N''-ethyl-N-methyl-guanidino)-1-phenyl-cyclohexylmethyl]-2-methoxy-benzamide | 448 |
| 607 | 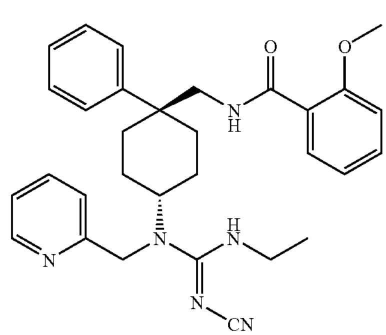 | Trans-N-[4-(N'-Cyano-N''-ethyl-N-pyridin-2-yl-methyl-guanidino)-1-phenyl-cyclohexylmethyl]-2-methoxy-benzamide | 525 |

| Ex. | Structure | Name | [M + 1] |
|---|---|---|---|
| 608 | 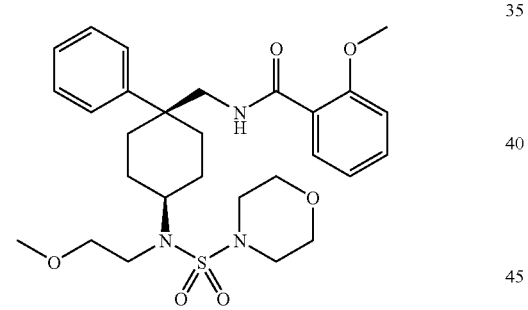 | Trans-N-[4-(N'-Cyano-N''-ethyl-N-pyridin-3-yl-methyl-guanidino)-1-phenyl-cyclohexylmethyl]-2-methoxy-benzamide | 525 |
| 609 | 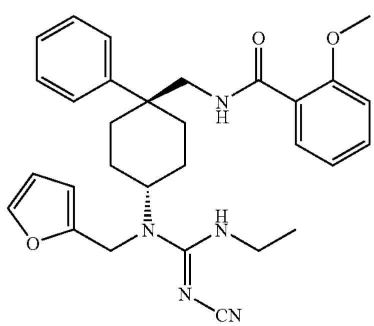 | Trans-N-[4-(N'-Cyano-N''-ethyl-N-furan-2-ylmethyl-guanidino)-1-phenyl-cyclohexylmethyl]-2-methoxy-benzamide | 514 |

EXAMPLE 610 cis-2-Methoxy-N-{4-[(2-methoxy-ethyl)-(morpholine-4-sulfonyl)-amino]-1-phenyl-cyclohexylmethyl}-benzamide Synthesis:

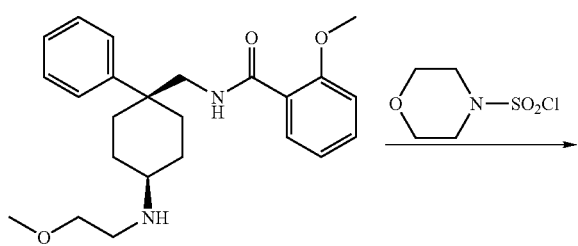

-continued

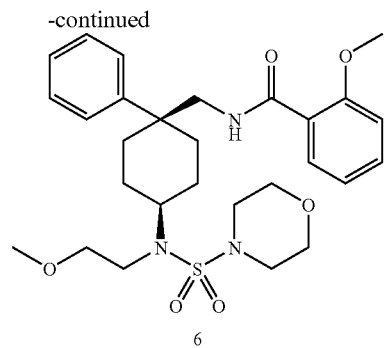

Compound 2: The synthesis of compound 2 is described in Example 599.

Compound 6: To a solution of the cis-isomer of the amine 2 (15 mg, 0.038 mmol) in dimethylformamide (0.5 mL) was added triethylamine (0.007 mL, 0.05 mmol) followed by morpholine-4-sulfonyl chloride (8.4 mg, 0.045 mmol) and a catalytic amount of DMAP. The reaction was stirred for 5 days then diluted with 50% EtOAc/hexanes (4 mL) and washed w/0.1N HCl (2 mL) and brine (2 mL). The organic phase was dried (Na$_2$SO$_4$), filtered and concentrated in vacuo. The residue was purified by prep TLC eluted with 3:25:72 MeOH/hexanes/EtOAc to give 6 (7.8 mg, 38% yield, HPLC Rt 2.30 min using Phenomenex 30×4.6 5 u column over 2 min gradient with 1 min hold time using flow rate of 5 mL/min. 0 to 100% Solvent B. Solvent A=10/90/0.1% MeOH/H2O/TFA. Solvent B=90/10/0.1%. M+H=546.1) as a white solid.

EXAMPLES 611–615

Examples 611 to 615 were prepared using methodology described in Example 610.

| Ex. | Structure | Name | [M + 1] |
|---|---|---|---|
| 611 | 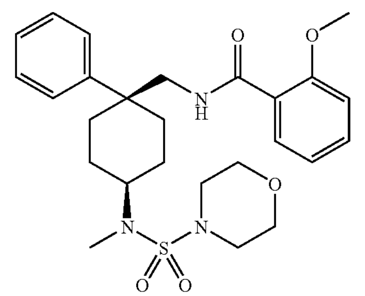 | Cis-2-Methoxy-N-{4-[methyl-(morpholine-4-sulfonyl)-amino]-1-phenyl-cyclohexylmethyl}-benzamide | 502 |
| 612 | 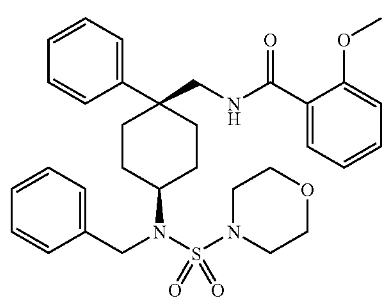 | Cis-N-{4-[Benzyl-(morpholine-4-sulfonyl)-amino]-1-phenyl-cyclohexylmethyl}-2-methoxy-benzamide | 578 |
| 613 | 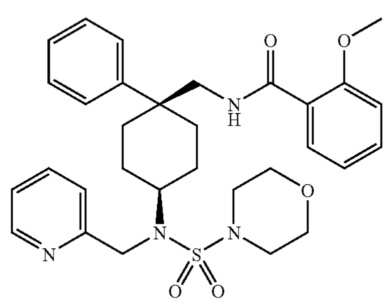 | Cis-2-Methoxy-N-{4-[(morpholine-4-sulfonyl)-pyridin-2-ylmethyl-amino]-1-phenyl-cyclohexylmethyl}-benzamide | 579 |
| 614 | 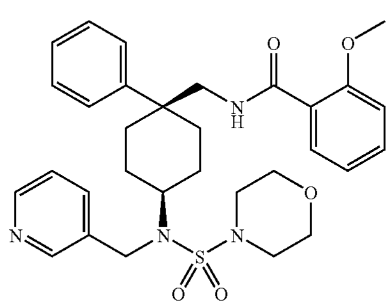 | Cis-2-Methoxy-N-{4-[(morpholine-4-sulfonyl)-pyridin-3-ylmethyl-amino]-1-phenyl-cyclohexylmethyl}-benzamide | 579 |

| Ex. | Structure | Name | [M + 1] |
|---|---|---|---|
| 615 | 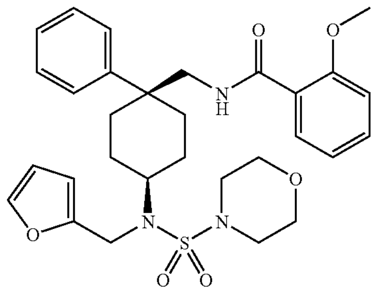 | Cis-N-{4-[Furan-2-yl-methyl-(morpholine-4-sulfonyl)-amino]-1-phenyl-cyclohexylmethyl}-2-methoxy-benzamide | 568 |

EXAMPLE 616 trans-2-Methoxy-N-{4-[(2-methoxy-ethyl)-(morpholine-4-sulfonyl)-amino]-1-phenyl-cyclohexylmethyl}-benzamide

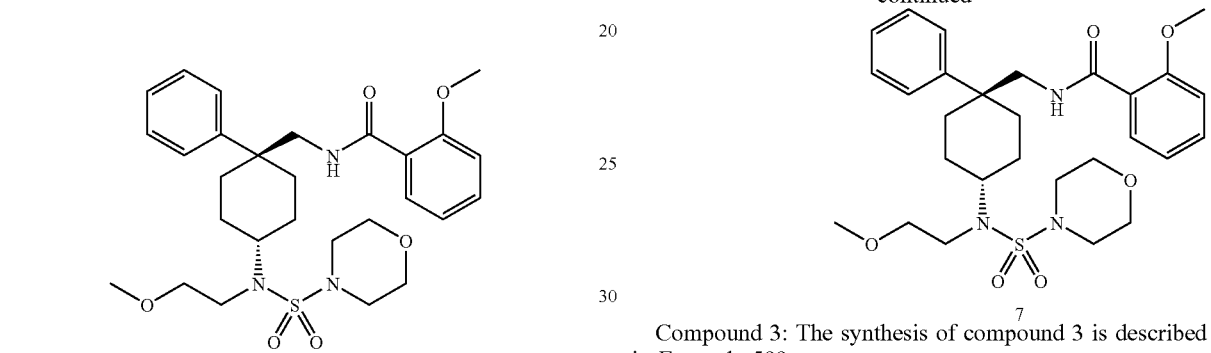

Compound 3: The synthesis of compound 3 is described in Example 599.

Compound 7: To a solution of the trans-isomer of the amine 3 (15 mg, 0.038 mmol) in dimethylformamide (0.5 mL) was added triethylamine (0.007 mL, 0.05 mmol) followed by morpholine-4-sulfonyl chloride (8.4 mg, 0.045 mmol) and a catalytic amount of DMAP. The reaction was stirred for 5 days then diluted with 50% EtOAc/hexanes (4 mL) and washed w/0.1N HCl (2 mL) and brine (2 mL). The organic phase was dried ($Na_2SO_4$), filtered and concentrated in vacuo. The residue was purified by prep TLC eluted with 3:25:72 MeOH/hexanes/EtOAc to give 7 (3.8 mg, 18% yield, HPLC Rt 2.20 min using Phenomenex 30×4.6 5 u column over 2 min gradient with 1 min hold time using flow rate of 5 mL/min. 0 to 100% Solvent B. Solvent A=10/90/0.1% MeOH/H2O/TFA. Solvent B=90/10/0.1%. M+H=546.1) as a white solid.

EXAMPLES 617–621

Examples 617 to 621 were prepared using methodology described in Example 616.

| Ex. | Structure | Name | [M + 1] |
|---|---|---|---|
| 617 | 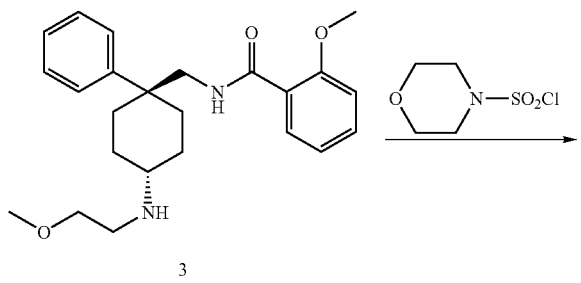 | Trans-2-Methoxy-N-{4-[methyl-(morpholine-4-sulfonyl)-amino]-1-phenyl-cyclohexylmethyl}-benzamide | 502 |

-continued

| Ex. | Structure | Name | [M + 1] |
|---|---|---|---|
| 618 | 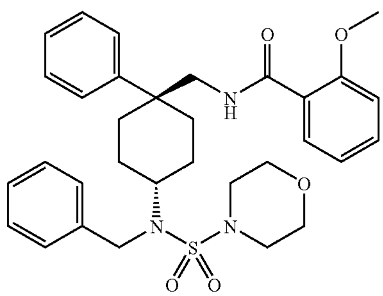 | Trans-N-{4-[Benzyl-(morpholine-4-sulfonyl)-amino]-1-phenyl-cyclohexylmethyl}-2-methoxy-benzamide | 578 |
| 619 | 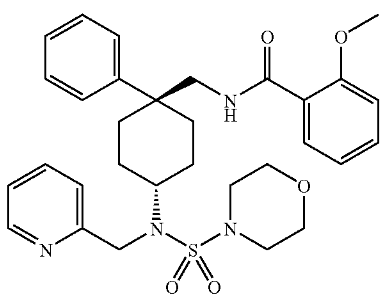 | Trans-2-Methoxy-N-{4-[(morpholine-4-sulfonyl)-pyridin-2-yl-methyl-amino]-1-phenyl-cyclohexylmethyl}-benzamide | 579 |
| 620 | 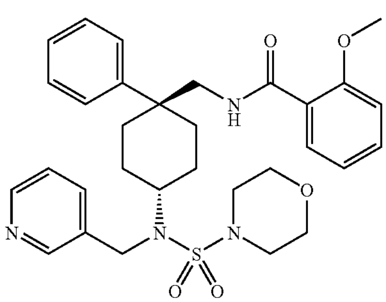 | Trans-2-Methoxy-N-{4-[(morpholine-4-sulfonyl)-pyridin-3-yl-methyl-amino]-1-phenyl-cyclohexylmethyl}-benzamide | 579 |
| 621 | 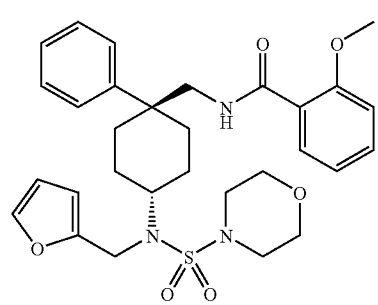 | Trans-N-{4-[Furan-2-yl-methyl-(morpholine-4-sulfonyl)-amino]-1-phenyl-cyclohexylmethyl}-2-methoxy-benzamide | 568 |

EXAMPLE 622

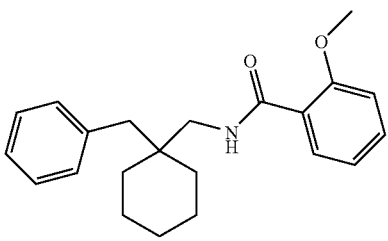

N-(1-Benzyl-cyclohexylmethyl)-2-methoxy-benzamide

Synthesis:

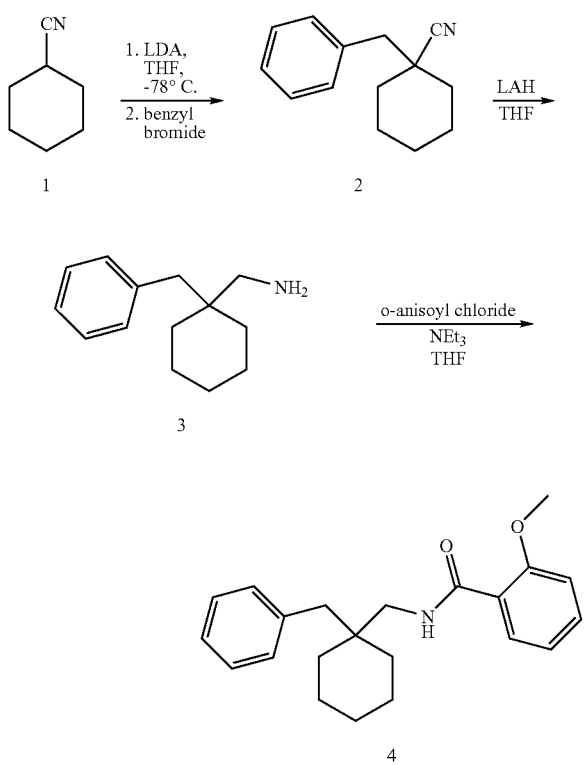

Compound 1: Compound 1 is commercially available.

Compound 2: A solution of cyclohexanecarbonitrile (6.14 g; 56.2 mmol) in tetrahydrofuran (40 mL) was cooled to −78° C. under argon and treated with a 2M solution of lithium diisopropylamide in THF/n-heptane (36 mL; 72 mmol). The cooling bath was removed and the reaction mixture was allowed to stir at room temperature for 10 minutes. The reaction mixture was cooled back to −78° C., treated with a solution of benzyl bromide (9.8 g; 57.3 mmol) in tetrahydrofuran (10 mL) and allowed to slowly warm to room temperature overnight. The reaction mixture was concentrated and the residue was portioned between ethyl ether and a 10% aqueous hydrochloric acid solution. The organic layer was separated, washed with saturated aqueous sodium chloride, dried (anhydrous sodium sulfate), filtered and concentrated. Column chromatography on silica gel using 9:1 hexane:ethyl acetate as the eluent gave 11 g of compound 2 as a clear oil. Mass Spec $[M+H]^+=200$.

Compound 3: A solution of compound 2 (3.8 g; 19.1 mmol) in tetrahydrofuran (40 mL) was cooled to 0° C. and treated with lithium aluminum hydride (3.8 g; 100.1 mmol) in portions. The reaction mixture was allowed to slowly warm to room temperature overnight. The reaction mixture was carefully quenched with 2N sodium hydroxide (approximately 2 mL), filtered through a plug of celite using ethyl acetate as the eluent, dried (anhydrous sodium sulfate), filtered and concentrated to give 3.8 g of compound 3 as a clear oil which was used in the next step with no additional purification. Mass Spec $[M+H]^+=204$.

Title Compound: A solution of compound 3 (0.38 g; 1.8 mmol) in tetrahydrofuran (20 mL) was treated with triethylamine (0.2 mL; 1.4 mmol) followed by o-anisoyl chloride (0.34 g; 2.0 mmol) at room temperature. The reaction was allowed to stir 48 h at which time the solvent was removed under reduced pressure. The residue was portioned between ethyl acetate and a 10% aqueous hydrochloric acid solution. The organic layer was separated, washed with saturated aqueous sodium chloride, dried (anhydrous sodium sulfate), filtered and concentrated. Column chromatography on silica gel using 8:1 hexane:ethyl acetate as the eluent gave 0.46 g of N-(1-benzyl-cyclohexylmethyl)-2-methoxy-benzamide as a clear oil. Mass Spec $[M+H]^+=338$.

EXAMPLES 623–647

Examples 623–647 may be prepared using methodology described in Example 622.

| Ex. | Structure | Name | $[M + H]^+$ |
|---|---|---|---|
| 623 | 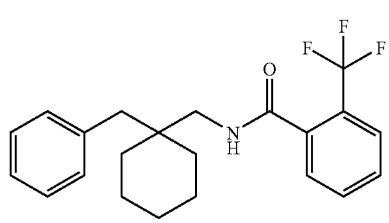 | N-(1-Benzyl-cyclo-hexylmethyl)-2-tri-fluoromethyl-benzamide | 376 |

-continued

| Ex. | Structure | Name | [M + H]+ |
|---|---|---|---|
| 624 | 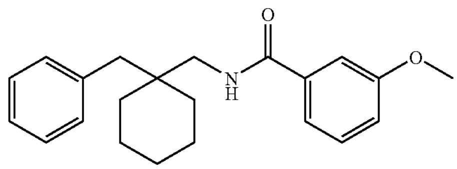 | N-(1-Benzyl-cyclo-hexylmethyl)-3-methoxy-benzamide | 338 |
| 625 | 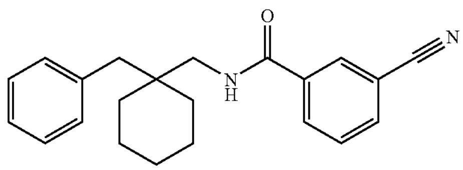 | N-(1-Benzyl-cyclo-hexylmethyl)-3-cyano-benzamide | 333 |
| 626 | 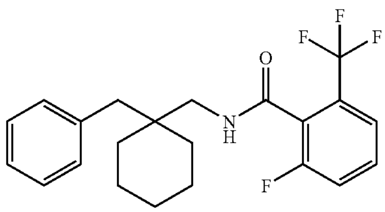 | N-(1-Benzyl-cyclo-hexylmethyl)-2-fluoro-6-trifluoromethyl-benzamide | 394 |
| 627 | 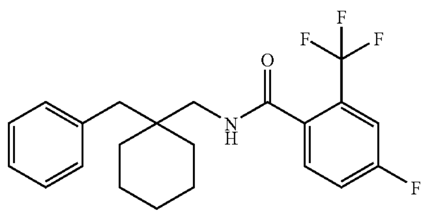 | N-(1-Benzyl-cyclo-hexylmethyl)-4-fluoro-2-trifluoromethyl-benzamide | 394 |
| 628 | 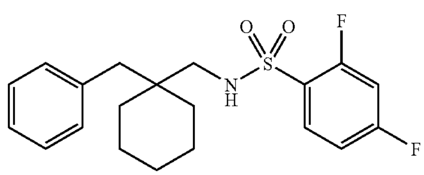 | N-(1-Benzyl-cyclo-hexylmethyl)-2,4-difluoro-benzenesulfonamide | 380 |
| 629 | 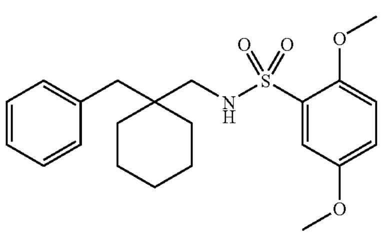 | N-(1-Benzyl-cyclo-hexylmethyl)-2,5-dimethoxy-benzene-sulfonamide | 404 |
| 630 | 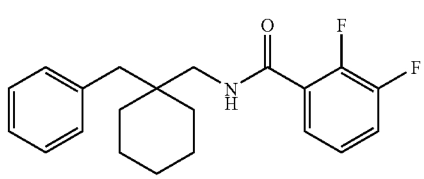 | N-(1-Benzyl-cyclo-hexylmethyl)-2,3-difluoro-benzamide | 344 |
| 631 | 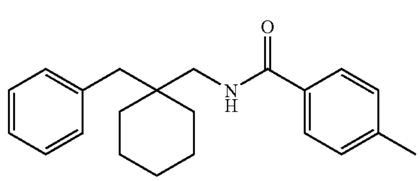 | N-(1-Benzyl-cyclo-hexylmethyl)-4-methyl-benzamide | 322 |

-continued

| Ex. | Structure | Name | [M + H]+ |
|---|---|---|---|
| 632 | 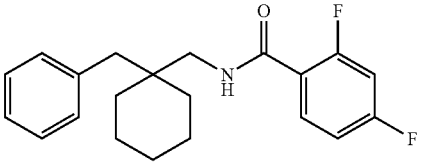 | N-(1-Benzyl-cyclo-hexylmethyl)-2,4-di-fluoro-benzamide | 344 |
| 633 | 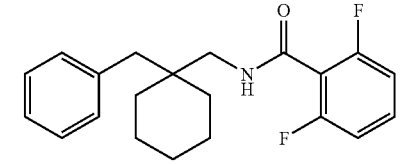 | N-(1-Benzyl-cyclo-hexylmethyl)-2,6-di-fluoro-benzamide | 344 |
| 634 | 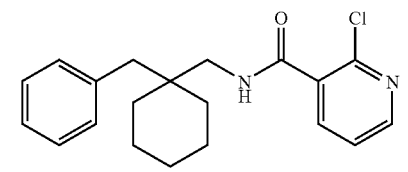 | N-(1-Benzyl-cyclo-hexylmethyl)-2-chloro-nico-tinamide | 343 |
| 635 | 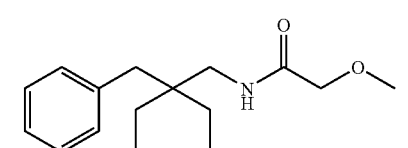 | N-(1-Benzyl-cyclo-hexylmethyl)-2-meth-oxy-acetamide | 276 |
| 636 | 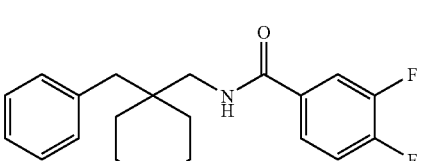 | N-(1-Benzyl-cyclo-hexylmethyl)-3,4-di-fluoro-benzamide | 344 |
| 637 | 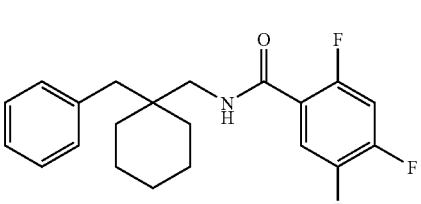 | N-(1-Benzyl-cyclo-hexylmethyl)-2,4,5-tri-fluoro-benzamide | 362 |
| 638 | 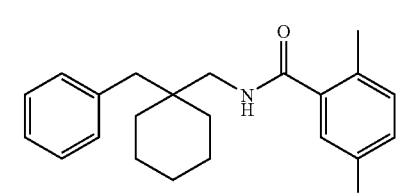 | N-(1-Benzyl-cyclo-hexylmethyl)-5-fluoro-2-meth-yl-benzamide | 340 |
| 639 | 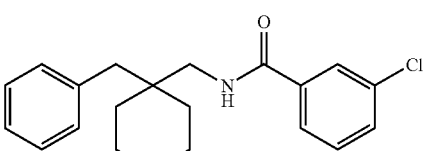 | N-(1-Benzyl-cyclo-hexylmethyl)-3-chloro-ben-zamide | 342 |

-continued

| Ex. | Structure | Name | [M + H]+ |
|---|---|---|---|
| 640 | 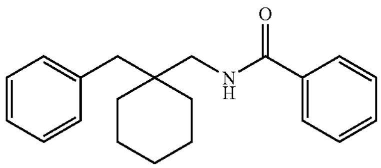 | N-(1-Benzyl-cyclo-hexylmethyl)-benzamide | 308 |
| 641 | 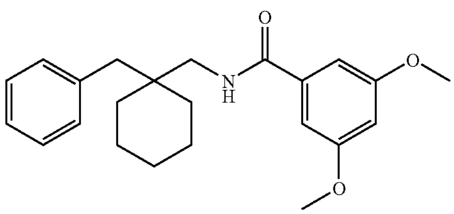 | N-(1-Benzyl-cyclo-hexylmethyl)-3,5-dimethoxy-benzamide | 368 |
| 642 | 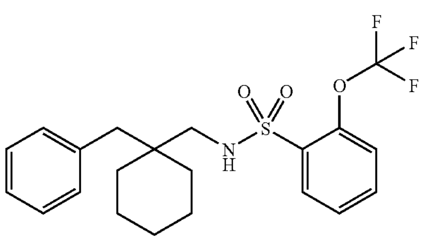 | N-(1-Benzyl-cyclo-hexylmethyl)-2-trifluoromethoxy-benzenesulfonamide | 428 |
| 643 | 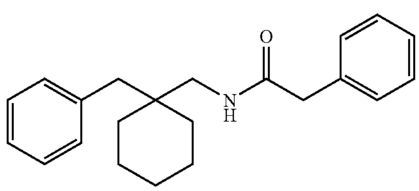 | N-(1-Benzyl-cyclo-hexylmethyl)-2-phenyl-acetamide | 322 |
| 644 | 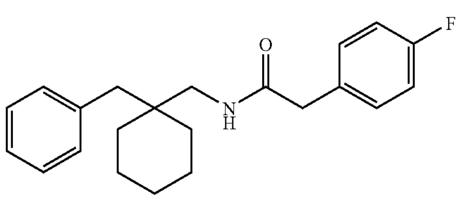 | N-(1-Benzyl-cyclo-hexylmethyl)-2-(4-fluoro-phenyl)-acetamide | 340 |
| 645 | 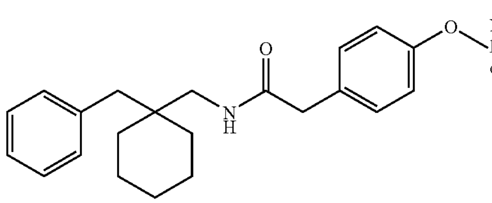 | N-(1-Benzyl-cyclo-hexylmethyl)-2-(4-methoxy-phenyl)-acetamide | 352 |

-continued

| Ex. | Structure | Name | [M + H]+ |
|---|---|---|---|
| 646 | 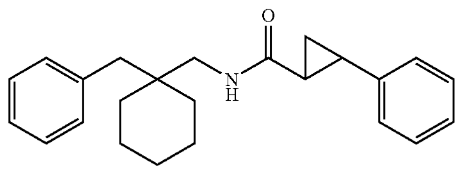 | 2-Phenyl-cyclo-propanecarboxylic acid (1-benzyl-cyclo-hexylmethyl)-amide | 348 |
| 648 | 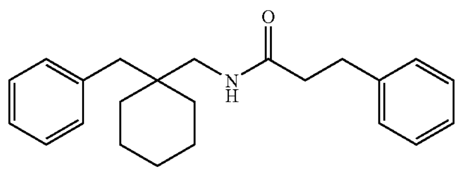 | N-(1-Benzyl-cyclo-hexylmethyl)-3-phe-nyl-propionamide | 336 |

EXAMPLE 648

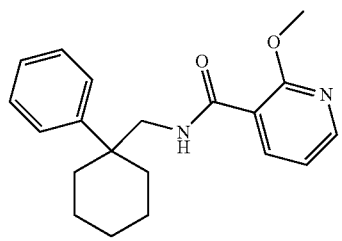

2-Methoxy-N-(1-phenyl-cyclohexylmethyl)-nicotinamide

Synthesis:

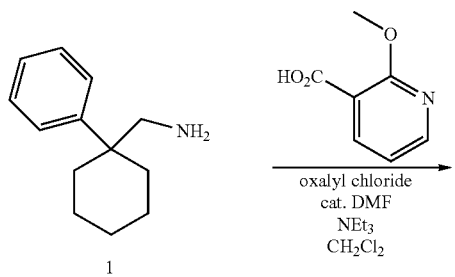

Compound 1: Compound 1 was prepared as described in Example 330.

Title Compound: A suspension of 2-methoxynicotinic acid (0.23 g; 1.5 mmol) in methylene chloride (15 ml) was treated with oxalyl chloride (0.14 mL; 1.6 mmol) and 2 drops of N,N-dimethylformamide. The reaction mixture was allowed to stir at room temperature for 30 minutes at which time triethylamine (0.3 mL; 2.2 mmol) and compound 1 (0.315 g; 1.66 mmol). After an additional 15 minutes of stirring the reaction mixture was washed with water and saturated aqueous sodium chloride, dried (magnesium sulfate) and concentrated. The crude residue was purified by column chromatography on silica gel using 7:3 hexane: ethyl acetate as the eluent to give 0.37 g of 2-Methoxy-N-(1-phenyl-cyclohexylmethyl)-nicotinamide as a white solid. Mass Spec [M+H]+=325.

EXAMPLE 649

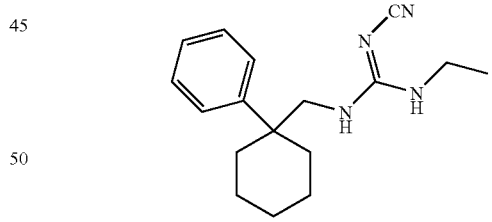

Synthesis:

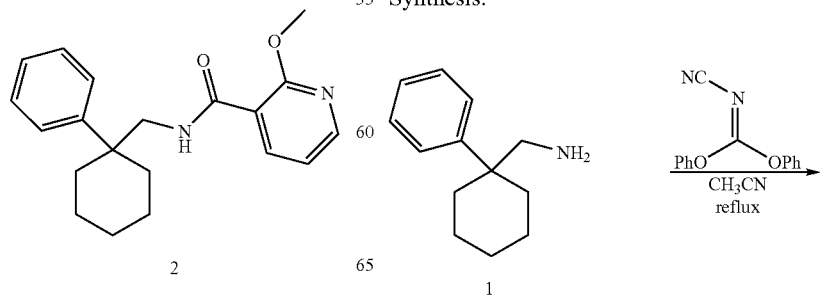

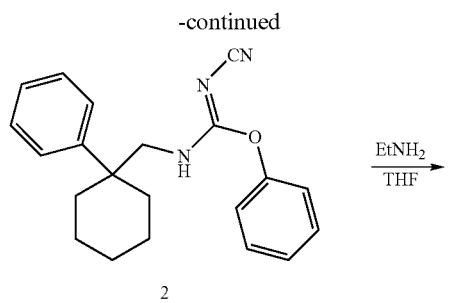

2

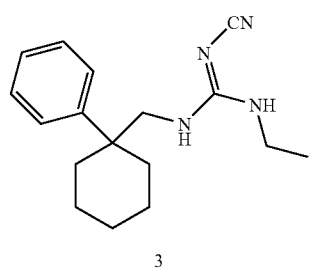

3

Compound 1: Compound 1 was prepared as described in Example 330.

Compound 2: A solution of compound 1 (1.2 g; 6.3 mmol) in anhydrous acetonitrile (30 mL) was treated with diphenyl N-cyanocarbonimidate (2.2 g; 9.2 mmol) and heated at 80° C. for 4 h. The reaction mixture was allowed to stand at room temperature overnight. The white precipitate that formed was collected by filtration and washed with hexane to provide 1.0 g of compound 2 as a white solid. Mass Spec [M+H]$^+$=334.

Title Compound: Compound 2 (0.027 g; 0.08 mmol) was treated with a 2 M solution of ethylamine in THF (0.5 mL; 1 mmol) and heated at 60° C. in a screw cap vial overnight. The solvent and excess ethylamine was removed be evaporation and the crude product was purified by preparative reverse-phase liquid chromatography to give 0.008 g of the title compound as a white solid. Mass Spec [M+H]$^+$=285.

EXAMPLES 650–660

Examples 650–660 were prepared using methodology described in Example 649.

| Ex. | Structure | [M + H]$^+$ |
|---|---|---|
| 650 | 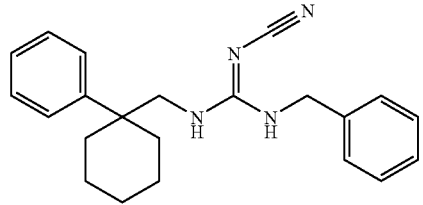 | 348 |
| 651 | 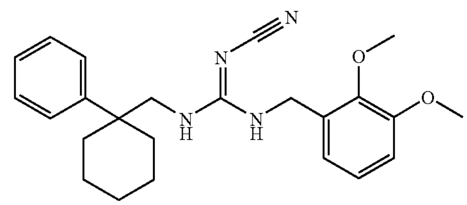 | 408 |
| 652 | 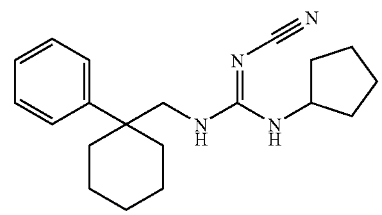 | 326 |
| 653 | 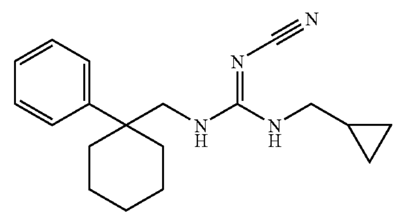 | 312 |
| 654 | 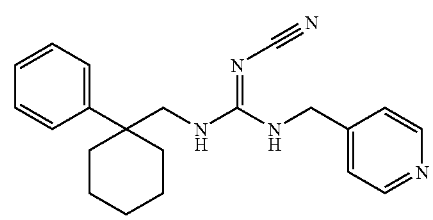 | 349 |
| 655 | 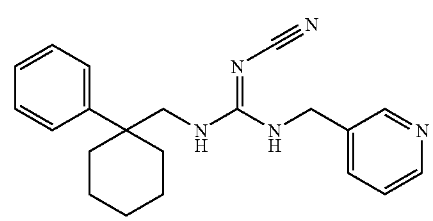 | 349 |
| 656 | 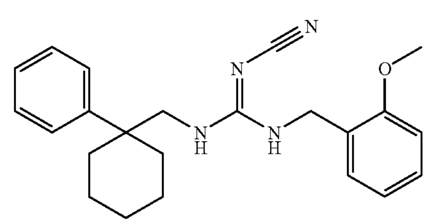 | 378 |
| 657 | 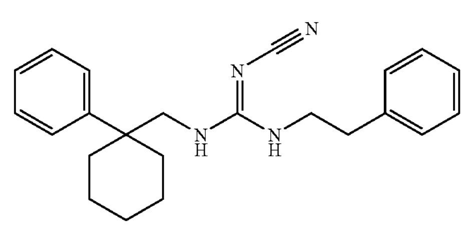 | 362 |

-continued

| Ex. | Structure | [M + H]+ |
|---|---|---|
| 658 | 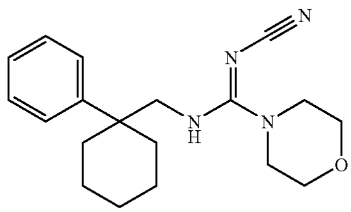 | 328 |
| 659 | 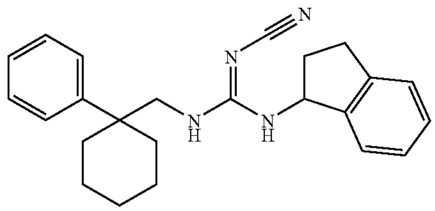 | 374 |
| 660 | 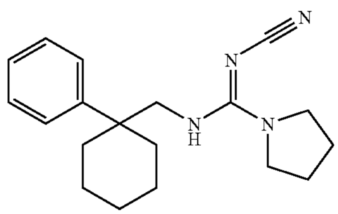 | 312 |

EXAMPLE 661

5-Benzyl-3-(1-phenyl-cyclohexylmethyl)-imidazolidine-2,4-dione

Synthesis:

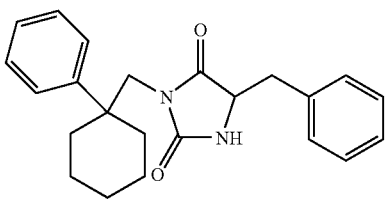

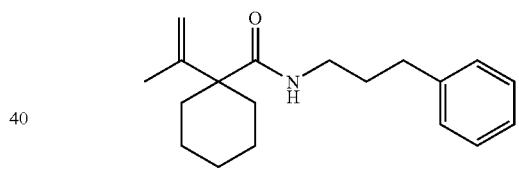

Compound 1: Compound 1 was prepared as described in Example 330.

Title Compound: A solution of compound 1 (0.255 g; 1.35 mmol) in anhydrous dichloromethane (8 mL) was treated with ethyl 2-isocyanato-3-phenylpropionate (0.325 g; 0.38 mmol) and stirred at room temperature overnight. The solvent was removed by evaporation, the residue was dissolved in ethanol (1 mL), 6N hydrochloric acid (0.5 mL) and water (0.5 mL) and the reaction mixture was heated to 50° C. After 3 h at 50° C., additional 6N hydrochloric acid (1 mL) was added and the reaction mixture was heated at 65° C. overnight. The reaction mixture was concentrated and the crude product was purified directly by column chromatography on silica gel using 1:1 ethyl acetate:hexane as the eluent to give 0.053 g of 5-Benzyl-3-(1-phenyl-cyclohexylmethyl)-imidazolidine-2,4-dione as a white solid. Mass Spec [M+H]+=363.

EXAMPLE 662

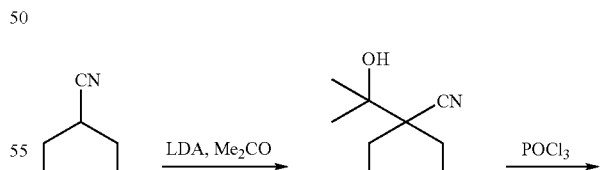

1-Isopropenyl-cyclohexanecarboxylic acid (3-phenyl-propyl)-amide

Synthesis:

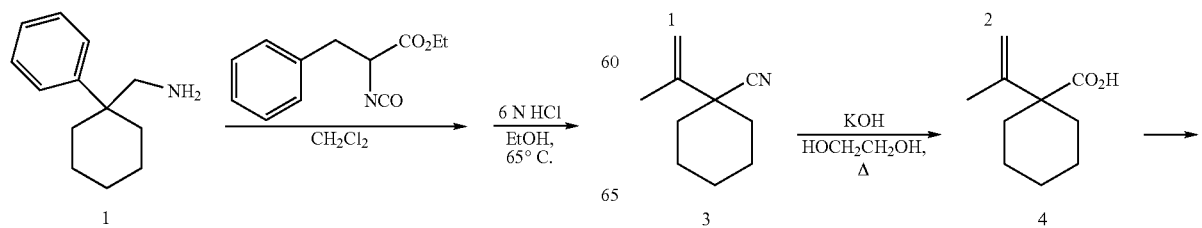

-continued

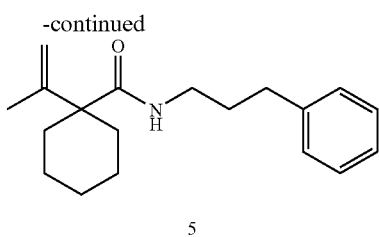

5

Compound 1: Compound 1 is commercially available.

Compound 2: To a solution of diisopropylamine (4.2 mL) in THF (30 mL) at 0° C. was added n-BuLi in hexanes (1.6 M, 19 mL). After stirring for 30 min., the reaction mixture was cooled to −78° C. and cyclohexanecarbonitrile (1.09 g, 10 mmol) in THF (10 mL) was added drop wise. After 2 h, acetone (1.16 g, 20 mmol) was added. The reaction mixture was stirred from −78° C. to rt overnight, diluted with Et$_2$O (100 mL), washed with 1N HCl, H$_2$O, brine and dried over anhydrous sodium sulfate. Purification by flash chromatography (1:1, hexanes-Et$_2$O) gave 1-(1-hydroxy-1-methyl-ethyl)-cyclohexanecarbonitrile (1.27 g, 76%) as a colorless oil. $^1$H NMR (CDCl$_3$, 300 MHz) δ (ppm) 0.86–1.91 (8H, m), 1.35 (6H, s), 2.01 (2H, d, J=12.8 Hz), 3.65 (1H, t, J=6.4 Hz). Mass Spec [M+H]$^+$=168.1.

Compound 3: Compound 2 (530 mg, 3.17 mmol) and phosphorus oxychloride (11.7 g, 76.1 mmol) in CHCl$_3$ (12 mL) was heated at reflux for 18 h then cooled to rt. Water (75 mL) was slowly added. The aqueous layer was extracted with CH$_2$Cl$_2$ (2×) and the combined extracts were dried over anhydrous sodium sulfate. Purification by flash chromatography (2:1, hexanes-CH$_2$Cl$_2$) gave 1-isopropenyl-cyclohexanecarbonitrile (1.27 g, 76%) as a colorless oil. $^1$H NMR (CDCl$_3$, 300 MHz) δ (ppm) 1.16–2.17 (13H, m), 4.96 (1H, s), 5.11 (1H, s). Mass Spec [M+H]$^+$=150.1.

Compound 4: Compound 3 (280 mg, 1.87 mmol) and KOH (460 mg, 8.20 mmol) in ethylene glycol (3.7 mL) was heated at 185° C. for 18 h then cooled to rt. The reaction mixture was diluted with H$_2$O then extracted with Et$_2$O (2×). The aqueous phase was acidified with 6N HCl then extracted with CH$_2$Cl$_2$ (3×) and dried over anhydrous sodium sulfate to give 1-isopropenyl-cyclohexanecarboxylic acid (234 mg, 74%) as a waxy white solid. $^1$H NMR (CDCl$_3$, 300 MHz) δ (ppm) 1.16–1.65 (9H, m), 1.79 (3H, s), 2.16–2.20 (2H, m), 4.99 (2H, s). Mass Spec [M+H]$^+$=169.1.

Title Compound: Compound 4 was made to react with 3-phenylpropylamine using methodology described in Example 74 to give 1-isopropenyl-cyclohexanecarboxylic acid (3-phenyl-propyl)-amide. Mass Spec [M+H]$^+$=286.1.

EXAMPLES 663–665

Examples 663–665 were prepared using methodology described in Example 662.

| Ex | Structure | Name | [M + H]$^+$ |
|---|---|---|---|
| 663 | 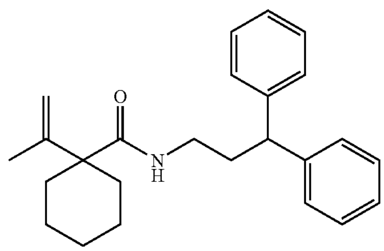 | 1-Isopropenyl-cyclohexanecarboxylic acid (3,3-diphenyl-propyl)-amide | 362 |
| 664 | 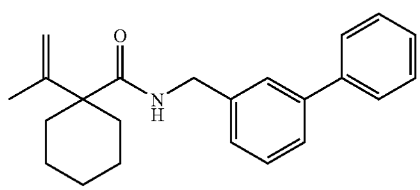 | 1-Isopropenyl-cyclohexanecarboxylic acid (biphenyl-3-ylmethyl)-amide | 334 |
| 665 | 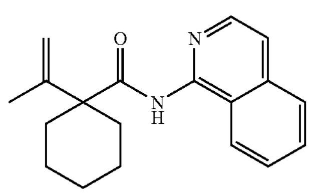 | 1-Isopropenyl-cyclohexanecarboxylic acid isoquinolin-1-ylamide | 295 |

EXAMPLE 666

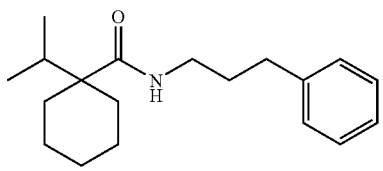

1-Isopropyl-cyclohexanecarboxylic acid (3-phenyl-propyl)-amide

Synthesis:

H₂, 10% Pd/C, EtOH

Compound 1: Compound 1 may be prepared as described in Example 662.

Title Compound: Compound 1 (33 mg, 0.12 mmol) and 10% Pd on carbon (30 mg), in EtOH (1 mL) was stirred under hydrogen for 18 h. The reaction mixture was filtered over celite and concentrated to give 1-isopropyl-cyclohexanecarboxylic acid (3-phenyl-propyl)-amide (33 mg, 100%) as a colorless oil. $^1$H NMR (CDCl$_3$, 300 MHz) δ (ppm) 0.86 (6H, d, J=6.8 Hz), 1.00–1.40 (5H, m), 1.50–1.65 (4H, m), 1.80–1.90 (4H, m), 2.67 (2H, t, J=7.5 Hz), 3.33–3.48 (2H, m), 5.59 (1H, s), 7.17–7.31 (5H, m). Mass Spec [M+H]$^+$ =288.

EXAMPLES 667–668

Examples 667–668 were prepared using methodology described in Example 666.

EXAMPLE 669

N-(1-Isopropenyl-cyclohexylmethyl)-2-methoxy-benzamide

Synthesis:

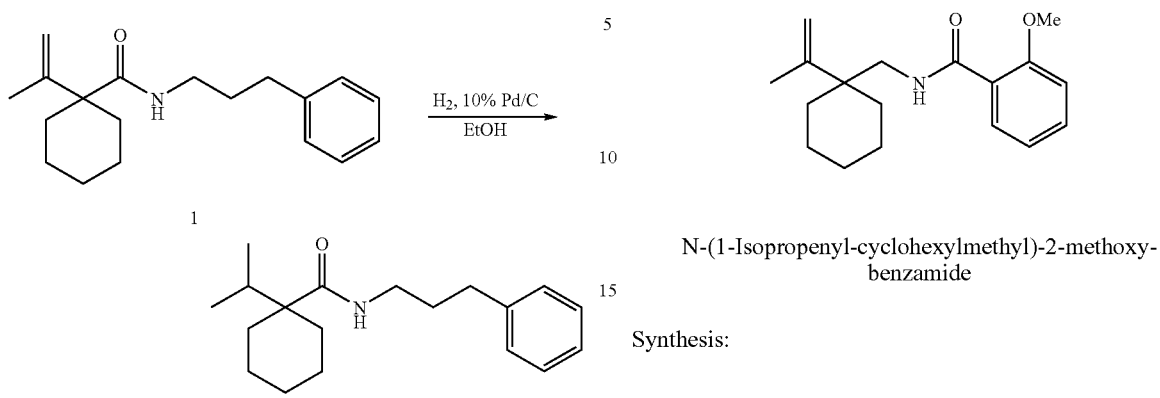

Compound 1: Compound 1 may be prepared as described in Example 662.

Compound 2: To Compound 1 (100 mg, 0.67 mmol) in THF (3 mL) cooled to 0° C. was added LAH (102 mg, 2.68

| Ex | Structure | Name | [M + H]$^+$ |
|----|-----------|------|-------------|
| 667 | | 1-Isopropyl-cyclohexanecarboxylic acid (3,3-diphenyl-propyl)-amide | 364 |
| 668 | | 1-Isopropyl-cyclohexanecarboxylic acid (biphenyl-3-ylmethyl)-amide | 336 | mmol). The reaction mixture was stirred from 0° C. to rt overnight then quenched with H$_2$O (0.1 mL), 15% NaOH (0.1 mL), H$_2$O (0.3 mL), filtered then dried over anhydrous sodium sulfate to give (1-isopropenyl-cyclohexyl)-methylamine (63 mg, 61% as a colorless oil. $^1$H NMR (CDCl$_3$, 300 MHz) δ (ppm) 1.05–1.80 (15H, m), 2.46 (2H, s), 4.76 (1H, s), 5.07 (1H, s). Mass Spec [M+H]$^+$=154.

Title Compound: Compound 2 was made to react with o-anisoyl chloride using methodology described in Example 1 to provide N-(1-isopropenyl-cyclohexylmethyl)-2-methoxy-benzamide. Mass Spec [M+H]$^+$=288.

EXAMPLE 670

Example 670 was prepared using methodology described in Example 669.

| Ex | Structure | Name | [M + H]$^+$ |
|---|---|---|---|
| 670 | 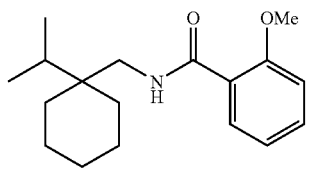 | N-Bicyclo-hexyl-1'-en-1-ylmethyl-2-methoxy-benzamide | 328 |

EXAMPLE 671

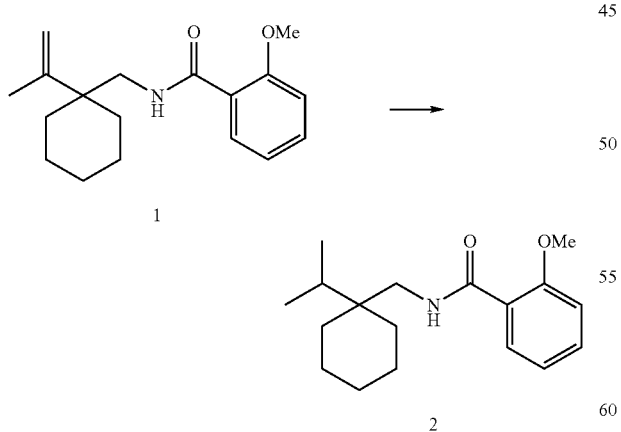

N-(1-Isopropyl-cyclohexylmethyl)-2-methoxy-benzamide

Synthesis:

Compound 1: Compound 1 was prepared as described in Example 669.

Title Compound: The title compound was prepared using methodology described in Example 669. Mass Spec [M+H]$^+$=290.

EXAMPLE 672

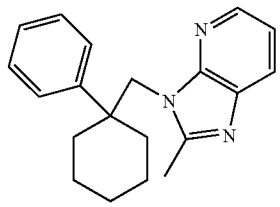

2-Methyl-3-(1-phenyl-cyclohexylmethyl)-3H-imidazo[4,5-b]pyridine

Synthesis:

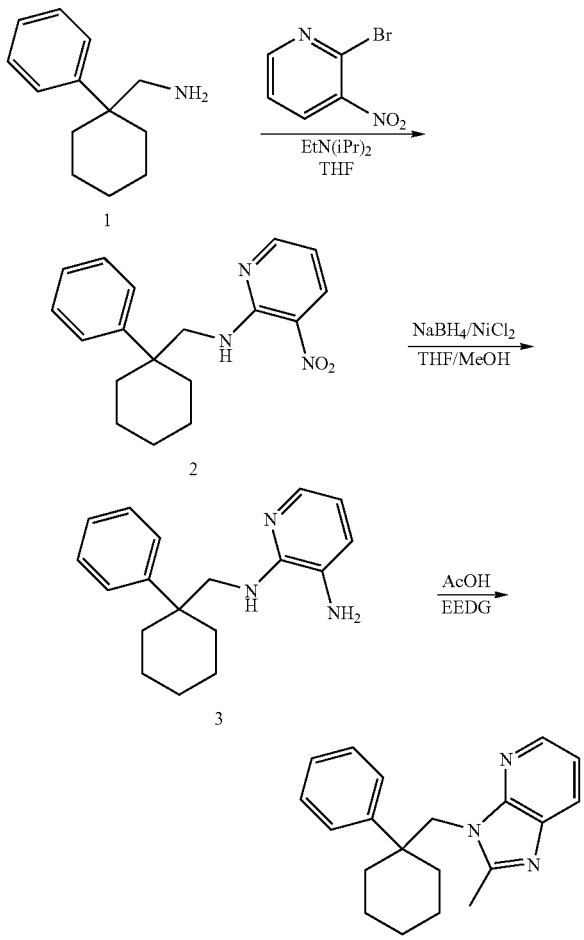

Compound 1: Compound 1 may be prepared as described in Example 330.

Compound 2: A solution of compound 1 (1.21 g; 6.39 mmol) in anhydrous tetrahydrofuran (30 mL) was treated with N,N-diisopropylethylamine (1 mL; 5.73 mmol) and 2-bromo-3-nitro-pyridine (1.18 g; 5.81 mmol). The reaction mixture was heated at 60° C. for 21 h. The solvent was removed under reduced pressure and the residue was treated with ethyl acetate and 10% aqueous hydrochloric acid. The organic layer was separated, washed with saturated aqueous sodium chloride, dried (anhydrous sodium sulfate), filtered and concentrated. The product was purified by recrystallization from a minimum amount of ethyl acetate to provide 1.3 g of (3-nitro-pyridin-2-yl)-(1-phenyl-cyclohexylmethyl)-amine as light tan solid. Mass Spec [M+H]$^+$=312.

Compound 3: A solution of compound 2 (0.96 g; 3.1 mmol) in tetrahydrofuran (25 mL) and methanol (10 mL) was cooled to 0° C. under argon. Sodium borohydride (0.62 g; 16.4 mmol) and nickel(II) chloride (0.06 g; 0.46 mmol) were added and the cooling bath was removed. The reaction mixture was stirred at room temperature for 1 h at which TLC analysis indicated no starting material remained. The reaction was quenched with 2N NaOH (5 mL) and the volatile components were removed under reduced pressure. The residue was treated with ethyl acetate and 1N NaOH. The organic layer was separated, washed with saturated aqueous sodium chloride, dried (anhydrous sodium sulfate), filtered and concentrated. The product was purified by recrystallization from a minimum amount of ethyl acetate and several drops of methanol to provide 0.47 g of (N2-(1-phenyl-cyclohexylmethyl)-pyridine-2,3-diamine as a white solid. Mass Spec [M+H]$^+$=282.

Title Compound: Compound 3 (0.087 g; 0.31 mmol), acetic acid (1 mL) and EEDQ (0.094 g; 0.38 mmol) were combined and heated to 120° C. under argon for 4 h. The reaction mixture was cooled to room temperature, diluted with acetonitrile and water, and purified by preparative reverse-phase liquid chromatography to provide 0.01 g of 2-methyl-3-(1-phenyl-cyclohexylmethyl)-3H-imidazo[4,5-b]pyridine as a white solid. Mass Spec [M+H]$^+$=306.

EXAMPLE 673

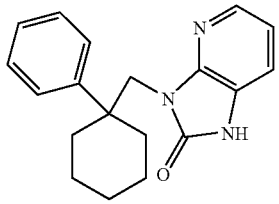

3-(1-Phenyl-cyclohexylmethyl)-1,3-dihydro-imidazo[4,5-b]pyridin-2-one

Synthesis:

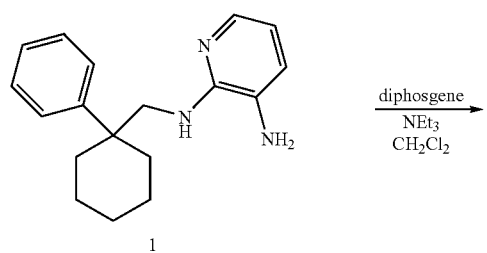

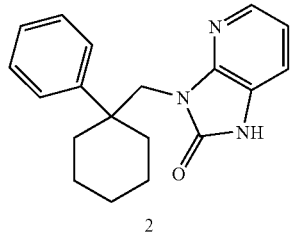

Compound 1: Compound 1 was prepared as described in Example 672.

Title Compound: A solution of compound 1 (0.095 g; 0.34 mmol) in dichloromethane (2 mL) was treated with triethylamine (0.05 mL; 0.36 mmol) and diphosgene (0.041 mL; 0.34 mmol) and allowed to stir at room temperature for 2 h. Additional dichloromethane and 5% aqueous hydrochloric acid was added to the reaction mixture. The organic layer was separated, washed with saturated aqueous sodium chloride and concentrated. The residue was dissolved in an acetonitrile/water mixture and lyophilized to provide 0.04 g of 3-(1-phenyl-cyclohexylmethyl)-1,3-dihydro-imidazo[4,5-b]pyridin-2-one as a white solid. Mass Spec [M+H]$^+$=308.

EXAMPLE 674

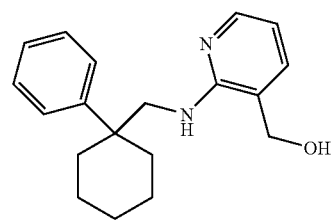

{2-[(1-Phenyl-cyclohexylmethyl)-amino]-pyridin-3-yl}-methanol

Synthesis:

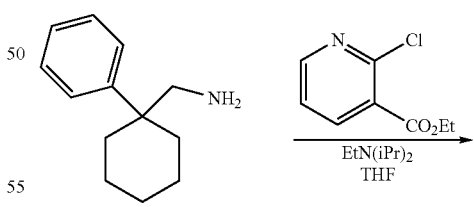

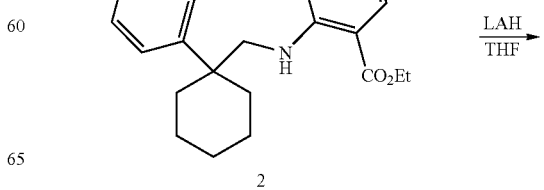

-continued

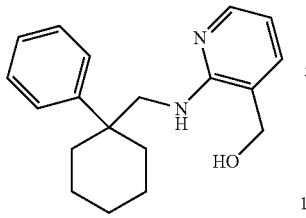

Compound 1: Compound 1 may be prepared as described in Example 330.

Compound 2: Compound 2 may be prepared using methodology described in Example 672 using ethyl 2-chloronicotinate instead of 2-bromo-3-nitro-pyridine. The product was isolated as a colorless oil by column chromatography on silica gel using 8:2 hexane:ethyl acetate as the eluent. Mass Spec [M+H]$^+$=339.

Title Compound: A solution of compound 2 (0.15 g; 0.43 mmol) in tetrahydrofuran (6 mL) was cooled to 0° C. under argon. Lithium aluminum hydride (0.073 g; 19.2 mmol) was added in 10 mg portions. After the addition was complete the cooling bath was removed and the reaction mixture was allowed to stir at room temperature for 0.5 h. The reaction was quenched with water (1 mL) and the reaction mixture was concentrated under reduced pressure. The residue was treated with ethyl acetate and saturated aqueous sodium bicarbonate. The organic layer was separated, washed with saturated aqueous sodium chloride, dried (anhydrous sodium sulfate), filtered and concentrated. Column chromatography on silica gel using 1:1 hexane:ethyl acetate as the eluent gave 0.06 g of {2-[(1-phenyl-cyclohexylmethyl)-amino]-pyridin-3-yl}-methanol as a white foam. Mass Spec [M+H]$^+$=297.

EXAMPLE 675

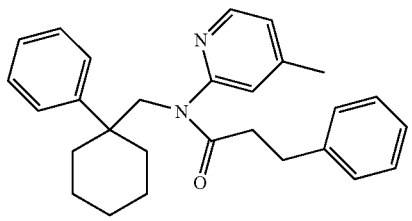

N-(4-Methyl-pyridin-2-yl)-3-phenyl-N-(1-phenyl-cyclohexylmethyl)-propionamide

Synthesis:

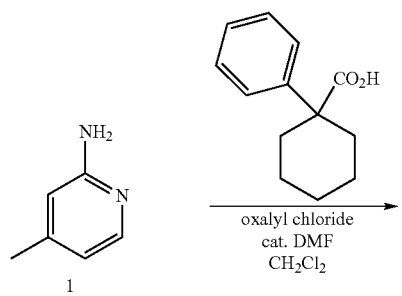

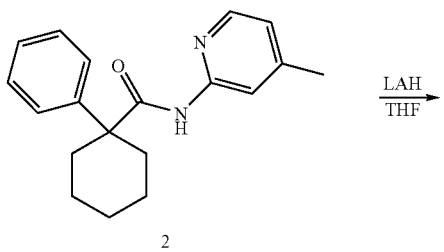

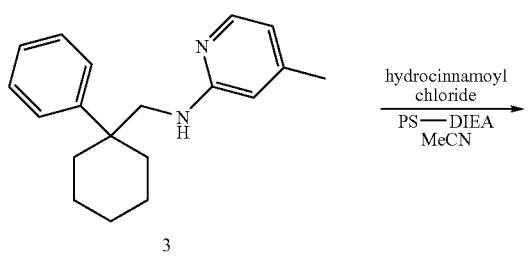

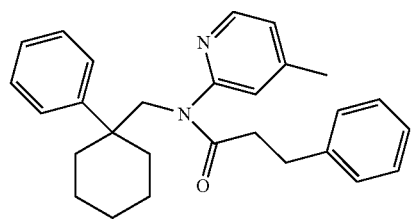

Compound 1: Compound 1 is commercially available.

Compound 2: Compound 2 may be prepared using methodology described in Example 325 using 4-methyl-pyridin-2-ylamine instead of isoquinolin-1-ylamine. The product was purified by recrystallization from a minimum amount of ethyl acetate, several drops of methanol and several drops of hexane to give compound 2 as a brown powder. Mass Spec [M+H]$^+$=295.

Compound 3: Compound 3 may be prepared using methodology described in Example 325. The product was isolated as a colorless oil. Mass Spec [M+H]$^+$=281.

Title compound: A solution of compound 3 (0.035 g; 0.13 mmol) in acetonitrile (2 mL) was treated with polystyrene-diisopropylethylamine (PS-DIEA) (200 mg) and hydrocinnamoyl chloride (0.05 g; 0.3 mmol). The reaction was allowed to shake for 6 h. The reaction mixture was purified directly by preparative reverse phase liquid chromatography to provide 0.02 g of N-(4-methyl-pyridin-2-yl)-3-phenyl-N-(1-phenyl-cyclohexylmethyl)-propionamide as a white solid. Mass Spec [M+H]$^+$=413.

EXAMPLES 676–680

Examples 675–680 were prepared using methodology described in Example 675.

| Ex | Structure | Name | [M + H]+ |
|---|---|---|---|
| 676 | 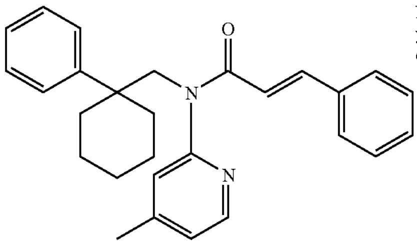 | N-(4-Methyl-pyridin-2-yl)-3-phenyl-N-(1-phenyl-cyclohexylmethyl)-acrylamide | 411 |
| 677 | 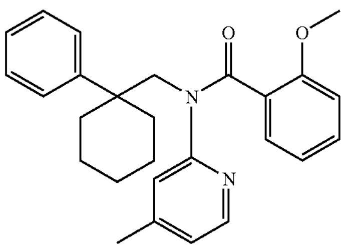 | 2-Methoxy-N-(4-methyl-pyridin-2-yl)-N-(1-phenyl-cyclohexylmethyl)-benzamide | 415 |
| 678 | 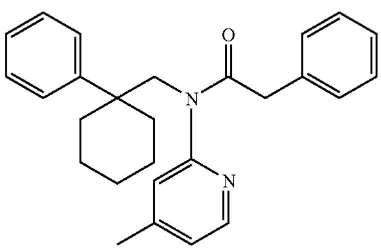 | N-(4-Methyl-pyridin-2-yl)-2-phenyl-N-(1-phenyl-cyclohexylmethyl)-acetamide | 399 |
| 679 | 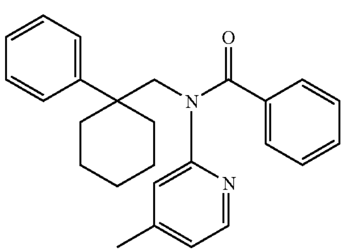 | N-(4-Methyl-pyridin-2-yl)-N-(1-phenyl-cyclohexylmethyl)-benzamide | 385 |
| 680 | 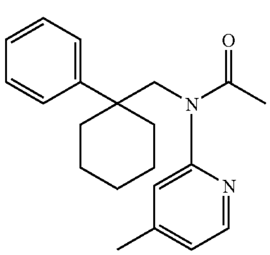 | N-(4-Methyl-pyridin-2-yl)-N-(1-phenyl-cyclohexylmethyl)-acetamide | 323 |

EXAMPLE 681

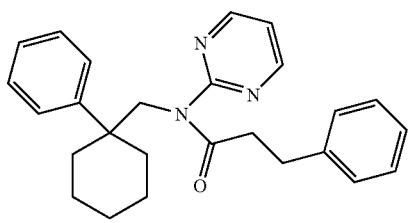

3-Phenyl-N-(1-phenyl-cyclohexylmethyl)-N-pyrimidin-2-yl-propionamide

Synthesis:

EXAMPLE 682

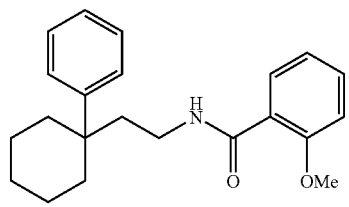

2-Methoxy-N-[2-(1-phenyl-cyclohexyl)-ethyl]-benzamide

Synthesis:

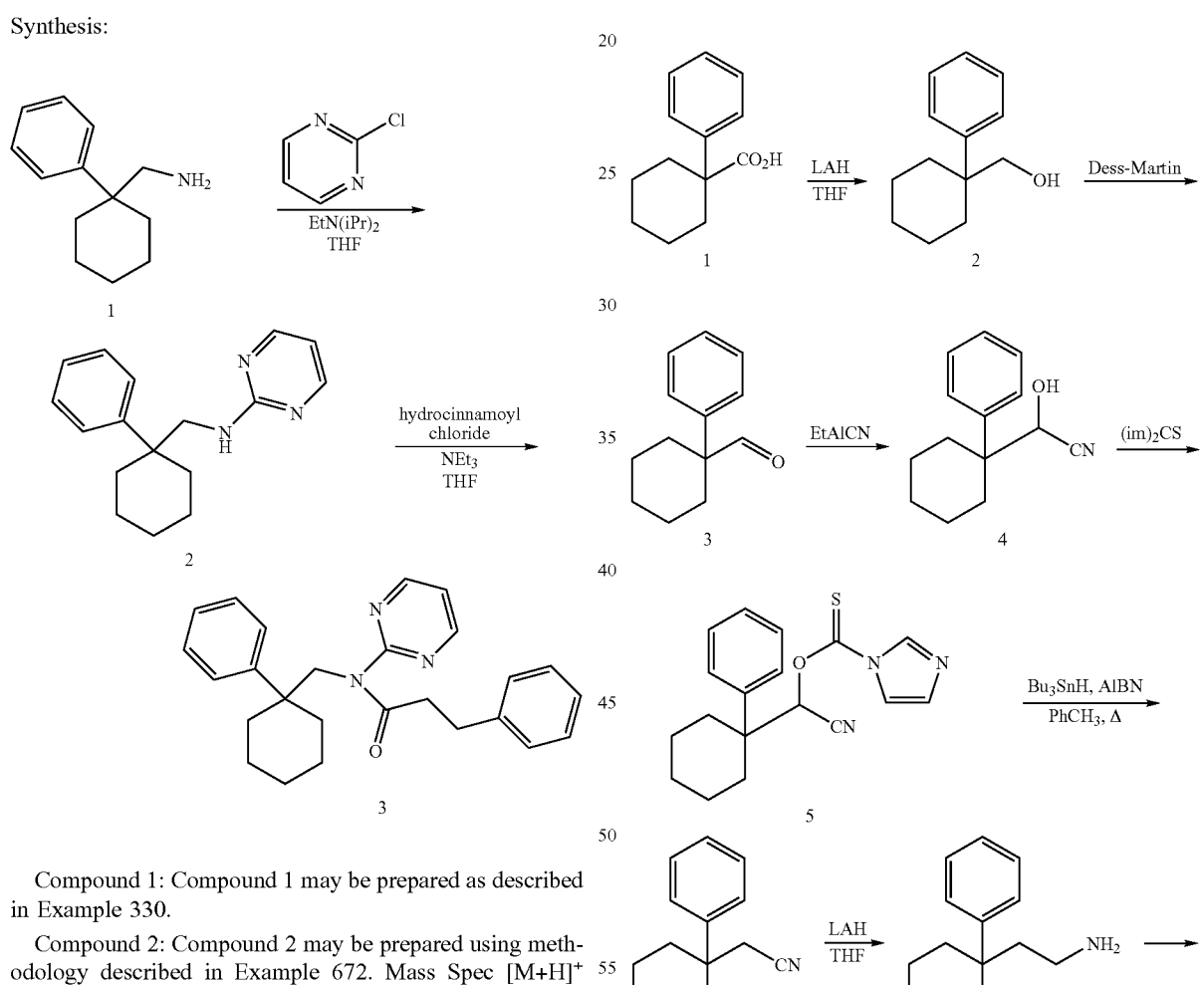

Compound 1: Compound 1 may be prepared as described in Example 330.

Compound 2: Compound 2 may be prepared using methodology described in Example 672. Mass Spec [M+H]$^+$ =268.

Compound 3: A solution of compound 2 (0.1 g; 0.37 mmol) in tetrahydrofuran (2 mL) was treated with triethylamine (0.1 mL; 0.72 mmol) and hydrocinnamoyl chloride (0.08 g; 0.47 mmol). The reaction mixture was allowed to stir at room temperature for 48 h. The solvent was removed by evaporation and the residue purified directly by preparative reverse phase liquid chromatography to provide 0.018 g of 3-phenyl-N-(1-phenyl-cyclohexylmethyl)-N-pyrimidin-2-yl-propionamide as a white solid. Mass Spec [M+H]$^+$= 400.

Compound 1: Compound 1 is commercially available.

Compound 2: To a suspension of LAH (3.8 g, 0.1 mol) cooled to 0° C. was slowly added 1-phenyl-cyclohexanecarboxylic acid (10.2 g, 50.0 mmol). After stirring from 0° C. to rt overnight, the reaction mixture was quenched with $H_2O$ (3.8 mL), 15% NaOH (3.8 mL), $H_2O$ (11.4 mL) and filtered. The salt was washed with $Et_2O$ and the combined organic phase dried over anhydrous sodium sulfate to give (1-phenyl-cyclohexyl)-methanol (8.48 g, 89%) as a white solid. $^1H$ NMR ($CDCl_3$, 300 MHz) δ (ppm) 1.30–1.70 (9H, m), 2.15–2.36 (2H, m), 3.51 (2H, s), 7.20–7.27 (1H, m), 7.34–7.41 (4H, m). Mass Spec $[M+H]^+=191.1$.

Compound 3: To compound 2 (5.0 g, 26.3 mmol) in $CH_2Cl_2$ (50 mL) was added 13.4 g (31.6 mmol) of Dess-Martin periodinane. After 2 h, sodium thiosulfate (58 g) followed by sat. $NaHCO_3$ (200 mL) was added. After stirring for 1 h, the reaction mixture was diluted with EtOAc then washed with $H_2O$, brine and dried over anhydrous sodium sulfate. Purification by flash chromatography (3:1, hexane-EtOAc) gave 1-phenyl-cyclohexanecarbaldehyde (4.47 g, 90%) as a colorless oil. Mass Spec $[M+H]^+=189.1$.

Compound 4: To compound 3 (4.47 g, 23.7 mmol) in $PhCH_3$ (130 mL) at 0° C. was added 36 mL of diethylaluminium cyanide (1.0 M/$PhCH_3$). After stirring for 3 h at 0° C. the reaction mixture was quenched with sat. Rochelle's salt and stirred at rt for 2 h. The aqueous layer was extracted with $CH_2Cl_2$ (2×) and the combined extracts dried over anhydrous sodium sulfate. Hydroxy-(1-phenyl-cyclohexyl)-acetonitrile was used without purification. Mass Spec $[M+H]^+=216.1$.

Compound 5: To compound 4 (23.7 mmol) in $CH_2Cl_2$ (80 mL) was added 5.07 g (28.4 mmol) of 1,1'-thiocarbonyldiimidazole followed by DMAP (0.579 g, 4.74 mmol). After stirring overnight the reaction mixture was washed with H2O and dried over anhydrous sodium sulfate. Purification by flash chromatography (3:1, hexane-EtOAc) gave imidazole-1-carbothioic acid O-[cyano-(1-phenyl-cyclohexyl)-methyl]ester (6.27 g, 81%) as a yellow syrup. Mass Spec $[M+H]^+=326.1$.

Compound 6: Compound 5 (6.27 g, 19.3 mmol), $Bu_3SnH$ (16.8 g, 57.8 mmol) and AIBN (0.63 g, 3.85 mmol) in $PhCH_3$ (100 mL) was heated at reflux for 1 h then concentrated. Purification by flash chromatography (hexane then 4:1, hexane-EtOAc) gave (1-phenyl-cyclohexyl)-acetonitrile (3.84 g, 100%) as a colorless oil. $^1H$ NMR ($CDCl_3$, 300 MHz) δ (ppm) 1.20–1.80 (8H, m), 2.25–2.49 (2H, m), 2.49 (2H, s), 7.35–7.46 (5H, m). Mass Spec $[M+H]^+=210.1$.

Compound 7: To compound 6 (500 mg, 2.51 mmol) in THF (10 mL) cooled at 0° C. was slowly added 382 mg (10.04 mmol) of LAH. After stirring from 0° C. to rt overnight, the reaction mixture was cooled to 0° C. then quenched with $H_2O$ (0.38 mL), 15% NaOH (0.38 mL), $H_2O$ (1.14 mL) and filtered. The salt was washed with $Et_2O$ and the combined organic phase dried over anhydrous sodium sulfate to give 2-(1-phenyl-cyclohexyl)-ethylamine (510 mg, 100%) as a colorless oil. Mass Spec $[M+H]^+=204.2$ Title Compound: 2-Methoxy-N-[2-(1-phenyl-cyclohexyl)-ethyl]-benzamide may be prepared using methodology described in Example 1. Mass Spec $[M+H]^+=338$.

EXAMPLE 683

Example 683 was prepared using methodology described in Example 682

| Ex | structure | Name | [M+H]+ |
|---|---|---|---|
| 683 | 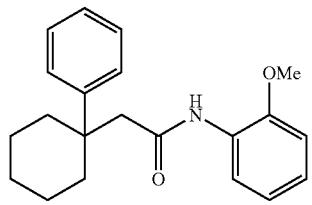 | 2-Hydroxy-6-methoxy-N-[2-(1-phenyl-cyclohexyl)-ethyl]-benzamide | 354 |

EXAMPLE 684

N-(2-Methoxy-phenyl)-2-(1-phenyl-cyclohexyl)-acetamide

Synthesis:

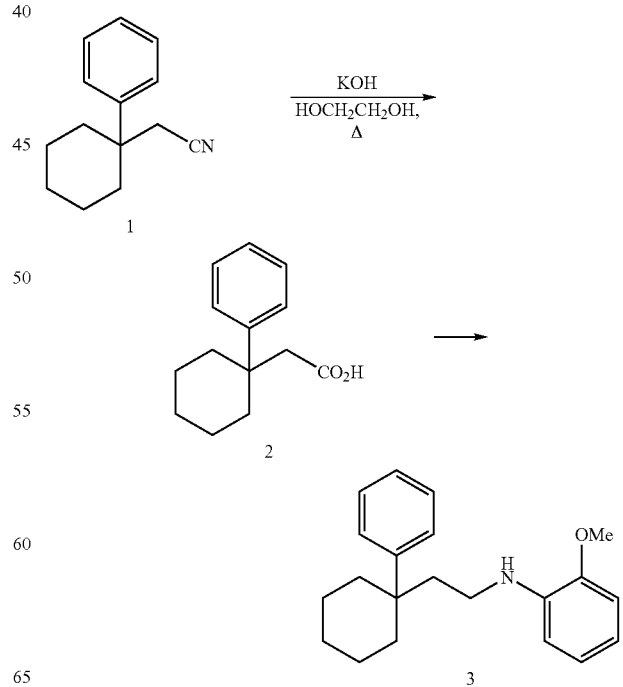

Compound 1: Compound 1 was prepared as described in Example 682.

Compound 2: Compound 1 (3.58 g, 17.96 mmol) and KOH (4.42 g, 78.77 mmol) in ethylene glycol (35 mL) was heated at 170° C. for 48 h then cooled to rt. The reaction mixture was diluted with H$_2$O then extracted with Et$_2$O (2×). The aqueous phase was acidified with 6N HCl then extracted with Et$_2$O (3×) and dried over anhydrous sodium sulfate to give (1-phenyl-cyclohexyl)-acetic acid (3.43 mg, 88%) as a tan solid. Mass Spec [M+H]$^+$=219.1.

Title Compound: To compound 2 (50 mg, 0.23 mmol) in CH$_2$Cl$_2$ (1 mL) was added 24 μL (0.27 mmol) of oxalyl chloride followed by one drop of DMF. After 1 h, o-anisidine (28 mg, 0.23 mmol) followed by Et$_3$N (97 μL, 0.27 mmol) was added. After stirring for 3 h, the reaction mixture was diluted with EtOAc, washed with 1 N HCl, 1 N NaOH, H$_2$O, brine and dried over anhydrous sodium sulfate. Purification by flash chromatography (9:1, hexane-EtOAc) gave N-(2-methoxy-phenyl)-2-(1-phenyl-cyclohexyl)-acetamide (37 mg, 50%) as a white solid. Mass Spec [M+H]$^+$=324.

Compound 1: Compound 1 was prepared as described in Example 684.

Compound 2: To compound 1 (100 mg, 0.046 mmol) in CH$_2$Cl$_2$ (2 mL) was added 48 μL (0.54 mmol) of oxalyl chloride followed by one drop of DMF. After 1.5 h, the resulting acid chloride was added to a solution of 1,2-phenylenediamine (28 mg, 0.23 mmol) Et$_3$N (190 μL, 0.1.38 mmol) was added. After stirring for 1 h, the reaction mixture was diluted with EtOAc, washed with 1 N HCl, 1 N NaOH, H$_2$O, brine and dried over anhydrous sodium sulfate. N-(2-Amino-phenyl)-2-(1-phenyl-cyclohexyl)-acetamide was used in next step without purification.

Title Compound: Compound 2 (0.46 mmol) in glacial AcOH (2 mL) was heated at 100° C. for 2 h then cooled to rt. The reaction mixture was concentrated and the residue purified by flash chromatography (1:1, hexane-EtOAc) to give 2-(1-phenyl-cyclohexylmethyl)-1H-benzoimidazole (73 mg, 54%) as a white solid. Mass Spec [M+H]$^+$=291.

EXAMPLE 685

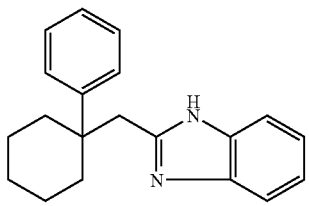

2-(1-Phenyl-cyclohexylmethyl)-1H-benzoimidazole

Synthesis:

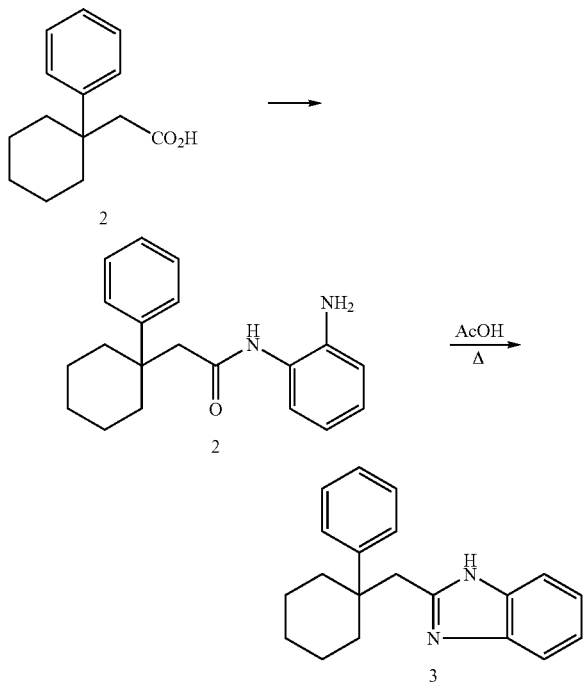

EXAMPLES 686–687

Examples 686–687 were prepared using methodology described in Example 685.

| Ex | structure | Name | [M + H]$^+$ |
|---|---|---|---|
| 686 | 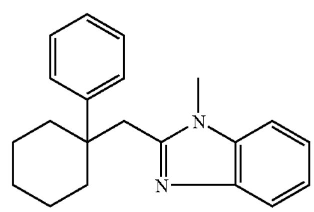 | 1-Methyl-2-(1-phenyl-cyclohexyl-methyl)-1H-benzoimidazole | 305 |
| 687 | 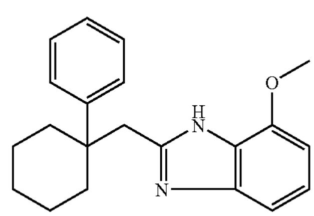 | 7-Methoxy-2-(1-phenyl-cyclohexyl-methyl)-1H-benzoimidazole | 321 |

EXAMPLE 688

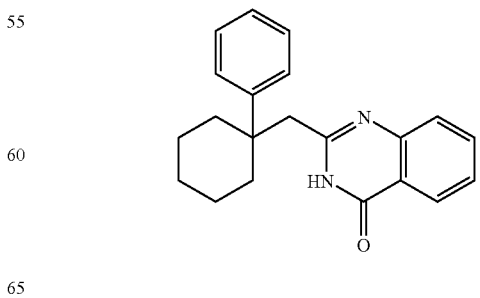

2-(1-Phenyl-cyclohexylmethyl)-3H-quinazolin-4-one

Synthesis:

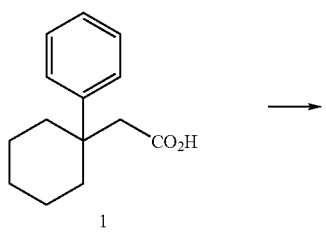

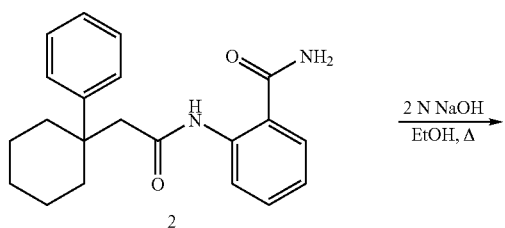

Compound 1: Compound 1 was prepared as described in Example 684.

Compound 2: To compound 2 (75 mg, 0.0.34 mmol) in CH$_2$Cl$_2$ (1 mL) was added 36 µL (0.0.41 mmol) of oxalyl chloride followed by one drop of DMF. After 1 h, anthranilamide (46 mg, 0.0.34 mmol) followed by Et$_3$N (150 µL, 1.02 mmol) was added. After stirring overnight, the reaction mixture was diluted with EtOAc, washed with 1 N HCl, 1 N NaOH, H$_2$O, brine and dried over anhydrous sodium sulfate. Purification by flash chromatography (1:1, hexane-EtOAc) gave 2-[2-(1-phenyl-cyclohexyl)-acetylamino]-benzamide (78 mg, 68%) as a white solid. Mass Spec [M+H]$^+$=337.2.

Title Compound: The amide (73 mg, 0.217 mmol) in EtOH (1 mL) and 2N NaOH (1 mL) was heated at 80° C. for 1 h. The reaction mixture was concentrated, extracted with CH$_2$Cl$_2$ (3×) then dried over anhydrous sodium sulfate. Purification by flash chromatography (1:1, hexane-EtOAc) gave 2-(1-phenyl-cyclohexylmethyl)-3H-quinazolin-4-one (66 mg, 96%) as a white solid. Mass Spec [M+H]$^+$=319.2.

EXAMPLE 689

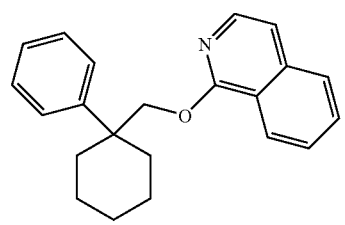

1-(1-Phenyl-cyclohexylmethoxy)-isoquinoline

Synthesis:

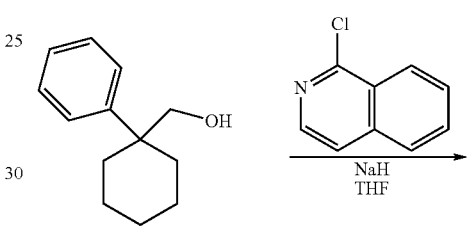

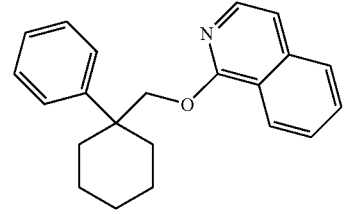

Compound 1: Compound 1 was prepared using methodology described in Example 682.

Title Compound: A solution of compound 1 (0.23 g; 1.23 mmol) in tetrahydrofuran (10 mL) was cooled to 0° C. under argon. Sodium hydride (0.080 g; 3.3 mmol) was slowly added in 5–10 mg portions. After the addition was complete the reaction mixture was allowed to stir at 0° C. for 0.25 h and 1-chloroisoquinoline (0.32 g; 2.0 mmol) was added. The reaction mixture was allowed to slowly warm to room temperature overnight. Additional sodium hydride (0.080 g; 3.3 mmol) was added and the reaction mixture was heated at 60° C. for 7 h. The solvent was removed by evaporation and the residue was purified by column chromatography on silica gel using 8:2 hexane:ethyl acetate as the eluent to provide 0.02 g of 1-(1-phenyl-cyclohexylmethoxy)-isoquinoline. Mass Spec [M+H]$^+$=318.

EXAMPLES 690–694

Examples 690–694 were prepared using methodology described in Example 325.

| Ex | structure | Name | [M + H]⁺ |
|---|---|---|---|
| 690 | 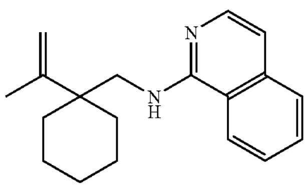 | (1-Isopropenyl-cyclohexylmethyl)-isoquinolin-1-yl-amine | 281 |
| 691 | 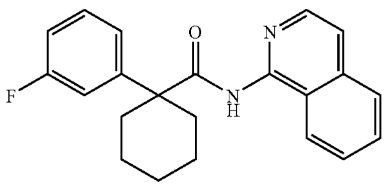 | 1-(3-Fluoro-phenyl)-cyclohexanecarboxylic acid isoquinolin-1-ylamide | 349 |
| 692 | 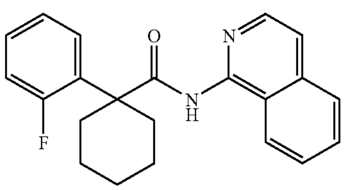 | 1-(2-Fluoro-phenyl)-cyclohexanecarboxylic acid isoquinolin-1-ylamide | 349 |
| 693 | 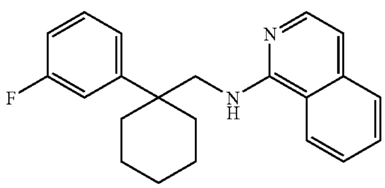 | [1-(3-Fluoro-phenyl)-cyclohexylmethyl]-isoquinolin-1-yl-amine | 335 |
| 694 | 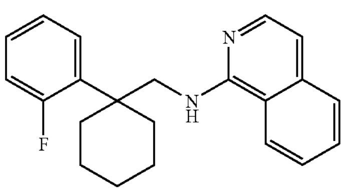 | [1-(2-Fluoro-phenyl)-cyclohexylmethyl]-isoquinolin-1-yl-amine | 335 |

We claim:

1. A compound of Formula I

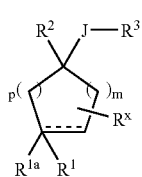

enantiomers, diastereomers, solvates or salts thereof wherein the dashed line represents an optional double bond, provided that $R^{1a}$ is absent when a double bond is present;

m and p are independently 0, 1, 2 or 3;

$R^1$ is

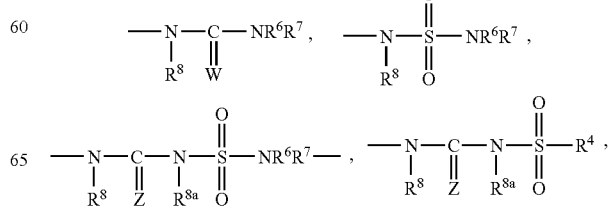

-continued

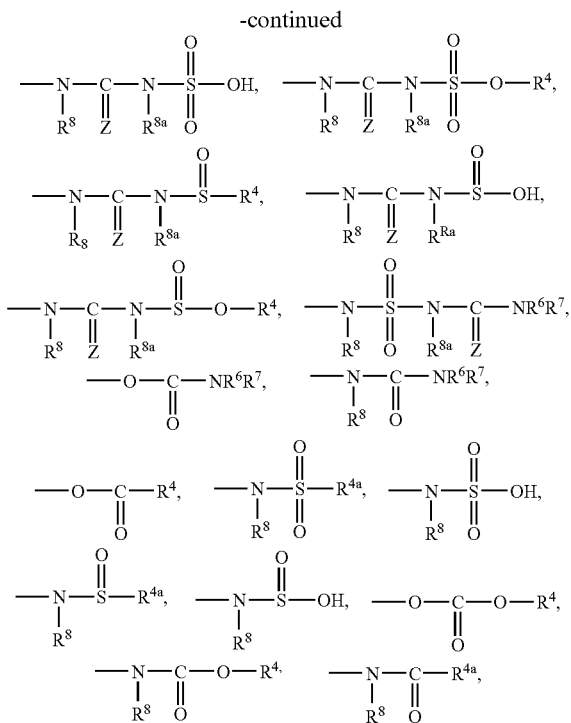

—N(R$^8$)R$^{14}$, —N(R$^8$)C(O)R$^{14}$, —SO$_2$R$^{8c}$, —OC(O)CCl$_3$, —NR$^6$R$^7$, —OC(O)NR$^6$R$^7$, —N$_3$, nitro, or hydroxy;

R$^{1a}$ is H;

R$^2$ is aryl, which may be optionally independently substituted with one or more groups T$^1$, T$^2$, or T$^3$;

J is a C$_{1-4}$ alkylene optionally independently substituted with one or more groups T$^{1a}$, T$^{2a}$ or T$^{3a}$;

R$^3$ is —R$^5$;

R$^4$ is alkyl, haloalkyl, alkenyl, cycloalkyl, heterocyclo, aryl, or heteroaryl any of which may be optionally independently substituted with one or more groups T$^{1b}$, T$^{2b}$ or T$^{3b}$;

R$^{4a}$ is R$^4$ or OR$^4$;

R$^5$ is —NR$^{6a}$R$^{7a}$;

R$^6$, R$^7$, R$^8$, R$^{8a}$, R$^{8a2}$, R$^{8a4}$, and R$^{8a5}$ are independently H, alkyl, hydroxy, alkoxy, aryloxy, heterocyclooxy, heteroaryloxy, (hydroxy)alkyl, (alkoxy)alkyl, (aryloxy)alkyl, (heterocyclooxy)alkyl, (heteroaryloxy)alkyl, (cyano)alkyl, (alkenyl)alkyl, (alkynyl)alkyl, cycloalkyl, (cycloalkyl)alkyl, aryl, (aryl)alkyl, heteroaryl, (heteroaryl)alkyl, heterocyclo, (heterocyclo)alkyl, —C(O)R$^{12}$, —CO$_2$R$^{12}$, —C(O)—NR$^{12}$R$^{13}$, or —NR$^{12}$R$^{13}$ any of which may be optionally independently substituted with one or more groups T$^{1d}$, T$^{2d}$ or T$^{3d}$;

or R$^6$ and R$^7$, together with the nitrogen atom to which they are attached may combine to form a saturated or unsaturated 4 to 8 membered ring optionally independently substituted with one or more groups T$^{1d}$, T$^{2d}$ or T$^{3d}$;

or one of R$^6$ or R$^7$, may combine with one of R$^8$ or R$^{8a}$ to form a saturated or unsaturated 5 to 8 membered ring optionally independently substituted with one or more groups T$^{1d}$, T$^{2d}$ or T$^{3d}$;

R$^{6a}$ is H;

R$^{7a}$ is heteroaryl, which may be optionally independently substituted with one or more groups T$^{1d}$, T$^{2d}$ or T$^{3d}$;

R$^{8b}$ is independently H, alkyl, aryl, cyano, nitro, acyl or —SO$_2$(alkyl);

R$^{8c}$ is independently H, alkyl, cycloalkyl, alkenyl, alkynyl, aryl, arylalkyl, cycloheteroalkyl, heteroaryl, amino or alkoxy;

R$^{8d}$ is R$^4$, COR$^4$, CO$_2$R$^4$, CONR$^6$R$^7$, or SO$_2$—NR$^6$R$^7$;

R$^{12}$ and R$^{13}$ are independently H, alkyl, hydroxy, alkoxy, aryloxy, heterocyclooxy, heteroaryloxy, (hydroxy)alkyl, (alkoxy)alkyl, (aryloxy)alkyl, (heterocyclooxy)alkyl, (heteroaryloxy)alkyl, cycloalkyl, (cycloalkyl)alkyl, aryl, (aryl)alkyl, heteroaryl, (heteroaryl)alkyl, heterocyclo, or (heterocyclo)alkyl any of which may be optionally independently substituted with one or more groups T$^{1f}$, T$^{2f}$ or T$^{3f}$ or R$^{12}$ and R$^{13}$ together with the nitrogen atom to which they are attached may combine to form a saturated or unsaturated ring which may be optionally independently substituted with one or more groups T$^{1f}$, T$^{2f}$ or T$^{3f}$;

W is =NR$^{8a2}$, =N—CO$_2$R$^{8a2}$, =N—COR$^{8a2}$, =N—CN, or =N—SO$_2$R$^{8a2}$;

Z and Z$^2$ are independently =O, =S, =NR$^{8a4}$ or =N—CN;

R$^{14}$ is independently

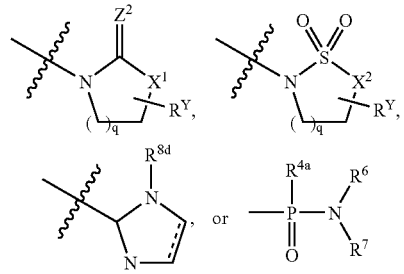

where q is 1, 2 or 3;

R$^Y$ is an optional oxo substituent attached to any available ring carbon atom;

X$^1$ is O, S, NR$^{8a5}$ or CH$_2$; and

X$^2$ is NR$^{8a5}$ or CH$_2$;

R$^X$ is one or more optional substituents, attached to any available ring carbon atom, independently selected from T$^{1g}$, T$^{2g}$ or T$^{3g}$;

T$^{1-1g}$, T$^{2-2g}$, and T$^{3-3g}$ are each independently (1) hydrogen or T$^6$, where T$^6$ is (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

(ii) a group (i) which is itself substituted by one or more of the same or different groups (i); or (iii) a group (i) or (ii) which is independently substituted by one or more (preferably 1 to 3) of the following groups (2) to (13) of the definition of T$^{1-1g}$, T$^{2-2g}$ and T$^{3-3g}$, (2) —OH or —OT$^6$, (3) —SH or —ST$^6$, (4) —C(O)$_t$H, —C(O)$_t$T$^6$, or —O—C(O)T$^6$, where t is 1 or 2;

(5) —SO$_3$H, —S(O)$_t$T$^6$, or S(O)$_t$N(T$^9$)T$^6$, (6) halo, (7) cyano,
(8) nitro,
(9) —$T^4$—$NT^7T^8$,
(10) —$T^4$—$N(T^9)$—$T^5$—$NT^7T^8$,
(11) —$T^4$—$N(T^{10})$—$T^5$—$T^6$,
(12) —$T^4$—$N(T^{10})$—$T^5$—H,
(13) oxo, $T^4$ and $T^5$ are each independently
(1) a single bond,
(2) —$T^{11}$—$S(O)_t$—$T^{12}$—,
(3) —$T^{11}$—$C(O)$—$T^{12}$—,
(4) —$T^{11}$—$C(S)$—$T^{12}$—,
(5) —$T^{11}$—O—$T^{12}$—,
(6) —$T^{11}$—S—$T^{12}$—,
(7) —$T^{11}$—O—$C(O)$—$T^{12}$—,
(8) —$T^{11}$—$C(O)$—O—$T^{12}$—,
(9) —$T^{11}$—$C(=NT^{9a})$—$T^{12}$—, or
(10) —$T^{11}$—$C(O)$—$C(O)$—$T^{12}$—

$T^7$, $T^8$, $T^9$, $T^{9a}$ and $T^{10}$
(1) are each independently hydrogen or a group provided in the definition of $T^6$, or
(2) $T^7$ and $T^8$ may together be alkylene or alkenylene, completing a 3- to 8-membered saturated or unsaturated ring together with the atoms to which they are attached, which ring is unsubstituted or substituted with one or more groups listed in the definition of $T^{1-1g}$, $T^{2-2g}$ and $T^{3-3g}$, or
(3) $T^7$ or $T^8$, together with $T^9$, may be alkylene or alkenylene completing a 3- to 8-membered saturated or unsaturated ring together with the nitrogen atoms to which they are attached, which ring is unsubstituted or substituted with one or more groups listed in the definition of $T^{1-1g}$, $T^{2-2g}$ and $T^{3-3g}$, or
(4) $T^7$ and $T^8$ or $T^9$ and $T^{10}$ together with the nitrogen atom to which they are attached may combine to form a group —N=$CT^{13}T^{14}$ where $T^{13}$ and $T^{14}$ are each independently H or a group provided in the definition of $T^6$;

$T^{11}$ and $T^{12}$ are each independently
(1) a single bond,
(2) alkylene,
(3) alkenylene, or
(4) alkynylene.

2. A compound of claim 1 wherein $R^1$ is

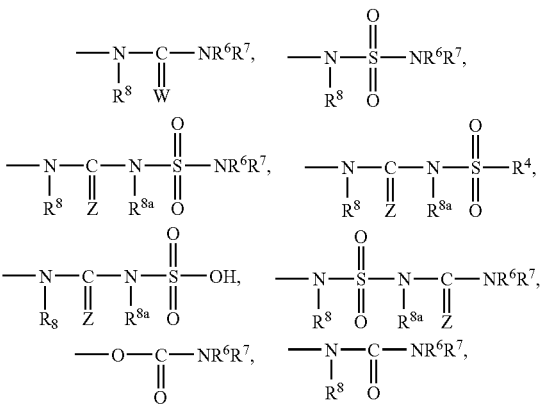

—$NR^6R^7$, or —$OC(O)NR^6R^7$;
where $R^7$ is heteroaryl.

3. A compound of claim 1 wherein $R^2$ is other than

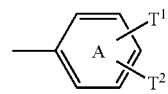

where A is phenyl.

4. A compound of claim 1 wherein
J is alkylene;
$R^1$ is

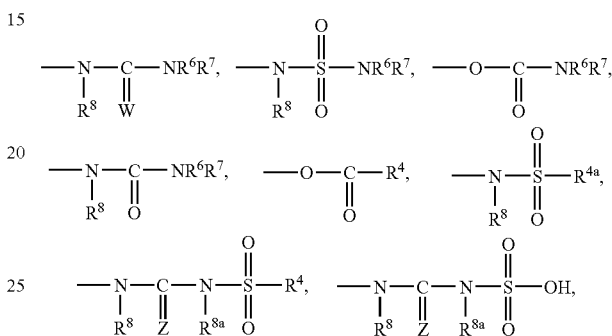

or hydroxy;
$R^2$ is phenyl, which may be optionally substituted with one or more groups $T^1$, $T^2$ or $T^3$.

5. A compound of claim 1 wherein $R^1$ is
(a) —$N(R^8)$—$SO_2$—$NR^6R^7$, or —$N(R^8)$—C(W)—$NR^6R^7$
where
$R^6$ and $R^7$ are independently
(i) H, or
(ii) alkyl, cycloalkyl, alkenyl, alkynyl, aryl, heteroaryl, heterocyclo, alkoxy, (aryl)alkyl, (cycloalkyl)alkyl, (heteroaryl)alkyl, (heterocyclo)alkyl, (alkoxy)alkyl, or $NR^{12}R^{13}$ any of which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl,
or $R^6$ and $R^7$ combine to form a heterocyclo ring optionally substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl; and
$R^8$ is
(i) H; or
(ii) alkyl, cycloalkyl, aryl, heteroaryl, heterocyclo, (cycloalkyl)alkyl, (aryl)alkyl, (heteroaryl)alkyl or (heterocyclo)alkyl any of which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl, or (b) —$N(R^8)$—C(Z)—$N(R^8)$—$SO_2$—$R^4$ or —$N(R^8)$—C(Z)—$N(R^{8a})$—$SO_2$—OH where $R^4$ is
(i) H, or
(ii) alkyl, cycloalkyl, alkenyl, alkynyl, aryl, heteroaryl, heterocyclo, alkoxy, (aryl)alkyl, (cycloalkyl)alkyl, (heteroaryl)alkyl, (heterocyclo)alkyl, (alkoxy)alkyl, or $NR^{12}R^{13}$ any of which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl; and $R^8$ and $R^{8a}$ are independently
(i) H; or
(ii) alkyl, cycloalkyl, aryl, heteroaryl, heterocyclo, (cycloalkyl)alkyl, (aryl)alkyl, (heteroaryl)alkyl or (heterocyclo)alkyl any of which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl;

$R^{1a}$ is H;

$R^2$ is phenyl, which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl; and J is methylene or ethylene $R^6$ and $R^7$ are independently H, optionally substituted aryl, optionally substituted heteroaryl, optionally substituted cycloalkyl, optionally substituted heterocyclo, optionally substituted (aryl)alkyl, optionally substituted (heteroaryl)alkyl, optionally substituted (heterocyclo)alkyl, optionally substituted alkyl, or $COR^{12}$;

or $R^6$ and $R^7$, together with the nitrogen to which they are attached combine to form an optionally substituted saturated or unsaturated 5 to 8 membered ring.

6. A compound of claim 1 wherein $R^1$ is
(a) hydroxy;
(b) —O—C(O)—$NR^6R^7$, —$N(R^8)$—$SO_2$—$NR^6R^7$, or —$N(R^8)$—C(W)—$NR^6R^7$ where $R^6$ and $R^7$ are independently
(i) H, or
(ii) alkyl, cycloalkyl, alkenyl, alkynyl, aryl, heteroaryl, heterocyclo, alkoxy, (aryl)alkyl, (cycloalkyl)alkyl, (heteroaryl)alkyl, (heterocyclo)alkyl, (alkoxy)alkyl, or $NR^{12}R^{13}$ any of which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl, or $R^6$ and $R^7$ combine to form a heterocyclo ring optionally substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl; and $R^8$ is
(i) H; or
(ii) alkyl, cycloalkyl, aryl, heteroaryl, heterocyclo, (cycloalkyl)alkyl, (aryl)alkyl, (heteroaryl)alkyl or (heterocyclo)alkyl any of which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl, or (c) —O—C(O)—$R^4$, —$N(R^8)$—C(Z)—$N(R^{8a})$—$SO_2$—$R^4$ or —$N(R^8)$—C(Z)—$N(R^{8a})$—$SO_2$OH where $R^4$ is
(i) H, or
(ii) alkyl, cycloalkyl, alkenyl, alkynyl, aryl, heteroaryl, heterocyclo, alkoxy, (aryl)alkyl, (cycloalkyl)alkyl, (heteroaryl)alkyl, (heterocyclo)alkyl, (alkoxy)alkyl, or $NR^{12}R^{13}$ any of which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl; and $R^8$ and $R^{8a}$ are independently
(i) H; or
(ii) alkyl, cycloalkyl, aryl, heteroaryl, heterocyclo, (cycloalkyl)alkyl, (aryl)alkyl, (heteroaryl)alkyl or (heterocyclo)alkyl any of which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl;

$R^{1a}$ is H;

$R^2$ is phenyl, which may be optionally independently substituted with one or more OH, SH, $OT^6$, $ST^6$, $C(O)_tT^6$, $NT^7T^8$, cyano, halo, oxo, alkyl, haloalkyl, aryl, heteroaryl, heterocyclo, (OH)alkyl, (SH)alkyl, ($OT^6$)alkyl, ($ST^6$)alkyl, ($C(O)_tT^6$)alkyl, ($NT^7T^8$)alkyl, (cyano)alkyl, (aryl)alkyl, (heteroaryl)alkyl or (heterocyclo)alkyl;

J is methylene or ethylene;

$R^6$ and $R^7$ are independently H, optionally substituted aryl, optionally substituted heteroaryl, optionally substituted cycloalkyl, optionally substituted heterocyclo, optionally substituted (aryl)alkyl, optionally substituted (heteroaryl)alkyl, optionally substituted (heterocyclo)alkyl, optionally substituted alkyl, or $COR^{12}$; or $R^6$ and $R^7$ together with the nitrogen to which they are attached combine to form an optionally substituted saturated or unsaturated 5 to 8 membered ring.

7. A pharmaceutical composition comprising at least one compound of claim 1 together with a suitable vehicle or carrier therefor.

8. A compound of Formula I

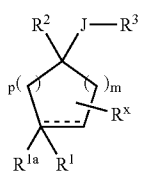

enantiomers, diastereomers or salts thereof wherein
the dashed line represents an optional double bond, provided that $R^{1a}$ is absent when a double bond is present;
m and p are independently 0, 1, 2 or 3;
$R^1$ is

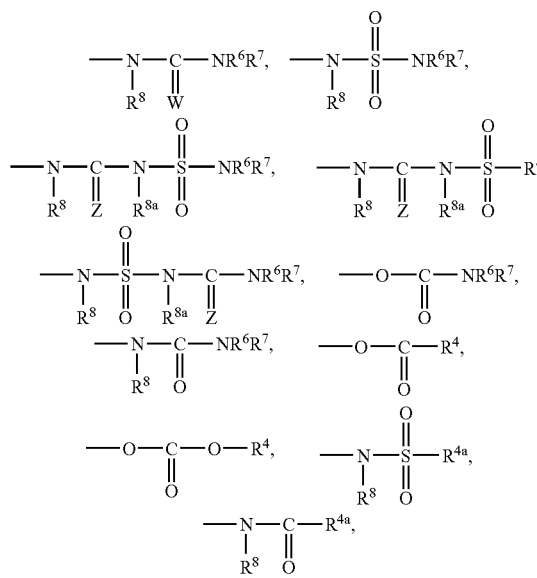

—$N(R^8)R^{14}$, —$N(R^8)C(O)R^{14}$, —$SO_2R^{8c}$, —$OC(O)CCl_3$, —$NR^6R^7$, —$OC(O)NR^6R^7$, —$N_3$, nitro, or hydroxy;

$R^{1a}$ is H;

$R^2$ is aryl, which may be optionally independently substituted with one or more groups $T^1$, $T^2$ or $T^3$;

J is $C_{1-4}$ alkylene optionally independently substituted with one or more groups $T^{1a}$, $T^{2a}$ or $T^{3a}$;

$R^3$ is —$R^5$;

$R^4$ is alkyl, haloalkyl, alkenyl, cycloalkyl, heterocyclo, aryl, or heteroaryl any of which may be optionally independently substituted with one or more groups $T^{1b}$, $T^{2b}$ or $T^{3b}$;

$R^{4a}$ is $R^4$ or $OR^4$;

$R^5$ is —$NR^{6a}R^{7a}$;

$R^6$, $R^7$, $R^8$, $R^{8a}$, $R^{8a2}$, $R^{8a4}$, and $R^{8a5}$ are independently H, alkyl, hydroxy, alkoxy, aryloxy, heterocyclooxy, heteroaryloxy, (hydroxy)alkyl, (alkoxy)alkyl, (aryloxy)alkyl, (heterocyclooxy)alkyl, (heteroaryloxy)alkyl, (cyano)alkyl, (alkenyl)alkyl, (alkynyl)alkyl, cycloalkyl, (cycloalkyl)alkyl, aryl, (aryl)alkyl, heteroaryl, (heteroaryl)alkyl, heterocyclo, (heterocyclo)alkyl, —$C(O)R^{12}$, —$C_2R^{12}$, —$C(O)$—$NR^{12}R^{13}$, or —$NR^{12}R^{13}$ any of which may be optionally independently substituted with one or more groups $T^{1d}$, $T^{2d}$ or $T^{3d}$;

or $R^6$ and $R^7$ together with the nitrogen atom to which they are attached may combine to form a saturated or unsaturated 4 to 8 membered ring optionally independently substituted with one or more groups $T^{1d}$, $T^{2d}$ or $T^{3d}$;

or one of $R^6$ or $R^7$, may combine with one of $R^8$, $R^{8a}$ or $R^9$ to form a saturated or unsaturated 5 to 8 membered ring optionally independently substituted with one or more groups $T^{1d}$, $T^{2d}$ or $T^{3d}$;

$R^{6a}$ is H;

$R^{7a}$ is heteroaryl, which may be optionally independently substituted with one or more groups $T^{1d}$, $T^{2d}$ or $T^{3d}$;

$R^{8b}$ is independently H, alkyl, aryl, cyano, nitro, acyl or —$SO_2$(alkyl);

$R^{8c}$ is independently H, alkyl, cycloalkyl, alkenyl, aryl, arylalkyl, cycloheteroalkyl, heteroaryl, amino or alkoxy;

$R^{8d}$ is $R^4$, $COR^4$, $CO_2R^4$, $SO_2R^4$, $CONR^6R^7$, or $SO_2$—$NR^6R^7$;

$R^{12}$ and $R^{13}$ are independently H, alkyl, hydroxy, alkoxy, aryloxy, heterocyclooxy, heteroaryloxy, (hydroxy)alkyl, (alkoxy)alkyl, (aryloxy)alkyl, (heterocyclooxy)alkyl, (heteroaryloxy)alkyl, cycloalkyl, (cycloalkyl)alkyl, aryl, (aryl)alkyl, heteroaryl, (heteroaryl)alkyl, heterocyclo, or (heterocyclo)alkyl any of which may be optionally independently substituted with one or more groups $T^{1f}$, $T^{2f}$ or $T^{3f}$;

or $R^{12}$ and $R^{13}$ together with the nitrogen atom to which they are attached may combine to form a saturated or unsaturated ring which may be optionally independently substituted with one or more groups $T^{1f}$, $T^{2f}$ or $T^{3f}$;

W is =$NR^{8a2}$, =$N$—$CO_2R^{8a2}$, =$N$—$COR^{8a2}$, =$N$—$CN$, or =$N$—$SO_2R^{8a2}$;

Z and $Z^2$ are independently =O, =S, =$NR^{8a4}$ or =$N$—$CN$;

$R^{14}$ is independently

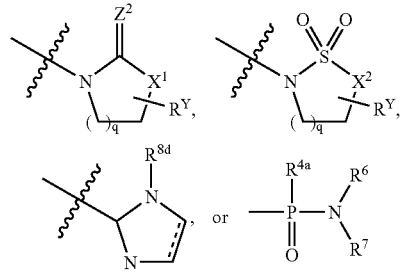

where q is 1, 2 or 3;

$R^Y$ is an optional oxo substituent attached to any available ring carbon atom;

$X^1$ is O, S, $NR^{8a5}$ or $CH_2$; and $X^2$ is $NR^{8a5}$ or $CH_2$;

$T^{1-1g}$, $T^{2-2g}$ and $T^{3-3g}$ are each independently
(1) hydrogen or $T^6$, where $T^6$ is
  (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (ii) a group (i) which is itself substituted by one or more of the same or different groups (i); or (iii) a group (i) or (ii) which is independently substituted by one or more (preferably 1 to 3) of the following groups (2) to (13) of the definition $T^{1-1g}$, $T^{2-2g}$ and $T^{3-3g}$,
(2) —OH or —OT$^6$,
(3) —SH or —ST$^6$,
(4) —C(O)$_t$H, —C(O)$_t$T$^6$, or —O—C(O)T$^6$, where t is 1 or 2;
(5) —SO$_3$H, —S(O)$_t$T$^6$, or S(O)$_t$N(T$^9$)T$^6$,
(6) halo,
(7) cyano,
(8) nitro,
(9) —T$^4$—NT$^7$T$^8$,
(10) —T$^4$—N(T$^9$)—T$^5$—NT$^7$T$^8$,
(11) —T$^4$—N(T$^{10}$)—T$^5$—T$^6$,
(12) —T$^4$—N(T$^{10}$)—T$^5$—H,
(13) oxo, $T^4$ and $T^5$ are each independently
(1) a single bond,
(2) —T$^{11}$—S(O)$_t$—T$^{12}$—,
(3) —T$^{11}$—C(O)—T$^{12}$—,
(4) —T$^{11}$—C(S)—T$^{12}$—,
(5) —T$^{11}$—O—T$^{12}$—,
(6) —T$^{11}$—S—T$^{12}$—,
(7) —T$^{11}$—O—C(O)—T$^{12}$—,
(8) —T$^{11}$—C(O)—O—T$^{12}$—,
(9) —T$^{11}$—C(=NT$^{9a}$)—T$^{12}$—, or
(10) —T$^{11}$—C(O)—C(O)—T$^{12}$—

$T^7$, $T^8$, $T^9$, $T^{9a}$ and $T^{10}$
(1) are each independently hydrogen or a group provided in the definition of $T^6$, or
(2) $T^7$ and $T^8$ may together be alkylene or alkenylene, completing a 3- to 8-membered saturated or unsaturated ring together with the atoms to which they are attached, which ring is unsubstituted or substituted with one or more groups listed in the definition $T^{1-1g}$, $T^{2-2g}$ and $T^{3-3g}$, or
(3) $T^7$ or $T^8$, together with $T^9$, may be alkylene or alkenylene completing a 3- to 8-membered saturated or unsaturated ring together with the nitrogen atoms to which they are attached, which ring is unsubstituted or substituted with one or more groups listed in the definition $T^{1-1g}$, $T^{2-2g}$ and $T^{3-3g}$, or
(4) $T^7$ and $T^8$ or $T^9$ and $T^{10}$ together with the nitrogen atom to which they are attached may combine to form a group —N=CT$^{13}$T$^{14}$ where $T^{13}$ and $T^{14}$ are each independently H or a group provided in the definition of $T^6$;

$T^{11}$ and $T^{12}$ are each independently
(1) a single bond,
(2) alkylene,
(3) alkenylene, or
(4) alkynylene.

9. The compound of claim 1 wherein $R^2$ is phenyl, which may be optionally independently substituted with one or more groups $T^1$, $T^2$ or $T^3$; and J is methylene.

* * * * *

UNITED STATES PATENT AND TRADEMARK OFFICE
CERTIFICATE OF CORRECTION

PATENT NO. : 7,202,253 B2
APPLICATION NO. : 10/997734
DATED : April 10, 2007
INVENTOR(S) : Lloyd et al.

It is certified that error appears in the above-identified patent and that said Letters Patent is hereby corrected as shown below:

Column 384, Lines 64-70:

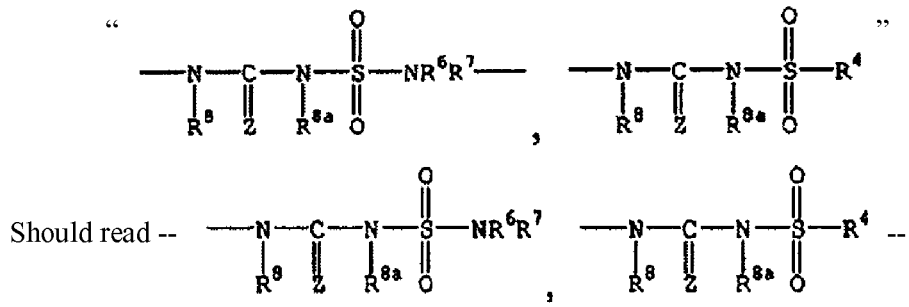

Column 386, Line 9:

"$R^{8d}$ is $R^4$, $COR^4$, $CO_2R^4$, $CONR^6R^7$, or $SO_2$-$NR^6R^7$;"

Should read: -- $R^{8d}$ is $R^4$, $COR^4$, $CO_2R^4$, $SO_2R^4$, $CONR^6R^7$, or $SO_2$-$NR^6R^7$; --

Column 386, Lines 58-59:

"(iii) a group (i) or (ii) which is independently substituted by one or more (preferably 1 to 3) of the"

Should read: -- (iii) a group (i) or (ii) which is independently substituted by one or more of the --

UNITED STATES PATENT AND TRADEMARK OFFICE
CERTIFICATE OF CORRECTION

PATENT NO.        : 7,202,253 B2
APPLICATION NO. : 10/997734
DATED             : April 10, 2007
INVENTOR(S)       : Lloyd et al.

It is certified that error appears in the above-identified patent and that said Letters Patent is hereby corrected as shown below:

Column 388, Line 55:

"$(C(O)^tT^6)$alkyl, $(NT^7T^8)$alkyl, (cyano)alkyl, (aryl)"

Should read: -- $(C(O)_tT^6)$alkyl, $(NT^7T^8)$alkyl, (cyano)alkyl, (aryl) --

Column 388, Line 57:

"$R^8$ is" should read: -- $R_8$ is --

Column 391, Line 64:

"alkyl, $-C(O)R^{12}$, $-C_2R^{12}$, $-C(O)-NR^{12}R^{13}$, or"

Should read: -- alkyl, $-C(O)R^{12}$, $-CO_2R^{12}$, $-C(O)-NR^{12}R^{13}$, or --

Column 392, Lines 15-17:

"$R^{8c}$ is independently H, alkyl, cycloalkyl, alkenyl, aryl, arylalkyl, cycloheteroalkyl, heteroaryl, amino or alkoxy;"

Should read: -- $R^{8c}$ is independently H, alkyl, cycloalkyl, alkenyl, alkynyl, aryl, arylalkyl, cycloheteroalkyl, heteroaryl, amino or alkoxy; --

UNITED STATES PATENT AND TRADEMARK OFFICE
CERTIFICATE OF CORRECTION

PATENT NO. : 7,202,253 B2
APPLICATION NO. : 10/997734
DATED : April 10, 2007
INVENTOR(S) : Lloyd et al.

It is certified that error appears in the above-identified patent and that said Letters Patent is hereby corrected as shown below:

Column 393, Lines 1-2:

"(iii)a group (i) or (ii) which is independently substituted by one or more (preferably 1 to 3) of the"

Should read: -- (iii)a group (i) or (ii) which is independently substituted by one or more of the --

Signed and Sealed this

Twenty-fourth Day of June, 2008

JON W. DUDAS
*Director of the United States Patent and Trademark Office*